US008916747B2

(12) United States Patent
Davies et al.

(10) Patent No.: US 8,916,747 B2
(45) Date of Patent: Dec. 23, 2014

(54) GENERATION OF PLANTS WITH ALTERED PROTEIN, FIBER, OR OIL CONTENT

(75) Inventors: John P. Davies, Portland, OR (US); Hein Tsoeng (Medard) Ng, Charlottesville, VA (US); D. Ry Wagner, Pleasant Hill, OR (US)

(73) Assignee: Agrigenetics, Inc., Indianapolis, IN (US)

( * ) Notice: Subject to any disclaimer, the term of this patent is extended or adjusted under 35 U.S.C. 154(b) by 302 days.

(21) Appl. No.: 13/480,275

(22) Filed: May 24, 2012

(65) Prior Publication Data

US 2012/0233724 A1    Sep. 13, 2012

Related U.S. Application Data

(62) Division of application No. 13/221,790, filed on Aug. 30, 2011, now Pat. No. 8,217,225, which is a division of application No. 11/940,270, filed on Nov. 14, 2007, now Pat. No. 8,034,993.

(60) Provisional application No. 60/866,056, filed on Nov. 15, 2006.

(51) Int. Cl.
*C12N 15/82* (2006.01)
*C12N 15/63* (2006.01)
*C12N 15/09* (2006.01)
*A01H 5/00* (2006.01)
*C07K 14/415* (2006.01)

(52) U.S. Cl.
CPC .......... *C12N 15/8261* (2013.01); *C07K 14/415* (2013.01)
USPC ........... 800/278; 800/284; 800/290; 800/306; 435/320.1; 536/23.1; 536/23.6

(58) Field of Classification Search
CPC ........ C12N 15/82; C12N 15/52; C12N 15/09; C12N 9/00; C12N 15/8247; C12N 15/8261; C07K 14/415
See application file for complete search history.

(56) References Cited

U.S. PATENT DOCUMENTS

| | | | |
|---|---|---|---|
| 5,322,783 A | 6/1994 | Tomes et al. | |
| 5,538,880 A | 7/1996 | Lundquist et al. | |
| 5,550,318 A | 8/1996 | Adams et al. | |
| 5,563,055 A | 10/1996 | Townsend et al. | |
| 5,610,042 A | 3/1997 | Chang et al. | |
| 5,639,790 A | 6/1997 | Voelker et al. | |
| 5,704,160 A | 1/1998 | Bergquist et al. | |
| 5,952,544 A | 9/1999 | Browse et al. | |
| 6,229,033 B1 | 5/2001 | Knowlton | |
| 6,248,939 B1 | 6/2001 | Leto et al. | |
| 6,750,046 B2 | 6/2004 | Moloney et al. | |
| 7,566,816 B2 | 7/2009 | Lightner et al. | |
| 2003/0046723 A1 | 3/2003 | Heard et al. | |
| 2004/0019927 A1 | 1/2004 | Sherman et al. | |
| 2004/0025202 A1 | 2/2004 | Laurie et al. | |
| 2006/0048240 A1 | 3/2006 | Alexandrov et al. | |
| 2006/0150283 A1 | 7/2006 | Alexandrov et al. | |
| 2006/0277630 A1 | 12/2006 | Lightner et al. | |
| 2009/0144860 A1 | 6/2009 | Beeckman et al. | |

FOREIGN PATENT DOCUMENTS

| | | |
|---|---|---|
| EP | 1033405 | 9/2000 |
| WO | WO 94/11516 | 5/1994 |
| WO | WO 95/06128 | 3/1995 |
| WO | WO 02/10210 | 2/2002 |
| WO | WO 2004/035798 | 4/2004 |
| WO | WO 2004/093528 | 11/2004 |
| WO | WO 2004/093532 | 11/2004 |
| WO | WO 2005/047516 | 5/2005 |
| WO | WO 2005/107437 | 11/2005 |
| WO | WO 2007/053482 | 5/2007 |

OTHER PUBLICATIONS

Anoop et al., "Modulation of citrate metabolism alters aluminum tolerance in yeast and transgenic canola overexpressing a mitochondrial citrate synthase," *Plant Physiol.*, 132:2205-2217, 2003.
Bateman et al., "Pfam 3.1: 1313 multiple alignments and profile HMMs match the majority of proteins," *Nucleic Acids Res.*, 27:260-262, 1999.
Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, 2003.
Browse et al., "Fluxes through the prokaryotic and eukaryotic pathways of lipid synthesis in the '16:3' plant *Arabidopsis thaliana*," *Biochem J.* 235:25-31, 1986.
Chapple and Carpita, "Plant cell walls as targets for biotechnology," *Current Opinion in Plant Biology*, 1:179-185 (1998).
Christensen et al., *9th International Conference on Arabidopsis Research*, Univ. of Wisconsin-Madison, Jun. 24-28, Abstract 165, 1998.
Christou et al., "Inheritance and expression of foreign genes in transgenic soybean plants," *Proc. Natl. Acad. Sci. USA*, 86:7500-7504, 1989.
Colbert et al., "High-throughput screening for induced point mutations," *Plant Physiol.* 126:480-484, 2001.
Database EMBL, "*Arabidopsis thaliana* genomic DNA, chromosome 3, P1 clone: MPN9," Database Accession No. AB025631; Apr. 9, 1999.
Database Uniprot, "Genomic DNA, chromosome 3, P1 clone: MPN9," Database Accession No. Q9LT22; Oct. 1, 2000.

(Continued)

*Primary Examiner* — Brent T Page
(74) *Attorney, Agent, or Firm* — Marcia I. Rosenfeld; Klarquist Sparkman, LLP.

(57) ABSTRACT

The present invention is directed to plants that display an improved oil quantity phenotype or an improved meal quality phenotype due to altered expression of an IMQ nucleic acid. The invention is further directed to methods of generating plants with an improved oil quantity phenotype or improved meal quality phenotype.

25 Claims, No Drawings

(56) References Cited

OTHER PUBLICATIONS

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701, 1989.
Dehesh et al., "Overexpression of 3-ketoacyl-acyl-carrier protein synthase IIIs in plants reduces the rate of lipid synthesis," *Plant Physiol.*, 125:1103-1114, 2001.
Douglas et al., "Nutritional evaluation of low phytate and high protein corns," *Poultry Sci.* 79:1586-1591, 2000.
Eastmond and Graham, "Re-examining the role of glyoxylate cycle in oilseeds," *Trends Plant Sci.*, 6(2):72-77, 2001.
Eccleston and Ohlrogge, "Expression of lauroyl-acyl carrier protein thioesterase in *Brassica napus* seeds induces pathways for both fatty acid oxidation and biosynthesis and implies a set point for triacylglycerol accumulation," *Plant Cell*. 10:613-621, 1998.
Edwards et al., "Protein and energy evaluation of soybean meals processed from genetically modified high-protein soybeans," *Poultry Sci.* 79:525-527, 1999.
Everett et al., "Genetic engineering of sunflower (*Helianthus annuus* L.)," *Bio/Technology*, 5:1201, 1987.
Falco et al., "Transgenic canola and soybean seeds with increased lysine," *Bio/Technology*, 13:577-582, 1995.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.
Feldmann et al., "A Dwarf Mutant of *Arabidopsis* Generated by T-DNA Insertion Mutagenesis," *Science*, 243:1351-1354, 1989.
Focks and Benning, "*wrinkled1*: a novel, low-seed-oil mutant of *Arabidopsis* with a deficiency in the seed-specific regulation of carbohydrate metabolism," *Plant Physiol.*, 118:91-101, 1998.
Fridborg et al., "The *Arabidopsis* dwarf mutant *shi* exhibits reduced gibberellin responses conferred by overexpression of a new putative zinc finger protein," *Plant Cell*, 11:1019-1032, 1999.
Girke et al., "Microarray analysis of developing *Arabidopsis* seeds," *Plant Physiol.*, 124:1570-1581, 2000.
Hayashi et al., "Activation of a plant gene by T-DNA tagging: auxin-independent growth in vitro," *Science*, 258:1350-1353, 1992.
Honig and Rackis, "Determination of the total pepsin-pancreatin indigestible content (dietary fiber) of soybean products, wheat bran, and corn bran," *J. Agri. Food Chem.*, 27:1262-1266, 1979.
Jako et al., "Seed-specific over-expression of an *Arabidopsis* cDNA encoding a diacylglycerol acyltransferase enhances seed oil content and seed weight," *Plant Physiol.*, 126(2):861-74, 2001.
James and Dooner, "Isolation of EMS-induced mutants in *Arabidopsis* altered in seed fatty acid composition," *Theor. Appl. Genet.*, 80:241-245, 1990.
Kardailsky et al., "Activation tagging of the floral inducer FT," *Science*, 286:1962-1965, 1999.
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.
Katavic et al., "Utility of the *Arabidopsis* FAE1 and yeast SLC1-1 genes for improvements in erucic acid and oil content in rapeseed," *Biochem Soc. Trans.*, 28(6):935-937, 2000.
Klein et al., "High velocity microprojectiles for delivering nucleic acids into living cells," *Nature*, 327:70-73, 1987.
Larson et al., "Acyl CoA profiles of transgenic plants that accumulate medium-chain fatty acids indicate inefficient storage lipid synthesis in developing oilseeds," *Plant J.*, 32:519-527, 2002.
Lemieux et al., "Mutants of *Arabidopsis* with alterations in seed lipid fatty acid composition," *Theor. Appl. Genet.*, 80:234-240, 1990.
Lin et al., "The Pex16p Homolog SSE1 and Storage Organelle Formation in *Arabidopsis* Seeds," *Science*, 284:328-330, 1999.
Lionneton et al., "Development of an AFLP-based linkage map and localization of QTLs for seed fatty acid content in condiment mustard (*Brassica juncea*)," *Genome*, 45:1203-15 (2002).

Liu and Butow, "A transcriptional switch in the expression of yeast tricarboxylic acid cycle genes in response to a reduction or loss of respiratory function," *Mol. Cell. Biol.*, 19:6720-6728, 1999.
McCallum et al., "Targeted screening for induced mutations," *Nature Biotechnology*, 18:455-457, 2000.
Mekhedov et al., "Toward a Functional Catalog of the Plant Genome. A Survey of Genes for Lipid Biosynthesis," *Plant Physiology*, 122:389-401, 2000.
Moire et al., "Impact of Unusual Fatty Acid Synthesis on Futile Cycling through β-Oxidation and on Gene Expression in Transgenic Plants," *Plant Physiology*, 134:432-442, 2004.
Moore et al., "Chromatography of Amino Acids on Sulfonated Polystyrene Resins," *Anal. Chem.*, 30:1185-1190, 1958.
Mulder et al., "The InterPro Database, 2003 brings increased coverage and new features," *Nucleic Acids Res.*, 31:315-318, 2003.
Neuhaus et al., "Nonphotosynthetic Metabolism in Plastids," *Annu. Rev. Plant Physiol. Plant Mol.*, 51:111-140, 2000.
O'Hara et al., "Fatty Acid and Lipid Biosynthetic Genes Are Expressed at Constant Molar Ratios But Different Absolute Levels during Embryogenesis," *Plant Physiology*, 129:310-320, 2002.
Okuley et al., "*Arabidopsis FAD2* gene encodes the enzyme that is essential for polyunsaturated lipid synthesis," *Plant Cell*, 6:147-158, 1994.
Parsons et al., "Nutritional evaluation of soybean meals varying in oligosaccharide content," *Poultry Sci.*, 79:1127-1131, 2000.
Pritchard et al., "Germination and storage reserve mobilization are regulated independently in *Arabidopsis*," *The Plant Journal*, 31(5):639-647, 2002.
Rangasamy and Ratledge, "Genetic enhancement of fatty acid synthesis by targeting rat liver ATP:citrate lyase into plastids of tobacco," *Plant Physiol.*, 122:1231-1238, 2000.
Rangasamy et al., "Compartmentation of ATP:Citrate Lyase in Plants," *Plant Physiology*, 122:1225-1230, 2000.
Ratledge et al., "Correlation of ATP/Citrate Lyase Activity with Lipid Accumulation in Developing Seeds of *Brassica napus* L.," Lipids, 32(1):7-12, 1997.
Rawsthorne, Stephen, "Carbon flux and fatty acid synthesis in plants," *Progress in Lipid Research*, 41:182-196, 2002.
Ruuska et al., "Contrapuntal Networks of Gene Expression during *Arabidopsis* Seed Filling," *The Plant Cell*, 14:1191-1206, 2002.
Rylott et al., "Co-ordinate regulation of genes involved in storage lipid mobilization in *Arabidopsis thaliana*," *Biochem Soc. Trans.*, 29:283-287, 2001.
Schaffer et al., "The late elongated hypocotyl mutation of *Arabidopsis* disrupts circadian rhythms and the photoperiodic control of flowering," *Cell*, 93:1219-1229, 1998.
Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.
Schnurr et al., "Characterization of an acyl-CoA synthetase from *Arabidopsis thaliana*," *Biochem Soc. Trans.*, 28(6):957-958, 2000.
Shewry, "Seed storage proteins: structures and biosynthesis," *Plant Cell*, 7:945-956, 1995.
Shockey et al., "Characterization of the AMP-binding protein gene family in *Arabidopsis thaliana*: will the real acyl-CoA synthetases please stand up?" *Biochem Soc. Trans.*, 28(6):955-957, 2000.
Thelen et al., "Biotin carboxyl carrier protein isoforms in *Brassicaceae* oilseeds," *Biochem. Soc. Trans.*, 28(6):595-598, 2000.
Weigel et al., "Activation tagging in *Arabidopsis*," *Plant Physiology*, 122:1003-1013, 2000.
White et al., "A new set of *Arabidopsis* expressed sequence tags from developing seeds. The metabolic pathway from carbohydrates to seed oil," *Plant Physiol.*, 124:1582-1594, 2000.
Wilson et al., "A Dissociation insertion causes a semidominant mutation that increases expression of TINY, an *Arabidopsis* gene related to APETALA2," *Plant Cell*, 8:659-671, 1996.
Yadav et al., "Cloning of higher plant omega-3 fatty acid desaturases," *Plant Physiol.*, 103:467-476, 1993.
Zou et al., "Modification of Seed Oil Content and Acyl Composition in the *Brassicaceae* by Expression of a Yeast *sn*-2 Acyltransferase Gene," *The Plant Cell*, 9:909-923, 1997.

GENERATION OF PLANTS WITH ALTERED PROTEIN, FIBER, OR OIL CONTENT

CROSS REFERENCE TO RELATED APPLICATIONS

This is a divisional of co-pending U.S. patent application Ser. No. 13/221,790, filed Aug. 30, 2011, which is a divisional of U.S. patent application Ser. No. 11/940,274, filed Nov. 14, 2007, now U.S. Pat. No. 8,034,993, issued Oct. 11, 2011, which claims the benefit of U.S. Provisional Application No. 60/866,056, filed Nov. 15, 2006, each of which is incorporated herein by reference in its entirety.

FIELD OF THE DISCLOSURE

The present disclosure is related to transgenic plants with altered oil, protein, and/or fiber content, as well as methods of making plants having altered oil, protein, and/or fiber content and producing oil from such plants.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on May 9, 2012, and having a size of ~322 kilobytes, as permitted under 37 CFR 1.821(c). The material in the aforementioned file is hereby incorporated by reference in its entirety.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmann et al., 1989, *Science* 243: 1351-1354) that detected altered fatty acid composition identified the omega 3 desaturase (FADS) and delta-12 desaturase (FAD2) genes (U.S. Pat. No. 5,952,544; Yadav et al., 1993, *Plant Physiol.* 103, 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9$^{th}$ *International Conference on Arabidopsis Research*, Univ. of Wisconsin-Madison, June 24-28, Abstract 165).

SUMMARY

Provided herein are transgenic plants having an Improved Seed Quality phenotype. Transgenic plants with an Improved Seed Quality phenotype may include an improved oil quantity and/or an improved meal quality. Transgenic plants with improved meal quality have an Improved Meal Quality (IMQ) phenotype and transgenic plants with improved oil quantity have an Improved Oil Quantity (IOQ) phenotype.

The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Examples of the disclosed transgenic plant are produced by a method that comprises introducing into progenitor cells of the plant a plant transformation vector comprising an IMQ nucleotide sequence that encodes, or is complementary to a sequence that encodes, an IMQ polypeptide, and growing the transformed progenitor cells to produce a transgenic plant, wherein the IMQ polynucleotide sequence is expressed, causing an IOQ phenotype and/or and IMQ phenotype in the transgenic plant. In some specific, non-limiting examples, the method produces transgenic plants wherein expression of the IMQ polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. In some embodiments of the method, the method employs candidate gene/QTL methodology or TILLING methodology.

Also provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "IMQ phenotype" refers to plants, or any part of a plant (for example, seeds, or meal produced from seeds), with an altered protein and/or fiber content (phenotype). As provided herein, altered protein and/or fiber content includes either an increased or decreased level of protein and/or fiber content in plants, seeds or seed meal. Any combination of these changes can lead to an IMQ phenotype. For example, in one specific non-limiting example, an IMQ phenotype can refer to increased protein and decreased fiber content. In another specific non-limiting example, an IMQ phenotype can refer to unchanged protein and decreased fiber content. In yet another specific non-limiting example, an IMQ phenotype can refer to increased protein and unchanged fiber content. It is also provided that any combination of these changes can lead to an increase in the AME (available metabolizable energy) from the seed or meal generated from the seed. An IMQ phenotype also includes an improved seed quality (ISQ) phenotype or an improved seed meal quality phenotype.

As used herein, the term "IOQ phenotype" refers to plants, or any part of a plant (for example, seeds), with an altered oil content (phenotype). As provided herein, altered oil content includes an increased, for example a high, oil content in plants or seeds. In some embodiments, a transgenic plant can express both an IOQ phenotype and an IMQ phenotype. In specific, non-limiting examples, a transgenic plant having a combination of an IOQ phenotype and an IMQ phenotype can lead to an increase in the AME (available metabolizable energy) from the seed or meal generated from the seed. An IOQ phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed protein and/or fiber content and without a decrease in seed oil content (seed oil content remains unchanged or is increased), resulting in an increase in the value of animal feed derived from the seed.

As used herein, the term "content" refers to the type and relative amount of, for instance, a seed or seed meal component.

As used herein, the term "fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include an IMQ nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant. Specific, non-limiting examples of a change in phenotype include an IMQ phenotype or an IOQ phenotype.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an IMQ phenotype or an IOQ phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified plant. A high protein phenotype refers to an increase in overall protein content. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified plant. A low fiber phenotype refers to decrease in overall fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having an Improved Seed Quality phenotype. Transgenic plants with an Improved Seed Quality phenotype may include an improved oil quantity and/or an improved meal quality. Transgenic plants with improved meal quality have an IMQ phenotype and transgenic plants with improved oil quantity have an IOQ phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods (see, for example, WO 2007/053482 and WO 2005/107437, which are incorporated herein by reference in their entirety).

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al. (*Plant J.* 4:833-840, 1993) and Misawa et al. (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock et al. (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., *Scientia Sinica* 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered protein, fiber and/or oil content (phenotype, for example, see columns 4, 5 and 6, respectively, of Table 1, below) and 2) the nucleic acid sequences identified in column 3 of Tables 2 and 3, wherein each nucleic acid sequence is provided with a gene alias or an IMQ designation (IMQ#; see column 1 in Tables 1, 2, and 3). Briefly, and as further described in the Examples, a large number of *Arabidopsis* plants were mutated with the pSKI015 vector, which comprises a T-DNA from the Ti plasmid of *Agrobacterium tumefaciens*, a viral enhancer element, and a selectable marker gene (Weigel et al., 2000, *Plant Physiology*, 122: 1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

Quantitative determination of fatty acid (FA) content (column 7, Table 1) in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 µl 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 µl of water and 400 µl of hexane were added to each vial, which was then shaken vigorously and allowed to phase separate. Reaction vials were loaded directly onto gas chromatography (GC) for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 µl of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Peaks were initially identified by comparison with standards. Integration and quantification were performed automatically, but all analyses were subsequently examined manually to verify correct peak identification and acceptable signal to noise ratio before inclusion of the derived results in the study.

The association of an IMQ nucleic acid sequence with an IMQ phenotype or an IOQ phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed IMQ nucleic acid sequences and/or polypeptides may be employed in the development of transgenic plants having an improved seed quality phenotype, including an IMQ phenotype and/or an IOQ phenotype. IMQ nucleic acid sequences may be used in the generation of transgenic plants, such as oilseed crops, that provide improved oil yield from oilseed processing and result in an increase in the quantity of oil recovered from seeds of the transgenic plant. IMQ nucleic acid sequences may also be used in the generation of transgenic plants, such as feed grain crops, that provide an IMQ phenotype resulting in increased energy for animal feeding, for example, seeds or seed meal with an altered protein and/or fiber content, resulting in an increase in AME. IMQ nucleic acid sequences may further be used to increase the oil content of specialty oil crops, in order to augment yield and/or recovery of desired unusual fatty acids. Transgenic plants that have been genetically modified to express IMQ polypeptides can be used in the production of seeds, wherein the transgenic plants are grown, and oil and seed meal are obtained from plant parts (e.g. seed) using standard methods.

IMQ Nucleic Acids and Polypeptides

The IMQ designation for each of the IMQ nucleic acid sequences discovered in the activation tagging screen described herein are listed in column 1 of Tables 1-3, below. The disclosed IMQ polypeptides are listed in column 5 of Table 2 and column 4 of Table 3. As used herein, the term "IMQ polypeptide" refers to any polypeptide that when expressed in a plant causes an IMQ phenotype and/or an IOQ phenotype in any part of the plant, for example the seeds. In one embodiment, an IMQ polypeptide refers to a full-length IMQ protein, or a fragment, derivative (variant), or ortholog thereof that is "functionally active," such that the protein fragment, derivative, or ortholog exhibits one or more or the functional activities associated with one or more of the disclosed full-length IMQ polypeptides, for example, the amino acid sequences provided in the GenBank entry referenced in column 5 of Table 2, which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof. In one preferred embodiment, a functionally active IMQ polypeptide causes an IMQ phenotype and/or an IOQ phenotype in a transgenic plant. In another embodiment, a functionally active IMQ polypeptide causes an altered oil, protein, and/or fiber content phenotype (for example, an altered seed meal content phenotype) when mis-expressed in a plant. In other preferred embodiments, mis-expression of the IMQ polypeptide causes a high oil (such as, increased oil), high protein (such as, increased protein), and/or low fiber (such as, decreased fiber) phenotype in a plant. In another embodiment, mis-expression of the IMQ polypeptide causes an improved AME of meal. In yet another embodiment, a functionally active IMQ polypeptide can rescue defective (including deficient) endogenous IMQ activity when expressed in a plant or in plant cells; the rescuing polypeptide may be from the same or from a different species as the species with the defective polypeptide activity. The disclosure also provides feed, meal, grain, food, or seed comprising the IMQ polypeptide, or a fragment, derivative (variant), or ortholog thereof.

In another embodiment, a functionally active fragment of a full length IMQ polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or a naturally occurring ortholog thereof) retains one or more of the biological properties associated with the full-length IMQ polypeptide, such as signaling activity, binding activity, catalytic activity, or cellular or extra-cellular localizing activity. An IMQ fragment preferably comprises an IMQ domain, such as a C- or N-terminal or catalytic domain, among others, and preferably comprises at least 10, preferably at least 20, more preferably at least 25, and most preferably at least 50 contiguous amino acids of an IMQ protein. Functional domains of IMQ genes are listed in column 8 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length IMQ polypeptides, or fragments thereof, include polypeptides with amino acid insertions, deletions, or substitutions that retain one of more of the biological properties associated with the full-length IMQ polypeptide. In some cases, variants are generated that change the post-translational processing of an IMQ polypeptide. For instance, variants may have altered protein transport or protein localization characteristics, or altered protein half-life, compared to the native polypeptide.

As used herein, the term "IMQ nucleic acid" refers to any polynucleotide that when expressed in a plant causes an IMQ phenotype and/or an IOQ phenotype in any part of the plant, for example the seeds. In one embodiment, an IMQ polynucleotide encompasses nucleic acids with the sequence provided in or complementary to the GenBank entry referenced in column 3 of Table 2, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, as well as functionally active fragments, derivatives, or orthologs thereof. An IMQ nucleic acid of this disclosure may be DNA, derived from genomic DNA or cDNA, or RNA. Genomic sequences of the genes listed in Table 2 are known and available in public databases such as GenBank.

In one embodiment, a functionally active IMQ nucleic acid encodes or is complementary to a nucleic acid that encodes a functionally active IMQ polypeptide. A functionally active IMQ nucleic acid also includes genomic DNA that serves as a template for a primary RNA transcript (i.e., an mRNA precursor) that requires processing, such as splicing, before encoding the functionally active IMQ polypeptide. An IMQ nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed IMQ polypeptide, or an intermediate form. An IMQ polynucleotide can also include heterologous coding sequences, for example, sequences that encode a marker included to facilitate the purification of the fused polypeptide, or a transformation marker. In another embodiment, a functionally active IMQ nucleic acid is capable of being used in the generation of loss-of-function IMQ phenotypes, for instance, via antisense suppression, co-suppression, etc. The disclosure also provides feed, meal, grain, food, or seed comprising a nucleic acid sequence that encodes an IMQ polypeptide.

In one preferred embodiment, an IMQ nucleic acid used in the disclosed methods comprises a nucleic acid sequence that encodes, or is complementary to a sequence that encodes, an IMQ polypeptide having at least 50%, 60%, 70%, 75%, 80%, 85%, 90%, 95%, 97%, 98%, or 99% sequence identity to a disclosed IMQ polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In another embodiment, an IMQ polypeptide comprises a polypeptide sequence with at least 50% or 60% identity to a disclosed IMQ polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100) and may have at least 70%, 80%, 85%, 90%, 95%, 97%, 98%, or 99% sequence identity to a disclosed IMQ polypeptide sequence. In a further embodiment, an IMQ polypeptide comprises 50%, 60%, 70%, 80%, 85%, 90%, 95%, 97%, 98%, or 99% sequence identity to a disclosed IMQ polypeptide sequence, and may include a conserved protein domain of the IMQ polypeptide (such as the protein domain(s) listed in column 8 of Table 2). In another embodiment, an IMQ polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, an IMQ polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 8 of Table 2.

In another aspect, an IMQ polynucleotide sequence is at least 50% to 60% identical over its entire length to a disclosed IMQ nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and may comprise at least 70%, 80%, 85%, 90%, 95%, 97%, 98%, or 99% sequence identity to the disclosed IMQ sequence, or a functionally active fragment thereof, or complementary sequences. In another embodiment, a disclosed IMQ nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and nucleic acid sequences that have substantial sequence homology to a such IMQ sequences. As used herein, the phrase "substantial sequence homology" refers to those nucleic acid sequences that have slight or inconsequential sequence variations from such IMQ sequences, i.e., the sequences function in substantially the same manner and encode an IMQ polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.*, 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed IMQ nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an IMQ polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs of a disclosed *Arabidopsis* IMQ nucleic acid sequence. Representative putative orthologs of each of the disclosed *Arabidopsis* IMQ genes are identified in column 3 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.*, 95:5849-5856; Huynen M A et al., 2000, *Genome Research*, 10:1204-1210).

Programs for multiple sequence alignment, such as CLUSTAL (Thompson J D et al., 1994, *Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* IMQ coding sequence may be used as a probe. IMQ ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known IMQ polypeptides are used for ortholog isolation (see, e.g., Harlow and Lane, 1988, 1999, *Antibodies: A Laboratory Manual*, Cold Spring Harbor Laboratory Press, New York). Western blot analysis can determine that an IMQ ortholog (i.e., a protein orthologous to a disclosed IMQ polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which IMQ nucleic acid and/or polypeptide sequences have been identified.

IMQ nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the IMQ nucleic acid into a plant expression vector for transformation of plant cells, and the IMQ polypeptide is expressed in the host plant. Transformed plants and plant cells expressing an IMQ polypeptide express an IMQ phenotype and/or an IOQ phenotype and, in one specific, non-limiting example, may have high (increased) oil, high (increased) protein, and/or low (decreased) fiber content.

An "isolated" IMQ nucleic acid molecule is other than in the form or setting in which it is found in nature, and is identified and separated from least one contaminant nucleic acid molecule with which it is ordinarily associated in the natural source of the IMQ nucleic acid. However, an isolated IMQ nucleic acid molecule includes IMQ nucleic acid molecules contained in cells that ordinarily express IMQ where, for example, the nucleic acid molecule is in a chromosomal location different from that of natural cells.

Generation of Genetically Modified Plants with an Improved Oil Quantity Phenotype and/or an Improved Meal Quality Phenotype The disclosed IMQ nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the IMQ gene in a plant is used to generate plants with a high oil content (phenotype). As used herein, an "altered protein content (phenotype)" may refer to altered protein content in any part of the plant. In a preferred embodiment, altered expression of the IMQ gene in a plant is used to generate plants with a high (or increased) protein content (phenotype). As used herein, an "altered fiber content (phenotype)" may refer to altered fiber content in any part of the plant. In a preferred embodiment, altered expression of the IMQ gene in a plant is used to generate plants with a low (or decreased) fiber content (phenotype). The altered oil, protein, and/or fiber content is often observed in seeds. Examples of a transgenic plant include plants comprising a plant transformation vector with a nucleotide sequence that encodes or is complementary to a sequence that encodes an IMQ polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the IMQ nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (Nicotiana), turfgrass (Poaceae family), other forage crops, and wild species may also be a source of unique fatty acids. In other embodiments, any plant expressing the IMQ nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an IMQ polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), sunflower (Everett et al., 1987, *Bio/Technology*, 5:1201), soybean (Christou et al., 1989, *Proc. Natl. Acad. Sci USA*, 86:7500-7504; Kline et al., 1987, *Nature*, 327:70), wheat, rice and oat.

Expression (including transcription and translation) of an IMQ nucleic acid sequence may be regulated with respect to the level of expression, the tissue type(s) where expression takes place and/or developmental stage of expression. A number of heterologous regulatory sequences (e.g., promoters and enhancers) are available for controlling the expression of an IMQ nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.*, 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (*U.S.A.*) 84:6624-6628, 1987), the sucrose synthase promoter (Yang et al., *Proc. Natl. Acad. Sci.* (*U.S.A.*) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol Biol.*, 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol Bio.*, 21:625-640).

In one preferred embodiment, expression of the IMQ nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-176, 1994), soybean α' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.*, 34(3):549-555, 1997). Also included are the zeins, which are a group of storage proteins found in corn endosperm. Genomic clones for zein genes have been isolated (Pedersen et al., *Cell*, 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10:1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus* napin, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus* oleosin (Keddie et al., 1994, *Plant Mol. Biol.* 24:327-40), *Arabidopsis* oleosin (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous IMQ nucleic acid sequence in a host cell. Exemplary methods for practicing this aspect of the invention include, but are not limited to antisense suppression (Smith, et al., 1988, *Nature*, 334:724-726; van der Krol et al., 1988, *BioTechniques*, 6:958-976); co-suppression (Napoli, et al., 1990, *Plant Cell*, 2:279-289); ribozymes (PCT Publication WO 97/10328); and combinations of sense and antisense (Waterhouse, et al., 1998, *Proc. Natl. Acad. Sci. USA*, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA*, 85:8805-8809), a partial cDNA sequence including fragments of 5' coding sequence, (Cannon et al., 1990, *Plant Mol. Biol.*, 15:39-47), or 3' non-coding sequences (Ch'ng et al., 1989, *Proc. Natl. Acad. Sci. USA*, 86:10006-10010). Cosuppression techniques may use the entire cDNA sequence (Napoli et al., 1990, *Plant Cell*, 2:279-289; van der Krol et al., 1990, *Plant Cell*, 2:291-299), or a partial cDNA sequence (Smith et al., 1990, *Mol. Gen. Genetics*, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe, *Arch. Virol. Suppl.* 15:189-201, 1999).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin et al., 1999, *Cur. Opin. Plant Biol.* 2(2):96-103; Dangond, *Physiol Genomics* (2000) 2:53-58; van Hal et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Improved Oil Quantity Phenotype and/or Improved Meal Quality Phenotype Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. For example, provided herein is a method of identifying plants that have mutations in the endogenous IMQ nucleic acid sequence that confer an IMQ phenotype and/or an IOQ phenotype and generating progeny of these plants with an IMQ and/or IOQ phenotype that are not genetically modified. In some embodiments, the plants have an IMQ phenotype with an altered protein and/or fiber content or seed meal content, or an IOQ phenotype, with an altered oil content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the IMQ nucleic acid sequence is used to identify whether a mutated plant has a mutation in the IMQ nucleic acid sequence. Plants having IMQ mutations may then be tested for altered oil, protein, and/or fiber content, or alternatively, plants may be tested for altered oil, protein, and/or fiber content, and then PCR amplification and sequencing of the IMQ nucleic acid sequence is used to determine whether a plant having altered oil, protein, and/or fiber content has a mutated IMQ nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the IMQ nucleic acid sequence or orthologs of the IMQ nucleic acid sequence that may confer altered oil, protein, and/or fiber content (see Bert et al., *Theor Appl Genet.*, 2003 June; 107 (1):181-9; and Lionneton et al., *Genome*, 2002 December; 45(6):1203-15). Thus, in a further aspect of the disclosure, an IMQ nucleic acid is used to identify whether a plant having altered oil, protein, and/or fiber content has a mutation an endogenous IMQ nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with an IMQ Phenotype and/or an IOQ Phenotype by Transformation with an Activation Tagging Construct This Example describes the generation of transgenic plants with altered oil, protein, and/or fiber content.

Mutants were generated using the activation tagging "ACTTAG" vector, pSKI015 (GI#6537289; Weigel D et al., 2000, *Plant Physiology*, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A fiber content predicting calibration was developed by measuring crude fiber content in a set of seed samples. Fiber content of in a known mass of seed was determined using the method of Honig and Rackis, (1979, *J. Agri. Food Chem.*, 27: 1262-1266). Digestible protein content of in a known mass of seed was determined by quantifying the individual amino acids liberated by an acid hydrolysis Steine and Moore (1958, *Anal. Chem.*, 30:1185-1190). The quantification was performed by the Amino Quant (Agilent). The undigested protein remaining associated with the non digestible fraction is measured by the same method described for the whole seed homogenate. Digestible protein content is determined by subtracting the amount of undigested protein associated with the non digestible fraction from the total amount of protein in the seed sample.

Seed oil, protein, digestible protein and fiber values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Promoters within 9 kb of the enhancers in the ACTTAG element are considered to be within "activation space." Genes with T-DNA inserts within coding sequences were not considered to be within "activation space." The ACTTAG lines with the above average oil and protein values, and below average fiber values were identified and are listed in column 3 of Table 1.

TABLE 1

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ42.3 | At3g19870 | W000093675 | 112.46% | 94.21% | 95.25% | |
| IMQ43.1 | At3g20170 | W000145325 | 114.17% | 89.64% | 94.52% | |
| IMQ43.2 | At3g20180 | W000145325 | 114.17% | 89.64% | 94.52% | |
| IMQ43.3 | At3g20190 | W000145325 | 114.17% | 89.64% | 94.52% | 97.33% |
| IMQ43.4 | At3g20200 | W000145325 | 114.17% | 89.64% | 94.52% | |
| IMQ43.5 | At3g20210 | W000145325 | 114.17% | 89.64% | 94.52% | |
| IMQ44.1 | At3g21300 | W000148155 | 114.84% | 91.54% | 93.83% | |
| IMQ44.2 | At3g21310 | W000148155 | 114.84% | 91.54% | 93.83% | |
| IMQ45.1 | At3g24570 | W000141484 | 113.59% | 92.03% | 99.29% | |
| IMQ45.2 | At3g24580 | W000141484 | 113.59% | 92.03% | 99.29% | |
| IMQ45.3 | At3g24590 | W000141484 | 113.59% | 92.03% | 99.29% | |
| IMQ45.4 | At3g24600 | W000141484 | 113.59% | 92.03% | 99.29% | |
| IMQ45.5 | At3g24610 | W000141484 | 113.59% | 92.03% | 99.29% | |
| IMQ46.1 | At3g26900 | W000109686 | 108.34% | 92.65% | 97.24% | |
| IMQ46.2 | At3g26910 | W000109686 | 108.34% | 92.65% | 97.24% | |
| IMQ46.2 | At3g26910 | W000109686 | 108.34% | 92.65% | 97.24% | |
| IMQ46.2 | At3g26910 | W000109686 | 108.34% | 92.65% | 97.24% | |
| IMQ46.3 | At3g26920 | W000109686 | 108.34% | 92.65% | 97.24% | |
| IMQ46.4 | At3g26930 | W000109686 | 108.34% | 92.65% | 97.24% | |
| IMQ47.1 | At3g27770 | W000194585 | 103.85% | 81.80% | 102.51% | |
| IMQ47.2 | At3g27785 | W000194585 | 103.85% | 81.80% | 102.51% | |
| IMQ48.1 | At3g44300 | W000160067 | 110.68% | 95.29% | 92.96% | |
| IMQ48.2 | At3g44310 | W000160067 | 110.68% | 95.29% | 92.96% | |
| IMQ48.2 | At3g44310 | W000160067 | 110.68% | 95.29% | 92.96% | |
| IMQ48.3 | At3g44320 | W000160067 | 110.68% | 95.29% | 92.96% | |
| IMQ49.1 | At3g45060 | W000185043 | 108.38% | 88.28% | 94.42% | |
| IMQ49.1 | At3g45060 | W000136337 | 124.01% | 89.52% | 88.72% | |
| IMQ49.2 | At3g45070 | W000185043 | 108.38% | 88.28% | 94.42% | |
| IMQ49.2 | At3g45070 | W000136337 | 124.01% | 89.52% | 88.72% | |
| IMQ49.3 | At3g45080 | W000185043 | 108.38% | 88.28% | 94.42% | |
| IMQ49.3 | At3g45080 | W000136337 | 124.01% | 89.52% | 88.72% | |
| IMQ49.4 | At3g45090 | W000185043 | 108.38% | 88.28% | 94.42% | |
| IMQ49.4 | At3g45090 | W000136337 | 124.01% | 89.52% | 88.72% | |
| IMQ49.4 | At3g45090 | W000185043 | 108.38% | 88.28% | 94.42% | |
| IMQ49.4 | At3g45090 | W000136337 | 124.01% | 89.52% | 88.72% | |
| IMQ49.5 | At3g45100 | W000136337 | 124.01% | 89.52% | 88.72% | |
| IMQ49.5 | At3g45100 | W000136337 | 124.01% | 89.52% | 88.72% | |
| IMQ49.5 | At3g45100 | W000136337 | 124.01% | 89.52% | 88.72% | |
| IMQ49.5 | At3g45100 | W000136337 | 124.01% | 89.52% | 88.72% | |
| IMQ49.6 | At3g45110 | W000136337 | 124.01% | 89.52% | 88.72% | |
| IMQ49.6 | At3g45110 | W000136337 | 124.01% | 89.52% | 88.72% | |
| IMQ50.1 | At3g46510 | W000185346 | 111.30% | 89.94% | 94.03% | |
| IMQ50.1 | At3g46510 | W000185346 | 111.30% | 89.94% | 94.03% | |
| IMQ50.2 | At3g46520 | W000185346 | 111.30% | 89.94% | 94.03% | |
| IMQ50.3 | At3g46530 | W000185346 | 111.30% | 89.94% | 94.03% | |
| IMQ50.4 | At3g46540 | W000185346 | 111.30% | 89.94% | 94.03% | |
| IMQ50.5 | At3g46550 | W000185346 | 111.30% | 89.94% | 94.03% | |
| IMQ50.6 | At3g46560 | W000185346 | 111.30% | 89.94% | 94.03% | |
| IMQ51.1 | At3g59410 | W000148125 | 110.29% | 91.22% | 96.30% | 97.59% |
| IMQ51.1 | At3g59410 | W000187558 | 103.08% | 88.95% | 99.29% | |
| IMQ51.2 | At3g59420 | W000148125 | 110.29% | 91.22% | 96.30% | |
| IMQ51.2 | At3g59420 | W000187558 | 103.08% | 88.95% | 99.29% | |
| IMQ51.3 | At3g59430 | W000148125 | 110.29% | 91.22% | 96.30% | 97.59% |
| IMQ51.3 | At3g59430 | W000187558 | 103.08% | 88.95% | 99.29% | |
| IMQ51.3 | At3g59430 | W000148125 | 110.29% | 91.22% | 96.30% | |
| IMQ51.3 | At3g59430 | W000187558 | 103.08% | 88.95% | 99.29% | |
| IMQ51.3 | At3g59430 | W000148125 | 110.29% | 91.22% | 96.30% | |
| IMQ51.3 | At3g59430 | W000187558 | 103.08% | 88.95% | 99.29% | |
| IMQ51.4 | At3g59440 | W000148125 | 110.29% | 91.22% | 96.30% | |
| IMQ51.4 | At3g59440 | W000187558 | 103.08% | 88.95% | 99.29% | |
| IMQ51.5 | At3g59450 | W000148125 | 110.29% | 91.22% | 96.30% | |
| IMQ51.5 | At3g59450 | W000187558 | 103.08% | 88.95% | 99.29% | |
| IMQ52.1 | At4g02010 | W000132781 | 119.33% | 90.32% | 92.13% | |
| IMQ52.2 | At4g02020 | W000132781 | 119.33% | 90.32% | 92.13% | |
| IMQ53.1 | At4g03470 | W000143264 | 127.95% | 94.43% | 89.75% | |

TABLE 2

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ42.3 | At3g19870 | gi\|30685527 | SEQ ID NO: 1 | gi\|15230976 | SEQ ID NO: 2 | unknown protein | |
| IMQ43.1 | At3g20170 | gi\|42565047 | SEQ ID NO: 3 | gi\|15231056 | SEQ ID NO: 4 | unknown protein | IPR000225 Armadillo; IPR000357 HEAT |
| IMQ43.2 | At3g20180 | gi\|18402522 | SEQ ID NO: 5 | gi\|15231057 | SEQ ID NO: 6 | unknown protein | IPR006121 Heavy metal transport/detoxification protein |
| IMQ43.3 | At3g20190 | gi\|42565048 | SEQ ID NO: 7 | gi\|42565049 | SEQ ID NO: 8 | ATP binding/kinase/ protein serine/threonine kinase | IPR001611 Leucine-rich repeat; IPR007090 Leucine-rich repeat, plant specific; IPR000719 Protein kinase; IPR008271 Serine/threonine protein kinase, active site |
| IMQ43.4 | At3g20200 | gi\|30685667 | SEQ ID NO: 9 | gi\|30685668 | SEQ ID NO: 10 | ATP binding/kinase/ protein kinase/protein serine/threonine kinase/protein-tyrosine kinase | IPR000719 Protein kinase; IPR008271 Serine/threonine protein kinase, active site; IPR006016 UspA |
| IMQ43.5 | At3g20210 | gi\|30685671 | SEQ ID NO: 11 | gi\|15231080 | SEQ ID NO: 12 | DELTA-VPE; cysteine-type endopeptidase | IPR001096 Peptidase C13, legumain |
| IMQ44.1 | At3g21300 | gi\|42565078 | SEQ ID NO: 13 | gi\|42565079 | SEQ ID NO: 14 | RNA binding/RNA methyltransferase | IPR000051 SAM (and some other nucleotide) binding motif; IPR001566 23S rRNA methyltransferase/RumA; IPR002792 Deoxyribonuclease/rho motif-related TRAM; IPR007848 Methyltransferase small; IPR010280 (Uracil-5)-methyltransferase |
| IMQ44.2 | At3g21310 | gi\|18402951 | SEQ ID NO: 15 | gi\|18402952 | SEQ ID NO: 16 | unknown protein | IPR004949 Protein of unknown function DUF266, plant |
| IMQ45.1 | At3g24570 | gi\|30687563 | SEQ ID NO: 17 | gi\|15230132 | SEQ ID NO: 18 | unknown protein | IPR007248 Mpv17/PMP22 |
| IMQ45.2 | At3g24580 | gi\|18404244 | SEQ ID NO: 19 | gi\|15230133 | SEQ ID NO: 20 | unknown protein | IPR006527 F-box protein interaction domain; IPR001810 Cyclin-like F-box |
| IMQ45.3 | At3g24590 | gi\|30687571 | SEQ ID NO: 21 | gi\|30687572 | SEQ ID NO: 22 | peptidase/serine-type peptidase | IPR011056 Peptidase S24 and S26, C-terminal region; IPR006198 Peptidase S24, S26A and S26B; IPR000223 Peptidase S26A, signal peptidase I |
| IMQ45.4 | At3g24600 | gi\|18404257 | SEQ ID NO: 23 | gi\|15230135 | SEQ ID NO: 24 | unknown protein | IPR010847 Harpin-induced 1 |
| IMQ45.5 | At3g24610 | gi\|18404260 | SEQ ID NO: 25 | gi\|15230136 | SEQ ID NO: 26 | unknown protein | IPR001810 Cyclin-like F-box; IPR006652 Kelch repeat |
| IMQ46.1 | At3g26900 | gi\|30688546 | SEQ ID NO: 27 | gi\|30688547 | SEQ ID NO: 28 | ATP binding/ shikimate kinase | IPR000623 Shikimate kinase |
| IMQ46.2 | At3g26910 | gi\|79313785 | SEQ ID NO: 29 | gi\|79313786 | SEQ ID NO: 30 | unknown protein | IPR006706 Extensin-like region |
| IMQ46.2 | At3g26910 | gi\|42565220 | SEQ ID NO: 31 | gi\|30688552 | SEQ ID NO: 32 | unknown protein | IPR006706 Extensin-like region |
| IMQ46.2 | At3g26910 | gi\|30685726 | SEQ ID NO: 33 | gi\|30685727 | SEQ ID NO: 34 | unknown protein | IPR006706 Extensin-like region |
| IMQ46.3 | At3g26920 | gi\|30688555 | SEQ ID NO: 35 | gi\|30688556 | SEQ ID NO: 36 | unknown protein | IPR001810 Cyclin-like F-box; IPR001611 Leucine-rich repeat |
| IMQ46.4 | At3g26930 | gi\|42565221 | SEQ ID NO: 37 | gi\|42565222 | SEQ ID NO: 38 | unknown protein | IPR006566 FBD; IPR001611 Leucine-rich repeat |
| IMQ47.1 | At3g27770 | gi\|30688916 | SEQ ID NO: 39 | gi\|18405512 | SEQ ID NO: 40 | unknown protein | |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ47.2 | At3g27785 | gi\|30688924 | SEQ ID NO: 41 | gi\|30688925 | SEQ ID NO: 42 | MYB118; DNA binding/transcription factor | IPR001005 Myb, DNA-binding |
| IMQ48.1 | At3g44300 | gi\|30692061 | SEQ ID NO: 43 | gi\|15229932 | SEQ ID NO: 44 | NIT2 (NITRILASE 2) | IPR003010 Nitrilase/cyanide hydratase and apolipoprotein N-acyltransferase; IPR000132 Nitrilase/cyanide hydratase |
| IMQ48.2 | At3g44310 | gi\|30692071 | SEQ ID NO: 45 | gi\|30692072 | SEQ ID NO: 46 | NIT1 (NITRILASE 1) | IPR003010 Nitrilase/cyanide hydratase and apolipoprotein N-acyltransferase; IPR000132 Nitrilase/cyanide hydratase |
| IMQ48.2 | At3g44310 | gi\|30692066 | SEQ ID NO: 47 | gi\|30692067 | SEQ ID NO: 48 | NIT1 (NITRILASE 1) | IPR003010 Nitrilase/cyanide hydratase and apolipoprotein N-acyltransferase; IPR000132 Nitrilase/cyanide hydratase |
| IMQ48.3 | At3g44320 | gi\|30692076 | SEQ ID NO: 49 | gi\|15229936 | SEQ ID NO: 50 | NIT3 (NITRILASE 3) | IPR003010 Nitrilase/cyanide hydratase and apolipoprotein N-acyltransferase; IPR000132 Nitrilase/cyanide hydratase |
| IMQ49.1 | At3g45060 | gi\|42565547 | SEQ ID NO: 51 | gi\|15230589 | SEQ ID NO: 52 | ATNRT2.6; nitrate transporter | IPR007114 Major facilitator superfamily; IPR011701 Major facilitator superfamily MFS_1; IPR004737 Nitrate transporter |
| IMQ49.2 | At3g45070 | gi\|30692514 | SEQ ID NO: 53 | gi\|15230602 | SEQ ID NO: 54 | sulfotransferase | IPR000863 Sulfotransferase |
| IMQ49.3 | At3g45080 | gi\|18407909 | SEQ ID NO: 55 | gi\|15230603 | SEQ ID NO: 56 | sulfotransferase | IPR000863 Sulfotransferase |
| IMQ49.4 | At3g45090 | gi\|42572582 | SEQ ID NO: 57 | gi\|42572583 | SEQ ID NO: 58 | unknown protein | IPR001093 IMP dehydrogenase/GMP reductase; IPR003593 AAA ATPase |
| IMQ49.4 | At3g45090 | gi\|18407910 | SEQ ID NO: 59 | gi\|18407911 | SEQ ID NO: 60 | unknown protein | IPR001093 IMP dehydrogenase/GMP reductase; IPR003593 AAA ATPase |
| IMQ49.5 | At3g45100 | gi\|30692534 | SEQ ID NO: 61 | gi\|30692535 | SEQ ID NO: 62 | SETH2; transferase, transferring glycosyl groups | IPR001296 Glycosyl transferase, group 1; IPR011835 Glycogen/starch synthases, ADP-glucose type |
| IMQ49.5 | At3g45100 | gi\|30692528 | SEQ ID NO: 63 | gi\|18407913 | SEQ ID NO: 64 | SETH2; transferase, transferring glycosyl groups | IPR001296 Glycosyl transferase, group 1; IPR011835 Glycogen/starch synthases, ADP-glucose type |
| IMQ49.6 | At3g45110 | gi\|18407915 | SEQ ID NO: 65 | gi\|15230607 | SEQ ID NO: 66 | unknown protein | |
| IMQ50.1 | At3g46510 | gi\|30692726 | SEQ ID NO: 67 | gi\|15231445 | SEQ ID NO: 68 | ubiquitin-protein ligase | IPR000225 Armadillo; IPR003613 U box |
| IMQ50.1 | At3g46510 | gi\|79527507 | SEQ ID NO: 69 | gi\|79527508 | SEQ ID NO: 70 | ubiquitin-protein ligase | IPR000225 Armadillo; IPR003613 U box; IPR001093 IMP dehydrogenase/GMP reductase |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ50.2 | At3g46520 | gi\|30692727 | SEQ ID NO: 71 | gi\|15231447 | SEQ ID NO: 72 | ACT12 (ACTIN-12); structural constituent of cytoskeleton | IPR004000 Actin/actin-like |
| IMQ50.3 | At3g46530 | gi\|30692728 | SEQ ID NO: 73 | gi\|15231449 | SEQ ID NO: 74 | RPP13 (RECOGNITION OF *PERONOSPORA PARASITICA* 13); ATP binding | IPR002182 NB-ARC; IPR003593 AAA ATPase; IPR007111 NACHT nucleoside triphosphatase |
| IMQ50.4 | At3g46540 | gi\|30692729 | SEQ ID NO: 75 | gi\|15231451 | SEQ ID NO: 76 | | IPR001026 Epsin, N-terminal |
| IMQ50.5 | At3g46550 | gi\|30692730 | SEQ ID NO: 77 | gi\|15231453 | SEQ ID NO: 78 | SOS5 (SALT OVERLY SENSITIVE 5) | IPR000782 Beta-Ig-H3/fasciclin |
| IMQ50.6 | At3g46560 | gi\|42565665 | SEQ ID NO: 79 | gi\|15231455 | SEQ ID NO: 80 | TIM9; protein translocase | IPR004217 Zinc finger, Tim10/DDP-type |
| IMQ51.1 | At3g59410 | gi\|30694991 | SEQ ID NO: 81 | gi\|30694992 | SEQ ID NO: 82 | ATP binding/protein kinase/protein serine/threonine kinase/protein-tyrosine kinase/tRNA ligase | IPR011009 Protein kinase-like; IPR000719 Protein kinase; IPR008271 Serine/threonine protein kinase, active site; IPR006575 RWD; IPR004154 Anticodon-binding; IPR04516 Histidyl-tRNA synthetase, class IIa |
| IMQ51.2 | At3g59420 | gi\|30694994 | SEQ ID NO: 83 | gi\|15231681 | SEQ ID NO: 84 | ACR4; kinase | IPR000719 Protein kinase; IPR008271 Serine/threonine protein kinase, active site; IPR001368 TNFR/CD27/30/40/95 cysteine-rich region; IPR009091 Regulator of chromosome condensation/beta-lactamase-inhibitor protein II |
| IMQ51.3 | At3g59430 | gi\|79315716 | SEQ ID NO: 85 | gi\|79315717 | SEQ ID NO: 86 | unknown protein | |
| IMQ51.3 | At3g59430 | gi\|42572730 | SEQ ID NO: 87 | gi\|42572731 | SEQ ID NO: 88 | unknown protein | |
| IMQ51.3 | At3g59430 | gi\|42566058 | SEQ ID NO: 89 | gi\|15231683 | SEQ ID NO: 90 | unknown protein | |
| IMQ51.4 | At3g59440 | gi\|30694998 | SEQ ID NO: 91 | gi\|15231685 | SEQ ID NO: 92 | calcium ion binding | IPR002048 Calcium-binding EF-hand |
| IMQ51.5 | At3g59450 | gi\|18411175 | SEQ ID NO: 93 | gi\|15231687 | SEQ ID NO: 94 | calcium ion binding | IPR002048 Calcium-binding EF-hand |
| IMQ52.1 | At4g02010 | gi\|30679030 | SEQ ID NO: 95 | gi\|30679031 | SEQ ID NO: 96 | kinase | IPR011009 Protein kinase-like; IPR000719 Protein kinase; IPR008271 Serine/threonine protein kinase, active site |
| IMQ52.2 | At4g02020 | gi\|30679033 | SEQ ID NO: 97 | gi\|18411808 | SEQ ID NO: 98 | EZA1; transcription factor | IPR001214 Nuclear protein SET |
| IMQ53.1 | At4g03470 | gi\|18412273 | SEQ ID NO: 99 | gi\|15236312 | SEQ ID NO: 100 | protein binding | IPR002110 Ankyrin |

TABLE 3

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ42.3 | At3g19870 | gi\|30685527 | gi\|15230976 | gi\|50916119 | gi\|50916120 | *Oryza sativa* (*japonica* cultivar-group) |
| | | | | gi\|66811721 | gi\|66811722 | *Dictyostelium discoideum* |
| | | | | gi\|47227243 | gi\|47227414 | *Tetraodon nigroviridis* |
| IMQ43.1 | At3g20170 | gi\|42565047 | gi\|15231056 | gi\|18406655 | gi\|18406656 | *Arabidopsis thaliana* |
| | | | | gi\|30695181 | gi\|15232303 | *Arabidopsis thaliana* |
| | | | | gi\|50303104 | gi\|50303105 | *Kluyveromyces lactis* NRRL Y-1140 |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ43.2 | At3g20180 | gi|18402522 | gi|15231057 | gi|50253060 | gi|50253093 | *Oryza sativa* (*japonica* cultivar-group) |
| | | | | gi|50253060 | gi|50253092 | *Oryza sativa* (*japonica* cultivar-group) |
| | | | | gi|50253060 | gi|50253091 | *Oryza sativa* (*japonica* cultivar-group) |
| IMQ43.3 | At3g20190 | gi|42565048 | gi|42565049 | gi|30694806 | gi|30694807 | *Arabidopsis thaliana* |
| | | | | gi|3015487 | gi|3015488 | *Lycopersicon esculentum* |
| | | | | gi|18421452 | gi|15238494 | *Arabidopsis thaliana* |
| IMQ43.4 | At3g20200 | gi|30685667 | gi|30685668 | gi|18394397 | gi|15219360 | *Arabidopsis thaliana* |
| | | | | gi|42563329 | gi|30699374 | *Arabidopsis thaliana* |
| | | | | gi|42567297 | gi|42567298 | *Arabidopsis thaliana* |
| IMQ43.5 | At3g20210 | gi|30685671 | gi|15231080 | gi|77799871 | gi|34530959 | *Homo sapiens* |
| | | | | gi|37542691 | gi|37542692 | *Glycine max* |
| | | | | gi|27544005 | gi|27544006 | *Nicotiana tabacum* |
| IMQ44.1 | At3g21300 | gi|42565078 | gi|42565079 | gi|34906469 | gi|34906470 | *Oryza sativa* (*japonica* cultivar-group) |
| | | | | gi|21672841 | gi|21672850 | *Chlorobium tepidum* TLS |
| | | | | gi|67938372 | gi|67938422 | *Chlorobium phaeobacteroides* BS1 |
| IMQ44.2 | At3g21310 | gi|18402951 | gi|18402952 | gi|18403668 | gi|15218028 | *Arabidopsis thaliana* |
| | | | | gi|30683761 | gi|15239155 | *Arabidopsis thaliana* |
| | | | | gi|50540715 | gi|50540730 | *Oryza sativa* (*japonica* cultivar-group) |
| IMQ45.1 | At3g24570 | gi|30687563 | gi|15230132 | gi|34904255 | gi|34904256 | *Oryza sativa* (*japonica* cultivar-group) |
| | | | | gi|66816890 | gi|66816891 | *Dictyostelium discoideum* |
| | | | | gi|46107693 | gi|46107694 | *Gibberella zeae* PH-1 |
| IMQ45.2 | At3g24580 | gi|18404244 | gi|15230133 | gi|18402249 | gi|18402250 | *Arabidopsis thaliana* |
| | | | | gi|18401581 | gi|15229086 | *Arabidopsis thaliana* |
| | | | | gi|42569113 | gi|42569114 | *Arabidopsis thaliana* |
| IMQ45.3 | At3g24590 | gi|30687571 | gi|30687572 | gi|45382012 | gi|50251480 | *Oryza sativa* (*japonica* cultivar-group) |
| | | | | gi|51535924 | gi|51535944 | *Oryza sativa* (*japonica* cultivar-group) |
| | | | | gi|50918990 | gi|50918991 | *Oryza sativa* (*japonica* cultivar-group) |
| IMQ45.4 | At3g24600 | gi|18404257 | gi|15230135 | gi|55741371 | gi|55741372 | *Oryza sativa* (*japonica* cultivar-group) |
| | | | | gi|34904259 | gi|34904260 | *Oryza sativa* (*japonica* cultivar-group) |
| | | | | gi|17385724 | gi|56784375 | *Oryza sativa* (*japonica* cultivar-group) |
| IMQ45.5 | At3g24610 | gi|18404260 | gi|15230136 | gi|18416176 | gi|15236530 | *Arabidopsis thaliana* |
| | | | | gi|18418316 | gi|18418317 | *Arabidopsis thaliana* |
| | | | | gi|18421782 | gi|15240973 | *Arabidopsis thaliana* |
| IMQ46.1 | At3g26900 | gi|30688546 | gi|30688547 | gi|55769656 | gi|55769657 | *Oryza sativa* (*japonica* cultivar-group) |
| | | | | gi|34894031 | gi|34894032 | *Oryza sativa* (*japonica* cultivar-group) |
| | | | | gi|50929064 | gi|50929065 | *Oryza sativa* (*japonica* cultivar-group) |
| IMQ46.2 | At3g26910 | gi|79313785 | gi|79313786 | gi|42565220 | gi|30688552 | *Arabidopsis thaliana* |
| | | | | gi|30693744 | gi|30693745 | *Arabidopsis thaliana* |
| | | | | gi|30693739 | gi|30693740 | *Arabidopsis thaliana* |
| IMQ46.2 | At3g26910 | gi|42565220 | gi|30688552 | gi|30693739 | gi|30693740 | *Arabidopsis thaliana* |
| | | | | gi|30693744 | gi|30693745 | *Arabidopsis thaliana* |
| | | | | gi|30685726 | gi|30685727 | *Arabidopsis thaliana* |
| IMQ46.2 | At3g26910 | gi|30685726 | gi|30685727 | gi|50923910 | gi|50923911 | *Oryza sativa* (*japonica* cultivar-group) |
| | | | | gi|42565220 | gi|30688552 | *Arabidopsis thaliana* |
| | | | | gi|52077544 | gi|51536022 | *Oryza sativa* (*japonica* cultivar-group) |
| IMQ46.3 | At3g26920 | gi|30688555 | gi|30688556 | gi|42565869 | gi|42565870 | *Arabidopsis thaliana* |
| | | | | gi|18408760 | gi|15229075 | *Arabidopsis thaliana* |
| | | | | gi|22328602 | gi|22328603 | *Arabidopsis thaliana* |
| IMQ46.4 | At3g26930 | gi|42565221 | gi|42565222 | gi|18405188 | gi|15221971 | *Arabidopsis thaliana* |
| | | | | gi|42565869 | gi|42565870 | *Arabidopsis thaliana* |
| | | | | gi|18408760 | gi|15229075 | *Arabidopsis thaliana* |
| IMQ47.1 | At3g27770 | gi|30688916 | gi|18405512 | gi|55770586 | gi|55770587 | *Oryza sativa* (*japonica* cultivar-group) |
| | | | | gi|42571426 | gi|42571427 | *Arabidopsis thaliana* |
| | | | | gi|42571424 | gi|42571425 | *Arabidopsis thaliana* |
| | | | | gi|42571428 | gi|42571429 | *Arabidopsis thaliana* |
| | | | | gi|30681842 | gi|15220184 | *Arabidopsis thaliana* |
| | | | | gi|42568719 | gi|42568720 | *Arabidopsis thaliana* |
| IMQ47.2 | At3g27785 | gi|30688924 | gi|30688925 | gi|18421976 | gi|18421977 | *Arabidopsis thaliana* |
| | | | | gi|30684524 | gi|15234013 | *Arabidopsis thaliana* |
| | | | | gi|77552765 | gi|77553798 | *Oryza sativa* (*japonica* cultivar-group) |
| IMQ48.1 | At3g44300 | gi|30692061 | gi|15229932 | gi|30692066 | gi|30692067 | *Arabidopsis thaliana* |
| | | | | gi|30692076 | gi|15229936 | *Arabidopsis thaliana* |
| | | | | gi|14211395 | gi|14211396 | *Brassica napus* |
| IMQ48.2 | At3g44310 | gi|30692071 | gi|30692072 | gi|30692066 | gi|30692067 | *Arabidopsis thaliana* |
| | | | | gi|30692061 | gi|15229932 | *Arabidopsis thaliana* |
| | | | | gi|30692076 | gi|15229936 | *Arabidopsis thaliana* |
| | | | | gi|42568008 | gi|15242205 | *Arabidopsis thaliana* |
| IMQ48.2 | At3g44310 | gi|30692066 | gi|30692067 | gi|30692061 | gi|15229932 | *Arabidopsis thaliana* |
| | | | | gi|30692076 | gi|15229936 | *Arabidopsis thaliana* |
| | | | | gi|14211395 | gi|14211396 | *Brassica napus* |
| IMQ48.3 | At3g44320 | gi|30692076 | gi|15229936 | gi|30692066 | gi|30692067 | *Arabidopsis thaliana* |
| | | | | gi|30692061 | gi|15229932 | *Arabidopsis thaliana* |
| | | | | gi|14211395 | gi|14211396 | *Brassica napus* |

TABLE 3-continued

|  |  |  |  | 5. Orthologous Genes: Nucleic Acid/Polypeptide seq. GI# | | |
|---|---|---|---|---|---|---|
| 1. Gene alias | 2. Tair | 3. Nucleic Acid seq. GI# | 4. Polypeptide seq. GI# | Nucleic Acid GI# | Polypeptide GI# | Species |
| IMQ49.1 | At3g45060 | gi\|42565547 | gi\|15230589 | gi\|18424396 | gi\|15239435 | *Arabidopsis thaliana* |
|  |  |  |  | gi\|48675348 | gi\|48675349 | *Prunus persica* |
|  |  |  |  | gi\|48675346 | gi\|48675347 | *Prunus persica* |
| IMQ49.2 | At3g45070 | gi\|30692514 | gi\|15230602 | gi\|18407909 | gi\|15230603 | *Arabidopsis thaliana* |
|  |  |  |  | gi\|30694345 | gi\|15239947 | *Arabidopsis thaliana* |
|  |  |  |  | gi\|30683282 | gi\|15222843 | *Arabidopsis thaliana* |
| IMQ49.3 | At3g45080 | gi\|18407909 | gi\|15230603 | gi\|30692514 | gi\|15230602 | *Arabidopsis thaliana* |
|  |  |  |  | gi\|30694345 | gi\|15239947 | *Arabidopsis thaliana* |
|  |  |  |  | gi\|30683282 | gi\|15222843 | *Arabidopsis thaliana* |
| IMQ49.4 | At3g45090 | gi\|42572582 | gi\|42572583 | gi\|18407910 | gi\|18407911 | *Arabidopsis thaliana* |
|  |  |  |  | gi\|30697427 | gi\|30697428 | *Arabidopsis thaliana* |
|  |  |  |  | gi\|40363800 | gi\|52076103 | *Oryza sativa* (*japonica* cultivar-group) |
| IMQ49.4 | At3g45090 | gi\|18407910 | gi\|18407911 | gi\|42572582 | gi\|42572583 | *Arabidopsis thaliana* |
|  |  |  |  | gi\|30697427 | gi\|30697428 | *Arabidopsis thaliana* |
|  |  |  |  | gi\|40363800 | gi\|52076103 | *Oryza sativa* (*japonica* cultivar-group) |
| IMQ49.5 | At3g45100 | gi\|30692534 | gi\|30692535 | gi\|30692528 | gi\|18407913 | *Arabidopsis thaliana* |
|  |  |  |  | gi\|50935714 | gi\|50935715 | *Oryza sativa* (*japonica* cultivar-group) |
|  |  |  |  | gi\|66810216 | gi\|66810217 | *Dictyostelium discoideum* |
|  |  |  |  | gi\|72083931 | gi\|72083932 | *Strongylocentrotus purpuratus* |
| IMQ49.5 | At3g45100 | gi\|30692528 | gi\|18407913 | gi\|30692534 | gi\|30692535 | *Arabidopsis thaliana* |
|  |  |  |  | gi\|50935714 | gi\|50935715 | *Oryza sativa* (*japonica* cultivar-group) |
|  |  |  |  | gi\|66810216 | gi\|66810217 | *Dictyostelium discoideum* |
|  |  |  |  | gi\|72083931 | gi\|72083932 | *Strongylocentrotus purpuratus* |
| IMQ49.6 | At3g45110 | gi\|18407915 | gi\|15230607 | gi\|48783781 | gi\|148784150 | *Burkholderia fungorum* LB400 |
|  |  |  |  | gi\|18407923 | gi\|15230616 | *Arabidopsis thaliana* |
|  |  |  |  | gi\|48786263 | gi\|48786365 | *Burkholderia fungorum* LB400 |
| IMQ50.1 | At3g46510 | gi\|30692726 | gi\|15231445 | gi\|30684026 | gi\|18401867 | *Arabidopsis thaliana* |
|  |  |  |  | gi\|51038702 | gi\|51038703 | *Oryza sativa* (*japonica* cultivar-group) |
|  |  |  |  | gi\|77552765 | gi\|77556856 | *Oryza sativa* (*japonica* cultivar-group) |
| IMQ50.1 | At3g46510 | gi\|79527507 | gi\|79527508 | gi\|50946934 | gi\|50946935 | *Oryza sativa* (*japonica* cultivar-group) |
|  |  |  |  | gi\|54291125 | gi\|54291136 | *Oryza sativa* (*japonica* cultivar-group) |
|  |  |  |  | gi\|30692726 | gi\|15231445 | *Arabidopsis thaliana* |
| IMQ50.2 | At3g46520 | gi\|30692727 | gi\|15231447 | gi\|30697210 | gi\|15238387 | *Arabidopsis thaliana* |
|  |  |  |  | gi\|3420238 | gi\|3420239 | *Gossypium hirsutum* |
|  |  |  |  | gi\|30693903 | gi\|18409908 | *Arabidopsis thaliana* |
|  |  |  |  | gi\|30687200 | gi\|30687201 | *Arabidopsis thaliana* |
| IMQ50.3 | At3g46530 | gi\|30692728 | gi\|15231449 | gi\|18408266 | gi\|15232624 | *Arabidopsis thaliana* |
|  |  |  |  | gi\|18408260 | gi\|15232622 | *Arabidopsis thaliana* |
|  |  |  |  | gi\|18406280 | gi\|15217954 | *Arabidopsis thaliana* |
| IMQ50.4 | At3g46540 | gi\|30692729 | gi\|15231451 | gi\|21104611 | gi\|56784669 | *Oryza sativa* (*japonica* cultivar-group) |
|  |  |  |  | gi\|34908157 | gi\|34908158 | *Oryza sativa* (*japonica* cultivar-group) |
|  |  |  |  | gi\|30680762 | gi\|22329424 | *Arabidopsis thaliana* |
| IMQ50.5 | At3g46550 | gi\|30692730 | gi\|15231453 | gi\|21104611 | gi\|56784671 | *Oryza sativa* (*japonica* cultivar-group) |
|  |  |  |  | gi\|34908161 | gi\|34908162 | *Oryza sativa* (*japonica* cultivar-group) |
|  |  |  |  | gi\|607773 | gi\|607774 | *Pinus taeda* |
| IMQ50.6 | At3g46560 | gi\|42565665 | gi\|15231455 | gi\|5107213 | gi\|5107214 | *Oryza sativa* |
|  |  |  |  | gi\|77552765 | gi\|77556866 | *Oryza sativa* (*japonica* cultivar-group) |
|  |  |  |  | gi\|5107211 | gi\|5107212 | *Mesembryanthemum crystallinum* |
| IMQ51.1 | At3g59410 | gi\|30694991 | gi\|30694992 | gi\|50925770 | gi\|50925771 | *Oryza sativa* (*japonica* cultivar-group) |
|  |  |  |  | gi\|74000019 | gi\|74000020 | *Canis familiaris* |
|  |  |  |  | gi\|50748343 | gi\|50748344 | *Gallus gallus* |
| IMQ51.2 | At3g59420 | gi\|30694994 | gi\|15231681 | gi\|40850572 | gi\|40850578 | *Musa acuminata* |
|  |  |  |  | gi\|50917202 | gi\|50917203 | *Oryza sativa* (*japonica* cultivar-group) |
|  |  |  |  | gi\|1597722 | gi\|1597723 | *Zea mays* |
| IMQ51.3 | At3g59430 | gi\|79315716 | gi\|79315717 | gi\|42572730 | gi\|42572731 | *Arabidopsis thaliana* |
|  |  |  |  | gi\|42566058 | gi\|15231683 | *Arabidopsis thaliana* |
| IMQ51.3 | At3g59430 | gi\|42572730 | gi\|42572731 | gi\|42566058 | gi\|15231683 | *Arabidopsis thaliana* |
|  |  |  |  | gi\|50725340 | gi\|50725357 | *Oryza sativa* (*japonica* cultivar-group) |
|  |  |  |  | gi\|74054322 | gi\|74054328 | *Streptococcus agalactiae* |
|  |  |  |  | gi\|56384961 | gi\|56384962 | *Streptococcus agalactiae* |
| IMQ51.3 | At3g59430 | gi\|42566058 | gi\|15231683 | gi\|42572730 | gi\|42572731 | *Arabidopsis thaliana* |
|  |  |  |  | gi\|50725340 | gi\|50725357 | *Oryza sativa* (*japonica* cultivar-group) |
|  |  |  |  | gi\|74054322 | gi\|74054328 | *Streptococcus agalactiae* |
|  |  |  |  | gi\|56384961 | gi\|56384962 | *Streptococcus agalactiae* |
| IMQ51.4 | At3g59440 | gi\|30694998 | gi\|15231685 | gi\|30689331 | gi\|18406202 | *Arabidopsis thaliana* |
|  |  |  |  | gi\|28301673 | gi\|28301674 | *Lotus corniculatus* var. *japonicus* |
|  |  |  |  | gi\|18397964 | gi\|15231470 | *Arabidopsis thaliana* |
| IMQ51.5 | At3g59450 | gi\|18411175 | gi\|15231687 | gi\|30694998 | gi\|15231685 | *Arabidopsis thaliana* |
|  |  |  |  | gi\|30689331 | gi\|18406202 | *Arabidopsis thaliana* |
|  |  |  |  | gi\|30679524 | gi\|15221358 | *Arabidopsis thaliana* |
| IMQ52.1 | At4g02010 | gi\|30679030 | gi\|30679031 | gi\|34902827 | gi\|34902828 | *Oryza sativa* (*japonica* cultivar-group) |
|  |  |  |  | gi\|6498456 | gi\|56783692 | *Oryza sativa* (*japonica* cultivar-group) |
|  |  |  |  | gi\|30696797 | gi\|22327898 | *Arabidopsis thaliana* |

TABLE 3-continued

| | | | | 5. Orthologous Genes: Nucleic Acid/Polypeptide seq. GI# | | |
|---|---|---|---|---|---|---|
| 1. Gene alias | 2. Tair | 3. Nucleic Acid seq. GI# | 4. Polypeptide seq. GI# | Nucleic Acid GI# | Polypeptide GI# | Species |
| IMQ52.2 | At4g02020 | gi\|30679033 | gi\|18411808 | gi\|20152908 | gi\|20152909 | *Zea mays* |
| | | | | gi\|22535906 | gi\|22535907 | *Oryza sativa* |
| | | | | gi\|29565494 | gi\|29565495 | *Oryza sativa* (*indica* cultivar-group) |
| IMQ53.1 | At4g03470 | gi\|18412273 | gi\|15236312 | gi\|18412781 | gi\|18412782 | *Arabidopsis thaliana* |
| | | | | gi\|42572834 | gi\|42572835 | *Arabidopsis thaliana* |
| | | | | gi\|42566786 | gi\|42566787 | *Arabidopsis thaliana* |
| | | | | gi\|30682836 | gi\|18414210 | *Arabidopsis thaliana* |

Example 2

Analysis of the *Arabidopsis* IMQ Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318.), PSORT (Nakai K, and Horton P, 1999, *Trends Biochem. Sci.* 24:34-6), and/or CLUSTAL (Thompson J D et al., 1994, *Nucleic Acids Res.* 22:4673-4680). Conserved domains for each protein are listed in column 8 of Table 2.

Table 4 lists constructs tested for causing a significant increase in oil, protein, digestible protein or a significant decrease in fiber were identified by a two-way Analysis of Variance (ANOVA) test at a p-value≤0.05. ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

TABLE 4

| 1. Gene | 2. TAIR | 3. Construct | 4. ANOVA Protein | 5. ANOVA Oil | 6. ANOVA Digestible Protein | 7. ANOVA Fiber | 8. Protein | 9. Oil | 10. Digestible Protein | 11. Fiber |
|---|---|---|---|---|---|---|---|---|---|---|
| IMQ43.3 | At3g20190 | CsVMV::At3g20190 | 0.659 | 0.336 | 0.005 | 0.002 | 100.6% | 101.6% | 101.9% | 96.1% |
| IMQ43.3 | At3g20190 | Pru::At3g20190 | 0.868 | 0.709 | 0.005 | 0.009 | 100.3% | 100.7% | 102.3% | 96.7% |
| IMQ47.1 | At3g27770 | Pru::At3g27770 | 0.404 | 0.143 | 0.033 | 0.004 | 99.2% | 102.2% | 101.1% | 97.3% |
| IMQ49.1 | At3g45060 | CsVMV::At3g45060 | 0.441 | 0.623 | 0.016 | 0.004 | 101.4% | 100.6% | 102.6% | 96.9% |
| IMQ49.1 | At3g45060 | Pru::At3g45060 | 0.779 | 0.842 | 0.023 | 0.070 | 100.2% | 100.9% | 101.2% | 98.6% |
| IMQ49.3 | At3g45080 | Pru::At3g45080 | 0.375 | 0.770 | 0.014 | 0.007 | 102.0% | 99.6% | 102.8% | 97.6% |
| IMQ50.5 | At3g46550 | Pru::At3g46550 | 0.038 | 0.171 | 0.240 | 0.013 | 102.9% | 102.6% | 101.1% | 97.1% |
| IMQ51.1 | At3g59410 | CsVMV::At3g59410 | 0.040 | 0.103 | 0.019 | 0.305 | 102.5% | 97.3% | 101.8% | 98.7% |
| IMQ51.3 | At3g59430 | CsVMV::At3g59430 | 0.034 | 0.035 | 0.347 | 0.538 | 95.5% | 104.2% | 99.2% | 99.4% |
| IMQ51.3 | At3g59430 | Pru::At3g59430 | 0.911 | 0.038 | 0.239 | 0.017 | 100.4% | 102.8% | 101.3% | 97.4% |

Example 3

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Example 4

To test whether over-expression of the genes identified in Tables 1-4 alter the seed composition phenotype, protein, digestible protein, oil, and fiber content in seeds from transgenic plants expressing these genes is compared with protein, digestible protein, oil and fiber content in seeds from non-transgenic control plants. Any one of the genes identified in Tables 1-4 is used to transform *Brassica napus* (canola). To do this, the genes are cloned into plant transformation vectors behind the strong constitutive CsVMV promoter and the seed specific phaseolin promoter. These constructs (which include a gene encoding a selection agent) are transformed into canola plants.

Transformation of canola is accomplished via *Agrobacterium*-mediated transformation. Seeds are surface-sterilized with 10% commercial bleach for 10 minutes and rinsed 3 times with sterile distilled water. The seeds are then placed on one half concentration of MS basal medium (Murashige and Skoog, *Physiol. Plant.* 15:473-497, 1962) and maintained under growth regime set at 25° C., and a photoperiod of 16 hrs light/8 hrs dark.

Hypocotyl segments (3-5 mm) are excised from 5-7 day old seedlings and placed on callus induction medium K1D1 (MS medium with 1 mg/l kinetin and 1 mg/l 2,4-D) for 3 days as pre-treatment. The segments are then transferred into a petri plate, treated with *Agrobacterium* Z7075 or LBA4404 strain containing pDAB721. The *Agrobacterium* is grown overnight at 28° C. in the dark on a shaker at 150 rpm and subsequently re-suspended in the culture medium.

After 30 minute treatment of the hypocotyl segments with Agrobacterium, these are placed back on the callus induction medium for 3 days. Following co-cultivation, the segments are placed on K1D1TC (callus induction medium containing 250 mg/l Carbenicillin and 300 mg/l Timentin) for one week of recovery. Alternately, the segments are placed directly on selection medium K1D1H1 (above medium with 1 mg/l selection agent, for example an herbicide). Carbenicillin and Timentin are antibiotics used to kill the Agrobacterium. The selection agent is used to allow the growth of the transformed cells.

Callus samples from independent events are tested by PCR. All the samples tested are positive for the presence of the transformed gene, whereas the non-transformed controls are negative. Callus samples are confirmed to express the appropriate protein as determined by ELISA.

Callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], mg/l silver nitrate, 1 mg/l selection agent, Carbenicillin and Timentin) shoot regeneration medium. After shoots start to regenerate (approximately 3 weeks), hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l selection agent, Carbenicillin and Timentin) for 3 weeks.

Shoots are excised from the hypocotyl segments and transferred to shoot elongation medium MESH10 (MS, 0.5 gm/l MES, 10 mg/l selection agent, Carbenicillin, Timentin) for 2-4 weeks. The elongated shoots are cultured for root induction on MSI.1 (MS with 0.1 mg/l Indolebutyric acid). Once the plants have a well established root system, these are transplanted into soil. The plants are acclimated under controlled environmental conditions in the Conviron for 1-2 weeks before transfer to the greenhouse. The transformed T0 plants self-pollinate in the greenhouse to obtain T1 seed. Transgenic plants are selected at the T1 generation based on resistance to a selection agent. T2 seed (from T1 plants) is harvested and sown in soil. T2 plants are grown to maturity, allowed to self-fertilize and set seed. T3 seed (from the T2 plants) is harvested in bulk for each line. Seed oil, protein, digestible protein, and fiber values are measured as discussed in Example 1.

It is claimed:

1. A transgenic plant, comprising a heterologous nucleotide sequence that encodes or is complementary to a sequence that encodes an IMQ polypeptide comprising an amino acid sequence at least 95% identical to the amino acid sequence as set forth in SEQ ID NO: 78, whereby the transgenic plant has an improved meal quality phenotype, relative to control plants.

2. The transgenic plant of claim 1, wherein the IMQ polypeptide comprises the amino acid sequence as set forth in SEQ ID NO: 78.

3. The transgenic plant of claim 1, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

4. The transgenic plant of claim 3, wherein the plant is canola.

5. The transgenic plant of claim 1, wherein an improved meal quality phenotype comprises an increase in available metabolizable energy in meal produced from seeds of the transgenic plant, relative to control plants.

6. The transgenic plant of claim 5, wherein an increase in available metabolizable energy comprises an altered protein and/or fiber content in the seeds of the transgenic plant.

7. The transgenic plant of claim 6, wherein the protein content is increased and/or the fiber content is decreased.

8. The transgenic plant of claim 5, wherein an increase in available metabolizable energy comprises a decreased fiber content in the seeds of the transgenic plant.

9. A plant part obtained from the transgenic plant according to claim 1, wherein the plant part comprises the heterologous nucleotide sequence.

10. The plant part of claim 9, which is a transgenic seed, wherein the transgenic seed comprises the heterologous nucleotide sequence.

11. Meal, feed, or food produced from the transgenic seed of claim 10.

12. A method of producing meal, comprising growing the transgenic plant of claim 1, and recovering meal from the plant,
thereby producing meal.

13. The method of claim 12, wherein the meal is produced from seeds of the plant.

14. A method of producing an improved meal quality phenotype in a plant, said method comprising:
 a) introducing into progenitor cells of the plant a heterologous nucleotide sequence that encodes or is complementary to a sequence that encodes an IMQ polypeptide comprising an amino acid sequence at least 95% identical to the amino acid sequence set forth in SEQ ID NO: 78; and
 b) growing the transformed progenitor cells to produce a transgenic plant, wherein the nucleotide sequence is expressed, and the transgenic plant exhibits an improved meal quality phenotype relative to control plants,
thereby producing the improved meal quality phenotype in the plant.

15. The method of claim 14, wherein the IMQ polypeptide comprises the amino acid sequence as set forth in SEQ ID NO: 78.

16. A plant obtained by a method of claim 14.

17. The plant of claim 16, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

18. The plant of claim 17, wherein the plant is canola.

19. The plant of claim 16, wherein the plant is selected from the group consisting of a plant grown from said progenitor cells, a plant that is the direct progeny of a plant grown from said progenitor cells, and a plant that is the indirect progeny of a plant grown from said progenitor cells.

20. A method of generating a plant having an improved meal quality phenotype, comprising:
 identifying a plant that has an allele in its ortholog of the *A. thaliana* IMQ gene which results in improved meal quality phenotype compared to plants lacking the allele, by employing candidate gene/QTL methodology or TILLING methodology, where the wildtype *A. thaliana* gene has the nucleic acid sequence set forth as SEQ ID NO: 77, wherein the ortholog comprises a nucleic acid sequence at least 80% identical to SEQ ID NO: 77, and
 generating progeny of said identified plant, wherein the generated progeny inherit the allele and have the improved meal quality phenotype,
thereby generating a plant having an improved meal quality phenotype.

21. A feed, meal, grain, food, or seed comprising a polypeptide encoded by a nucleic acid sequence at least 95% identical to the nucleic acid sequence as set forth in SEQ ID NO: 77.

22. A feed, meal, grain, food, or seed comprising a polypeptide comprising an amino acid sequence at least 95% identical to the amino acid sequence as set forth in SEQ ID NO: 78.

23. The feed, meal, grain, food, or seed of claim 21, wherein the recombinant polypeptide is encoded by the nucleic acid sequence as set forth in SEQ ID NO: 77.

24. The feed, meal, grain, food, or seed of claim 22, wherein the recombinant polypeptide comprises the amino acid sequence as set forth in SEQ ID NO: 78.

25. The method of claim 20, wherein the ortholog comprises a nucleic acid sequence at least 90% identical to the nucleic acid sequence set forth as SEQ ID NO: 77.

* * * * *

SEQUENCE LISTING

```
<160> NUMBER OF SEQ ID NOS: 100

<210> SEQ ID NO 1
<211> LENGTH: 3472
<212> TYPE: DNA
<213> ORGANISM: Arabidopsis thaliana

<400> SEQUENCE: 1
atgaccacga cgacgccgga gaagactccg gcgagacctc tctctatcca agattgggac      60
gttctcatcg acgacttccg cgacgccggc gctcctcgcg actggttcac ttccgttttc     120
cagattgatt ctctggtgga cttcgctctc tcgtctctcc tcaaaaaaga cttccctaca     180
ccagtgaagc tctcaatcct agtctttctc gatgaatttt ccccgatttt gtttgataat     240
tgtggtagcg atacctttga tcgcttcatc gatgttctcc ggacgatcgt gcaatctcca     300
actgatggat cgtcaggatt gaaagagcaa gctatggtct ctttcacgtc tgtgcttgta     360
tcgattgatt ctttctctgt aggtcacgtt gaagcagttg ttgatttgct tcttgcgctc     420
gttaatcgtc ctaaccacgg atttgatcga caagctcgtg ctatcgcctg tgagtgttta     480
cgtcagcttg agaaagcttt tcctggtttg ttatctgatg tcgctggtca tctttggtcg     540
ttgtgtcaag cggagagaac tcacgccgtg caagcttatc ttctcttgtt caccacaatt     600
gtctacaatg tggttaatca gaagcttaag gtttcacttc ttagtacctc tgtacctttg     660
gtgcctttta atgctcctaa ttggatgcgt gatgagagtt cgattatgag tcaaggtcaa     720
gggttggggc cagatcagaa ggaactgaga cgaacattgg cttttatgtt ggaatctccg     780
tatttgttta cttcttgtgc tatgatggaa tttatggta tggttgtgcc acttgcatcg      840
gcgttggagt tacaggcttc tatgttgaaa gttcagttct tggggatgat ttattcgttt     900
gatccaatgc tttgtcatgt tgtcttgctt atgtattctc ggttccctga tgcgtttgag     960
ggacaagaga aagagatcat gagacgtctt atgctctttt caaaggagac tcagatctat    1020
cttgttttcc gtttgcttgc gctgcactgg ttaatgggtt tgttgaataa gcatatgttg    1080
agtggggagc ttgagaagag gacatctgtt cttgagatgg gtcagaagtt tcatcctgtc    1140
gtttttgatc cactcgcttt gaaagcgttg aagcttgatc tgctggtaca atgctctgtg    1200
```

```
agttccaacg ctttgagtgg aggtgataac agtaaatctg ctggggattt gttgcaggac      1260
tgcttggtat cggtttcgga tttcaaatgg ttgcctccat ggagctcaga aactgaacta      1320
gcattccgca ctttacacaa gtttctgata tgtgcatcta cacattccga ctctgaccct      1380
tccaccacta gaatccttat ggagtctagc ctcttccaaa acgtgcaggg gttgctggta      1440
gacatgactt tggagtttca aatcttggtc cctgttattg tggcttttat tgagcggttg      1500
attcactgtc acaagcatca gtggttagga gagcggtttc ttcagatagt cgatgagaat      1560
ctgcttccca aacttaagaa aaaaaactta ttaacagctt acttcccgct tttccatcga      1620
atagccgaga atgatacaat acctccttct cgattgatag agctgcttac gaagtttgta      1680
atttcacttg ttgagaagcg cggacttgat gtggggttga aattgtggga tcaaggaact      1740
gaagttcttg gcatctgtcg aacattgatg agtcaccata agagctctag attatttctc      1800
ggactctctc gccttctttc cctcacatgt ctctatttcc ctgatctgga ggtccgagac      1860
aatgctagga tatatctgag gatgctggtc tgtataccag gacagagaat taagaacatt      1920
ttgaagccgg cagatgctgt cactccatca acccattctt ctacattttt tagtgttcaa      1980
agtcctcgtt ttcgtcatga tcctagtaaa tctcggaacc tttcatccta tattcatctt      2040
gaacgggtta cgcccctact cgtgaaacag tcatggtcat tgtctctacc atctctaagt      2100 gttgaactg atggatatag cattatagaa aacaaaatcc aggtagatga agttgagccg       2160
gatggcagtc aagaacttca gattttgcca gaagctcgaa gaattgaatc aggaaaacct      2220
acgttaaggg taatggactc aaagattgca gagattctag aaagattaag aagatatttc      2280
tctgtgattc ctgatttcaa acacatgcca ggaattaagg ttagaataac gtgtactttg      2340
agattggatg ctgaaccata tagcagtata tggggaagtg aaactcagaa aatcgattta      2400
gagaaagtcg actcacctcc tgcgattttc gcgacggtgc tcaaattctc atcttcagcc      2460
ccttatggct ctattccctc atgtcgcata cctttccttc tcggtgagcc tcattggaac      2520
agcaatgtac ccaatgaaga agtttcttta gacattgtcg tggtagaaaa cacactgaaa      2580
gaggaggaaa aagatggctt gagaggagca cctgtaacag tggaactgga acctagagaa      2640
cctacaccag gtttggtcga ggtttcaatg gaagcaaatg cagagaatgg tcagatgatt      2700
cagggaaaac tcgagagtgt ccctgtgggg attgaagaca tgttcctaaa agctcttgct      2760
ccaccggacg aacctgaaga tacaataccg agctactact cagatctatt caatgctttg      2820
tgggaagtgt gtggttcttc gtccagcact gcacacgaaa catttgcact aaaaggtggc      2880
aaaatggctg cagcagtcag cgggactcgg tcagtaaaac tgcttgaagt ccctgcggaa      2940
actgtaatac aggccactga gcttcgttta gcgccctttg tggtggctat cagtggagaa      3000
cagcttgtaa acattgtaag agacggagga attattgaga acattgtgtg gaaggaagag      3060
gaagaagaac aagggaatca cacaaatgcg gaccagcctt cttcatcctc ggtgggatta      3120
aaccgaggcc ctcttcgtct gacatacatt ggatatggag atgaccaaga ggttccgatg      3180
acgagaagta gggggaaaat gggaacgata agatgctga tgtttctgcc gccaagatat       3240
catctaatgt ttgaaatgga agttgggcaa ggatcgacat tggtgcatat aagaacagat      3300
tattggcctt gcttagctta tgttgatgat tacttagaag ctttgttttt gtaataatag      3360
cagagacttt cactattttc ttcttattct ttgggcccaa cctacatgta aagttttacc      3420
caaacgaaca aacacaaatt ctgttttttg agaagtttat ttttattggg at             3472
```

<210> SEQ ID NO 2

```
<211> LENGTH: 1117
<212> TYPE: PRT
<213> ORGANISM: Arabidopsis thaliana

<400> SEQUENCE: 2

Met Thr Thr Thr Thr Pro Glu Lys Thr Pro Ala Arg Pro Leu Ser Ile
1               5                   10                  15

Gln Asp Trp Asp Val Leu Ile Asp Asp Phe Arg Asp Ala Gly Ala Pro
            20                  25                  30

Arg Asp Trp Phe Thr Ser Val Phe Gln Ile Asp Ser Leu Val Asp Phe
        35                  40                  45

Ala Leu Ser Ser Leu Leu Lys Lys Asp Phe Pro Thr Pro Val Lys Leu
    50                  55                  60

Ser Ile Leu Val Phe Leu Asp Glu Phe Ser Pro Ile Leu Phe Asp Asn
65                  70                  75                  80

Cys Gly Ser Asp Thr Phe Asp Arg Phe Ile Asp Val Leu Arg Thr Ile
                85                  90                  95

Val Gln Ser Pro Thr Asp Gly Ser Ser Gly Leu Lys Glu Gln Ala Met
            100                 105                 110

Val Ser Phe Thr Ser Val Leu Val Ser Ile Asp Ser Phe Ser Val Gly
        115                 120                 125

His Val Glu Ala Val Val Asp Leu Leu Leu Ala Leu Val Asn Arg Pro
    130                 135                 140

Asn His Gly Phe Asp Arg Gln Ala Arg Ala Ile Ala Cys Glu Cys Leu
145                 150                 155                 160

Arg Gln Leu Glu Lys Ala Phe Pro Gly Leu Leu Ser Asp Val Ala Gly
                165                 170                 175

His Leu Trp Ser Leu Cys Gln Ala Glu Arg Thr His Ala Val Gln Ala
            180                 185                 190

Tyr Leu Leu Leu Phe Thr Thr Ile Val Tyr Asn Val Asn Gln Lys
        195                 200                 205

Leu Lys Val Ser Leu Leu Ser Thr Ser Val Pro Leu Val Pro Phe Asn
    210                 215                 220

Ala Pro Asn Trp Met Arg Asp Glu Ser Ser Ile Met Ser Gln Gly Gln
225                 230                 235                 240

Gly Leu Gly Pro Asp Gln Lys Glu Leu Arg Arg Thr Leu Ala Phe Met
                245                 250                 255

Leu Glu Ser Pro Tyr Leu Phe Thr Ser Cys Ala Met Met Glu Phe Met
            260                 265                 270

Gly Met Val Val Pro Leu Ala Ser Ala Leu Glu Leu Gln Ala Ser Met
        275                 280                 285

Leu Lys Val Gln Phe Leu Gly Met Ile Tyr Ser Phe Asp Pro Met Leu
    290                 295                 300

Cys His Val Val Leu Leu Met Tyr Ser Arg Phe Pro Asp Ala Phe Glu
305                 310                 315                 320

Gly Gln Glu Lys Glu Ile Met Arg Arg Leu Met Leu Phe Ser Lys Glu
                325                 330                 335

Thr Gln Ile Tyr Leu Val Phe Arg Leu Leu Ala Leu His Trp Leu Met
            340                 345                 350

Gly Leu Leu Asn Lys His Met Leu Ser Gly Glu Leu Glu Lys Arg Thr
        355                 360                 365

Ser Val Leu Glu Met Gly Gln Lys Phe His Pro Val Val Phe Asp Pro
    370                 375                 380

Leu Ala Leu Lys Ala Leu Lys Leu Asp Leu Leu Val Gln Cys Ser Val
```

-continued

```
            385                 390                 395                 400
        Ser Ser Asn Ala Leu Ser Gly Gly Asp Asn Ser Lys Ser Ala Gly Asp
                        405                 410                 415

Leu Leu Gln Asp Cys Leu Val Ser Val Ser Asp Phe Lys Trp Leu Pro
                        420                 425                 430

Pro Trp Ser Ser Glu Thr Glu Leu Ala Phe Arg Thr Leu His Lys Phe
                        435                 440                 445

Leu Ile Cys Ala Ser Thr His Ser Asp Ser Asp Pro Ser Thr Thr Arg
        450                 455                 460

Ile Leu Met Glu Ser Ser Leu Phe Gln Asn Val Gln Gly Leu Leu Val
        465                 470                 475                 480

Asp Met Thr Leu Glu Phe Gln Ile Leu Val Pro Val Ile Val Ala Phe
                        485                 490                 495

Ile Glu Arg Leu Ile His Cys His Lys His Gln Trp Leu Gly Glu Arg
                        500                 505                 510

Phe Leu Gln Ile Val Asp Glu Asn Leu Leu Pro Lys Leu Lys Lys Lys
                        515                 520                 525

Asn Leu Leu Thr Ala Tyr Phe Pro Leu Phe His Arg Ile Ala Glu Asn
        530                 535                 540

Asp Thr Ile Pro Pro Ser Arg Leu Ile Glu Leu Leu Thr Lys Phe Val
        545                 550                 555                 560

Ile Ser Leu Val Glu Lys Arg Gly Leu Asp Val Gly Leu Lys Leu Trp
                        565                 570                 575

Asp Gln Gly Thr Glu Val Leu Gly Ile Cys Arg Thr Leu Met Ser His
                        580                 585                 590

His Lys Ser Ser Arg Leu Phe Leu Gly Leu Ser Arg Leu Leu Ser Leu
                        595                 600                 605

Thr Cys Leu Tyr Phe Pro Asp Leu Glu Val Arg Asp Asn Ala Arg Ile
                        610                 615                 620

Tyr Leu Arg Met Leu Val Cys Ile Pro Gly Gln Arg Ile Lys Asn Ile
        625                 630                 635                 640

Leu Lys Pro Ala Asp Ala Val Thr Pro Ser Thr His Ser Ser Thr Phe
                        645                 650                 655

Phe Ser Val Gln Ser Pro Arg Phe Arg His Asp Pro Ser Lys Ser Arg
                        660                 665                 670

Asn Leu Ser Ser Tyr Ile His Leu Glu Arg Val Thr Pro Leu Leu Val
                        675                 680                 685

Lys Gln Ser Trp Ser Leu Ser Leu Pro Ser Leu Ser Val Gly Thr Asp
                        690                 695                 700

Gly Tyr Ser Ile Ile Glu Asn Lys Ile Gln Val Asp Glu Val Glu Pro
        705                 710                 715                 720

Asp Gly Ser Gln Glu Leu Gln Ile Leu Pro Glu Ala Arg Arg Ile Glu
                        725                 730                 735

Ser Gly Lys Pro Thr Leu Arg Val Met Asp Ser Lys Ile Ala Glu Ile
                        740                 745                 750

Leu Glu Arg Leu Arg Arg Tyr Phe Ser Val Ile Pro Asp Phe Lys His
                        755                 760                 765

Met Pro Gly Ile Lys Val Arg Ile Thr Cys Thr Leu Arg Leu Asp Ala
                        770                 775                 780

Glu Pro Tyr Ser Ser Ile Trp Gly Ser Glu Thr Gln Lys Ile Asp Leu
        785                 790                 795                 800

Glu Lys Val Asp Ser Pro Pro Ala Ile Phe Ala Thr Val Leu Lys Phe
                        805                 810                 815
```

Ser Ser Ser Ala Pro Tyr Gly Ser Ile Pro Ser Cys Arg Ile Pro Phe
                820                 825                 830

Leu Leu Gly Glu Pro His Trp Asn Ser Asn Val Pro Asn Glu Glu Val
            835                 840                 845

Ser Leu Asp Ile Val Val Glu Asn Thr Leu Lys Glu Glu Glu Lys
        850                 855                 860

Asp Gly Leu Arg Gly Ala Pro Val Thr Val Glu Leu Glu Pro Arg Glu
865                 870                 875                 880

Pro Thr Pro Gly Leu Val Glu Val Ser Met Glu Ala Asn Ala Glu Asn
                885                 890                 895

Gly Gln Met Ile Gln Gly Lys Leu Glu Ser Val Pro Val Gly Ile Glu
            900                 905                 910

Asp Met Phe Leu Lys Ala Leu Ala Pro Pro Asp Glu Pro Glu Asp Thr
        915                 920                 925

Ile Pro Ser Tyr Tyr Ser Asp Leu Phe Asn Ala Leu Trp Glu Val Cys
    930                 935                 940

Gly Ser Ser Ser Ser Thr Ala His Glu Thr Phe Ala Leu Lys Gly Gly
945                 950                 955                 960

Lys Met Ala Ala Ala Val Ser Gly Thr Arg Ser Val Lys Leu Leu Glu
                965                 970                 975

Val Pro Ala Glu Thr Val Ile Gln Ala Thr Glu Leu Arg Leu Ala Pro
            980                 985                 990

Phe Val Val Ala Ile Ser Gly Glu Gln Leu Val Asn Ile Val Arg Asp
        995                 1000                1005

Gly Gly Ile Ile Glu Asn Ile Val Trp Lys Glu Glu Glu Glu
        1010                1015                1020

Gln Gly Asp His Thr Asn Ala Asp Gln Pro Ser Ser Ser Ser Val
        1025                1030                1035

Gly Leu Asn Arg Gly Pro Leu Arg Leu Thr Tyr Ile Gly Tyr Gly
        1040                1045                1050

Asp Asp Gln Glu Val Pro Met Thr Arg Ser Arg Gly Lys Met Gly
        1055                1060                1065

Thr Ile Lys Met Leu Met Phe Leu Pro Pro Arg Tyr His Leu Met
        1070                1075                1080

Phe Glu Met Glu Val Gly Gln Gly Ser Thr Leu Val His Ile Arg
        1085                1090                1095

Thr Asp Tyr Trp Pro Cys Leu Ala Tyr Val Asp Asp Tyr Leu Glu
        1100                1105                1110

Ala Leu Phe Leu
        1115

<210> SEQ ID NO 3
<211> LENGTH: 1615
<212> TYPE: DNA
<213> ORGANISM: Arabidopsis thaliana

<400> SEQUENCE: 3
atttcgtgct actactctct tgataattcg aagctttttc gttatctcca gaaatgggtt      60
cttcagaaac ggaaagtgaa agcagaggtt ttcaaaaccc agattgggaa acagagttta    120
accgattcga aaacgcgatt tcgtctggtt ctgcttcaat tcgtgtaaga tccgttttaa    180
agttatcaga tttgacgaat cgagtacctg agagctatat atcccgtgca attccgattc    240
tcgccggtct tcttcgtgtc tcagacgact ccaatcgttc cgttcaagct gccgccgctc    300

-continued

```
attgcttgaa atgtattacc tgttgcggcg gtgaagaaag tggatttgcg gtgacgatgg    360
ggaggtgtgg tgtgattgct agcttattag ggttgttact tgaagcgaat acggatggta    420
atgtgtttcg aaggatttgg gtgaaatgtt tgtggagctt agttactttt ggatcttcga    480
ttcgagttgg tttggctagg ttaggtggtt tagagattgt gattcgtgag ttgaataatt    540
gggaagatga tggaagtaga tggtacttgt tagagatcct tagtgctttg acgacgatta    600
gagagagcag acgcgttctt gttcattcag gtgggcttaa gtttcttgta aagctgcta    660
aagttgggaa cttggcctca agagagagag cttgtcatgc tatcggactg atcggtgtta    720
ctagacgagc tcggcgaata ctggttgaag caggagtgat tccagcactt gtggatctgt    780
atcgagatgg ggatgataag gcaaagcttt tagctggtaa tgccttaggg atcatatctg    840
ctcagactga gtacattagg cctgtcactg aagctggttc cattcctttg tatgtcgagc    900
ttctctcggg acaagatccc atggggaaag atattgcaga ggatgtgttc tgtatattag   960
ctgtagctga aggtaatgct gttttgatag cggaacaact ggtgaggatc ttgagagcag   1020
gggataacga agccaagctt gcagcttctg atgtgttatg gatcttgcg ggttataggc    1080
attctgtatc tgttattaga gggtctggcg caattccttt gcttattgag cttctgagag   1140
atgggtcact tgagttcaga gagaggattt ctggagctat ttctcagttg agttacaatg   1200
agaacgaccg tgaggccttt tctgattccg gtatgatacc gattctgatt gaatggttgg   1260
gggatgagtc ggaagagctc agggataacg cagctgaggc acttattaat ttttctgaag   1320
accaagagca ttatgctaga gtgcgtgagg caataggcca tcctgtgttt cagagtatgc   1380
agagcagact ggctagaatc cgagcttccc atgaactgat ggttcgatca atgcgaaggg   1440
ttacaatcca acatcttgcc catgaccatg atcttccatg atctgaaggg caaattaagc   1500
ttcccatctg ttttgatgta tgtttataat ctgacttgga aaagaaaag actcaattgc    1560
tgtttgattt ctgcaatttg tatttgatac gtttgtatac atgtactaaa agatt         1615
```

<210> SEQ ID NO 4
<211> LENGTH: 475
<212> TYPE: PRT
<213> ORGANISM: Arabidopsis thaliana

<400> SEQUENCE: 4

```
Met Gly Ser Ser Glu Thr Glu Ser Glu Ser Arg Gly Phe Gln Asn Pro
1               5                   10                  15

Asp Trp Glu Thr Glu Phe Asn Arg Phe Glu Asn Ala Ile Ser Ser Gly
            20                  25                  30

Ser Ala Ser Ile Arg Val Arg Ser Val Leu Lys Leu Ser Asp Leu Thr
        35                  40                  45

Asn Arg Val Pro Glu Ser Tyr Ile Ser Arg Ala Ile Pro Ile Leu Ala
    50                  55                  60

Gly Leu Leu Arg Val Ser Asp Asp Ser Asn Arg Ser Val Gln Ala Ala
65                  70                  75                  80

Ala Ala His Cys Leu Lys Cys Ile Thr Cys Cys Gly Glu Glu Ser
                85                  90                  95

Gly Phe Ala Val Thr Met Gly Arg Cys Gly Val Ile Ala Ser Leu Leu
            100                 105                 110

Gly Leu Leu Leu Glu Ala Asn Thr Asp Gly Asn Val Phe Arg Arg Ile
        115                 120                 125

Trp Val Lys Cys Leu Trp Ser Leu Val Thr Phe Gly Ser Ser Ile Arg
    130                 135                 140
```

Val Gly Leu Ala Arg Leu Gly Gly Leu Glu Ile Val Ile Arg Glu Leu
145                 150                 155                 160

Asn Asn Trp Glu Asp Asp Gly Ser Arg Trp Tyr Leu Leu Glu Ile Leu
                165                 170                 175

Ser Ala Leu Thr Thr Ile Arg Glu Ser Arg Val Leu Val His Ser
            180                 185                 190

Gly Gly Leu Lys Phe Leu Val Glu Ala Ala Lys Val Gly Asn Leu Ala
            195                 200                 205

Ser Arg Glu Arg Ala Cys His Ala Ile Gly Leu Ile Gly Val Thr Arg
            210                 215                 220

Arg Ala Arg Arg Ile Leu Val Glu Ala Gly Val Ile Pro Ala Leu Val
225                 230                 235                 240

Asp Leu Tyr Arg Asp Gly Asp Lys Ala Lys Leu Leu Ala Gly Asn
            245                 250                 255

Ala Leu Gly Ile Ile Ser Ala Gln Thr Glu Tyr Ile Arg Pro Val Thr
            260                 265                 270

Glu Ala Gly Ser Ile Pro Leu Tyr Val Glu Leu Ser Gly Gln Asp
            275                 280                 285

Pro Met Gly Lys Asp Ile Ala Glu Asp Val Phe Cys Ile Leu Ala Val
            290                 295                 300

Ala Glu Gly Asn Ala Val Leu Ile Ala Glu Gln Leu Val Arg Ile Leu
305                 310                 315                 320

Arg Ala Gly Asp Asn Glu Ala Lys Leu Ala Ala Ser Asp Val Leu Trp
            325                 330                 335

Asp Leu Ala Gly Tyr Arg His Ser Val Ser Val Ile Arg Gly Ser Gly
            340                 345                 350

Ala Ile Pro Leu Leu Ile Glu Leu Leu Arg Asp Gly Ser Leu Glu Phe
            355                 360                 365

Arg Glu Arg Ile Ser Gly Ala Ile Ser Gln Leu Ser Tyr Asn Glu Asn
            370                 375                 380

Asp Arg Glu Ala Phe Ser Asp Ser Gly Met Ile Pro Ile Leu Ile Glu
385                 390                 395                 400

Trp Leu Gly Asp Glu Ser Glu Glu Leu Arg Asp Asn Ala Ala Glu Ala
            405                 410                 415

Leu Ile Asn Phe Ser Glu Asp Gln Glu His Tyr Ala Arg Val Arg Glu
            420                 425                 430

Ala Ile Gly His Pro Val Phe Gln Ser Met Gln Ser Arg Leu Ala Arg
            435                 440                 445

Ile Arg Ala Ser His Glu Leu Met Val Arg Ser Met Arg Arg Val Thr
            450                 455                 460

Ile Gln His Leu Ala His Asp His Asp Leu Pro
465                 470                 475

<210> SEQ ID NO 5
<211> LENGTH: 357
<212> TYPE: DNA
<213> ORGANISM: Arabidopsis thaliana

<400> SEQUENCE: 5
atgcgtatca aactgtcagt gaatagtgaa aaatgcagga agaaggcaat gcaagtagca      60
gttgctgcag atggtgtaac ttcagtggcc atggaaggag aatttcagga tgagcttgtg     120
gttgttggag atggagtgga ttcagcttct tgattatgg ccttaaggaa gaaagcatgt      180
catgtcactc ttgagactct tgaagaagtg aagaagccac aggtcgaaga gaagtctatt     240

```
acaccgcatt gctgcatagc tcaatgtcct gtggttagca atgagcagcc aaggcctgag      300
gtttatagaa tagtgcatga ttcttatggt ccaaccactg ggtgcttagt tatgtaa         357
```

<210> SEQ ID NO 6
<211> LENGTH: 118
<212> TYPE: PRT
<213> ORGANISM: Arabidopsis thaliana

<400> SEQUENCE: 6

```
Met Arg Ile Lys Leu Ser Val Asn Ser Glu Lys Cys Arg Lys Lys Ala
1               5                   10                  15

Met Gln Val Ala Val Ala Ala Asp Gly Val Thr Ser Val Ala Met Glu
            20                  25                  30

Gly Glu Phe Gln Asp Glu Leu Val Val Gly Asp Gly Val Asp Ser
        35                  40                  45

Ala Ser Leu Ile Met Ala Leu Arg Lys Lys Ala Cys His Val Thr Leu
    50                  55                  60

Glu Thr Leu Glu Glu Val Lys Lys Pro Gln Val Glu Glu Lys Ser Ile
65                  70                  75                  80

Thr Pro His Cys Cys Ile Ala Gln Cys Pro Val Val Ser Asn Glu Gln
                85                  90                  95

Pro Arg Pro Glu Val Tyr Arg Ile Val His Asp Ser Tyr Gly Pro Thr
            100                 105                 110

Thr Gly Cys Leu Val Met
        115
```

<210> SEQ ID NO 7
<211> LENGTH: 2271
<212> TYPE: DNA
<213> ORGANISM: Arabidopsis thaliana

<400> SEQUENCE: 7

```
aaagaggtaa gattgttctt gaagaatcga ttctatagag cgtgttagct tcaatgctaa       60
cttgggagac cccagttatg cttgcaagca acaccgcctc aaccaaaaag ctagccttca      120
ttaccacctt tctcatcatt gtgttatgtc cggtcacaat ggtcatgtct cagccgcagg      180
cggatgtttt gccactgcca gcctcagacg cagattgcct cttgagattt aaagatactt      240
tggttaatgc atcgttcatt agcagttggg atccttccat ctccccgtgt aagcgaaact      300
cagagaattg gttcggtgtt ctctgtgtta ccggtaatgt ttggggccta caactcgaag      360
gaatgggctt aaccgggaag cttgaccttg aaccattagc tgcaatcaag aatctacgaa      420
ccttgagctt catgaacaac aaatttaacg gttcaatgcc atctgtcaag aattttggtg      480
cgttgaaatc attgtacttg tctaacaacc ggtttacagg ggagataccc gcggatgcgt      540 tgatggtat gcatcatttg aagaagcttc tgttggctaa caacgcgttt cgagggagta      600
tcccttcttc tttagcttat ttgccaatgc ttttagagtt gaggctaaat gggaatcagt      660
ttcatgggga ataccttat tttaaacaaa aggaccttaa gttggctagc ttcgaaaaca      720
atgacctcga gggacctata ccggaaagcc ttagcaacat ggatcctgtc tccttttcag      780
ggaacaagaa cttgtgtggt cctccactaa gcccatgttc gagtgattca ggatcttctc      840
cggatctccc ttctagtccc acggaaaaga acaagaacca atctttcttc atcattgcaa      900
ttgttctgat tgtcattggg ataatactga tgatcatttc gcttgtggtc tgtatccttc      960
ataccagaag acgcaagagt ttgtcggctt atccatccgc gggtcaggac aggacagaga     1020
aatacaacta cgatcaatct acggacaagg ataaagctgc agattctgta acgagttaca     1080
```

-continued

```
ctagtagaag aggagcagta ccggatcaga ataaactctt gttttttgcaa gatgacattc   1140 aaagatttga ccttcaagat cttcttagag cctctgctga agttcttggg agcggaagct   1200
ttggctcttc ttataaaact gggataaata gcggacagat gctggtcgtg aagaggtata   1260
aacatatgaa caatgttgga agagatgagt tcatgagcat atgagacgg ttagggagat   1320 tgaaacatcc gaatctgttg cctattgtgg cttactatta ccgcagagaa gagaagctct   1380
tgatcgctga gttcatgcca aatcgtagct tggcaagcca tcttcacgcg aatcattctg   1440
tggatcaacc gggattggat tggccaacaa ggctaaagat tatacaagga gtggctaagg   1500
gtttaggtta cttgttcaac gagctaacaa ccctaacaat ccctcacggt catctcaagt   1560
catcgaacgt tgtattggac gaatcatttg agccactcct aaccgattat gcactaagac   1620
cagtgatgaa ctcagagcag tctcacaatc taatgatctc ttataaatca ccagagtata   1680
gcttaaaggg acatctaact aaaaagacag atgtttggtg cctgggggta ttgatcttgg   1740
agcttttaac aggtaggttt ccggagaatt atctaagcca agggtacgat gctaacatga   1800
gcctcgtaac ttgggtgagc aacatggtta aggagaagaa aacaggtgac gtgtttgaca   1860
aggaaatgac tggaagaaa aactgcaaag cagagatgct aaaccttttg aaaatcgggt   1920
tgagttgttg cgaagaagat gaagaaagga ggatggagat gagagatgct gtggagaaga   1980
tagagaggtt aaaagaagga gagtttgaca atgatttcgc atcgacgaca cataatgtct   2040
ttgcttctcg gttgatagac gacgatgact ttggtttcgc catgaatcga tgatgaaact   2100
gatcagtctt ctccagaaca atggaaaaag ctaaacaatt tgtaatcttt gatgccaaat   2160
aaaaagaaga actttctttt tcttctttgt tatgtaactt tttccattct tataaatcat   2220
tctcttcgtg taattgtaaa tccatttttgc agagttttga aaatttttact c          2271
```

<210> SEQ ID NO 8
<211> LENGTH: 679
<212> TYPE: PRT
<213> ORGANISM: Arabidopsis thaliana

<400> SEQUENCE: 8

```
Met Leu Thr Trp Glu Thr Pro Val Met Leu Ala Ser Asn Thr Ala Ser
1               5                   10                  15

Thr Lys Lys Leu Ala Phe Ile Thr Thr Phe Leu Ile Ile Val Leu Cys
            20                  25                  30

Pro Val Thr Met Val Met Ser Gln Pro Gln Ala Asp Val Leu Pro Leu
        35                  40                  45

Pro Ala Ser Asp Ala Asp Cys Leu Leu Arg Phe Lys Asp Thr Leu Val
    50                  55                  60

Asn Ala Ser Phe Ile Ser Ser Trp Asp Pro Ser Ile Ser Pro Cys Lys
65                  70                  75                  80

Arg Asn Ser Glu Asn Trp Phe Gly Val Leu Cys Val Thr Gly Asn Val
                85                  90                  95

Trp Gly Leu Gln Leu Glu Gly Met Gly Leu Thr Gly Lys Leu Asp Leu
            100                 105                 110

Glu Pro Leu Ala Ala Ile Lys Asn Leu Arg Thr Leu Ser Phe Met Asn
        115                 120                 125

Asn Lys Phe Asn Gly Ser Met Pro Ser Val Lys Asn Phe Gly Ala Leu
    130                 135                 140

Lys Ser Leu Tyr Leu Ser Asn Asn Arg Phe Thr Gly Glu Ile Pro Ala
145                 150                 155                 160
```

```
Asp Ala Phe Asp Gly Met His His Leu Lys Lys Leu Leu Leu Ala Asn
            165                 170                 175

Asn Ala Phe Arg Gly Ser Ile Pro Ser Ser Leu Ala Tyr Leu Pro Met
            180                 185                 190

Leu Leu Glu Leu Arg Leu Asn Gly Asn Gln Phe His Gly Glu Ile Pro
            195                 200                 205

Tyr Phe Lys Gln Lys Asp Leu Lys Leu Ala Ser Phe Glu Asn Asn Asp
            210                 215                 220

Leu Glu Gly Pro Ile Pro Glu Ser Leu Ser Asn Met Asp Pro Val Ser
225                 230                 235                 240

Phe Ser Gly Asn Lys Asn Leu Cys Gly Pro Pro Leu Ser Pro Cys Ser
            245                 250                 255

Ser Asp Ser Gly Ser Ser Pro Asp Leu Pro Ser Ser Pro Thr Glu Lys
            260                 265                 270

Asn Lys Asn Gln Ser Phe Phe Ile Ala Ile Val Leu Ile Val Ile
            275                 280                 285

Gly Ile Ile Leu Met Ile Ile Ser Leu Val Val Cys Ile Leu His Thr
            290                 295                 300

Arg Arg Arg Lys Ser Leu Ser Ala Tyr Pro Ser Ala Gly Gln Asp Arg
305                 310                 315                 320

Thr Glu Lys Tyr Asn Tyr Asp Gln Ser Thr Asp Lys Asp Lys Ala Ala
            325                 330                 335

Asp Ser Val Thr Ser Tyr Thr Ser Arg Arg Gly Ala Val Pro Asp Gln
            340                 345                 350

Asn Lys Leu Leu Phe Leu Gln Asp Asp Ile Gln Arg Phe Asp Leu Gln
            355                 360                 365

Asp Leu Leu Arg Ala Ser Ala Glu Val Leu Gly Ser Gly Ser Phe Gly
            370                 375                 380

Ser Ser Tyr Lys Thr Gly Ile Asn Ser Gly Gln Met Leu Val Val Lys
385                 390                 395                 400

Arg Tyr Lys His Met Asn Asn Val Gly Arg Asp Glu Phe His Glu His
            405                 410                 415

Met Arg Arg Leu Gly Arg Leu Lys His Pro Asn Leu Leu Pro Ile Val
            420                 425                 430

Ala Tyr Tyr Tyr Arg Arg Glu Glu Lys Leu Leu Ile Ala Glu Phe Met
            435                 440                 445

Pro Asn Arg Ser Leu Ala Ser His Leu His Ala Asn His Ser Val Asp
450                 455                 460

Gln Pro Gly Leu Asp Trp Pro Thr Arg Leu Lys Ile Ile Gln Gly Val
465                 470                 475                 480

Ala Lys Gly Leu Gly Tyr Leu Phe Asn Glu Leu Thr Thr Leu Thr Ile
            485                 490                 495

Pro His Gly His Leu Lys Ser Ser Asn Val Val Leu Asp Glu Ser Phe
            500                 505                 510

Glu Pro Leu Leu Thr Asp Tyr Ala Leu Arg Pro Val Met Asn Ser Glu
            515                 520                 525

Gln Ser His Asn Leu Met Ile Ser Tyr Lys Ser Pro Glu Tyr Ser Leu
            530                 535                 540

Lys Gly His Leu Thr Lys Lys Thr Asp Val Trp Cys Leu Gly Val Leu
545                 550                 555                 560

Ile Leu Glu Leu Leu Thr Gly Arg Phe Pro Glu Asn Tyr Leu Ser Gln
            565                 570                 575

Gly Tyr Asp Ala Asn Met Ser Leu Val Thr Trp Val Ser Asn Met Val
```

```
            580             585             590
Lys Glu Lys Lys Thr Gly Asp Val Phe Asp Lys Glu Met Thr Gly Lys
            595             600             605

Lys Asn Cys Lys Ala Glu Met Leu Asn Leu Leu Lys Ile Gly Leu Ser
            610             615             620

Cys Cys Glu Glu Asp Glu Arg Arg Met Glu Met Arg Asp Ala Val
625             630             635             640

Glu Lys Ile Glu Arg Leu Lys Glu Gly Glu Phe Asp Asn Asp Phe Ala
            645             650             655

Ser Thr Thr His Asn Val Phe Ala Ser Arg Leu Ile Asp Asp Asp Asp
            660             665             670

Phe Gly Phe Ala Met Asn Arg
            675

<210> SEQ ID NO 9
<211> LENGTH: 2772
<212> TYPE: DNA
<213> ORGANISM: Arabidopsis thaliana

<400> SEQUENCE: 9
ataaactaat tactatggcg gagaattcgc ggctacgaga gctacggaga cacagatgat     60
gaaagagaga agagagagaga gagagagaga gaatgtgagg ttaaaattat ccattgttgt    120
tcttcagtgc accactgaat cgaagttttc taatttggag aaagaggatt ctcaaaacc     180 cctaatttag gaagaccgca gatttcttta gtattgagaa tgagattctc cgagaagatg    240
gattagtgaa tcgagaggtt gatatcgtta atgcggggga ttttgcaatc tagggttctt    300
aagcattgta atcgatgaag gctcaaaagg gaagctcgaa gaagaaaggt acgaattctg    360
ggttagtcgc tgtagcagtg gataacaata aggaagcca acatgctctc aaatgggctg    420
ctgatcatct tgtctctaaa ggacaaacca ttatcctcct ccatgttatc cttaggtcat    480
cctctgattc aggtgagatt actgcagaga acataagca agctgaaaat cttttttgtga    540 catttcattg ctactgcagt cgaaaagaga tacaatgcct tgatgtcacg cttgaggatg    600
acaacattgt caagtccctt gcggaatatg tttcctctgg tgtgattgag aatttgattc    660
ttggtgctcc ttcgaggcat ggattcatga ggaaatttaa gatttctgat acaccgagca    720
atgtagcgaa agcagcacct gatttctgta cagtttacgt tatttcaaaa gggaagatat    780
catctgtccg ccatgcctca cgagctgctc catatcggtc tccgcttatg ggtcagattg    840
aaaaccactc tgaaatcata aactacgaaa agttcagaaa caccatgagc tttagagata    900
gggctcctcc caggtcttcg actgctagct ccattgaaga ttatggaaag tcacctatgg    960
caaggacgtc aaattacgca aactcattct ttgatttgga agattccgaa acgacatat    1020 catttgtttg ctcaggcagg ccaagtaccg caagctcagg ccggccaagt acaagtaccg   1080
gaaggtctga catatctttt gtgagctcag gcaggccgag tacaagcacc actgaagcc   1140 cttccttcat ctacgatttt cctgattctg gtttaactcc gagagagtcg acgagctctg   1200
gacactctat gcgtctagga atcaggttca atgacacaaa tatccaacat gatttctcat   1260
tcgtctcaca agatagcggt cggtcatctt gttcttgttc accacaaaac ttggaagaag   1320
tggaagctga gatgcggaga ttgaagcagg aactgaaaca cgcaattgac atgtatggat   1380
cagcttgcag agaagcacta gctgcaaagc aagaggcgaa ggagctccaa cgtcagaaaa   1440
ttgaagagga agggtgggtg caagaaggac agttatcaga gaaatctaca aagtccatag   1500
tggaaaaaga gagagcacat aaagctgcga aggatgcttc tgaaacagca ggcaagatag   1560
```

-continued

```
cagagctcga aacacaaaga agagctatag aagctgcagg ttctttctct gattccagtt     1620
taaggtatcg aaggtatgtc attggtgaga ttgaagaagc cacaaactca ttcgacaagg     1680
ctaataaaat aggcgaaggc gggtatggtc ctgtctataa gggttatctt gatcataccc     1740
ctgttgctat taaggctttg aaagcagatg cagttcaagg aagatctcaa tttcaaagag     1800
aggtagaagt tcttagctgc ataagacacc cacacatggt actactaatt ggagcatgtc     1860
cagagtatgg agtgcttgta tatgagtata tggccaaagg gagtttagct gataggctct     1920
ataagtatgg aaacacacca ccactctcgt gggagctcag gttccgaatt gcagccgaag     1980
ttgcgacggg tctgctcttc ctacaccaga cgaaacccga gcctatagtg caccgtgatc     2040
ttaaacccgg aaacattttg attgaccaga actacgtaag caaaataggg gacgttggat     2100
tagccaaact agtgcctgca gttgctgaaa acgtcacgca gtgccacgtg tcatcaaccg     2160
ctgggacttt ctgttacatt gaccctgagt accaacaaac tggaatgcta ggtgtgaaat     2220
ctgatgtcta ctcttttggt atcttgcttc tcgaactgct cacagcgaaa aggccgacgg     2280
gtttggctta taccgttgag caagcaatgg agcaagggaa attcaaggat atgttagacc     2340
cagcagtgcc taactggccg gtggaagaag ctatgtcttt ggcaaagatt gctcttaaat     2400
gtgcacagct gagaaggaaa gaccgaccag acctcggaaa agaggtttta ccagagctca     2460
ataaattgag agctcgtgca gatacgaata tggaatggat gatgttcaac ttaagtagag     2520
gtcgtctaac accaaatcat agccaagtgt ccttgccacc agttgatgaa ctaagtgtat     2580
gctcggataa gtcttataca cattcaagca ctgtatccga cacagagaag aactcagacc     2640
aaaacgaaga ggattagcat attttgtgtg ttgaaggaaa tggagtgaga ccattgttaa     2700
agcttatgta attgtgaata ttgttgtatg tatgtatgta tataattcgt aaaggaagaa     2760 ataactgaa gg                                                          2772
```

<210> SEQ ID NO 10
<211> LENGTH: 780
<212> TYPE: PRT
<213> ORGANISM: Arabidopsis thaliana

<400> SEQUENCE: 10

```
Met Lys Ala Gln Lys Gly Ser Ser Lys Lys Gly Thr Asn Ser Gly
1               5                   10                  15

Leu Val Ala Val Ala Val Asp Asn Asn Lys Gly Ser Gln His Ala Leu
                20                  25                  30

Lys Trp Ala Ala Asp His Leu Val Ser Lys Gly Gln Thr Ile Ile Leu
            35                  40                  45

Leu His Val Ile Leu Arg Ser Ser Asp Ser Gly Glu Ile Thr Ala
        50                  55                  60

Glu Lys His Lys Gln Ala Glu Asn Leu Phe Val Thr Phe His Cys Tyr
65              70                  75                  80

Cys Ser Arg Lys Glu Ile Gln Cys Leu Asp Val Thr Leu Glu Asp Asp
                85                  90                  95

Asn Ile Val Lys Ser Leu Ala Glu Tyr Val Ser Gly Val Ile Glu
                100                 105                 110

Asn Leu Ile Leu Gly Ala Pro Ser Arg His Gly Phe Met Arg Lys Phe
            115                 120                 125

Lys Ile Ser Asp Thr Pro Ser Asn Val Ala Lys Ala Ala Pro Asp Phe
        130                 135                 140

Cys Thr Val Tyr Val Ile Ser Lys Gly Lys Ile Ser Ser Val Arg His
```

```
            145                 150                 155                 160
        Ala Ser Arg Ala Ala Pro Tyr Arg Ser Pro Leu Met Gly Gln Ile Glu
                        165                 170                 175

Asn His Ser Glu Ile Ile Asn Tyr Glu Lys Phe Arg Asn Thr Met Ser
                        180                 185                 190

Phe Arg Asp Arg Ala Pro Pro Arg Ser Ser Thr Ala Ser Ser Ile Glu
                        195                 200                 205

Asp Tyr Gly Lys Ser Pro Met Ala Arg Thr Ser Asn Tyr Ala Asn Ser
                210                 215                 220

Phe Phe Asp Leu Glu Asp Ser Glu Asn Asp Ile Ser Phe Val Cys Ser
        225                 230                 235                 240

Gly Arg Pro Ser Thr Ala Ser Ser Gly Arg Pro Ser Thr Ser Thr Gly
                        245                 250                 255

Arg Ser Asp Ile Ser Phe Val Ser Ser Gly Arg Pro Ser Thr Ser Thr
                        260                 265                 270

Thr Gly Ser Pro Ser Phe Ile Tyr Asp Phe Pro Asp Ser Gly Leu Thr
                        275                 280                 285

Pro Arg Glu Ser Thr Ser Ser Gly His Ser Met Arg Leu Gly Ile Arg
                        290                 295                 300

Phe Asn Asp Thr Asn Ile Gln His Asp Phe Ser Phe Val Ser Gln Asp
        305                 310                 315                 320

Ser Gly Arg Ser Ser Cys Ser Cys Ser Pro Gln Asn Leu Glu Glu Val
                        325                 330                 335

Glu Ala Glu Met Arg Arg Leu Lys Gln Glu Leu Lys His Ala Ile Asp
                        340                 345                 350

Met Tyr Gly Ser Ala Cys Arg Glu Ala Leu Ala Ala Lys Gln Glu Ala
                        355                 360                 365

Lys Glu Leu Gln Arg Gln Lys Ile Glu Glu Gly Trp Val Gln Glu
                        370                 375                 380

Gly Gln Leu Ser Glu Lys Ser Thr Lys Ser Ile Val Glu Lys Glu Arg
        385                 390                 395                 400

Ala His Lys Ala Ala Lys Asp Ala Ser Glu Thr Ala Gly Lys Ile Ala
                        405                 410                 415

Glu Leu Glu Thr Gln Arg Arg Ala Ile Glu Ala Ala Gly Ser Phe Ser
                        420                 425                 430

Asp Ser Ser Leu Arg Tyr Arg Arg Tyr Val Ile Gly Glu Ile Glu Glu
                        435                 440                 445

Ala Thr Asn Ser Phe Asp Lys Ala Asn Lys Ile Gly Glu Gly Gly Tyr
                450                 455                 460

Gly Pro Val Tyr Lys Gly Tyr Leu Asp His Thr Pro Val Ala Ile Lys
        465                 470                 475                 480

Ala Leu Lys Ala Asp Ala Val Gln Gly Arg Ser Gln Phe Gln Arg Glu
                        485                 490                 495

Val Glu Val Leu Ser Cys Ile Arg His Pro His Met Val Leu Leu Ile
                        500                 505                 510

Gly Ala Cys Pro Glu Tyr Gly Val Leu Val Tyr Glu Tyr Met Ala Lys
                        515                 520                 525

Gly Ser Leu Ala Asp Arg Leu Tyr Lys Tyr Gly Asn Thr Pro Pro Leu
                        530                 535                 540

Ser Trp Glu Leu Arg Phe Arg Ile Ala Ala Glu Val Ala Thr Gly Leu
        545                 550                 555                 560

Leu Phe Leu His Gln Thr Lys Pro Glu Pro Ile Val His Arg Asp Leu
                        565                 570                 575
```

Lys Pro Gly Asn Ile Leu Ile Asp Gln Asn Tyr Val Ser Lys Ile Gly
            580                 585                 590

Asp Val Gly Leu Ala Lys Leu Val Pro Ala Val Ala Glu Asn Val Thr
        595                 600                 605

Gln Cys His Val Ser Ser Thr Ala Gly Thr Phe Cys Tyr Ile Asp Pro
    610                 615                 620

Glu Tyr Gln Gln Thr Gly Met Leu Gly Val Lys Ser Asp Val Tyr Ser
625                 630                 635                 640

Phe Gly Ile Leu Leu Leu Glu Leu Leu Thr Ala Lys Arg Pro Thr Gly
                645                 650                 655

Leu Ala Tyr Thr Val Glu Gln Ala Met Glu Gln Gly Lys Phe Lys Asp
            660                 665                 670

Met Leu Asp Pro Ala Val Pro Asn Trp Pro Val Glu Glu Ala Met Ser
        675                 680                 685

Leu Ala Lys Ile Ala Leu Lys Cys Ala Gln Leu Arg Arg Lys Asp Arg
    690                 695                 700

Pro Asp Leu Gly Lys Glu Val Leu Pro Glu Leu Asn Lys Leu Arg Ala
705                 710                 715                 720

Arg Ala Asp Thr Asn Met Glu Trp Met Met Phe Asn Leu Ser Arg Gly
                725                 730                 735

Arg Leu Thr Pro Asn His Ser Gln Val Ser Leu Pro Pro Val Asp Glu
            740                 745                 750

Leu Ser Val Cys Ser Asp Lys Ser Tyr Thr His Ser Ser Thr Val Ser
        755                 760                 765

Asp Thr Glu Lys Asn Ser Asp Gln Asn Glu Glu Asp
    770                 775                 780

<210> SEQ ID NO 11
<211> LENGTH: 1681
<212> TYPE: DNA
<213> ORGANISM: Arabidopsis thaliana

<400> SEQUENCE: 11
aatcatcatc caaaaacatt cttctcacaa gaatcagatt caagatagaa gttttcaaa       60 caatgtctag tcctcttggt cactttcaga ttcttgtttt tcttcatgct ttgcttatct      120
tctcagctga gtcccgcaaa acccaattgc tgaacgataa tgatgttgaa tctagcgaca      180
agagtgcaaa aggcacacga tgggctgttt tagttgctgg atcaaatgaa tattataact      240
acaggcatca ggctgacata tgccacgcgt atcagatact ccgaaaaggc ggtttaaaag      300
atgaaaacat cattgtgttt atgtatgatg atatcgcgtt ttcctcggag aatcctaggc      360
ctggagttat cattaataaa ccagatggag aagatgttta taaggagtt cctaaggact       420 acactaaaga agctgttaat gttcaaaact tctacaatgt gttacttgga aatgaaagtg      480
gcgtcacagg aggaaatggc aaagttgtga aaagtggtcc taatgataat atcttcatct      540
attatgctga ccatggagct cctggcttaa tagcgatgcc cactggtgat gaagttatgg      600
caaaagattt caatgaagtc ttggagaaga tgcataagag aaaaaaatac aacaagatgg      660
tgatctatgt tgaagcatgt gaatcaggaa gtatgtttga agggatttta agaaaaaatc      720
tcaacatata cgcagtgact gctgctaatt ctaaagagag cagctgggga gtttactgtc      780
ctgagtcata tcctcctcct ccttctgaga ttggaacttg tctcggcgat acatttagca      840
tctcttggct tgaggacagt gaccttcatg acatgagcaa agagactttg gagcaacaat      900
accacgttgt aaagagaaga gtaggatctg atgtaccaga gacttctcat gtatgccgtt      960

```
tcggaacaga gaagatgctt aaagattatc tttcctctta cattggaaga aatcctgaaa    1020
acgataactt cactttcacg gaatccttt cctcaccaat ctctaattct ggcttggtca    1080
atccgcgcga tattcctctg ctataccctcc agagaaagat tcaaaaagct ccaatgggat    1140
cacttgaaag caaagaagct cagaagaaat tgcttgacga aaagaatcat aggaaacaaa    1200
tcgatcagag cattacagac attctgcggc tttcagttaa acaaaccaat gtcttaaatc    1260
tcttaacttc cacaagaaca acaggacagc ctcttgtaga cgattgggat tgcttcaaga    1320
ctctagttaa tagcttcaag aatcactgcg gtgcaacggt gcattacgga ttgaagtata    1380
caggagcgct tgccaatatc tgcaatatgg gagtggatgt gaagcaaact gtttcagcca    1440
ttgaacaagc ttgttcgatg taatgatttg caaaacaatg tgatattcga ctttaaaaat    1500
atcaaagtta atttcaataa aactcgatgt agagatggtt ggttcatgat actacttta     1560 catgaaaagc tttttaatcg atgataacgc gaaagtcttg gtctaaattt gtgaattgga    1620
ttcatggaac aataacctcg taccaactgt acggtacgga cggctgtact ttggttgagt    1680
t                                                                    1681
```

<210> SEQ ID NO 12
<211> LENGTH: 466
<212> TYPE: PRT
<213> ORGANISM: Arabidopsis thaliana

<400> SEQUENCE: 12

```
Met Ser Ser Pro Leu Gly His Phe Gln Ile Leu Val Phe Leu His Ala
1               5                   10                  15

Leu Leu Ile Phe Ser Ala Glu Ser Arg Lys Thr Gln Leu Leu Asn Asp
            20                  25                  30

Asn Asp Val Glu Ser Ser Asp Lys Ser Ala Lys Gly Thr Arg Trp Ala
        35                  40                  45

Val Leu Val Ala Gly Ser Asn Glu Tyr Tyr Asn Tyr Arg His Gln Ala
    50                  55                  60

Asp Ile Cys His Ala Tyr Gln Ile Leu Arg Lys Gly Gly Leu Lys Asp
65                  70                  75                  80

Glu Asn Ile Ile Val Phe Met Tyr Asp Asp Ile Ala Phe Ser Ser Glu
                85                  90                  95

Asn Pro Arg Pro Gly Val Ile Ile Asn Lys Pro Asp Gly Glu Asp Val
            100                 105                 110

Tyr Lys Gly Val Pro Lys Asp Tyr Thr Lys Glu Ala Val Asn Val Gln
        115                 120                 125

Asn Phe Tyr Asn Val Leu Leu Gly Asn Glu Ser Gly Val Thr Gly Gly
    130                 135                 140

Asn Gly Lys Val Val Lys Ser Gly Pro Asn Asp Asn Ile Phe Ile Tyr
145                 150                 155                 160

Tyr Ala Asp His Gly Ala Pro Gly Leu Ile Ala Met Pro Thr Gly Asp
                165                 170                 175

Glu Val Met Ala Lys Asp Phe Asn Glu Val Leu Glu Lys Met His Lys
            180                 185                 190

Arg Lys Lys Tyr Asn Lys Met Val Ile Tyr Val Glu Ala Cys Glu Ser
        195                 200                 205

Gly Ser Met Phe Glu Gly Ile Leu Lys Lys Asn Leu Asn Ile Tyr Ala
    210                 215                 220

Val Thr Ala Ala Asn Ser Lys Glu Ser Ser Trp Gly Val Tyr Cys Pro
225                 230                 235                 240
```

Glu Ser Tyr Pro Pro Pro Ser Glu Ile Gly Thr Cys Leu Gly Asp
            245                 250                 255

Thr Phe Ser Ile Ser Trp Leu Glu Asp Ser Asp Leu His Asp Met Ser
                260                 265                 270

Lys Glu Thr Leu Glu Gln Gln Tyr His Val Val Lys Arg Arg Val Gly
            275                 280                 285

Ser Asp Val Pro Glu Thr Ser His Val Cys Arg Phe Gly Thr Glu Lys
        290                 295                 300

Met Leu Lys Asp Tyr Leu Ser Ser Tyr Ile Gly Arg Asn Pro Glu Asn
305                 310                 315                 320

Asp Asn Phe Thr Phe Thr Glu Ser Phe Ser Pro Ile Ser Asn Ser
                325                 330                 335

Gly Leu Val Asn Pro Arg Asp Ile Pro Leu Leu Tyr Leu Gln Arg Lys
            340                 345                 350

Ile Gln Lys Ala Pro Met Gly Ser Leu Glu Ser Lys Glu Ala Gln Lys
        355                 360                 365

Lys Leu Leu Asp Glu Lys Asn His Arg Lys Gln Ile Asp Gln Ser Ile
370                 375                 380

Thr Asp Ile Leu Arg Leu Ser Val Lys Gln Thr Asn Val Leu Asn Leu
385                 390                 395                 400

Leu Thr Ser Thr Arg Thr Thr Gly Gln Pro Leu Val Asp Asp Trp Asp
                405                 410                 415

Cys Phe Lys Thr Leu Val Asn Ser Phe Lys Asn His Cys Gly Ala Thr
            420                 425                 430

Val His Tyr Gly Leu Lys Tyr Thr Gly Ala Leu Ala Asn Ile Cys Asn
        435                 440                 445

Met Gly Val Asp Val Lys Gln Thr Val Ser Ala Ile Glu Gln Ala Cys
    450                 455                 460

Ser Met
465

<210> SEQ ID NO 13
<211> LENGTH: 1912
<212> TYPE: DNA
<213> ORGANISM: Arabidopsis thaliana

<400> SEQUENCE: 13
agaaattagc acccgactcg ggctccgttt caatgttggc cgcgacgcct gctcatggac      60
tcaggtacgt ggtggtgccc acacgctcat ggcttcatag gtttcgatgc tgctcgtctt     120
ctctcgctcc tctctcccct tctgaattct cgggcggtaa taaagcccag aagaagctca     180
acgacgagaa caacaccaac gtaagcaatg agaaaacggc gccgtattat ccgaaacgag     240
gagaaacagt ggagcttgtg tgcgagagtt taggattcaa aggcaaagga atctgtaaag     300
ttgatggaac tggctacgtc gttatgtgtg accgagctct tcccggcgaa cgttttcttg     360
gccgtgtcac tcgccgcaaa ggcagctatg ctgaagtgac aaaaatgaag acaatatctc     420
cacataagga cttagtagaa gctccatgtg agtatgcatc ttactgtggt ggttgcaaaa     480
ctcagaatct ctcttatgaa gctcagctta gagctaaaga gagcaagtt  catgagctta     540 tcagacatgt tggaaggttt tctgataaca atcctggcct tgagattgtc ttgaagccta     600
ttgttgcttg cgatattcaa ttccattatc ggaataagat ggagttttca tttggtccac     660
aaagatggct tccgattgaa atgttaaacg agagacaaga tggtcctaag aactttgcat     720
tggggctcca tgcacctgga tttttgata aggttttaaa tgttgataag tgcttattac     780

```
agagcgagcc aggaaacttg gttcttgctg ctgtccaaga ttgctggaga gatcctgaat    840
taagtctttc accatatgat tgtcgttcac atgttgggtt tcttaaacat ttgatgctga    900
gaactggaag gaatgtggag actggttcac tagaacttat ggtcaatttt gtgacatcgt    960
cttataagcc agagctgttg aaaccnctgg ttgataggat ttcatcaatt cctcaagtgg   1020
taagcattat gaataatgta aattcttcgg taggaaacac atccgttggc gaaaaggaat   1080
atactcttta tgggaaggat acaatcacag aggtcttaag agggcttaca tttcaaattt   1140
cagccaactc tttctttcag actaacactc atcaggctga agttttatat aagcttattg   1200
aggaatctgc tggacttaaa ggagatggct cagaagtcgt gctcgatctt ttctgtggaa   1260
ctggtaccat aggccttaca cttgccagaa gggcgaaaca cgtgtatggt tatgaagtag   1320
taccacaagc aataacagat gcacacaaga atgcccaaat aaacggcata gagaatgcaa   1380
cattcatcca aggggatcta aacaaaatag agaagattt tgggaacaat ttccctaagc   1440
ctgatatcgt tatttctgat cccaatcgac ctggtatgca catgaagttg atcaagtttc   1500
tgctaaagct taaatctcca cggatcattt atgtttcctg taatcctgca acctgcgcca   1560
gggatctcga ttacctctgt cacggcgtgg aggagaagaa tctaaaaggt tgctacaaac   1620
tgatgagtgt tcagccagtg gatatgttcc ctcacactcc tcacatcgaa tgtgtctgct   1680
tgttagagct tgcttgagct ctattgtcac catggctgct tcatttggtc tctaatcaga   1740
tgagagacaa atgaaaacag agatttttt agattgaggg agttttggtt ttccattaga   1800
gttaagtatc tgtaatcttt ttcatcgagt tctttaatag cattcataga caagaatgta   1860
aacgtttttt aaaaagttaa aatcccacca aggcaagtgg tctttaagag tt           1912
```

<210> SEQ ID NO 14
<211> LENGTH: 554
<212> TYPE: PRT
<213> ORGANISM: Arabidopsis thaliana

<400> SEQUENCE: 14

```
Met Leu Ala Ala Thr Pro Ala His Gly Leu Arg Tyr Val Val Pro
1               5                   10                  15

Thr Arg Ser Trp Leu His Arg Phe Arg Cys Cys Ser Ser Leu Ala
            20                  25                  30

Pro Leu Ser Pro Ser Glu Phe Ser Gly Gly Asn Lys Ala Gln Lys Lys
        35                  40                  45

Leu Asn Asp Glu Asn Asn Thr Asn Val Ser Asn Glu Lys Thr Ala Pro
    50                  55                  60

Tyr Tyr Pro Lys Arg Gly Glu Thr Val Glu Leu Val Cys Glu Ser Leu
65                  70                  75                  80

Gly Phe Lys Gly Lys Gly Ile Cys Lys Val Asp Gly Thr Gly Tyr Val
                85                  90                  95

Val Met Cys Asp Arg Ala Leu Pro Gly Glu Arg Phe Leu Gly Arg Val
            100                 105                 110

Thr Arg Arg Lys Gly Ser Tyr Ala Glu Val Thr Lys Met Lys Thr Ile
        115                 120                 125

Ser Pro His Lys Asp Leu Val Glu Ala Pro Cys Glu Tyr Ala Ser Tyr
    130                 135                 140

Cys Gly Gly Cys Lys Thr Gln Asn Leu Ser Tyr Glu Ala Gln Leu Arg
145                 150                 155                 160

Ala Lys Glu Glu Gln Val His Glu Leu Ile Arg His Val Gly Arg Phe
                165                 170                 175
```

Ser Asp Asn Asn Pro Gly Leu Glu Ile Val Leu Lys Pro Ile Val Ala
            180                 185                 190

Cys Asp Ile Gln Phe His Tyr Arg Asn Lys Met Glu Phe Ser Phe Gly
            195                 200                 205

Pro Gln Arg Trp Leu Pro Ile Glu Met Leu Asn Glu Arg Gln Asp Gly
        210                 215                 220

Pro Lys Asn Phe Ala Leu Gly Leu His Ala Pro Gly Phe Phe Asp Lys
225                 230                 235                 240

Val Leu Asn Val Asp Lys Cys Leu Leu Gln Ser Glu Pro Gly Asn Leu
                245                 250                 255

Val Leu Ala Ala Val Gln Asp Cys Trp Arg Asp Pro Glu Leu Ser Leu
            260                 265                 270

Ser Pro Tyr Asp Cys Arg Ser His Val Gly Phe Leu Lys His Leu Met
            275                 280                 285

Leu Arg Thr Gly Arg Asn Val Glu Thr Gly Ser Leu Glu Leu Met Val
        290                 295                 300

Asn Phe Val Thr Ser Ser Tyr Lys Pro Glu Leu Leu Lys Pro Leu Val
305                 310                 315                 320

Asp Arg Ile Ser Ser Ile Pro Gln Val Val Ser Ile Met Asn Asn Val
                325                 330                 335

Asn Ser Ser Val Gly Asn Thr Ser Val Gly Glu Lys Glu Tyr Thr Leu
            340                 345                 350

Tyr Gly Lys Asp Thr Ile Thr Glu Val Leu Arg Gly Leu Thr Phe Gln
        355                 360                 365

Ile Ser Ala Asn Ser Phe Phe Gln Thr Asn Thr His Gln Ala Glu Val
            370                 375                 380

Leu Tyr Lys Leu Ile Glu Glu Ser Ala Gly Leu Lys Gly Asp Gly Ser
385                 390                 395                 400

Glu Val Val Leu Asp Leu Phe Cys Gly Thr Gly Thr Ile Gly Leu Thr
                405                 410                 415

Leu Ala Arg Arg Ala Lys His Val Tyr Gly Tyr Glu Val Val Pro Gln
            420                 425                 430

Ala Ile Thr Asp Ala His Lys Asn Ala Gln Ile Asn Gly Ile Glu Asn
        435                 440                 445

Ala Thr Phe Ile Gln Gly Asp Leu Asn Lys Ile Gly Glu Asp Phe Gly
        450                 455                 460

Asn Asn Phe Pro Lys Pro Asp Ile Val Ile Ser Asp Pro Asn Arg Pro
465                 470                 475                 480

Gly Met His Met Lys Leu Ile Lys Phe Leu Lys Leu Lys Ser Pro
                485                 490                 495

Arg Ile Ile Tyr Val Ser Cys Asn Pro Ala Thr Cys Ala Arg Asp Leu
        500                 505                 510

Asp Tyr Leu Cys His Gly Val Glu Glu Lys Asn Leu Lys Gly Cys Tyr
            515                 520                 525

Lys Leu Met Ser Val Gln Pro Val Asp Met Phe Pro His Thr Pro His
        530                 535                 540

Ile Glu Cys Val Cys Leu Leu Glu Leu Ala
545                 550

<210> SEQ ID NO 15
<211> LENGTH: 1584
<212> TYPE: DNA
<213> ORGANISM: Arabidopsis thaliana

<400> SEQUENCE: 15

```
accaaaatca gattagagtt tcagagacat ctctcgaata cgatcatcag acaagactta      60
acctccattt gcacgtcttc ctgctcacga cagacaaatc atgaacgaat ccgacagctg     120
aacgaattgc gtgtctgaga agatccaaat cctaattttc tacctttttt ttttgggaac     180
taaggttaga atttggagct tctcgtacgt ttttgcttgc ctacgtttcc ggacaaaacc     240
ctatttgcat ataaacagaa caggttctgt tcatcaagac actgaagcct gatggggatg     300
gaggaaggga ttaaagataa tgctgcatca gctcccaatt caagacctac aaaccaactt     360
aaagctcttt taccgatgcg ggtgcttcaa gttttcttgt tgttctttgt tttggttctt     420
ggaatctcag tcattagtat gcacatgatc aagtacttaa agattcaaac tttagctcca     480
tcgacattga tctctactta tgatgagaga attacgttag agagcctta t caagcctcca    540
ttgaatggtt ggcattccat gaatgacagt gagcttcttt ggcgtgcttc gatggagcct     600
cggatacttg actatccatt taaaagagtt cctaaaatgg cattcatgtt tctcaccaaa     660
ggaccttgtgc catttgctcc actttgggaa aggttttttca aagggcatga gggcttttac     720
tcaatctatg ttcatacttt gccaaattat agatcagatt tcccaagctc atctgtgttt     780
tacagaagac agatcccaag tcagcatgta gcttggggag agatgagtat gtgtgatgct     840
gaaaggaggc ttttggctaa cgcgttgctc gatatctcta acgaatggtt tgttttacta     900
tctgaagcgt gtattcctct tcgcggtttc aactttgtct accgttatgt ctctagatca     960
agatatagtt tcatgggttc tgttgacgag gacgggcctt acgggagagg cagatatagc    1020
tatgcaatgg gaccagaagt aagtctaaac gagtggagaa aagggtctca gtggtttgaa    1080
ataaacagag cacttgctgt tgatattgtt gaagacatgg tttactataa caaattcaaa    1140
gagttttgta gacctccttg ttatgtagat gaacattact tcccaacaat gctctctatt    1200
ggatatccgg attttctcgc taatcggaca ttgacttgga cagattggtc aagggtggt     1260
gctcatccag ctacttttgg caaggctgat ataacagaga agttcatcaa gaagctgtca    1320
agaggtaaag cttgcttcta caatgatcag ccatctcaag tttgttatct ttttgcaaga    1380
aagtttgctc caagcgcatt gaagcctta cttaaacttg caccaaaggt tcttgggttc    1440
taattaatgg atctcttgtc ttctttttgt tcttggtttt tgttctgaaa tgttcttgaa    1500
cttgagtgta gcttcgtata gcatggacac aactctgatc cttattgtct ccttccacat    1560
tgataatata gatacttcaa tggc                                           1584
```

<210> SEQ ID NO 16
<211> LENGTH: 383
<212> TYPE: PRT
<213> ORGANISM: Arabidopsis thaliana

<400> SEQUENCE: 16

```
Met Gly Met Glu Glu Gly Ile Lys Asp Asn Ala Ala Ser Ala Pro Asn
1               5                   10                  15

Ser Arg Pro Thr Asn Gln Leu Lys Ala Leu Leu Pro Met Arg Val Leu
            20                  25                  30

Gln Val Phe Leu Leu Phe Phe Val Leu Val Leu Gly Ile Ser Val Ile
        35                  40                  45

Ser Met His Met Ile Lys Tyr Leu Lys Ile Gln Thr Leu Ala Pro Ser
    50                  55                  60

Thr Leu Ile Ser Thr Tyr Asp Glu Arg Ile Thr Leu Glu Ser Leu Ile
65                  70                  75                  80
```

```
Lys Pro Pro Leu Asn Gly Trp His Ser Met Asn Asp Ser Glu Leu Leu
                85                  90                  95

Trp Arg Ala Ser Met Glu Pro Arg Ile Leu Asp Tyr Pro Phe Lys Arg
            100                 105                 110

Val Pro Lys Met Ala Phe Met Phe Leu Thr Lys Gly Pro Leu Pro Phe
        115                 120                 125

Ala Pro Leu Trp Glu Arg Phe Phe Lys Gly His Glu Gly Phe Tyr Ser
    130                 135                 140

Ile Tyr Val His Thr Leu Pro Asn Tyr Arg Ser Asp Phe Pro Ser Ser
145                 150                 155                 160

Ser Val Phe Tyr Arg Arg Gln Ile Pro Ser Gln His Val Ala Trp Gly
                165                 170                 175

Glu Met Ser Met Cys Asp Ala Glu Arg Arg Leu Leu Ala Asn Ala Leu
            180                 185                 190

Leu Asp Ile Ser Asn Glu Trp Phe Val Leu Leu Ser Glu Ala Cys Ile
        195                 200                 205

Pro Leu Arg Gly Phe Asn Phe Val Tyr Arg Tyr Val Ser Arg Ser Arg
    210                 215                 220

Tyr Ser Phe Met Gly Ser Val Asp Glu Asp Gly Pro Tyr Gly Arg Gly
225                 230                 235                 240

Arg Tyr Ser Tyr Ala Met Gly Pro Glu Val Ser Leu Asn Glu Trp Arg
                245                 250                 255

Lys Gly Ser Gln Trp Phe Glu Ile Asn Arg Ala Leu Ala Val Asp Ile
            260                 265                 270

Val Glu Asp Met Val Tyr Tyr Asn Lys Phe Lys Glu Phe Cys Arg Pro
        275                 280                 285

Pro Cys Tyr Val Asp Glu His Tyr Phe Pro Thr Met Leu Ser Ile Gly
    290                 295                 300

Tyr Pro Asp Phe Leu Ala Asn Arg Thr Leu Thr Trp Thr Asp Trp Ser
305                 310                 315                 320

Arg Gly Gly Ala His Pro Ala Thr Phe Gly Lys Ala Asp Ile Thr Glu
                325                 330                 335

Lys Phe Ile Lys Lys Leu Ser Arg Gly Lys Ala Cys Phe Tyr Asn Asp
            340                 345                 350

Gln Pro Ser Gln Val Cys Tyr Leu Phe Ala Arg Lys Phe Ala Pro Ser
        355                 360                 365

Ala Leu Lys Pro Leu Leu Lys Leu Ala Pro Lys Val Leu Gly Phe
    370                 375                 380

<210> SEQ ID NO 17
<211> LENGTH: 1064
<212> TYPE: DNA
<213> ORGANISM: Arabidopsis thaliana

<400> SEQUENCE: 17
aagcactgta tcaacctctt tcttctaacc aatcacaatc gccttcttcc acggcggctc      60
tccgtcacag gtgacaggtc ccaatctctc tctctcgcgg cgacggcgaa tacggctggt     120
acataatgtt gaagctttgg agatggtacc agcgatgcct gacggttcat cctgtgaaaa     180
ctcaggtcat cagttctgga tttctttggg gattggcgca tgtcaccgct caatacatca     240
ctcattccac tgcgaaacgt cgtcttcttc gtctcaccga acaaataaaa gatgctgacg     300
cagatgcaga aattaaggtc aagtggaagc aagatgcaga attcaaagtc aactggaagc     360
gagtagctat cacgagcatg tttggatttg gttttgtcgg acctgttggc cacttctggt     420
```

-continued

```
acgaaggctt ggataaattc ataaaactga agcttcgata tgtaccaaag tcaacacgtt    480
ttgtagctgc aaaagttgca atggatggtc ttatctttgg acctgtagat ctactggtgt    540
tcttcacata catgggattc gccacaggaa agaacacagc tgaagtgaaa gaaggactca    600
agagagattt tcttccggct ctagctcttg aaggcggagc atggccactt cttcagattg    660
caaacttcag atatgttccc gtgcaatacc agttgcttta cgtcaacatc ttttgcctag    720
tagacagtgc cttcctctca tgggtcgagc aacagaagga cgcagcttgg aagcaatggt    780
ttacttcatc atttcaacca ttaaaagaac gaggtggcca aggcggagta tgatcgtttt    840
ccctgtcata aactttgaat gaaaacaaaa acgagtgtaa ttggcgattt tcaataacgg    900
aagttgccta ggatacagat tcttgaatca atattattt cgtttcacga gaattcagta    960
caagtgaata aatgtctgtt agtattgaat gaatgcaaca tgatatggct agactagaga   1020
aatgagctat gaccgcctcc gagtggtatt cttggaagaa acac                    1064
```

<210> SEQ ID NO 18
<211> LENGTH: 235
<212> TYPE: PRT
<213> ORGANISM: Arabidopsis thaliana

<400> SEQUENCE: 18

```
Met Leu Lys Leu Trp Arg Trp Tyr Gln Arg Cys Leu Thr Val His Pro
1               5                   10                  15

Val Lys Thr Gln Val Ile Ser Ser Gly Phe Leu Trp Gly Phe Gly Asp
            20                  25                  30

Val Thr Ala Gln Tyr Ile Thr His Ser Thr Ala Lys Arg Arg Leu Leu
        35                  40                  45

Arg Leu Thr Glu Thr Asn Lys Asp Ala Asp Ala Glu Ile Lys
    50                  55                  60

Val Lys Trp Lys Gln Asp Ala Glu Phe Lys Val Asn Trp Lys Arg Val
65                  70                  75                  80

Ala Ile Thr Ser Met Phe Gly Phe Gly Phe Val Gly Pro Val Gly His
                85                  90                  95

Phe Trp Tyr Glu Gly Leu Asp Lys Phe Ile Lys Leu Lys Leu Arg Tyr
            100                 105                 110

Val Pro Lys Ser Thr Arg Phe Val Ala Ala Lys Val Ala Met Asp Gly
        115                 120                 125

Leu Ile Phe Gly Pro Val Asp Leu Leu Val Phe Phe Thr Tyr Met Gly
    130                 135                 140

Phe Ala Thr Gly Lys Asn Thr Ala Glu Val Lys Glu Gly Leu Lys Arg
145                 150                 155                 160

Asp Phe Leu Pro Ala Leu Ala Leu Glu Gly Gly Ala Trp Pro Leu Leu
                165                 170                 175

Gln Ile Ala Asn Phe Arg Tyr Val Pro Val Gln Tyr Gln Leu Leu Tyr
            180                 185                 190

Val Asn Ile Phe Cys Leu Val Asp Ser Ala Phe Leu Ser Trp Val Glu
        195                 200                 205

Gln Gln Lys Asp Ala Ala Trp Lys Gln Trp Phe Thr Ser Ser Phe Gln
    210                 215                 220

Pro Leu Lys Glu Arg Gly Gly Gln Gly Gly Val
225                 230                 235
```

<210> SEQ ID NO 19
<211> LENGTH: 1137
<212> TYPE: DNA

<213> ORGANISM: Arabidopsis thaliana

<400> SEQUENCE: 19

```
atgacgaaga tgtctaatct ccctaatgat ttggcggaag aggtgctctc tagggtttcg      60
ttaacatctc tgagaaacgt ccgacttact tgtaaagatt ggaatacttt atctaaaggt     120
gagagctttg caagaatca ccttggttat caagcaatag tagcagcgaa ggaaaaagag     180
tttatgatgg tcctgatgat ggattttagg gtttatttga ttcgagtcaa cgttcacaat     240
gacattgagt cgtgtattaa gcctgaaggt gagcttatta gcttgggcga tgaagtcgat     300
gtatctcaag tctttcactg cgacggttta ttgctatgca tcacggaaga taacgaagat     360
aacgctaagg tcgttctttg aacccgtat tgggggcaaa cacggtggat cgagtctaca     420
aataatttcc acaaattgga catgtatacg tatgctctcg gatacaagaa gagcagcaaa     480
tcaagccgca gctacaaaat cttgagattt attgattttt ctcccacttg ttctgagttc     540
aaaatctaca atatcaactc tgattcatgg aaggttcttg atgtgtctcc agactggaag     600
atagattctt atattcgtgg cgtgtctctc aagggaaata catactggat gctagagag     660
aggcacggat acggccatac tttcttagtc tgttttgatt tcacaagaga gagatttagg     720
tcgcgtttac ctctgccgag tcagccgtgt gttttagata ccgtgagtct atctagtgtt     780
agagaagagc agcttgctgt tttatttcag tgctcaagta cattggagat gcagatctgg     840
gtaacaacca aaattgagcc caatgcggtg ttgtggaaca gcaaggtgtt cttagctgtg     900
gatatgcact cacttaagtt tcagtttcaa gttagagctt cgagtttctt tatcgacgag     960
gagaagagag ttgttgttgt ttttgataaa gaaaaacgtt atttagcgtc ctctcgcaac    1020
aaagcttaca tcgttggagt ggatggaacc tgggaacaag tggaccttgg aatgtctgta    1080
gacaaatttg tttacccact tgtgtgctct tatgttccaa gtttagtgca ttttga       1137
```

<210> SEQ ID NO 20
<211> LENGTH: 378
<212> TYPE: PRT
<213> ORGANISM: Arabidopsis thaliana

<400> SEQUENCE: 20

```
Met Thr Lys Met Ser Asn Leu Pro Asn Asp Leu Ala Glu Glu Val Leu
1               5                   10                  15

Ser Arg Val Ser Leu Thr Ser Leu Arg Asn Val Arg Leu Thr Cys Lys
            20                  25                  30

Asp Trp Asn Thr Leu Ser Lys Gly Glu Ser Phe Ala Lys Asn His Leu
        35                  40                  45

Gly Tyr Gln Ala Ile Val Ala Ala Lys Glu Lys Glu Phe Met Met Val
    50                  55                  60

Leu Met Met Asp Phe Arg Val Tyr Leu Ile Arg Val Asn Val His Asn
65                  70                  75                  80

Asp Ile Glu Ser Cys Ile Lys Pro Glu Gly Glu Leu Ile Ser Leu Gly
                85                  90                  95

Asp Glu Val Asp Val Ser Gln Val Phe His Cys Asp Gly Leu Leu Leu
            100                 105                 110

Cys Ile Thr Glu Asp Asn Glu Asp Asn Ala Lys Val Val Leu Trp Asn
        115                 120                 125

Pro Tyr Trp Gly Gln Thr Arg Trp Ile Glu Ser Thr Asn Asn Phe His
    130                 135                 140

Lys Leu Asp Met Tyr Thr Tyr Ala Leu Gly Tyr Lys Lys Ser Ser Lys
145                 150                 155                 160
```

```
Ser Ser Arg Ser Tyr Lys Ile Leu Arg Phe Ile Asp Phe Ser Pro Thr
            165                 170                 175

Cys Ser Glu Phe Lys Ile Tyr Asn Ile Asn Ser Asp Ser Trp Lys Val
        180                 185                 190

Leu Asp Val Ser Pro Asp Trp Lys Ile Asp Ser Tyr Ile Arg Gly Val
        195                 200                 205

Ser Leu Lys Gly Asn Thr Tyr Trp Ile Ala Arg Glu Arg His Gly Tyr
    210                 215                 220

Gly His Thr Phe Leu Val Cys Phe Asp Phe Thr Arg Glu Arg Phe Arg
225                 230                 235                 240

Ser Arg Leu Pro Leu Pro Ser Gln Pro Cys Val Leu Asp Thr Val Ser
                245                 250                 255

Leu Ser Ser Val Arg Glu Glu Gln Leu Ala Val Leu Phe Gln Cys Ser
            260                 265                 270

Ser Thr Leu Glu Met Gln Ile Trp Val Thr Thr Lys Ile Glu Pro Asn
    275                 280                 285

Ala Val Leu Trp Asn Ser Lys Val Phe Leu Ala Val Asp Met His Ser
290                 295                 300

Leu Lys Phe Gln Phe Gln Val Arg Ala Ser Ser Phe Phe Ile Asp Glu
305                 310                 315                 320

Glu Lys Arg Val Val Val Phe Asp Lys Glu Lys Arg Tyr Leu Ala
                325                 330                 335

Ser Ser Arg Asn Lys Ala Tyr Ile Val Gly Val Asp Gly Thr Trp Glu
            340                 345                 350

Gln Val Asp Leu Gly Met Ser Val Asp Lys Phe Val Tyr Pro Leu Val
    355                 360                 365

Cys Ser Tyr Val Pro Ser Leu Val His Phe
370                 375

<210> SEQ ID NO 21
<211> LENGTH: 1046
<212> TYPE: DNA
<213> ORGANISM: Arabidopsis thaliana

<400> SEQUENCE: 21
gagaaagcca ttgtttcagt tgatgatggt gatgatatct cttcacttct ctactccgcc      60
gctagctttt ctcaaatctg attccaattc cagatttctc aagaacccta atcctaattt     120
tatccaattc accccaaaat cccaacttct ttcccccaa cgtctcaatt caacaccgg      180
aacaaattta aaccggcgaa ctctgagttg ctatgggatt aaggattcaa gtgagacaac     240
gaagtctgcg ccgtcattag actccggcga cggtggcggc ggagatggtg gtgatgatga     300
taaaggtgaa gtggaggaaa aaaacagact ttttccggaa tggttggatt ttacctcgga     360
tgatgcacag actgtgtttg tggctatagc tgtatcgttg gcgtttcgtt attttatcgc     420
agaaccaaga tatattcctt ctttgtctat gtatcctact tttgatgttg agacagatt     480
agttgcagag aaggtgagtt attatttcag gaagccttgt gcaaatgata ttgtcatctt     540
taaaagtcca ccagttcttc aggaagttgg gtatactgat gccgatgtat ttattaaacg     600
gattgttgcc aaagaaggtg accttgtgga ggtacataat gggaaactga tggttaatgg     660
tgttgctagg aatgaaaaat tcatcttaga gcctcctggt tatgaaatga ccaattag      720
ggtaccggaa aattcagtct ttgtgatggg tgataaccgg aataacagtt atgattcgca     780
cgtatgggt cctctgcctt tgaagaatat tattggacgg tcggtttttc ggtattggcc     840
```

```
accaaacaga gtaagcggga cagtgctaga aggtggctgt gctgtggata agcaatagaa      900
catattgtaa cgttttgatt cggcatgtct tcatttgaaa cacttgtgca gataaaaacg      960
aaaacaatgt accttttat gaaggagaga gttgcacatt tgaattagat tgcagattaa     1020
tgaggaaaca agaaattctt atttgc                                          1046
```

```
<210> SEQ ID NO 22
<211> LENGTH: 291
<212> TYPE: PRT
<213> ORGANISM: Arabidopsis thaliana

<400> SEQUENCE: 22
```

| Met | Met | Val | Met | Ile | Ser | Leu | His | Phe | Ser | Thr | Pro | Pro | Leu | Ala | Phe |
|---|---|---|---|---|---|---|---|---|---|---|---|---|---|---|---|
| 1 | | | | 5 | | | | | 10 | | | | | 15 | |

| Leu | Lys | Ser | Asp | Ser | Asn | Ser | Arg | Phe | Leu | Lys | Asn | Pro | Asn | Pro | Asn |
| | | | 20 | | | | | 25 | | | | | 30 | | |

| Phe | Ile | Gln | Phe | Thr | Pro | Lys | Ser | Gln | Leu | Leu | Phe | Pro | Gln | Arg | Leu |
| | | | 35 | | | | | 40 | | | | | 45 | | |

| Asn | Phe | Asn | Thr | Gly | Thr | Asn | Leu | Asn | Arg | Arg | Thr | Leu | Ser | Cys | Tyr |
| | 50 | | | | | 55 | | | | | 60 | | | | |

| Gly | Ile | Lys | Asp | Ser | Ser | Glu | Thr | Thr | Lys | Ser | Ala | Pro | Ser | Leu | Asp |
| 65 | | | | | 70 | | | | | 75 | | | | | 80 |

| Ser | Gly | Asp | Gly | Gly | Gly | Gly | Asp | Gly | Asp | Asp | Lys | Gly | Glu |
| | | | | 85 | | | | | 90 | | | | | 95 |

| Val | Glu | Glu | Lys | Asn | Arg | Leu | Phe | Pro | Glu | Trp | Leu | Asp | Phe | Thr | Ser |
| | | | 100 | | | | | 105 | | | | | 110 | | |

| Asp | Asp | Ala | Gln | Thr | Val | Phe | Val | Ala | Ile | Ala | Val | Ser | Leu | Ala | Phe |
| | | | 115 | | | | | 120 | | | | | 125 | | |

| Arg | Tyr | Phe | Ile | Ala | Glu | Pro | Arg | Tyr | Ile | Pro | Ser | Leu | Ser | Met | Tyr |
| | | 130 | | | | | 135 | | | | | 140 | | | |

| Pro | Thr | Phe | Asp | Val | Gly | Asp | Arg | Leu | Val | Ala | Glu | Lys | Val | Ser | Tyr |
| 145 | | | | | 150 | | | | | 155 | | | | | 160 |

| Tyr | Phe | Arg | Lys | Pro | Cys | Ala | Asn | Asp | Ile | Val | Ile | Phe | Lys | Ser | Pro |
| | | | 165 | | | | | 170 | | | | | 175 | | |

| Pro | Val | Leu | Gln | Glu | Val | Gly | Tyr | Thr | Asp | Ala | Asp | Val | Phe | Ile | Lys |
| | | | 180 | | | | | 185 | | | | | 190 | | |

| Arg | Ile | Val | Ala | Lys | Glu | Gly | Asp | Leu | Val | Glu | Val | His | Asn | Gly | Lys |
| | | | 195 | | | | | 200 | | | | | 205 | | |

| Leu | Met | Val | Asn | Gly | Val | Ala | Arg | Asn | Glu | Lys | Phe | Ile | Leu | Glu | Pro |
| | | 210 | | | | | 215 | | | | | 220 | | | |

| Pro | Gly | Tyr | Glu | Met | Thr | Pro | Ile | Arg | Val | Pro | Glu | Asn | Ser | Val | Phe |
| 225 | | | | | 230 | | | | | 235 | | | | | 240 |

| Val | Met | Gly | Asp | Asn | Arg | Asn | Asn | Ser | Tyr | Asp | Ser | His | Val | Trp | Gly |
| | | | 245 | | | | | 250 | | | | | 255 | | |

| Pro | Leu | Pro | Leu | Lys | Asn | Ile | Ile | Gly | Arg | Ser | Val | Phe | Arg | Tyr | Trp |
| | | | 260 | | | | | 265 | | | | | 270 | | |

| Pro | Pro | Asn | Arg | Val | Ser | Gly | Thr | Val | Leu | Glu | Gly | Gly | Cys | Ala | Val |
| | | | 275 | | | | | 280 | | | | | 285 | | |

| Asp | Lys | Gln |
| | 290 | |

```
<210> SEQ ID NO 23
<211> LENGTH: 1521
<212> TYPE: DNA
<213> ORGANISM: Arabidopsis thaliana
```

<400> SEQUENCE: 23

```
atgaagatgt acccaaaatc tgactcagac gtcacaagcc tcgacctatc atcaccaaaa      60
cgtcctactt actacgttca aagcccatca cgtgactccg acaagtcttc ctcggtggca     120
ctgactactc atcaaaccac tcccacagag tcgccgtcac acccatcaat tgctagccgg     180
gtatccaatg gcggtggtgg cggtttccgg tggaagggac ggaggaaata tcacggcggg     240
atatggtggc cggctgataa ggaggaaggt ggtgatggag gtacgagga tctttatgag      300
gacaacagag gagtctccat tgttacttgt agacttattt gggagttgt tgcgacattg      360
agtatctttt ttcttctttg ttctgttctc tttggtgctt ctcaatcttc tcctccaatc     420
gtctacatca agggtgtgaa tgtgagaagt ttttactacg agaaggttc agacaataca      480
ggagttccaa caaagatcat gaacgttaaa tgttcagtgg tgatcacaac acacaatcct     540
tctacattat tcggcatcca tgttagctcc actgccgtca gcctcatata ctctcgtcaa     600
ttcacacttg cgaatgcgcg gctgaagagt atcaccaac caaaacaaag caaccacaca      660
tctaggatca accttattgg ctccaaggtt ccactatatg gagcaggagc cgagttagtt     720
gcttcggaca cagtggtgg agttcccgtt cataccccaa actacaccat tctcagtgag      780
tcacgtctct cctcttcgag ccgtacctct aatgggacaa gcggtatggg atttcgatgg     840
aaaggaagct cccggaggag taatatgtat tggccggaga agccatacac gattaatgaa     900
gatgaggttt atgatgataa cagaggatta tcagtgggac aatgtagagc ggttttggta     960
atattaggta ctgtggttgt gttctctgtt ttttgctctg ttttgtgggg agcttctcat    1020
cctttctctc ctatcgtctc cgttaagagc gttgacatcc atagcttcta ttacggagaa    1080
ggaatagaca gaacaggagt cgccaccaag attctaagct taacagttc agtgaaggtg    1140
acaatagaca gtcctgctcc ttactttggc atccatgtct cttcttctac cttcaaactc    1200
actttctctg ctctcacact cgccactggt cagctaaaga gctattacca accaagaaag    1260
agtaagcaca tatcaattgt aaagctcact ggcgcagagg ttcctctgta tggagcagga    1320
ccacacttag cagcttccga caagaagggt aaagttccag tgaagctgga gtttgagatc    1380
agatcaagag gtaatctatt ggggaagcta gtcaagtcga agcacgagaa tcacgtatca    1440
tgctctttct tcatctcctc ctccaagact tccaaaccca tagaattcac tcacaagacc    1500
tgtaaactcg ttaccaagta a                                              1521
```

<210> SEQ ID NO 24
<211> LENGTH: 506
<212> TYPE: PRT
<213> ORGANISM: Arabidopsis thaliana

<400> SEQUENCE: 24

```
Met Lys Met Tyr Pro Lys Ser Asp Ser Asp Val Thr Ser Leu Asp Leu
1               5                   10                  15

Ser Ser Pro Lys Arg Pro Thr Tyr Tyr Val Gln Ser Pro Ser Arg Asp
            20                  25                  30

Ser Asp Lys Ser Ser Ser Val Ala Leu Thr Thr His Gln Thr Thr Pro
        35                  40                  45

Thr Glu Ser Pro Ser His Pro Ser Ile Ala Ser Arg Val Ser Asn Gly
    50                  55                  60

Gly Gly Gly Gly Phe Arg Trp Lys Gly Arg Arg Lys Tyr His Gly Gly
65                  70                  75                  80

Ile Trp Trp Pro Ala Asp Lys Glu Glu Gly Gly Asp Gly Arg Tyr Glu
                85                  90                  95
```

-continued

```
Asp Leu Tyr Glu Asp Asn Arg Gly Val Ser Ile Val Thr Cys Arg Leu
            100                 105                 110

Ile Leu Gly Val Val Ala Thr Leu Ser Ile Phe Phe Leu Leu Cys Ser
        115                 120                 125

Val Leu Phe Gly Ala Ser Gln Ser Ser Pro Pro Ile Val Tyr Ile Lys
    130                 135                 140

Gly Val Asn Val Arg Ser Phe Tyr Tyr Gly Gly Ser Asp Asn Thr
145                 150                 155                 160

Gly Val Pro Thr Lys Ile Met Asn Val Lys Cys Ser Val Val Ile Thr
                165                 170                 175

Thr His Asn Pro Ser Thr Leu Phe Gly Ile His Val Ser Thr Ala
                180                 185                 190

Val Ser Leu Ile Tyr Ser Arg Gln Phe Thr Leu Ala Asn Ala Arg Leu
            195                 200                 205

Lys Ser Tyr His Gln Pro Lys Gln Ser Asn His Thr Ser Arg Ile Asn
    210                 215                 220

Leu Ile Gly Ser Lys Val Pro Leu Tyr Gly Ala Gly Ala Glu Leu Val
225                 230                 235                 240

Ala Ser Asp Asn Ser Gly Gly Val Pro Val His Thr Pro Asn Tyr Thr
                245                 250                 255

Ile Leu Ser Glu Ser Arg Leu Ser Ser Ser Arg Thr Ser Asn Gly
            260                 265                 270

Thr Ser Gly Met Gly Phe Arg Trp Lys Gly Ser Ser Arg Arg Ser Asn
        275                 280                 285

Met Tyr Trp Pro Glu Lys Pro Tyr Thr Ile Asn Glu Asp Glu Val Tyr
    290                 295                 300

Asp Asp Asn Arg Gly Leu Ser Val Gly Gln Cys Arg Ala Val Leu Val
305                 310                 315                 320

Ile Leu Gly Thr Val Val Phe Ser Val Phe Cys Ser Val Leu Trp
                325                 330                 335

Gly Ala Ser His Pro Phe Ser Pro Ile Val Ser Val Lys Ser Val Asp
            340                 345                 350

Ile His Ser Phe Tyr Tyr Gly Glu Gly Ile Asp Arg Thr Gly Val Ala
        355                 360                 365

Thr Lys Ile Leu Ser Phe Asn Ser Ser Val Lys Val Thr Ile Asp Ser
    370                 375                 380

Pro Ala Pro Tyr Phe Gly Ile His Val Ser Ser Ser Thr Phe Lys Leu
385                 390                 395                 400

Thr Phe Ser Ala Leu Thr Leu Ala Thr Gly Gln Leu Lys Ser Tyr Tyr
                405                 410                 415

Gln Pro Arg Lys Ser Lys His Ile Ser Ile Val Lys Leu Thr Gly Ala
            420                 425                 430

Glu Val Pro Leu Tyr Gly Ala Gly Pro His Leu Ala Ala Ser Asp Lys
        435                 440                 445

Lys Gly Lys Val Pro Val Lys Leu Glu Phe Glu Ile Arg Ser Arg Gly
    450                 455                 460

Asn Leu Leu Gly Lys Leu Val Lys Ser Lys His Glu Asn His Val Ser
465                 470                 475                 480

Cys Ser Phe Phe Ile Ser Ser Lys Thr Ser Lys Pro Ile Glu Phe
                485                 490                 495

Thr His Lys Thr Cys Lys Leu Val Thr Lys
            500                 505
```

<210> SEQ ID NO 25
<211> LENGTH: 1338
<212> TYPE: DNA
<213> ORGANISM: Arabidopsis thaliana

<400> SEQUENCE: 25

| | | | | | |
|---|---|---|---|---|---|
| atggattcgg | ttggagcgga | cagatcaggt | gatcttgtag | ccgttcaagt | gcttcctcct | 60 |
| tctttcgtcg | tgcttgttct | cgatgaaggt | tctcgagagg | ttaggcttca | ctccttgtac | 120 |
| ttgcttcaga | tcttttctga | ggtggcagat | gttatttcgg | gttggctgtg | ggcagccgta | 180 |
| gtaaatctct | cgcaggtgc | ttttgaggag | gagtttttct | tgccgctta | tgctcttagg | 240 |
| gaatcatggt | tttacttggt | tgtggccttg | tgggaaaaa | ctttaatcga | gcaaagtcag | 300 |
| aagtgtgtga | caatgtccaa | tgaggctccc | gaagtggaac | cacatagtaa | gaggaggaag | 360 |
| aaagaggcat | ctccgtcgtc | atcttcaggg | tttctacaat | cttttgccaga | agcggtggct | 420 |
| atgatttgct | tggcccgcgt | atcaagattg | gaccatgcag | ccttatctct | cgtctccaag | 480 |
| agctgccggt | caatggttct | tcacccgag | ctctaccaga | cacgatcgtt | gataggttac | 540 |
| gctgagaagt | tcctctactg | gcaccacgtg | acctccatga | gagtggctcg | tgtttcccct | 600 |
| gaagtcagtg | tagtggacgg | aaagataaac | gtgtggggag | gctgcaagta | caagcattac | 660 |
| tacgactggg | gagaagtgtt | cgatccaaag | acacaaactt | gggctgatat | gtcaattcca | 720 |
| aagccagtgc | gggaagaaaa | gatatacgtg | gtggattcat | gggatgttgg | aagctattac | 780 |
| tacttgccga | gcaagagtat | atgggaaaaa | gggaatcaag | attcaaagcg | tagcaaggat | 840 |
| tggtgtctaa | tagataagtt | gatatatagt | tgtggtaacg | atggaggtat | atattggtgt | 900 |
| gaggcagggg | agttggattg | tgtgacgca | gtagggatag | attggaggga | agtgtttggt | 960 |
| ttggagtttc | tgtcaaagga | gctccgtgaa | tcgagagtgg | tctactttgg | tgggaaaatg | 1020 |
| gtgaaagtgt | gggagtccta | caagatcatg | tacaatatta | gcttaaacct | tgaagaatta | 1080 |
| cttcccgaga | cccaattgac | caacttgacc | gaacttggtc | ataatgtttt | ggtcttttgg | 1140 |
| gaaaagctcg | aatgttgttg | tgatggtttt | aagatcttgg | agatttggtg | tgcggagatt | 1200 |
| tcgttggaaa | ggtgggaggg | aggcgagatt | ttggggaggt | gtgattggtg | ccatcctatc | 1260 |
| ctcgcaatca | atcttctcac | ggtcgatcct | ctcttctacc | actctatggt | cttgtattct | 1320 |
| atccctgttg | atgtttga | | | | | 1338 |

<210> SEQ ID NO 26
<211> LENGTH: 445
<212> TYPE: PRT
<213> ORGANISM: Arabidopsis thaliana

<400> SEQUENCE: 26

Met Asp Ser Val Gly Ala Asp Arg Ser Gly Asp Leu Val Ala Val Gln
1               5                   10                  15

Val Leu Pro Pro Ser Phe Val Val Leu Val Leu Asp Glu Gly Ser Arg
            20                  25                  30

Glu Val Arg Leu His Ser Leu Tyr Leu Leu Gln Ile Phe Ser Glu Val
        35                  40                  45

Ala Asp Val Ile Ser Gly Trp Leu Trp Ala Ala Val Val Asn Leu Phe
    50                  55                  60

Ala Gly Ala Phe Glu Glu Glu Phe Phe Phe Ala Ala Tyr Ala Leu Arg
65                  70                  75                  80

Glu Ser Trp Phe Tyr Leu Val Val Ala Leu Trp Gly Lys Thr Leu Ile
                85                  90                  95

Glu Gln Ser Gln Lys Cys Val Thr Met Ser Asn Glu Ala Pro Glu Val
            100                 105                 110

Glu Pro His Ser Lys Arg Arg Lys Glu Ala Ser Pro Ser Ser Ser
            115                 120                 125

Ser Gly Phe Leu Gln Ser Leu Pro Glu Ala Val Ala Met Ile Cys Leu
130                 135                 140

Ala Arg Val Ser Arg Leu Asp His Ala Ala Leu Ser Leu Val Ser Lys
145                 150                 155                 160

Ser Cys Arg Ser Met Val Leu Ser Pro Glu Leu Tyr Gln Thr Arg Ser
                165                 170                 175

Leu Ile Gly Tyr Ala Glu Lys Phe Leu Tyr Trp His His Val Thr Ser
            180                 185                 190

Met Arg Val Ala Arg Val Ser Pro Glu Val Ser Val Val Asp Gly Lys
            195                 200                 205

Ile Asn Val Trp Gly Gly Cys Lys Tyr Lys His Tyr Tyr Asp Trp Gly
210                 215                 220

Glu Val Phe Asp Pro Lys Thr Gln Thr Trp Ala Asp Met Ser Ile Pro
225                 230                 235                 240

Lys Pro Val Arg Glu Gly Lys Ile Tyr Val Val Asp Ser Trp Asp Val
                245                 250                 255

Gly Ser Tyr Tyr Tyr Leu Pro Ser Lys Ser Ile Trp Glu Lys Gly Asn
            260                 265                 270

Gln Asp Ser Lys Arg Ser Lys Asp Trp Cys Leu Ile Asp Lys Leu Ile
            275                 280                 285

Tyr Ser Cys Gly Asn Asp Gly Gly Ile Tyr Trp Cys Glu Ala Gly Glu
290                 295                 300

Leu Asp Trp Cys Asp Ala Val Gly Ile Asp Trp Arg Glu Val Phe Gly
305                 310                 315                 320

Leu Glu Phe Leu Ser Lys Glu Leu Arg Glu Ser Arg Val Val Tyr Phe
                325                 330                 335

Gly Gly Lys Met Val Lys Val Trp Glu Ser Tyr Lys Ile Met Tyr Asn
            340                 345                 350

Ile Ser Leu Asn Leu Glu Glu Leu Leu Pro Glu Thr Gln Leu Thr Asn
            355                 360                 365

Leu Thr Glu Leu Gly His Asn Val Leu Val Phe Trp Glu Lys Leu Glu
370                 375                 380

Cys Cys Cys Asp Gly Phe Lys Ile Leu Glu Ile Trp Cys Ala Glu Ile
385                 390                 395                 400

Ser Leu Glu Arg Trp Glu Gly Gly Glu Ile Leu Gly Arg Cys Asp Trp
                405                 410                 415

Cys His Pro Ile Leu Ala Ile Asn Leu Leu Thr Val Asp Pro Leu Phe
            420                 425                 430

Tyr His Ser Met Val Leu Tyr Ser Ile Pro Val Asp Val
            435                 440                 445

<210> SEQ ID NO 27
<211> LENGTH: 999
<212> TYPE: DNA
<213> ORGANISM: Arabidopsis thaliana

<400> SEQUENCE: 27
gggactagag gaaggaggga gagaaggagc ttaagagagc attcgtcgtc gtcaatggag     60
atcttctctg cgtctgcttc tctaacttta actggattcg ttcctcgtct tcttcccttg    120

```
ctctctcctc aagctcgaac tactctctgc aagccgttgc tgtcttcttc ttctactaga    180
ctcatttctt gtcacagtcg tatagctccg tctcggtctc tcgcagatca atccgcctct    240
actgggatca gtgttgttga ttcggatccc attgatgttg taaagaggaa agctatggac    300 atagccctg aactgaaagg agcttccata tttctggttg gaattaataa ctctattaaa     360
acgaacacgg ggaagctttt ggctgaggca ttacgatatt actactttga tagtgataat    420
ttgatcacag aggcggctgg tggaaatgtg tctgctcaag cttgaagga agctgatgag     480 aaggcttttc aagaatcaga gactgaagtg ctgaagcagc tatcatctat gggtcggctt    540
gtagtttgcg ctggagatgg tgcggtccaa agcttgagaa tcttgcact cttagacac     600 gggatctcca tatggatcga tgttcctctg gatatcactg ctaaagggga tgatgattca    660
ttccactcag aaccttcccc tgagttgttt gacacactaa aagcgagtta cgagaaatca    720
agaaagggtt acgaaacagc agatgtatcc atttcccttg aaaaaatagc tacaaagcta    780
gaatttgaag acttggaagc agtaacttct gaagacattg ctttggagat tctgaaagaa    840
atagagaagt tgacaagagt gaagaaaatg atggaagaag cttctcgacc tttctaggtc    900
gattttacac tctcattcat agtatgattt atgttgtata tcatctcgac attaatatag    960
ctttttttgc ataaaatcac tcatatgatt tttaatttc                           999
```

<210> SEQ ID NO 28
<211> LENGTH: 280
<212> TYPE: PRT
<213> ORGANISM: Arabidopsis thaliana

<400> SEQUENCE: 28

```
Met Glu Ile Phe Ser Ala Ser Ala Ser Leu Thr Leu Thr Gly Phe Val
1               5                   10                  15

Pro Arg Leu Leu Pro Leu Leu Ser Pro Gln Ala Arg Thr Thr Leu Cys
            20                  25                  30

Lys Pro Leu Leu Ser Ser Ser Ser Thr Arg Leu Ile Ser Cys His Ser
        35                  40                  45

Arg Ile Ala Pro Ser Arg Ser Leu Ala Asp Gln Ser Ala Ser Thr Gly
    50                  55                  60

Ile Ser Val Val Asp Ser Asp Pro Ile Asp Val Val Lys Arg Lys Ala
65                  70                  75                  80

Met Asp Ile Ala Pro Glu Leu Lys Gly Ala Ser Ile Phe Leu Val Gly
                85                  90                  95

Ile Asn Asn Ser Ile Lys Thr Asn Thr Gly Lys Leu Leu Ala Glu Ala
            100                 105                 110

Leu Arg Tyr Tyr Tyr Phe Asp Ser Asp Asn Leu Ile Thr Glu Ala Ala
        115                 120                 125

Gly Gly Asn Val Ser Ala Gln Ala Leu Lys Glu Asp Glu Lys Ala
    130                 135                 140

Phe Gln Glu Ser Glu Thr Glu Val Leu Lys Gln Leu Ser Ser Met Gly
145                 150                 155                 160

Arg Leu Val Val Cys Ala Gly Asp Gly Ala Val Gln Ser Leu Arg Asn
                165                 170                 175

Leu Ala Leu Leu Arg His Gly Ile Ser Ile Trp Ile Asp Val Pro Leu
            180                 185                 190

Asp Ile Thr Ala Lys Gly Asp Asp Ser Phe His Ser Glu Pro Ser
        195                 200                 205

Pro Glu Leu Phe Asp Thr Leu Lys Ala Ser Tyr Glu Lys Ser Arg Lys
    210                 215                 220
```

```
Gly Tyr Glu Thr Ala Asp Val Ser Ile Ser Leu Glu Lys Ile Ala Thr
225                 230                 235                 240

Lys Leu Glu Phe Glu Asp Leu Glu Ala Val Thr Ser Glu Asp Ile Ala
            245                 250                 255

Leu Glu Ile Leu Lys Glu Ile Gly Lys Leu Thr Arg Val Lys Lys Met
        260                 265                 270

Met Glu Glu Ala Ser Arg Pro Phe
        275                 280

<210> SEQ ID NO 29
<211> LENGTH: 2253
<212> TYPE: DNA
<213> ORGANISM: Arabidopsis thaliana

<400> SEQUENCE: 29
aaagaaactt tttttttttg gtcttcctta ttctttcttc aatgtcgttg aacatatctg      60
acgatacttg aatctcactc tttcttctct tctattctct gtttttagtc acaatttcat     120
ctatatctcc tctcactttt gttttgaga  attttcgatc ccaagctttt ctcagagaat     180
tttgactgga aatttcgtaa ttagggtttt tgatttgagg cattattcta cgatgaaagc     240
ttcgattgag aagttaagga gattaacatc gcattcacat aaggttgatg tgaaggagaa     300
aggagatgtc atggctacaa cacaaatcga cgaactcgat cgagccggga aggatatgca     360
agatatgaga gaatgttacg atagactact cgctgcagct gctgccacgg caaatagcgc     420
atatgagttc tctgagtcgt tgggagaaat gggttcttgt ttggagcaaa tcgcgcctca     480
taacgacgaa gagagcagta gaatcttgtt tatgttgggt aaagtacaga gtgagcttca     540
aagacttctt gacacatatc gtagtcatat attcgaaact attacatccc cgtccgaggc     600
gcttctcaag gacctcagat atgttgagga tatgaagcaa caatgcgacg ggaagaggaa     660
tgtgtatgag atgtcgctag tgaaagagaa aggaaggcct aaaagcagta aggagagag     720 acatattcct cctgagtctc gacctgctta cagtgagttt catgatgaag ccacaatgtg     780
catttttcga ttgaaatcgc ttaaagaagg acaagctcgt agtctcctaa tacaagcagt     840
ccgtcaccac actgctcaga tgcgtttgtt tcacactgga ctgaaatcgc tcgaggcagt     900
tgagcgtcat gtaaaagttg ctgtagagaa acaacacatt gactgtgatc tatctgttca     960
tgggaacgag atggaagcta gcgaggatga tgatgatgat ggccgataca tgaatagaga    1020
aggagaactc agttttgatt acagaacaaa tgagcagaag gtagaagctt cttctctctc    1080
tacaccatgg gccacaaaga tggatgatac agacctctcg tttcctcgcc cttctacaac    1140
aagaccagca gcggtaaatg ctgatcatag agaagaatat ccagtttcaa cccgcgataa    1200
gtatttgagc agccattcag ctccgttgtt cccagaaaag aaacctgatg tatcagagag    1260
gttgagacag gcgaatccat cttttaatgc ctacgtatta ccaacaccaa atgattcaag    1320
gtactcaaaa ccggtttccc aagcattaaa tccgaggcca acaaaccaca gtgccggaaa    1380
catatggcat tcatctccgt tagagccgat aaaaagcggg aaagatggga agacgccga    1440 aagcaacagc ttctacggcc gcctccctcg gccttctaca acagacacgc atcatcatca    1500
gcagcaagca gcaggaagac atgcattttc tggacctctc agaccgtcct caacaaaacc    1560
catcaccatg gctgacagtt attcaggcgc ttttttgtcct ctgccgactc ctccagtact    1620
ccaatctcac cctcattcat catcttctcc aagagtctcc cctaccgctt cacctcctcc    1680
tgcttcttcc ccaaggctca acgagcttca cgagcttcca agacccccag gccactttgc    1740
```

```
accacctcca agacgagcca agtccctgg tctggttggt cactcagcgc ctctaaccgc    1800
atggaaccaa gaaagaagca ctgtcactgt tgctgttccg tccgccacca acattgtggc    1860
ctcgccgctt ccggttcctc cgttggttgt ccctagaagc tactctatac cttcaagaaa    1920
ccagagagtt gtttctcaac ggctggtcga aggagagat gatatagtag catccccacc     1980
gttaacacca atgagcctgt ctaggccact tcctcaagcc acaggagttg ctcagaccag    2040
tcaaatcaga ggagtaggaa agctgatcga acgatgaggc ttccgcgtct gcgtcacgtt    2100
tgaccaaaac gctgattgta caaattcaga gatcttcaca agtgaatata gaagtcagta    2160
tatgtattat tctttagttg gttaatctcc tttttttttt cccattgtaa atctgaagcc    2220
tctgctcttt attcccttt cattttcaat ccc                                 2253
```

<210> SEQ ID NO 30
<211> LENGTH: 614
<212> TYPE: PRT
<213> ORGANISM: Arabidopsis thaliana

<400> SEQUENCE: 30

```
Met Lys Ala Ser Ile Glu Lys Leu Arg Arg Leu Thr Ser His Ser His
1               5                   10                  15

Lys Val Asp Val Lys Glu Lys Gly Asp Val Met Ala Thr Thr Gln Ile
                20                  25                  30

Asp Glu Leu Asp Arg Ala Gly Lys Asp Met Gln Asp Met Arg Glu Cys
            35                  40                  45

Tyr Asp Arg Leu Leu Ala Ala Ala Ala Thr Ala Asn Ser Ala Tyr
        50                  55                  60

Glu Phe Ser Glu Ser Leu Gly Glu Met Gly Ser Cys Leu Glu Gln Ile
65                  70                  75                  80

Ala Pro His Asn Asp Glu Glu Ser Ser Arg Ile Leu Phe Met Leu Gly
                85                  90                  95

Lys Val Gln Ser Glu Leu Gln Arg Leu Leu Asp Thr Tyr Arg Ser His
                100                 105                 110

Ile Phe Glu Thr Ile Thr Ser Pro Ser Glu Ala Leu Leu Lys Asp Leu
            115                 120                 125

Arg Tyr Val Glu Asp Met Lys Gln Gln Cys Asp Gly Lys Arg Asn Val
        130                 135                 140

Tyr Glu Met Ser Leu Val Lys Glu Lys Gly Arg Pro Lys Ser Ser Lys
145                 150                 155                 160

Gly Glu Arg His Ile Pro Pro Glu Ser Arg Pro Ala Tyr Ser Glu Phe
                165                 170                 175

His Asp Glu Ala Thr Met Cys Ile Phe Arg Leu Lys Ser Leu Lys Glu
                180                 185                 190

Gly Gln Ala Arg Ser Leu Leu Ile Gln Ala Val Arg His His Thr Ala
        195                 200                 205

Gln Met Arg Leu Phe His Thr Gly Leu Lys Ser Leu Glu Ala Val Glu
    210                 215                 220

Arg His Val Lys Val Ala Val Glu Lys Gln His Ile Asp Cys Asp Leu
225                 230                 235                 240

Ser Val His Gly Asn Glu Met Glu Ala Ser Glu Asp Asp Asp Asp
                245                 250                 255

Gly Arg Tyr Met Asn Arg Glu Gly Glu Leu Ser Phe Asp Tyr Arg Thr
            260                 265                 270

Asn Glu Gln Lys Val Glu Ala Ser Ser Leu Ser Thr Pro Trp Ala Thr
        275                 280                 285
```

Lys Met Asp Asp Thr Asp Leu Ser Phe Pro Arg Pro Ser Thr Thr Arg
        290                 295                 300
Pro Ala Ala Val Asn Ala Asp His Arg Glu Glu Tyr Pro Val Ser Thr
305                 310                 315                 320
Arg Asp Lys Tyr Leu Ser Ser His Ser Ala Pro Leu Phe Pro Glu Lys
                325                 330                 335
Lys Pro Asp Val Ser Glu Arg Leu Arg Gln Ala Asn Pro Ser Phe Asn
            340                 345                 350
Ala Tyr Val Leu Pro Thr Pro Asn Asp Ser Arg Tyr Ser Lys Pro Val
        355                 360                 365
Ser Gln Ala Leu Asn Pro Arg Pro Thr Asn His Ser Ala Gly Asn Ile
370                 375                 380
Trp His Ser Ser Pro Leu Glu Pro Ile Lys Ser Gly Lys Asp Gly Lys
385                 390                 395                 400
Asp Ala Glu Ser Asn Ser Phe Tyr Gly Arg Leu Pro Arg Pro Ser Thr
                405                 410                 415
Thr Asp Thr His His His Gln Gln Gln Ala Ala Gly Arg His Ala Phe
            420                 425                 430
Ser Gly Pro Leu Arg Pro Ser Ser Thr Lys Pro Ile Thr Met Ala Asp
        435                 440                 445
Ser Tyr Ser Gly Ala Phe Cys Pro Leu Pro Thr Pro Val Leu Gln
450                 455                 460
Ser His Pro His Ser Ser Ser Pro Arg Val Ser Pro Thr Ala Ser
465                 470                 475                 480
Pro Pro Pro Ala Ser Ser Pro Arg Leu Asn Glu Leu His Glu Leu Pro
                485                 490                 495
Arg Pro Pro Gly His Phe Ala Pro Pro Arg Arg Ala Lys Ser Pro
            500                 505                 510
Gly Leu Val Gly His Ser Ala Pro Leu Thr Ala Trp Asn Gln Glu Arg
        515                 520                 525
Ser Thr Val Thr Val Ala Val Pro Ser Ala Thr Asn Ile Val Ala Ser
530                 535                 540
Pro Leu Pro Val Pro Pro Leu Val Val Pro Arg Ser Tyr Ser Ile Pro
545                 550                 555                 560
Ser Arg Asn Gln Arg Val Val Ser Gln Arg Leu Val Glu Arg Asp
                565                 570                 575
Asp Ile Val Ala Ser Pro Pro Leu Thr Pro Met Ser Leu Ser Arg Pro
            580                 585                 590
Leu Pro Gln Ala Thr Gly Val Ala Gln Thr Ser Gln Ile Arg Gly Val
        595                 600                 605
Gly Lys Leu Ile Glu Arg
    610

<210> SEQ ID NO 31
<211> LENGTH: 2215
<212> TYPE: DNA
<213> ORGANISM: Arabidopsis thaliana

<400> SEQUENCE: 31
aaactttttt ttttggtct tccttattct ttcttcaatg tcgttgaaca tatctgacga    60
tacttgaatc tcactctttc ttctcttcta ttctctgttt ttagtcacaa tttcatctat   120
atctcctctc acttttgttt ttgagaattt tcgatcccaa gctttctca gagaattttg    180 actggaaatt tcgtaattag ggttttgat ttgaggcatt attctacgat gaaagcttcg    240

```
attgagaagt taaggagatt aacatcgcat tcacataagg ttgatgtgaa ggagaaagga      300
gatgtcatgg ctacaacaca aatcgacgaa ctcgatcgag ccgggaagga tatgcaagat      360
atgagagaat gttacgatag actactcgct gcagctgctg ccacggcaaa tagcgcatat      420
gagttctctg agtcgttggg agaaatgggt tcttgtttgg agcaaatcgc gcctcataac      480
gacgaagaga gcagtagaat cttgtttatg ttgggtaaag tacagagtga gcttcaaaga      540
cttcttgaca catatcgtag tcatatattc gaaactatta catccccgtc cgaggcgctt      600
ctcaaggacc tcagatatgt tgaggatatg aagcaacaat gcgacgggaa gaggaatgtg      660
tatgagatgt cgctagtgaa agagaaagga aggcctaaaa gcagtaaagg agagagacat      720
attcctcctg agtctcgacc tgcttacagt gagtttcatg atgaagccac aatgtgcatt      780
tttcgattga aatcgcttaa agaaggacaa gctcgtagtc tcctaataca agcagtccgt      840
caccacactg ctcagatgcg tttgtttcac actggactga aatcgctcga ggcagttgag      900
cgtcatgtaa aagttgctgt agagaaacaa cacattgact gtgatctatc tgttcatggg      960
aacgagatgg aagctagcga ggatgatgat gatgatggcc gatacatgaa tagagaagga     1020
gaactcagtt ttgattacag aacaaatgag cagaaggtag aagcttcttc tctctctaca     1080
ccatgggcca caaagatgga tgatacagac ctctcgtttc ctcgcccttc tacaacaaga     1140
ccagcagcgg taaatgctga tcatagagaa gaatatccag tttcaacccg cgataagtat     1200
ttgagcagcc attcagctcc gttgttccca gaaaagaaac ctgatgtatc agagaggttg     1260
agacaggcga atccatcttt taatgcctac gtattaccaa caccaaatga ttcaaggtac     1320
tcaaaaccgg tttcccaagc attaaatccg aggccaacaa accacagtgc cggaaacata     1380
tggcattcat ctccgttaga gccgataaaa agcgggaaag atgggaaaga cgccgaaagc     1440
aacagcttct acggccgcct ccctcggcct tctacaacag acacgcatca tcatcagcag     1500
caagcagcag gaagacatgc atttctgga cctctcagac cgtcctcaac aaaacccatc     1560
accatggctg acagttattc aggcgctttt tgtcctctgc cgactcctcc agtactccaa     1620
tctcaccctc attcatcatc ttctccaaga gtctccccta ccgcttcacc tcctcctgct     1680
tcttccccaa ggctcaacga gcttcacgag cttccaagac ccccaggcca ctttgcacca     1740
cctccaagac gagccaagtc ccctggtctg gttggtcact cagcgcctct aaccgcatgg     1800
aaccaagaaa gaagcactgt cactgttgct gttccgtccg ccaccaacat gtggcctcg     1860
ccgcttccgg ttcctccgtt ggttgtccct agaagctact ctataccttc aagaaaccag     1920
agagttgttt ctcaacggct ggtcgaaagg agagatgata tagtagcatc cccaccgtta     1980
acaccaatga gcctgtctag gccacttcct caagccacag gagttgctca gaccagtcaa     2040
atcagaggtt attaatcatg caggagtagg aaagctgatc gaacgatgag gcttccgcgt     2100
ctgcgtcacg tttgaccaaa acgctgattg tacaaattca gagatcttca caagtgaata     2160
tagaagtcag tatatgtatt attctttagt tggttaatct ccttttttt ttccc           2215
```

<210> SEQ ID NO 32
<211> LENGTH: 608
<212> TYPE: PRT
<213> ORGANISM: Arabidopsis thaliana

<400> SEQUENCE: 32

Met Lys Ala Ser Ile Glu Lys Leu Arg Arg Leu Thr Ser His Ser His
1               5                   10                  15

Lys Val Asp Val Lys Glu Lys Gly Asp Val Met Ala Thr Thr Gln Ile

-continued

```
                20                  25                  30
Asp Glu Leu Asp Arg Ala Gly Lys Asp Met Gln Asp Met Arg Glu Cys
                35                  40                  45

Tyr Asp Arg Leu Leu Ala Ala Ala Ala Thr Ala Asn Ser Ala Tyr
 50                  55                  60

Glu Phe Ser Glu Ser Leu Gly Glu Met Gly Ser Cys Leu Glu Gln Ile
 65                  70                  75                  80

Ala Pro His Asn Asp Glu Glu Ser Ser Arg Ile Leu Phe Met Leu Gly
                85                  90                  95

Lys Val Gln Ser Glu Leu Gln Arg Leu Leu Asp Thr Tyr Arg Ser His
                100                 105                 110

Ile Phe Glu Thr Ile Thr Ser Pro Ser Glu Ala Leu Leu Lys Asp Leu
                115                 120                 125

Arg Tyr Val Glu Asp Met Lys Gln Gln Cys Asp Gly Lys Arg Asn Val
                130                 135                 140

Tyr Glu Met Ser Leu Val Lys Glu Lys Gly Arg Pro Lys Ser Ser Lys
145                 150                 155                 160

Gly Glu Arg His Ile Pro Pro Glu Ser Arg Pro Ala Tyr Ser Glu Phe
                165                 170                 175

His Asp Glu Ala Thr Met Cys Ile Phe Arg Leu Lys Ser Leu Lys Glu
                180                 185                 190

Gly Gln Ala Arg Ser Leu Leu Ile Gln Ala Val Arg His His Thr Ala
                195                 200                 205

Gln Met Arg Leu Phe His Thr Gly Leu Lys Ser Leu Glu Ala Val Glu
                210                 215                 220

Arg His Val Lys Val Ala Val Glu Lys Gln His Ile Asp Cys Asp Leu
225                 230                 235                 240

Ser Val His Gly Asn Glu Met Glu Ala Ser Glu Asp Asp Asp Asp
                245                 250                 255

Gly Arg Tyr Met Asn Arg Glu Gly Glu Leu Ser Phe Asp Tyr Arg Thr
                260                 265                 270

Asn Glu Gln Lys Val Glu Ala Ser Ser Leu Ser Thr Pro Trp Ala Thr
                275                 280                 285

Lys Met Asp Asp Thr Asp Leu Ser Phe Pro Arg Pro Ser Thr Thr Arg
                290                 295                 300

Pro Ala Ala Val Asn Ala Asp His Arg Glu Glu Tyr Pro Val Ser Thr
305                 310                 315                 320

Arg Asp Lys Tyr Leu Ser Ser His Ser Ala Pro Leu Phe Pro Glu Lys
                325                 330                 335

Lys Pro Asp Val Ser Glu Arg Leu Arg Gln Ala Asn Pro Ser Phe Asn
                340                 345                 350

Ala Tyr Val Leu Pro Thr Pro Asn Asp Ser Arg Tyr Ser Lys Pro Val
                355                 360                 365

Ser Gln Ala Leu Asn Pro Arg Pro Thr Asn His Ser Ala Gly Asn Ile
                370                 375                 380

Trp His Ser Ser Pro Leu Glu Pro Ile Lys Ser Gly Lys Asp Gly Lys
385                 390                 395                 400

Asp Ala Glu Ser Asn Ser Phe Tyr Gly Arg Leu Pro Arg Pro Ser Thr
                405                 410                 415

Thr Asp Thr His His His Gln Gln Gln Ala Ala Gly Arg His Ala Phe
                420                 425                 430

Ser Gly Pro Leu Arg Pro Ser Ser Thr Lys Pro Ile Thr Met Ala Asp
                435                 440                 445
```

```
Ser Tyr Ser Gly Ala Phe Cys Pro Leu Pro Thr Pro Pro Val Leu Gln
    450                 455                 460

Ser His Pro His Ser Ser Ser Pro Arg Val Ser Pro Thr Ala Ser
465                 470                 475                 480

Pro Pro Pro Ala Ser Ser Pro Arg Leu Asn Glu Leu His Glu Leu Pro
                485                 490                 495

Arg Pro Pro Gly His Phe Ala Pro Pro Arg Arg Ala Lys Ser Pro
                500                 505                 510

Gly Leu Val Gly His Ser Ala Pro Leu Thr Ala Trp Asn Gln Glu Arg
            515                 520                 525

Ser Thr Val Thr Val Ala Val Pro Ser Ala Thr Asn Ile Val Ala Ser
    530                 535                 540

Pro Leu Pro Val Pro Pro Leu Val Val Pro Arg Ser Tyr Ser Ile Pro
545                 550                 555                 560

Ser Arg Asn Gln Arg Val Val Ser Gln Arg Leu Val Glu Arg Arg Asp
                565                 570                 575

Asp Ile Val Ala Ser Pro Pro Leu Thr Pro Met Ser Leu Ser Arg Pro
                580                 585                 590

Leu Pro Gln Ala Thr Gly Val Ala Gln Thr Ser Gln Ile Arg Gly Tyr
            595                 600                 605

<210> SEQ ID NO 33
<211> LENGTH: 2075
<212> TYPE: DNA
<213> ORGANISM: Arabidopsis thaliana

<400> SEQUENCE: 33
atgaaaacct ctctccgacg gttacgaggt gtgcttcaca agcatgaatc taaagaccgg      60
agagatcttc gagctctggt tcagaaagat gagcttgccc aagcttctca ggacgtagaa     120
gacatgagag attgctatga tagcttgctc aatgccgctg ctgctactgc caatagtgct     180
tatgaatttt ctgaatcttt gcgagaacta ggtgcttgtc ttcttgagaa aactgcgcta     240
aatgatgatg aagaaagtgg tagagtgttg attatgctgg gaaagttgca gtttgaattg     300
caaaaacttg ttgataaata tcgttctcat atttttcaaa caatcacaat ccctcagag     360 tcacttctaa atgaactccg catagttgag gagatgcagc ggctttgtga tgagaaaagg     420
aatgtttatg aaggcatgct acaagacaa agagagaaag ggagatcaaa gggtgggaaa     480
ggagaaactt tttcgccaca gcaactacaa gaagctcatg atgattatga aaacgagacg     540
actttatttg ttttccgttt aaaatccctg aaacaagggc aaacacgtag tcttttgact     600
caggcagcaa ggcaccatgc agcacagtta tgcttcttca agaaggctct tagttccctt     660
gaagaagtgg acccacatgt acagatggta accgagtcac agcatattga ttaccatttc     720
agcggattag aagatgatga cggggatgat gaaattgaaa acaatgagaa cgatggttct     780
gaggtgcatg atgatggaga gttgagtttt gaatatagag ttaatgacaa ggaccaagat     840
gcggattctt cagctggtgg ctcctcagag ttgggtaact cagacatcac atttccacaa     900
attggaggac catatactgc acaggaaaat gaggaaggaa attacagaaa atctcattcg     960
tttaggagag atgtaagggc agtgagccaa tcagcaccac tttttcccga gaaccgcaca    1020
actcctcctt cagaaaagct gttacggatg cgatcaactc tgacacggaa attcaacact    1080
tatgcattgc caactcctgt ggaaacaaca agaagtccct catctactac aagtccaggt    1140
cacaaaaacg tggggtcatc taatcctaca aaggcaatta caaagcagat ttggtattca    1200
```

```
tccccacttg aaactcgcgg acctgcaaag gtttcctcaa gatcaatggt agccttgaaa      1260
gaacaagtcc tgagagagag taacaagaat acatctcggt tgcctccgcc tttagcagat      1320
ggactcttgt tctctcgtct cggtacactc aagagacgat ccttctctgg tccactgaca      1380
agtaaaccgt taccgaacaa gcctctctct acaacatctc acttatactc tggtccgatc      1440
ccaaggaatc cagtttctaa attgccaaaa gtgtcatcat ctccaactgc ttcccctaca      1500
tttgtctcaa ccccaaaaat aagtgagctc catgagcttc ctagaccacc accaagaagc      1560
tctactaagt cctctaggga attgggatat tcagctccct tggtttcgag gagccaattg      1620
cttagtaaac ctcttattac aaattcagct tctcctcttc ctataccacc tgcaatcact      1680
cgtagcttct ctatacctac tagcaacctt agagcatcag atttagatat gtctaagaca      1740
agtctgggca ctaaaaagtt aggcactccc tcgcctcctt aaccccaat gtcattgatc       1800
catccaccgc cacaggctct tcccgaacgt gcagaccacc taatgatgtc caaacaagag      1860
aggaggattt aagatgtaag gtgtaagacg tttgtagctg cctaaaaact gtaggaggaa      1920
ggcattccct atagttgcag atatatgtaa atatcctcca atttttagtc tcatggatga      1980
tcttagttgt atattacata tagtagttga tccctttga gaatgatgac aaaaatagag       2040
gcaaacagag ttaataataa ttgcctgagg aattt                                 2075
```

```
<210> SEQ ID NO 34
<211> LENGTH: 623
<212> TYPE: PRT
<213> ORGANISM: Arabidopsis thaliana

<400> SEQUENCE: 34

Met Lys Thr Ser Leu Arg Arg Leu Arg Gly Val Leu His Lys His Glu
1               5                   10                  15

Ser Lys Asp Arg Arg Asp Leu Arg Ala Leu Val Gln Lys Asp Glu Leu
            20                  25                  30

Ala Gln Ala Ser Gln Asp Val Glu Asp Met Arg Asp Cys Tyr Asp Ser
        35                  40                  45

Leu Leu Asn Ala Ala Ala Ala Thr Ala Asn Ser Ala Tyr Glu Phe Ser
    50                  55                  60

Glu Ser Leu Arg Glu Leu Gly Ala Cys Leu Leu Glu Lys Thr Ala Leu
65                  70                  75                  80

Asn Asp Asp Glu Glu Ser Gly Arg Val Leu Ile Met Leu Gly Lys Leu
                85                  90                  95

Gln Phe Glu Leu Gln Lys Leu Val Asp Lys Tyr Arg Ser His Ile Phe
            100                 105                 110

Gln Thr Ile Thr Ile Pro Ser Glu Ser Leu Leu Asn Glu Leu Arg Ile
        115                 120                 125

Val Glu Glu Met Gln Arg Leu Cys Asp Glu Lys Arg Asn Val Tyr Glu
    130                 135                 140

Gly Met Leu Thr Arg Gln Arg Glu Lys Gly Arg Ser Lys Gly Gly Lys
145                 150                 155                 160

Gly Glu Thr Phe Ser Pro Gln Gln Leu Gln Glu Ala His Asp Asp Tyr
                165                 170                 175

Glu Asn Glu Thr Thr Leu Phe Val Phe Arg Leu Lys Ser Leu Lys Gln
            180                 185                 190

Gly Gln Thr Arg Ser Leu Leu Thr Gln Ala Ala Arg His His Ala Ala
        195                 200                 205

Gln Leu Cys Phe Phe Lys Lys Ala Leu Ser Ser Leu Glu Glu Val Asp
    210                 215                 220
```

Pro His Val Gln Met Val Thr Glu Ser Gln His Ile Asp Tyr His Phe
225                 230                 235                 240

Ser Gly Leu Glu Asp Asp Gly Asp Asp Glu Ile Glu Asn Asn Glu
            245                 250                 255

Asn Asp Gly Ser Glu Val His Asp Asp Gly Glu Leu Ser Phe Glu Tyr
            260                 265                 270

Arg Val Asn Asp Lys Asp Gln Asp Ala Asp Ser Ser Ala Gly Gly Ser
            275                 280                 285

Ser Glu Leu Gly Asn Ser Asp Ile Thr Phe Pro Gln Ile Gly Gly Pro
            290                 295                 300

Tyr Thr Ala Gln Glu Asn Glu Glu Gly Asn Tyr Arg Lys Ser His Ser
305                 310                 315                 320

Phe Arg Arg Asp Val Arg Ala Val Ser Gln Ser Ala Pro Leu Phe Pro
                325                 330                 335

Glu Asn Arg Thr Thr Pro Pro Ser Glu Lys Leu Leu Arg Met Arg Ser
            340                 345                 350

Thr Leu Thr Arg Lys Phe Asn Thr Tyr Ala Leu Pro Thr Pro Val Glu
            355                 360                 365

Thr Thr Arg Ser Pro Ser Ser Thr Thr Ser Pro Gly His Lys Asn Val
370                 375                 380

Gly Ser Ser Asn Pro Thr Lys Ala Ile Thr Lys Gln Ile Trp Tyr Ser
385                 390                 395                 400

Ser Pro Leu Glu Thr Arg Gly Pro Ala Lys Val Ser Arg Ser Met
            405                 410                 415

Val Ala Leu Lys Glu Gln Val Leu Arg Glu Ser Asn Lys Asn Thr Ser
            420                 425                 430

Arg Leu Pro Pro Pro Leu Ala Asp Gly Leu Leu Phe Ser Arg Leu Gly
            435                 440                 445

Thr Leu Lys Arg Arg Ser Phe Ser Gly Pro Leu Thr Ser Lys Pro Leu
            450                 455                 460

Pro Asn Lys Pro Leu Ser Thr Thr Ser His Leu Tyr Ser Gly Pro Ile
465                 470                 475                 480

Pro Arg Asn Pro Val Ser Lys Leu Pro Lys Val Ser Ser Ser Pro Thr
                485                 490                 495

Ala Ser Pro Thr Phe Val Ser Thr Pro Lys Ile Ser Glu Leu His Glu
            500                 505                 510

Leu Pro Arg Pro Pro Arg Ser Ser Thr Lys Ser Ser Arg Glu Leu
            515                 520                 525

Gly Tyr Ser Ala Pro Leu Val Ser Arg Ser Gln Leu Leu Ser Lys Pro
            530                 535                 540

Leu Ile Thr Asn Ser Ala Ser Pro Leu Pro Ile Pro Pro Ala Ile Thr
545                 550                 555                 560

Arg Ser Phe Ser Ile Pro Thr Ser Asn Leu Arg Ala Ser Asp Leu Asp
                565                 570                 575

Met Ser Lys Thr Ser Leu Gly Thr Lys Lys Leu Gly Thr Pro Ser Pro
            580                 585                 590

Pro Leu Thr Pro Met Ser Leu Ile His Pro Pro Gln Ala Leu Pro
            595                 600                 605

Glu Arg Ala Asp His Leu Met Met Ser Lys Gln Glu Arg Arg Ile
610                 615                 620

<210> SEQ ID NO 35
<211> LENGTH: 1760

<212> TYPE: DNA
<213> ORGANISM: Arabidopsis thaliana

<400> SEQUENCE: 35

```
ataatgtcag caagtgtttg ttttcacatc aagctccgtt tctacagagt ttgcatctca      60
atatgaactt tgggtgtgac cctcgtataa tggattttga gatattgatt ggaattgcgt     120
ttggacgcca actgcgtaag ttggtactca agtttactc tggggattgg ttcaaatttc     180
ctacaagttt gtataactcc gaaactctag agaccttgga actctaccat tgcattctta     240
tagatgtccc ttttccggtt tgtctcaagt cccttagaac tctaaacctt cacgaagtgg     300
agtttgtaaa cgatgaatca gttgttaacc ttttagctgg ttgtattagc ctggaaaatt     360
tggtgattca tcaaactaca gatcttaatg tgaagacttt tactattgcg gtaccatcct     420
tgcagaggtt aacagttatt gttgagtatt atgaagagtt ttctgtcttt gtggtaaata     480
ctccatcttt gaaatacttg aagattgaag gtattattgt agatgatagg acttgtataa     540
ttgagaatac acctgagctg gtggaggcaa gtattattga tgtgtctttt aaagtctttg     600
agagcattct tggatccctt gcttcagtcc aacgtctttc cttgaaggtt tcactcgtgg     660
agtctcagga acagaggcct tgggagaaat ggaatgaacc gaagaatgtt cctgaatgtt     720
tgttgctcca cctcgaaaca tttgtgtgga catgttatga agggaaacta gaaaatgaga     780
tagagctggc gaaatatatc ctaaggaacg ctaggcgttt gaaaaaggca actttctcca     840
taattgaaat taatccggac aagagagttg agatggttga caggatcagt gacttgcccg     900
aagctctgct tctgcagata ttgtctatgc ttccagtaaa agatgttgtt accactagtg     960
ttttgtctaa accatggagg tctctctgga agttggtacc tacactcaag tttgattatg    1020
aaaacaatca agtgaagat gagacatact cagagattgt ttgcaggctt ttgcttttcca    1080
ataaagctcc ttttcttgag agtttgcatc tcggattcag gtttggcgaa tgtcgttcgg    1140
tggaagttgg aatgtggatt ggaattgcat acgcacgcca tgtgcgtgat ttggtactcc    1200
atgttgaatc tgtgaaaggg tctttcatat ttcctacagg cttgtataac tgtgaaacac    1260
tagagagctt gacactgagg agttgggtac tcgttgatgt cccttctccg gcttgtctca    1320
agtctcttag aactctgcgt cttgagaatg tggattacaa atacgatgat tcggtttata    1380
acctttatc tggctgccct aatcttgaaa atttggttgt gtatcgagga aatctactgg    1440
aagtggagac tttcactatt gcagtgccat ctttacagag actaacaatt tatgatgaca    1500
atgatggaga atactgtacg ggctatgtga taaatgctcc ttcattgaag tacttgaaga    1560
ttgatgggtt taaggctctc gagtcttgtc tgattgagaa cgcaccggag ttggtggagg    1620
caactattat gaatgtctct aagataatca atgagaagct tttggaaacc ctcacttcag    1680
tcaaacgtct ttccttggct ttatcaccct tggagttaaa gttttcttgc ataattatt    1740
cgggtcactt gttgttatga                                                1760
```

<210> SEQ ID NO 36
<211> LENGTH: 565
<212> TYPE: PRT
<213> ORGANISM: Arabidopsis thaliana

<400> SEQUENCE: 36

```
Met Asn Phe Gly Cys Asp Pro Arg Ile Met Asp Phe Glu Ile Leu Ile
1               5                   10                  15

Gly Ile Ala Phe Gly Arg Gln Leu Arg Lys Leu Val Leu Lys Val Tyr
            20                  25                  30
```

```
Ser Gly Asp Trp Phe Lys Phe Pro Thr Ser Leu Tyr Asn Ser Glu Thr
         35                  40                  45

Leu Glu Thr Leu Glu Leu Tyr His Cys Ile Leu Ile Asp Val Pro Phe
 50                  55                  60

Pro Val Cys Leu Lys Ser Leu Arg Thr Leu Asn Leu His Glu Val Glu
 65                  70                  75                  80

Phe Val Asn Asp Glu Ser Val Val Asn Leu Leu Ala Gly Cys Ile Ser
                 85                  90                  95

Leu Glu Asn Leu Val Ile His Gln Thr Thr Asp Leu Asn Val Lys Thr
            100                 105                 110

Phe Thr Ile Ala Val Pro Ser Leu Gln Arg Leu Thr Val Ile Val Glu
            115                 120                 125

Tyr Tyr Glu Glu Phe Ser Val Phe Val Val Asn Thr Pro Ser Leu Lys
130                 135                 140

Tyr Leu Lys Ile Glu Gly Ile Ile Val Asp Asp Arg Thr Cys Ile Ile
145                 150                 155                 160

Glu Asn Thr Pro Glu Leu Val Glu Ala Ser Ile Ile Asp Val Ser Phe
                165                 170                 175

Lys Val Phe Glu Ser Ile Leu Gly Ser Leu Ala Ser Val Gln Arg Leu
            180                 185                 190

Ser Leu Lys Val Ser Leu Val Glu Ser Gln Glu Gln Arg Pro Trp Glu
            195                 200                 205

Lys Trp Asn Glu Pro Lys Asn Val Pro Glu Cys Leu Leu His Leu
            210                 215                 220

Glu Thr Phe Val Trp Thr Cys Tyr Glu Gly Lys Leu Glu Asn Glu Ile
225                 230                 235                 240

Glu Leu Ala Lys Tyr Ile Leu Arg Asn Ala Arg Arg Leu Lys Lys Ala
                245                 250                 255

Thr Phe Ser Ile Ile Glu Ile Asn Pro Asp Lys Arg Val Glu Met Val
            260                 265                 270

Asp Arg Ile Ser Asp Leu Pro Glu Ala Leu Leu Leu Gln Ile Leu Ser
            275                 280                 285

Met Leu Pro Val Lys Asp Val Val Thr Thr Ser Val Leu Ser Lys Pro
290                 295                 300

Trp Arg Ser Leu Trp Lys Leu Val Pro Thr Leu Lys Phe Asp Tyr Glu
305                 310                 315                 320

Asn Asn Gln Ser Glu Asp Glu Thr Tyr Ser Glu Ile Val Cys Arg Leu
                325                 330                 335

Leu Leu Ser Asn Lys Ala Pro Phe Leu Glu Ser Leu His Leu Gly Phe
            340                 345                 350

Arg Phe Gly Glu Cys Arg Ser Val Glu Val Gly Met Trp Ile Gly Ile
            355                 360                 365

Ala Tyr Ala Arg His Val Arg Asp Leu Val Leu His Val Glu Ser Val
370                 375                 380

Lys Gly Ser Phe Ile Phe Pro Thr Gly Leu Tyr Asn Cys Glu Thr Leu
385                 390                 395                 400

Glu Ser Leu Thr Leu Arg Ser Trp Val Leu Val Asp Val Pro Ser Pro
                405                 410                 415

Ala Cys Leu Lys Ser Leu Arg Thr Leu Arg Leu Glu Asn Val Asp Tyr
            420                 425                 430

Lys Tyr Asp Asp Ser Val Tyr Asn Leu Leu Ser Gly Cys Pro Asn Leu
            435                 440                 445

Glu Asn Leu Val Val Tyr Arg Gly Asn Leu Leu Glu Val Glu Thr Phe
```

```
                450             455             460
Thr Ile Ala Val Pro Ser Leu Gln Arg Leu Thr Ile Tyr Asp Asp Asn
465                 470                 475                 480

Asp Gly Glu Tyr Cys Thr Gly Tyr Val Ile Asn Ala Pro Ser Leu Lys
                485                 490                 495

Tyr Leu Lys Ile Asp Gly Phe Lys Ala Leu Glu Ser Cys Leu Ile Glu
            500                 505                 510

Asn Ala Pro Glu Leu Val Glu Ala Thr Ile Met Asn Val Ser Lys Ile
        515                 520                 525

Ile Asn Glu Lys Leu Leu Glu Thr Leu Thr Ser Val Lys Arg Leu Ser
    530                 535                 540

Leu Ala Leu Ser Pro Leu Glu Leu Lys Phe Ser Cys Asn Asn Tyr Ser
545                 550                 555                 560

Gly His Leu Leu Leu
            565

<210> SEQ ID NO 37
<211> LENGTH: 1230
<212> TYPE: DNA
<213> ORGANISM: Arabidopsis thaliana

<400> SEQUENCE: 37
atgagtgtct tgtctaaacg atggaggtct ctttggaaga tgttgcctcg gcttaagttt      60
gatgattgga tgtttcctga taatgtcaac aggtgtttgc tttcacatca agcttcgttt     120
ctacagagtt tgcatcttgt aatagattat gattttgtgt ctcatatgca tactgggata     180
ttgatgggaa ttgcgtttgg acgccatata cgtgagctgg tactctatgt taatggcttt     240
caagagtcct ttacatttcc tttaagcttg tgtaactgcg aatcactaga gacattgaca     300
ctcggtcata acgttcttat agatgtccct tctccggttt ttttgaagtc tcttagaact     360
ctacacctag atggggttga gtacacagac gatgaatcag ttgttaacct tttatctggt     420
tgtattagcc tggaaaattt ggtggtccat cgagttatac aagctgatgt gacaactttc     480
actattgcgg tgccatcctt gaagaggcta acacttacta ctgaatttga tgatgatgaa     540
gactcagtct atgtgataaa tgctccttct ttgaaatact tgaagatttt aggtgacaag     600
gcttatctga ttgagaattc acctgagttg gtggaggtaa gtctgacaga taggcaagtt     660
actgtggatg gttatcccat cgcttcatac gttgagaacc ttcttagatc tcttacttca     720
gtcaaacgca tgtctttgaa gatatcatca tacttagaga ttaagtttcc aactggtagc     780
atcttctatc agttggtatc tttggagcta tatacaaata aagcagagtg gtggaatctg     840
cttgtgttga tgctcgatag ttctcctaaa ttgcaagtcc tcaagctcaa cggtaaattg     900
tctggtgaaa caatcatttt agccagtatg aattgggatc aaccaaagaa tattcctgga     960
tgtttgttgt ttaatctcga cattcatt tggaaaggct gcaaaggat aggagaagat    1020 gaaaaagagg tggcgaaata catcctaagg aacacaaatc gtttgaagag gcgactttc    1080 accagagaaa tctatgaaga gaacaattct caagacatgt ttgagaatct tgaaatggtg   1140
gaggaattgg aaagtgtggt cagagcttca aagtcatgca agcttgtgtt cgaatctacc   1200
ttgtggtcac tatccaatta tgatgtttaa                                    1230

<210> SEQ ID NO 38
<211> LENGTH: 409
<212> TYPE: PRT
<213> ORGANISM: Arabidopsis thaliana
```

-continued

```
<400> SEQUENCE: 38

Met Ser Val Leu Ser Lys Arg Trp Arg Ser Leu Trp Lys Met Leu Pro
1               5                   10                  15

Arg Leu Lys Phe Asp Asp Trp Met Phe Pro Asp Asn Val Asn Arg Cys
            20                  25                  30

Leu Leu Ser His Gln Ala Ser Phe Leu Gln Ser Leu His Leu Val Ile
        35                  40                  45

Asp Tyr Asp Phe Val Ser His Met His Thr Gly Ile Leu Met Gly Ile
    50                  55                  60

Ala Phe Gly Arg His Ile Arg Glu Leu Val Leu Tyr Val Asn Gly Phe
65                  70                  75                  80

Gln Glu Ser Phe Thr Phe Pro Leu Ser Leu Cys Asn Cys Glu Ser Leu
                85                  90                  95

Glu Thr Leu Thr Leu Gly His Asn Val Leu Ile Asp Val Pro Ser Pro
            100                 105                 110

Val Phe Leu Lys Ser Leu Arg Thr Leu His Leu Asp Gly Val Glu Tyr
        115                 120                 125

Thr Asp Asp Glu Ser Val Val Asn Leu Leu Ser Gly Cys Ile Ser Leu
    130                 135                 140

Glu Asn Leu Val Val His Arg Val Ile Gln Ala Asp Val Thr Thr Phe
145                 150                 155                 160

Thr Ile Ala Val Pro Ser Leu Lys Arg Leu Thr Leu Thr Thr Glu Phe
                165                 170                 175

Asp Asp Asp Glu Asp Ser Val Tyr Val Ile Asn Ala Pro Ser Leu Lys
            180                 185                 190

Tyr Leu Lys Ile Leu Gly Asp Lys Ala Tyr Leu Ile Glu Asn Ser Pro
        195                 200                 205

Glu Leu Val Glu Val Ser Leu Thr Asp Arg Gln Val Thr Val Asp Gly
    210                 215                 220

Tyr Pro Ile Ala Ser Tyr Val Glu Asn Leu Leu Arg Ser Leu Thr Ser
225                 230                 235                 240

Val Lys Arg Met Ser Leu Lys Ile Ser Ser Tyr Leu Glu Ile Lys Phe
                245                 250                 255

Pro Thr Gly Ser Ile Phe Tyr Gln Leu Val Ser Leu Glu Leu Tyr Thr
            260                 265                 270

Asn Lys Ala Glu Trp Trp Asn Leu Leu Val Leu Met Leu Asp Ser Ser
        275                 280                 285

Pro Lys Leu Gln Val Leu Lys Leu Asn Gly Lys Leu Ser Gly Glu Asn
    290                 295                 300

Asn His Leu Ala Ser Met Asn Trp Asp Gln Pro Lys Asn Ile Pro Gly
305                 310                 315                 320

Cys Leu Leu Phe Asn Leu Glu Thr Phe Ile Trp Lys Gly Cys Lys Arg
                325                 330                 335

Ile Gly Glu Asp Glu Lys Glu Val Ala Lys Tyr Ile Leu Arg Asn Thr
            340                 345                 350

Asn Arg Leu Lys Arg Ala Thr Phe Thr Arg Glu Ile Tyr Glu Glu Asn
        355                 360                 365

Asn Ser Gln Asp Met Phe Glu Asn Leu Glu Met Val Glu Glu Leu Glu
    370                 375                 380

Ser Val Val Arg Ala Ser Lys Ser Cys Lys Leu Val Phe Glu Ser Thr
385                 390                 395                 400

Leu Trp Ser Leu Ser Asn Tyr Asp Val
                405
```

<210> SEQ ID NO 39
<211> LENGTH: 2113
<212> TYPE: DNA
<213> ORGANISM: Arabidopsis thaliana

<400> SEQUENCE: 39

| | | | | | |
|---|---|---|---|---|---|
| aagtttcaat | ttgacttctc | catcacacac | aacaacaaga | acaaggacaa | gcttctacat | 60 |
| ttctcttaac | ataacagaca | gttttgatc | tgggttttca | agtccggtgt | tgatcccatt | 120 |
| gagtttcgga | tctaaaagat | ccgaatattc | agacggatca | acaagagaac | aagaaaaaaa | 180 |
| aaatgaatct | tgagaatgtt | ttggaattca | ccagctttga | ttactggttt | aattggagag | 240 |
| tgttactatg | tgctatatgg | gtaatagttc | caatgattgt | ttctttatta | gtcttatgga | 300 |
| agtatgaaga | tagttcagtt | caaactcaac | catcacttaa | tggtaatgat | gttttgtgca | 360 |
| ttgatgatgt | ttggagacct | tgttttgaac | gaatccatcc | gggttggttg | ttgggttttc | 420 |
| gggttctcgg | gttttgtttc | cttcttgcta | acaatattgc | ccggtttgct | aatcgtggat | 480 |
| ggcgtattta | ctactattat | actcagtgga | cattcacttt | gatagcaatc | tacttcggga | 540 |
| tgggatcatt | gctttcaatt | tatggatgtt | acaatacaa | gaagcaaggg | aacactggac | 600 |
| ttatcgctga | tcaagtagga | atcgatgcag | agaacgggtt | tcgttcgcct | cttatagatg | 660 |
| gtgacaacat | ggtttcgttc | gagaagagaa | aaacttctgg | ttcggaagca | ctaaagtcat | 720 |
| atgttcatct | cttccagatt | atatatcaga | tgggtgctgg | agcagctgtg | cttacagaca | 780 |
| gtatatattg | gaccgtgatt | tcccgtttc | tgtctttaca | ggactatgag | atgagtttca | 840 |
| tgactgtgaa | tttgcacaca | agcaacctcg | ttttgctgct | tattgacacg | tttctaaacc | 900 |
| gtctgaaatt | tccattgttc | aggttctctt | acttcatctt | atggacagga | tgtttcgttc | 960 |
| ttttccagtg | gattctccac | atgtttatct | ccgttgggtg | gccatatcca | tttctcaacc | 1020 |
| tgtcattaga | catggctcca | gtgtggtatt | tgttggtggc | actcctgcat | cttccttctt | 1080 |
| atggcctctt | tgcattaatc | gtcaaaatca | aatacaaact | catttcttga | agtcatttcg | 1140 |
| aatccaagag | tttctgcccc | gtaagagtca | gtgctcaagg | gttacaacaa | tcaaagaaac | 1200 |
| aatttttac | cccatatgtc | taaaatcttc | aaaacagatc | attgtaaacg | ccacaacatt | 1260 |
| tcaatgcata | aactatttac | ttccgatcca | attcgcatat | cgcaatgaac | catttcgtaa | 1320 |
| attttcgct | acccgaattg | atttcagctc | gaaccaaatc | gaaagaacta | accatagcaa | 1380 |
| cagaatatag | tgcaatcttt | gccaaaagtg | tatgaactta | atcaaaaacc | gaaccaaacc | 1440 |
| aaaccgaaaa | cccgaaaatt | caaggtttta | gaattgaaga | tttgagtgag | acttgagaag | 1500 |
| ccaagtctgg | ctctcctagt | ctcaagagac | ccttactcaa | aacctcagcg | acatactcat | 1560 |
| cagcctccca | tgactcagac | ccccaaccac | tttccctcat | caaggtataa | acccctaacca | 1620 |
| ccgactctct | cctctcagct | ccaaccacag | ccctaatcaa | cttagctaaa | gccttatcat | 1680 |
| cacttctttg | atcaattcca | tcaatttcac | caataagacg | atctatctca | tcgaactctt | 1740 |
| tattcctcgt | aagagcatta | acaatgtctg | cgtatagaac | aaggtcaaga | ggaggatact | 1800 |
| ctgtacggag | agtggagagt | acatggacag | cgagtgtgca | atagtcttga | cggagaagct | 1860 |
| cacggaggac | ggagatgaga | tcggatttta | tgagacggcg | gagaggacgg | agggtaaggg | 1920 |
| agagggagac | accggttcga | tgagctcgtt | tgagagattg | gattgattgg | attgcttcgg | 1980 |
| tgcttaggat | tcggcctttg | agaagtggtc | cgcggttgtc | tcgtggaccg | catcggatcg | 2040 |
| aaacgaacgt | tctcttagga | acgatgacgc | taagggtatg | gctatggcta | aggcttggtg | 2100 |

```
gtcgagtctg gct                                                      2113
```

<210> SEQ ID NO 40
<211> LENGTH: 315
<212> TYPE: PRT
<213> ORGANISM: Arabidopsis thaliana

<400> SEQUENCE: 40

```
Met Asn Leu Glu Asn Val Leu Glu Phe Thr Ser Phe Asp Tyr Trp Phe
1               5                   10                  15

Asn Trp Arg Val Leu Leu Cys Ala Ile Trp Val Ile Val Pro Met Ile
            20                  25                  30

Val Ser Leu Leu Val Leu Trp Lys Tyr Glu Asp Ser Ser Val Gln Thr
        35                  40                  45

Gln Pro Ser Leu Asn Gly Asn Asp Val Leu Cys Ile Asp Asp Val Trp
    50                  55                  60

Arg Pro Cys Phe Glu Arg Ile His Pro Gly Trp Leu Leu Gly Phe Arg
65                  70                  75                  80

Val Leu Gly Phe Cys Phe Leu Leu Ala Asn Asn Ile Ala Arg Phe Ala
                85                  90                  95

Asn Arg Gly Trp Arg Ile Tyr Tyr Tyr Tyr Thr Gln Trp Thr Phe Thr
            100                 105                 110

Leu Ile Ala Ile Tyr Phe Gly Met Gly Ser Leu Leu Ser Ile Tyr Gly
        115                 120                 125

Cys Leu Gln Tyr Lys Lys Gln Gly Asn Thr Gly Leu Ile Ala Asp Gln
    130                 135                 140

Val Gly Ile Asp Ala Glu Asn Gly Phe Arg Ser Pro Leu Ile Asp Gly
145                 150                 155                 160

Asp Asn Met Val Ser Phe Glu Lys Arg Lys Thr Ser Gly Ser Glu Ala
                165                 170                 175

Leu Lys Ser Tyr Val His Leu Phe Gln Ile Ile Tyr Gln Met Gly Ala
            180                 185                 190

Gly Ala Ala Val Leu Thr Asp Ser Ile Tyr Trp Thr Val Ile Phe Pro
        195                 200                 205

Phe Leu Ser Leu Gln Asp Tyr Glu Met Ser Phe Met Thr Val Asn Leu
    210                 215                 220

His Thr Ser Asn Leu Val Leu Leu Ile Asp Thr Phe Leu Asn Arg
225                 230                 235                 240

Leu Lys Phe Pro Leu Phe Arg Phe Ser Tyr Phe Ile Leu Trp Thr Gly
                245                 250                 255

Cys Phe Val Leu Phe Gln Trp Ile Leu His Met Phe Ile Ser Val Gly
            260                 265                 270

Trp Pro Tyr Pro Phe Leu Asn Leu Ser Leu Asp Met Ala Pro Val Trp
        275                 280                 285

Tyr Leu Leu Val Ala Leu Leu His Leu Pro Ser Tyr Gly Leu Phe Ala
    290                 295                 300

Leu Ile Val Lys Ile Lys Tyr Lys Leu Ile Ser
305                 310                 315
```

<210> SEQ ID NO 41
<211> LENGTH: 1700
<212> TYPE: DNA
<213> ORGANISM: Arabidopsis thaliana

<400> SEQUENCE: 41

```
ctaatcaatt actttcctcg ttatcctttt ttgcagtcaa gttaaattgc tctctttcaa     60
```

-continued

```
gacttgtgtt ctttaaacca aaaaaaaaaa aaaagtatct gtgttcatca ccaactcatt      120
cttctttcag atctagggtt tcatgcttca ctcaattttt ttttgtttag gtagttccat      180
cttctaaacg ttgtatttt tttttttgc catcataatc atatggagtt cgagtcagtg       240
ttcaaaatgc attatccgta tctcgcagcc gttatctacg atgatagctc cactttaaaa      300
gattttcatc catctcttac cgatgatttt tcttgtgtac acaatgtgca tcacaaacca      360
tcgatgcctc acacatatga aataccatca aagaaaccca ttaggggcat cactccttct      420
ccatgcactg aagctttcga ggcatgtttt catggcacat ccaacgacca tgttttttt      480 ggcatggcct ataccacccc accaactatt gaacccaacg tttcacatgt ctcacatgac      540
aatactatgt gggaaaacga tcaaaaccaa ggattcatct ttggaaccga gtcaaccctc      600
aatcaagcca tggcggactc taatcaattc aatatgccaa accactctt gagcgcaaac      660 gaagacacca tcatgaatcg acgtcaaaat aaccaggtaa tgatcaagac cgagcagatc      720
aagaagaaga acaagagatt tcagatgagg aggatatgta aacccacaaa aaaagctagc      780
atcatcaaag acaatggac tcctgaagaa gacaagttat tggtgcagct agtggacctt      840
cacggaacta aaaaatggtc tcagattgct aagatgcttc aaggacgagt tggaaaacag      900
tgcagagaaa ggtggcataa ccatctccgt cccgatatca agaaagatgg atggactgaa      960
gaagaggata taatactgat aaaagcccat aaggagattg ggaacagatg ggctgagata     1020
gctcgaaaac tcccgggacg cactgaaaat acgatcaaga accattggaa cgcgactaaa     1080
cgtcgacaac actcgaggag gactaaagga aaagatgaaa tttcccttc acttggtagc     1140 aacactcttc agaactacat taggtctgtt acctacaatg atgatccttt catgaccgca     1200
aatgcaaacg caaacattgg tccaagaaac atgagaggta aagtaagaa tgtaatggtt     1260 gcggtctcgg agtatgatga gggtgaatgt aagtatattg tggatggtgt gaataacttg     1320
ggtttagaag atggaaggat caagatgccg tcattggcgg ctatgtcggc tccggatca     1380 gcgtctactt ctggttctgc gtctggttct ggaagtggtg tgaccatgga gattgatgag     1440
ccgatgactg atagctggat ggtgatgcat ggatgtgatg aagttatgat gaacgagatt     1500
gctttgctgg agatgattgc tcatggtcgt ctttagaccg tgcaatataa acaagtcgaa     1560
cttgattata tctacctata taattatgct atttatgaaa ttatgtttgt gcttttaatt     1620
gaagaattgg acatgtaata tatattgtgg tttaattgaa ggtttctttt ggactaaaca     1680
aaaattgaag gttttcttgc                                                 1700
```

<210> SEQ ID NO 42
<211> LENGTH: 437
<212> TYPE: PRT
<213> ORGANISM: Arabidopsis thaliana

<400> SEQUENCE: 42

```
Met Glu Phe Glu Ser Val Phe Lys Met His Tyr Pro Tyr Leu Ala Ala
1               5                   10                  15

Val Ile Tyr Asp Asp Ser Ser Thr Leu Lys Asp Phe His Pro Ser Leu
            20                  25                  30

Thr Asp Asp Phe Ser Cys Val His Asn Val His Lys Pro Ser Met
        35                  40                  45

Pro His Thr Tyr Glu Ile Pro Ser Lys Glu Thr Ile Arg Gly Ile Thr
    50                  55                  60

Pro Ser Pro Cys Thr Glu Ala Phe Glu Ala Cys Phe His Gly Thr Ser
65                  70                  75                  80
```

```
Asn Asp His Val Phe Phe Gly Met Ala Tyr Thr Thr Pro Pro Thr Ile
                85                  90                  95
Glu Pro Asn Val Ser His Val Ser His Asp Asn Thr Met Trp Glu Asn
            100                 105                 110
Asp Gln Asn Gln Gly Phe Ile Phe Gly Thr Glu Ser Thr Leu Asn Gln
        115                 120                 125
Ala Met Ala Asp Ser Asn Gln Phe Asn Met Pro Lys Pro Leu Leu Ser
130                 135                 140
Ala Asn Glu Asp Thr Ile Met Asn Arg Arg Gln Asn Asn Gln Val Met
145                 150                 155                 160
Ile Lys Thr Glu Gln Ile Lys Lys Lys Asn Lys Arg Phe Gln Met Arg
                165                 170                 175
Arg Ile Cys Lys Pro Thr Lys Lys Ala Ser Ile Ile Lys Gly Gln Trp
            180                 185                 190
Thr Pro Glu Glu Asp Lys Leu Leu Val Gln Leu Val Asp Leu His Gly
        195                 200                 205
Thr Lys Lys Trp Ser Gln Ile Ala Lys Met Leu Gln Gly Arg Val Gly
210                 215                 220
Lys Gln Cys Arg Glu Arg Trp His Asn His Leu Arg Pro Asp Ile Lys
225                 230                 235                 240
Lys Asp Gly Trp Thr Glu Glu Asp Ile Ile Leu Ile Lys Ala His
                245                 250                 255
Lys Glu Ile Gly Asn Arg Trp Ala Glu Ile Ala Arg Lys Leu Pro Gly
            260                 265                 270
Arg Thr Glu Asn Thr Ile Lys Asn His Trp Asn Ala Thr Lys Arg Arg
        275                 280                 285
Gln His Ser Arg Arg Thr Lys Gly Lys Asp Glu Ile Ser Leu Ser Leu
290                 295                 300
Gly Ser Asn Thr Leu Gln Asn Tyr Ile Arg Ser Val Thr Tyr Asn Asp
305                 310                 315                 320
Asp Pro Phe Met Thr Ala Asn Ala Asn Ala Asn Ile Gly Pro Arg Asn
                325                 330                 335
Met Arg Gly Lys Gly Lys Asn Val Met Val Ala Val Ser Glu Tyr Asp
            340                 345                 350
Glu Gly Glu Cys Lys Tyr Ile Val Asp Gly Val Asn Asn Leu Gly Leu
        355                 360                 365
Glu Asp Gly Arg Ile Lys Met Pro Ser Leu Ala Ala Met Ser Ala Ser
370                 375                 380
Gly Ser Ala Ser Thr Ser Gly Ser Ala Ser Gly Ser Gly Ser Gly Val
385                 390                 395                 400
Thr Met Glu Ile Asp Glu Pro Met Thr Asp Ser Trp Met Val Met His
                405                 410                 415
Gly Cys Asp Glu Val Met Met Asn Glu Ile Ala Leu Leu Glu Met Ile
            420                 425                 430
Ala His Gly Arg Leu
        435

<210> SEQ ID NO 43
<211> LENGTH: 1423
<212> TYPE: DNA
<213> ORGANISM: Arabidopsis thaliana

<400> SEQUENCE: 43
atatcgaagt aagactaaag ctcaagttaa aacagaaaaa atgtcaactt cagaaaacac   60
```

```
tccgtttaat ggcgttgcct catccaccat tgttcgagct accattgtcc aagcctccac    120
cgtctacaac gatactcccg ccactctaga aaaggcgaac aagtttattg tggaggctgc    180
aagcaaggga tcggagctgg ttgtgttccc ggaggcgttt atcggtggtt atcctcgagg    240
ttttaggttt ggtttagggg tgggagttca taacgaagaa gggcgtgatg agttccgcaa    300
gtaccatgct tctgctatta aagttcctgg ccctgaagta gaaaagttgg cggagttggc    360
cgggaagaac aatgtgtact tggtaatggg agcgatagag aaggatgggt atacactcta    420
ttgcacagca ctttcttca gtccacaagg tcagttcttg ggtaagcacc gtaaactcat    480
gcccacaagt ttggaacgtt gcatttgggg tcaaggagac ggatcaacca tccccgttta    540
cgacactccg attggaaaac tcggtgctgc tatttgctgg agaataggga tgcccctcta    600
cagaactgct ttgtacgcca aaggcattga gctttattgt gcacctactg ctgatggttc    660
gaaagaatgg caatcgtcga tgcttcacat tgcgatcgaa ggtggatgtt cgtattgtc    720
ggcttgccag ttctgccttc gtaaagattt ccctgatcat cctgactact tgtttaccga    780
ttggtacgac gacaaagagc ctgactctat tgtttcccaa ggtggaagtg ttattatttc    840
acctttggga caggttcttg cgggaccaaa ctttgaatca gagggtctca tcacagctga    900
tcttgatctt ggtgatgtag caagagctaa gttgtacttc gattcggttg acattactc    960
gagaccagat gttttacact tgaccgtaaa tgagcacccg aagaaaccgg tcacattcat   1020
ttcgaaggtg gagaaagcgg aagatgactc aaacaagtaa tcggttgtga ttcgtcagtt   1080
catgtcactc ctatgaagga gtcaagttca aatgttatg ttgagtttca aacttttatg   1140
ctaaactttt tttcttaatt ttcgttaata atggaagaga accaattctc ttgtatctaa   1200
agattatcca tctatcatcc aatttgagtg ttcaattctg gatgttgtgt accctacat   1260
tctacaacca tgtagccaat tattatgaat ctggctttga tttcagttgt gttctttct   1320
ttttttcctt tgcatatttg catttagaat gtttaataat taagttactg tatttccaca   1380
tacattagtt ccaagaatat acatatatta atttattttt ctt                    1423
```

<210> SEQ ID NO 44
<211> LENGTH: 339
<212> TYPE: PRT
<213> ORGANISM: Arabidopsis thaliana

<400> SEQUENCE: 44

```
Met Ser Thr Ser Glu Asn Thr Pro Phe Asn Gly Val Ala Ser Ser Thr
 1               5                  10                  15

Ile Val Arg Ala Thr Ile Val Gln Ala Ser Thr Val Tyr Asn Asp Thr
            20                  25                  30

Pro Ala Thr Leu Glu Lys Ala Asn Lys Phe Ile Val Glu Ala Ala Ser
        35                  40                  45

Lys Gly Ser Glu Leu Val Val Phe Pro Glu Ala Phe Ile Gly Gly Tyr
    50                  55                  60

Pro Arg Gly Phe Arg Phe Gly Leu Gly Val Gly Val His Asn Glu Glu
65                  70                  75                  80

Gly Arg Asp Glu Phe Arg Lys Tyr His Ala Ser Ala Ile Lys Val Pro
                85                  90                  95

Gly Pro Glu Val Glu Lys Leu Ala Glu Leu Ala Gly Lys Asn Asn Val
            100                 105                 110

Tyr Leu Val Met Gly Ala Ile Glu Lys Asp Gly Tyr Thr Leu Tyr Cys
        115                 120                 125
```

```
Thr Ala Leu Phe Phe Ser Pro Gln Gly Gln Phe Leu Gly Lys His Arg
    130                 135                 140

Lys Leu Met Pro Thr Ser Leu Glu Arg Cys Ile Trp Gly Gln Gly Asp
145                 150                 155                 160

Gly Ser Thr Ile Pro Val Tyr Asp Thr Pro Ile Gly Lys Leu Gly Ala
                165                 170                 175

Ala Ile Cys Trp Glu Asn Arg Met Pro Leu Tyr Arg Thr Ala Leu Tyr
            180                 185                 190

Ala Lys Gly Ile Glu Leu Tyr Cys Ala Pro Thr Ala Asp Gly Ser Lys
        195                 200                 205

Glu Trp Gln Ser Ser Met Leu His Ile Ala Ile Glu Gly Gly Cys Phe
    210                 215                 220

Val Leu Ser Ala Cys Gln Phe Cys Leu Arg Lys Asp Phe Pro Asp His
225                 230                 235                 240

Pro Asp Tyr Leu Phe Thr Asp Trp Tyr Asp Asp Lys Glu Pro Asp Ser
                245                 250                 255

Ile Val Ser Gln Gly Gly Ser Val Ile Ile Ser Pro Leu Gly Gln Val
            260                 265                 270

Leu Ala Gly Pro Asn Phe Glu Ser Glu Gly Leu Ile Thr Ala Asp Leu
        275                 280                 285

Asp Leu Gly Asp Val Ala Arg Ala Lys Leu Tyr Phe Asp Ser Val Gly
    290                 295                 300

His Tyr Ser Arg Pro Asp Val Leu His Leu Thr Val Asn Glu His Pro
305                 310                 315                 320

Lys Lys Pro Val Thr Phe Ile Ser Lys Val Glu Lys Ala Glu Asp Asp
                325                 330                 335

Ser Asn Lys

<210> SEQ ID NO 45
<211> LENGTH: 1121
<212> TYPE: DNA
<213> ORGANISM: Arabidopsis thaliana

<400> SEQUENCE: 45 atttttgat   atgtaaaatt   tatcgaaaac   gttccatttc   aatatgtaga   caaagcggag     60
aagtatattg   tggaggcggc   aagcaaggga   gcagagctag   tgttgttccc   ggagggtttt    120
atcggtggct   atcctcgagg   ttttaggttc   ggtttagcgg   ttggcgttca   taacgaagaa    180
gggcgtgatg   agtttcggaa   gtaccatgct   tctgctattc   atgttcctgg   ccctgaagta    240
gcaagattgg   ctgacgtggc   taggaaaaac   catgtgtact   tggtaatggg   agccatagag    300
aaggaagggt   ataccctcta   ttgcacagtt   cttttcttta   gtccacaggg   tcagttcttg    360
ggcaagcacc   gtaaactcat   gcccacaagt   ttggaacgtt   gcatttgggg   ccaagggac    420 ggatcaacca   tccccgttta   cgacactccc   attggaaaac   tcggtgctgc   tatttgctgg    480
gagaatagga   tgcccctcta   cagaactgca   ttgtacgcca   aaggcattga   gctttattgt    540
gcacctactg   ctgatggttc   gaaagaatgg   caatcgtcga   tgcttcacat   tgcgatcgaa    600
ggtggatgtt   tcgtcttgtc   ggcttgccaa   ttctgccagc   gtaaacattt   ccctgatcat    660
cctgactact   tgtttaccga   ttggtacgac   gacaaagaac   atgattctat   tgtctcccaa    720
ggtggaagtg   tcattatttc   acctttggga   caagttctcg   ccggaccaaa   ctttgaatca    780
gagggtctcg   tcacagctga   tattgatctt   ggtgatatag   caagagccaa   gttatacttc    840
gattcggttg   gacattactc   gagaccagat   gttttacact   tgaccgtaaa   tgagcacccg    900
```

```
aggaaatcgg ttacattcgt gacgaaggtg gagaaagctg aggatgactc aaacaaatag    960
taagagactt gaagttcgta tctgctggag ttatgtcaat cgtatggagt caagtccaaa   1020
atgttctgtt gcgttttcat tttatgttca agtttattta tctttctctt caatggtaag   1080
atctatggag tcaagtaata atggtaagac ttatgttgtt g                       1121
```

<210> SEQ ID NO 46
<211> LENGTH: 224
<212> TYPE: PRT
<213> ORGANISM: Arabidopsis thaliana

<400> SEQUENCE: 46

```
Met Gly Ala Ile Glu Lys Glu Gly Tyr Thr Leu Tyr Cys Thr Val Leu
1               5                  10                  15

Phe Phe Ser Pro Gln Gly Gln Phe Leu Gly Lys His Arg Lys Leu Met
            20                  25                  30

Pro Thr Ser Leu Glu Arg Cys Ile Trp Gly Gln Gly Asp Gly Ser Thr
        35                  40                  45

Ile Pro Val Tyr Asp Thr Pro Ile Gly Lys Leu Gly Ala Ala Ile Cys
    50                  55                  60

Trp Glu Asn Arg Met Pro Leu Tyr Arg Thr Ala Leu Tyr Ala Lys Gly
65                  70                  75                  80

Ile Glu Leu Tyr Cys Ala Pro Thr Ala Asp Gly Ser Lys Glu Trp Gln
                85                  90                  95

Ser Ser Met Leu His Ile Ala Ile Glu Gly Gly Cys Phe Val Leu Ser
            100                 105                 110

Ala Cys Gln Phe Cys Gln Arg Lys His Phe Pro Asp His Pro Asp Tyr
        115                 120                 125

Leu Phe Thr Asp Trp Tyr Asp Asp Lys Glu His Asp Ser Ile Val Ser
    130                 135                 140

Gln Gly Gly Ser Val Ile Ile Ser Pro Leu Gly Gln Val Leu Ala Gly
145                 150                 155                 160

Pro Asn Phe Glu Ser Glu Gly Leu Val Thr Ala Asp Ile Asp Leu Gly
                165                 170                 175

Asp Ile Ala Arg Ala Lys Leu Tyr Phe Asp Ser Val Gly His Tyr Ser
            180                 185                 190

Arg Pro Asp Val Leu His Leu Thr Val Asn Glu His Pro Arg Lys Ser
        195                 200                 205

Val Thr Phe Val Thr Lys Val Glu Lys Ala Glu Asp Asp Ser Asn Lys
    210                 215                 220
```

<210> SEQ ID NO 47
<211> LENGTH: 1338
<212> TYPE: DNA
<213> ORGANISM: Arabidopsis thaliana

<400> SEQUENCE: 47

```
atgaaccaaa gtaaaaaaca aagactcgag ttgatatgtc tagtactaaa gatatgtcaa     60
ctgtccaaaa cgcaactcct tttaacggcg ttgccccatc caccaccgtg cgagttacaa    120
tcgtccaatc ctccaccgtc tataacgata ctcctgccac tatagacaaa gcggagaagt    180
atattgtgga ggcggcaagc aagggagcag agctagtgtt gttcccggag gggtttatcg    240
gtggctatcc tcgaggtttt aggttcggtt tagcggttgg cgttcataac gaagaagggc    300
gtgatgagtt tcggaagtac catgcttctg ctattcatgt tcctggccct gaagtagcaa    360
gattggctga cgtggctagg aaaaaccatg tgtacttggt aatgggagcc atagagaagg    420
```

```
aagggtatac cctctattgc acagttcttt tctttagtcc acagggtcag ttcttgggca     480
agcaccgtaa actcatgccc acaagtttgg aacgttgcat ttggggccaa ggggacggat     540
caaccatccc cgtttacgac actcccattg gaaaactcgg tgctgctatt tgctgggaga     600
ataggatgcc cctctacaga actgcattgt acgccaaagg cattgagctt tattgtgcac     660
ctactgctga tggttcgaaa gaatggcaat cgtcgatgct tcacattgcg atcgaaggtg     720
gatgtttcgt cttgtcggct tgccaattct gccagcgtaa acatttccct gatcatcctg     780
actacttgtt taccgattgg tacgacgaca agaacatga ttctattgtc tcccaaggtg      840
gaagtgtcat tatttcacct ttgggacaag ttctcgccgg accaaacttt gaatcagagg     900
gtctcgtcac agctgatatt gatcttggtg atatagcaag agccaagtta tacttcgatt     960
cggttggaca ttactcgaga ccagatgttt tacacttgac cgtaaatgag cacccgagga    1020
aatcggttac attcgtgacg aaggtggaga aagctgagga tgactcaaac aaatagtaag    1080
agacttgaag ttcgtatctg ctggagttat gtcaatcgta tggagtcaag tccaaaatgt    1140
tctgttgcgt tttcatttta tgttcaagtt tatttatctt tctcttcaat ggtaagatct    1200
atggagtcaa gtaataatgg taagacttat gttgttgaat aaaacgaatt ggttctctcc    1260
tcttgtattt taaaactgtg ccattatgtt tatctaattt gggcgttggg cgttgaatct    1320
caattgttgt tcagccgt                                                  1338

<210> SEQ ID NO 48
<211> LENGTH: 346
<212> TYPE: PRT
<213> ORGANISM: Arabidopsis thaliana

<400> SEQUENCE: 48

Met Ser Ser Thr Lys Asp Met Ser Thr Val Gln Asn Ala Thr Pro Phe
1               5                   10                  15

Asn Gly Val Ala Pro Ser Thr Thr Val Arg Val Thr Ile Val Gln Ser
                20                  25                  30

Ser Thr Val Tyr Asn Asp Thr Pro Ala Thr Ile Asp Lys Ala Glu Lys
            35                  40                  45

Tyr Ile Val Glu Ala Ala Ser Lys Gly Ala Glu Leu Val Leu Phe Pro
    50                  55                  60

Glu Gly Phe Ile Gly Gly Tyr Pro Arg Gly Phe Arg Phe Gly Leu Ala
65                  70                  75                  80

Val Gly Val His Asn Glu Glu Gly Arg Asp Glu Phe Arg Lys Tyr His
                85                  90                  95

Ala Ser Ala Ile His Val Pro Gly Pro Glu Val Ala Arg Leu Ala Asp
            100                 105                 110

Val Ala Arg Lys Asn His Val Tyr Leu Val Met Gly Ala Ile Glu Lys
        115                 120                 125

Glu Gly Tyr Thr Leu Tyr Cys Thr Val Leu Phe Phe Ser Pro Gln Gly
    130                 135                 140

Gln Phe Leu Gly Lys His Arg Lys Leu Met Pro Thr Ser Leu Glu Arg
145                 150                 155                 160

Cys Ile Trp Gly Gln Gly Asp Gly Ser Thr Ile Pro Val Tyr Asp Thr
                165                 170                 175

Pro Ile Gly Lys Leu Gly Ala Ala Ile Cys Trp Glu Asn Arg Met Pro
            180                 185                 190

Leu Tyr Arg Thr Ala Leu Tyr Ala Lys Gly Ile Glu Leu Tyr Cys Ala
        195                 200                 205
```

```
Pro Thr Ala Asp Gly Ser Lys Glu Trp Gln Ser Ser Met Leu His Ile
    210                 215                 220
Ala Ile Glu Gly Gly Cys Phe Val Leu Ser Ala Cys Gln Phe Cys Gln
225                 230                 235                 240
Arg Lys His Phe Pro Asp His Pro Asp Tyr Leu Phe Thr Asp Trp Tyr
                245                 250                 255
Asp Asp Lys Glu His Asp Ser Ile Val Ser Gln Gly Gly Ser Val Ile
                260                 265                 270
Ile Ser Pro Leu Gly Gln Val Leu Ala Gly Pro Asn Phe Glu Ser Glu
            275                 280                 285
Gly Leu Val Thr Ala Asp Ile Asp Leu Gly Asp Ile Ala Arg Ala Lys
290                 295                 300
Leu Tyr Phe Asp Ser Val Gly His Tyr Ser Arg Pro Asp Val Leu His
305                 310                 315                 320
Leu Thr Val Asn Glu His Pro Arg Lys Ser Val Thr Phe Val Thr Lys
                325                 330                 335
Val Glu Lys Ala Glu Asp Asp Ser Asn Lys
                340                 345

<210> SEQ ID NO 49
<211> LENGTH: 1396
<212> TYPE: DNA
<213> ORGANISM: Arabidopsis thaliana

<400> SEQUENCE: 49
atcaaagtat aaagtaaaaa caaagactcg agttaatatg tctagtactg aagaaatgtc      60
atcagtcaaa aacacaactc aggttattgg cgttgaccca tcctccaccg tacgagttac     120
catcgttcaa tcttccaccg tctataatga taccccggcc actttagaca aggcggagaa     180
gtttattgtg gaggcggcga gcaaaggagc gaagttggtg ttgtttcccg aggcgttcat     240
cggcggttat cctcgaggtt ttaggtttgg tttagcggtg ggagttcata cgaagaagg      300 gcgtgatgag tttcgtaact accatgcttc tgctattaaa gtccctggcc ctgaagtgga     360
aagattggct gagttggccg ggaaaaataa tgtgcacttg gtaatggggg ctatagagaa     420
ggatggttat acactctatt gcacagctct tttcttcagt ccacaaggtc agttttagg      480 taagcaccgt aaagtcatgc ccacatcttt ggaacgttgc atatgggtc aaggggacgg     540 atcaaccatc cccgtttacg acactcctat tggcaaaatc ggtgctgcta tttgctggga     600
gaataggatg ccctctaca gaactgcatt gtacgctaaa ggcattgaga tttattgtgc     660
acctactgct gattattcgt tggaatggca agcatcgatg attcacattg cggtagaagg     720
tggatgtttc gtgttgtcag cgcaccagtt ctgcaagcgt agagagttcc ctgaacatcc     780
tgattacttg tttaatgaca tagtagacac taaagaacat gatcctactg tctccggagg     840
tggaagtgtc attatttcac ctttgggaaa ggttctcgcc ggaccaaact atgaatcaga     900
gggtctcgtc acagctgatc ttgatcttgg tgatatagca agagccaagt tatacttcga     960
tgtggttgga cattactcaa agccagatat ttttaacttg accgtaaatg agcacccgaa    1020
gaaaccggtt acattcatga cgaaggtcga gaaagcagag gatgaatcaa acaaatagtc    1080
aagatttgca attcgtctac tgaagttaag tcaagttcga atgtttttt tttcagtttt    1140 aaagttgatg ttcaagttta ttttctttc tcttcaataa tgtaagagga ctatttcgat    1200
atgttaaaat aaaaccaatt ggttctctcc tcttgtattc aattgtcgtg taataatgtt    1260
ttgttcaatt cgagtgttga ttaagttgta ttctttattt ttcctttgca tgtcaaacac    1320
```

```
agatttttg ctgtttaaat aagttgctag ctaagtctag atgtgagttt gaaaagtcac    1380
tacaaaacta cttaat                                                   1396
```

<210> SEQ ID NO 50
<211> LENGTH: 346
<212> TYPE: PRT
<213> ORGANISM: Arabidopsis thaliana

<400> SEQUENCE: 50

```
Met Ser Ser Thr Glu Glu Met Ser Ser Val Lys Asn Thr Thr Gln Val
1               5                   10                  15

Ile Gly Val Asp Pro Ser Ser Thr Val Arg Val Thr Ile Val Gln Ser
            20                  25                  30

Ser Thr Val Tyr Asn Asp Thr Pro Ala Thr Leu Asp Lys Ala Glu Lys
        35                  40                  45

Phe Ile Val Glu Ala Ala Ser Lys Gly Ala Lys Leu Val Leu Phe Pro
    50                  55                  60

Glu Ala Phe Ile Gly Gly Tyr Pro Arg Gly Phe Arg Phe Gly Leu Ala
65                  70                  75                  80

Val Gly Val His Asn Glu Glu Gly Arg Asp Glu Phe Arg Asn Tyr His
                85                  90                  95

Ala Ser Ala Ile Lys Val Pro Gly Pro Glu Val Glu Arg Leu Ala Glu
            100                 105                 110

Leu Ala Gly Lys Asn Asn Val His Leu Val Met Gly Ala Ile Glu Lys
        115                 120                 125

Asp Gly Tyr Thr Leu Tyr Cys Thr Ala Leu Phe Phe Ser Pro Gln Gly
    130                 135                 140

Gln Phe Leu Gly Lys His Arg Lys Val Met Pro Thr Ser Leu Glu Arg
145                 150                 155                 160

Cys Ile Trp Gly Gln Gly Asp Gly Ser Thr Ile Pro Val Tyr Asp Thr
                165                 170                 175

Pro Ile Gly Lys Ile Gly Ala Ala Ile Cys Trp Glu Asn Arg Met Pro
            180                 185                 190

Leu Tyr Arg Thr Ala Leu Tyr Ala Lys Gly Ile Glu Ile Tyr Cys Ala
        195                 200                 205

Pro Thr Ala Asp Tyr Ser Leu Glu Trp Gln Ala Ser Met Ile His Ile
    210                 215                 220

Ala Val Glu Gly Gly Cys Phe Val Leu Ser His Gln Phe Cys Lys
225                 230                 235                 240

Arg Arg Glu Phe Pro Glu His Pro Asp Tyr Leu Phe Asn Asp Ile Val
                245                 250                 255

Asp Thr Lys Glu His Asp Pro Thr Val Ser Gly Gly Gly Ser Val Ile
            260                 265                 270

Ile Ser Pro Leu Gly Lys Val Leu Ala Gly Pro Asn Tyr Glu Ser Glu
        275                 280                 285

Gly Leu Val Thr Ala Asp Leu Asp Leu Gly Asp Ile Ala Arg Ala Lys
    290                 295                 300

Leu Tyr Phe Asp Val Val Gly His Tyr Ser Lys Pro Asp Ile Phe Asn
305                 310                 315                 320

Leu Thr Val Asn Glu His Pro Lys Lys Pro Val Thr Phe Met Thr Lys
                325                 330                 335

Val Glu Lys Ala Glu Asp Glu Ser Asn Lys
            340                 345
```

<210> SEQ ID NO 51
<211> LENGTH: 1725
<212> TYPE: DNA
<213> ORGANISM: Arabidopsis thaliana

<400> SEQUENCE: 51

```
caaaggccac aaagaagaag aaaaccttct tcaacgttta aagtctcttc tctctctctc      60
tcttaacttc tcccattttc tttgaactaa agatcaatgg ctcacaacca ttctaatgaa     120
gacggctcta ttggaacctc cttgcatgga gtcacggcaa gggagcaagt cttctccttc     180
tccgtccaag aagatgtccc ttcatctcaa gccgtccgaa caaacgatcc aacggctaag     240
tttgccctac cagtggactc cgaacatagg gcaaaagtgt tcaaaccact atcattcgct     300
aaaccacata tgagagcctt ccacttagga tggatctctt tcttcacttg cttcatctcc     360
accttcgcag ccgcacctct agtccccgtc attcgcgaca atctcgacct gaccaaaacc     420
gacatcggaa atgctggagt tgcatcagtt tccggcgcca ttttctcgag actcgctatg     480
ggtgctgtat gtgaccttct aggggcacgt tatggaaccg ccttctcact tatgcttaca     540
gctccagcag ttttctccat gtcgttcgta gctgacgcgg aagctactt agccgtaagg     600
ttcatgatcg gttttttgctt agcaacgttc gtatcatgtc agtactggac gagtgttatg     660
ttcactggaa agattatcgg actcgttaac ggatgtgctg gagggtgggg agatatggga     720
ggaggagtga ctcagctact aatgccaatg gtcttccacg tcatcaaact caccggagcc     780
actcccttca cggcttggag gttcgccttc ttcatcccccg gcattcttca gatagttatg     840
ggtattctcg ttctcactct cggccaagat cttcccgatg gtaacctcag tactctccaa     900
aagagtggtc aagtttctaa agacaaattc tccaaggtct tttggttcgc tgtgaaaaac     960
tatagaacat ggatcttatt catgctctat ggattttcta tgggagttga attaacgatc    1020
aacaacgtta tatctggata cttctacgat aggtttaacc ttacgcttca cacagctggt    1080
attatagcag ccagctttgg tatggcaaac ttctttgccc gtcctttgg tggctacgct    1140
tcagatgtag ctgcacggct cttcggtatg aggggacggt tatggatctt gtggatctta    1200
caaactgttg gagctctctt ttgcatctgg cttggtcgtg ctagttcact acctatagct    1260
atcttagcca tgatgctttt ttccatgggc acacaagctg cttgtggagc tctctttggt    1320
gttgctcctt tgtttcccg ccgttctctt ggacttatct cgggattaac tggtgctggt    1380
ggaaattttg ggtcgggagt tactcaactt cttttcttct cttcctcgag gtttagtacg    1440
gcggaaggac tatcgttgat gggcgttatg gctgttgtgt gctctcttcc ggttgcgttt    1500
atacattttc cgcagtgggg aagcatgttc ttgaggccat acaagatgg agagaaatca    1560
aaggaagagc attactatgg agcggaatgg acagaggaag agaagagctt aggactacac    1620
gaaggaagca ttaaatttgc tgaaaacagc cggtcagaga gaggccgcaa ggcgatgttg    1680
gctgatattc caacgccgga aaccggatct ccggctcatg tctag                    1725
```

<210> SEQ ID NO 52
<211> LENGTH: 542
<212> TYPE: PRT
<213> ORGANISM: Arabidopsis thaliana

<400> SEQUENCE: 52

```
Met Ala His Asn His Ser Asn Glu Asp Gly Ser Ile Gly Thr Ser Leu
1               5                   10                  15

His Gly Val Thr Ala Arg Glu Gln Val Phe Ser Phe Ser Val Gln Glu
            20                  25                  30
```

```
Asp Val Pro Ser Ser Gln Ala Val Arg Thr Asn Asp Pro Thr Ala Lys
         35                  40                  45

Phe Ala Leu Pro Val Asp Ser Glu His Arg Ala Lys Val Phe Lys Pro
 50                  55                  60

Leu Ser Phe Ala Lys Pro His Met Arg Ala Phe His Leu Gly Trp Ile
 65                  70                  75                  80

Ser Phe Phe Thr Cys Phe Ile Ser Thr Phe Ala Ala Pro Leu Val
                 85                  90                  95

Pro Val Ile Arg Asp Asn Leu Asp Leu Thr Lys Thr Asp Ile Gly Asn
                100                 105                 110

Ala Gly Val Ala Ser Val Ser Gly Ala Ile Phe Ser Arg Leu Ala Met
             115                 120                 125

Gly Ala Val Cys Asp Leu Leu Gly Ala Arg Tyr Gly Thr Ala Phe Ser
         130                 135                 140

Leu Met Leu Thr Ala Pro Ala Val Phe Ser Met Ser Phe Val Ala Asp
145                 150                 155                 160

Ala Gly Ser Tyr Leu Ala Val Arg Phe Met Ile Gly Phe Cys Leu Ala
                165                 170                 175

Thr Phe Val Ser Cys Gln Tyr Trp Thr Ser Val Met Phe Thr Gly Lys
             180                 185                 190

Ile Ile Gly Leu Val Asn Gly Cys Ala Gly Gly Trp Gly Asp Met Gly
         195                 200                 205

Gly Gly Val Thr Gln Leu Leu Met Pro Met Val Phe His Val Ile Lys
         210                 215                 220

Leu Thr Gly Ala Thr Pro Phe Thr Ala Trp Arg Phe Ala Phe Phe Ile
225                 230                 235                 240

Pro Gly Ile Leu Gln Ile Val Met Gly Ile Leu Val Leu Thr Leu Gly
                245                 250                 255

Gln Asp Leu Pro Asp Gly Asn Leu Ser Thr Leu Gln Lys Ser Gly Gln
             260                 265                 270

Val Ser Lys Asp Lys Phe Ser Lys Val Phe Trp Phe Ala Val Lys Asn
         275                 280                 285

Tyr Arg Thr Trp Ile Leu Phe Met Leu Tyr Gly Phe Ser Met Gly Val
         290                 295                 300

Glu Leu Thr Ile Asn Asn Val Ile Ser Gly Tyr Phe Tyr Asp Arg Phe
305                 310                 315                 320

Asn Leu Thr Leu His Thr Ala Gly Ile Ile Ala Ala Ser Phe Gly Met
                325                 330                 335

Ala Asn Phe Phe Ala Arg Pro Phe Gly Gly Tyr Ala Ser Asp Val Ala
             340                 345                 350

Ala Arg Leu Phe Gly Met Arg Gly Arg Leu Trp Ile Leu Trp Ile Leu
         355                 360                 365

Gln Thr Val Gly Ala Leu Phe Cys Ile Trp Leu Gly Arg Ala Ser Ser
         370                 375                 380

Leu Pro Ile Ala Ile Leu Ala Met Met Leu Phe Ser Met Gly Thr Gln
385                 390                 395                 400

Ala Ala Cys Gly Ala Leu Phe Gly Val Ala Pro Phe Val Ser Arg Arg
             405                 410                 415

Ser Leu Gly Leu Ile Ser Gly Leu Thr Gly Ala Gly Gly Asn Phe Gly
                420                 425                 430

Ser Gly Val Thr Gln Leu Leu Phe Phe Ser Ser Arg Phe Ser Thr
             435                 440                 445
```

Ala Glu Gly Leu Ser Leu Met Gly Val Met Ala Val Val Cys Ser Leu
         450                 455                 460

Pro Val Ala Phe Ile His Phe Pro Gln Trp Gly Ser Met Phe Leu Arg
465                 470                 475                 480

Pro Ser Gln Asp Gly Glu Lys Ser Lys Glu Glu His Tyr Tyr Gly Ala
                485                 490                 495

Glu Trp Thr Glu Glu Glu Lys Ser Leu Gly Leu His Glu Gly Ser Ile
            500                 505                 510

Lys Phe Ala Glu Asn Ser Arg Ser Glu Arg Gly Arg Lys Ala Met Leu
515                 520                 525

Ala Asp Ile Pro Thr Pro Glu Thr Gly Ser Pro Ala His Val
        530                 535                 540

<210> SEQ ID NO 53
<211> LENGTH: 1067
<212> TYPE: DNA
<213> ORGANISM: Arabidopsis thaliana

<400> SEQUENCE: 53
atggagatga acttgagaat tgaagaccta acgaagaaa caaagactct aatctcttca    60
cttccttcag acaagagatt cactgggaaa actatttgca agtatcaagg atgttggtat   120
actcacaatg ttcttcaagc tgtcctcaat ttccagaaaa gcttcaagcc tcaagacacc   180
gatatcatcg ttgcttcgtt ccctaaatgc ggcaccactt ggctcaaggc gcttacattc   240
gcactccttc atagatcaaa acagccttct catgatgatg atcatcctct tctttctaat   300
aatccacacg ttcttgtacc ctactttgag atagatctct atctacgtag cgaaaatcct   360
gaccttacca agttctcatc atctccgagg ctgttttcga cacacgtgcc gtcacatacg   420
ttgcaagaag gtctcaaagg ttctacttgt aaaattgtgt atatatctag aaacgtaaaa   480
gacacattgg tttcatattg gcatttcttt actaagaaac aaaccgatga aaaaataata   540
agcagtttcg aggatacgtt tgagatgttt tgtaggggag tcagcatttt cgggcctttt   600
tgggatcatg tcttaagcta ttggagagga agcttggaag atccaaacca tgtgcttttt   660
atgaagtttg aagagatgaa agcagaacct cgtgaccaga tcaagaaatt tgccgagttc   720
ttaggttgtc cttttactaa ggaagaagaa gagagcggat cggtggatga gattatcgat   780
ctttgttctc tacgtaatct gagcagtttg gagatcaata agaccggaaa attgaattct   840
ggtagagaaa acaaaatgtt tttccgtaaa ggagaagttg gtgattggaa gaactatttg   900
actcctgaaa tggagaacaa aatcgacatg atcattcaag agaaacttca aaactctggt   960
ttgaaattct gagtttgtgc attgtaataa taagactacc tcttatgctg ttgttctatt  1020
ccttttgatg taataatgat tatgaataat ggtctttgtt ttcgttc                1067

<210> SEQ ID NO 54
<211> LENGTH: 323
<212> TYPE: PRT
<213> ORGANISM: Arabidopsis thaliana

<400> SEQUENCE: 54

Met Glu Met Asn Leu Arg Ile Glu Asp Leu Asn Glu Glu Thr Lys Thr
1               5                   10                  15

Leu Ile Ser Ser Leu Pro Ser Asp Lys Asp Phe Thr Gly Lys Thr Ile
            20                  25                  30

Cys Lys Tyr Gln Gly Cys Trp Tyr Thr His Asn Val Leu Gln Ala Val
        35                  40                  45

```
Leu Asn Phe Gln Lys Ser Phe Lys Pro Gln Asp Thr Asp Ile Ile Val
    50              55                  60
Ala Ser Phe Pro Lys Cys Gly Thr Thr Trp Leu Lys Ala Leu Thr Phe
 65              70                  75                  80
Ala Leu Leu His Arg Ser Lys Gln Pro Ser His Asp Asp Asp His Pro
                 85                  90                  95
Leu Leu Ser Asn Asn Pro His Val Leu Val Pro Tyr Phe Glu Ile Asp
            100                 105                 110
Leu Tyr Leu Arg Ser Glu Asn Pro Asp Leu Thr Lys Phe Ser Ser Ser
            115                 120                 125
Pro Arg Leu Phe Ser Thr His Val Pro Ser His Thr Leu Gln Glu Gly
130                 135                 140
Leu Lys Gly Ser Thr Cys Lys Ile Val Tyr Ile Ser Arg Asn Val Lys
145                 150                 155                 160
Asp Thr Leu Val Ser Tyr Trp His Phe Phe Thr Lys Lys Gln Thr Asp
                165                 170                 175
Glu Lys Ile Ile Ser Ser Phe Glu Asp Thr Phe Glu Met Phe Cys Arg
            180                 185                 190
Gly Val Ser Ile Phe Gly Pro Phe Trp Asp His Val Leu Ser Tyr Trp
            195                 200                 205
Arg Gly Ser Leu Glu Asp Pro Asn His Val Leu Phe Met Lys Phe Glu
210                 215                 220
Glu Met Lys Ala Glu Pro Arg Asp Gln Ile Lys Lys Phe Ala Glu Phe
225                 230                 235                 240
Leu Gly Cys Pro Phe Thr Lys Glu Glu Glu Ser Gly Ser Val Asp
                245                 250                 255
Glu Ile Ile Asp Leu Cys Ser Leu Arg Asn Leu Ser Ser Leu Glu Ile
            260                 265                 270
Asn Lys Thr Gly Lys Leu Asn Ser Gly Arg Glu Asn Lys Met Phe Phe
            275                 280                 285
Arg Lys Gly Glu Val Gly Asp Trp Lys Asn Tyr Leu Thr Pro Glu Met
            290                 295                 300
Glu Asn Lys Ile Asp Met Ile Ile Gln Glu Lys Leu Gln Asn Ser Gly
305                 310                 315                 320
Leu Lys Phe

<210> SEQ ID NO 55
<211> LENGTH: 990
<212> TYPE: DNA
<213> ORGANISM: Arabidopsis thaliana

<400> SEQUENCE: 55
atggatgaga aaagattac gatgaacgtg agaaacgatg agttaagcga agaatcaaaa     60
actctaatct cttcacttcc ttcagacaaa aattccactg gggtaaatgt ttgtaagtac    120
caaggatgtt ggtatactcc gcctattctc caaggtgtcc tcaatttcca gaaaactttt    180
aagcctcaag acaccgatat catcgttgct tcgttcccta atgcggcac cacttggctc    240 aaggcgctta cattcgcact cgttcgtaga tcgaagcacc cttctcatga tgatcatcat    300
ccacttcttt ctgataatcc acacgttctt tcaccctccc ttgagatgta tctctatcta    360
tgtagcgaaa atcccgacct taccaagttc tcatcatctt cgaggctgtt ttcgacacac    420
atgccgtcac atacattgca agaaggtctc aaaggttcta cttgtaaaat tgtgtatatg    480
tctagaaacg taaagacac attggtttca tattggcatt tcttttgtaa gaaacaaacc    540
```

-continued

```
gatgataaca taataagcag tgtcgaggat acatttgaga tgttttgtag gggagtcaac    600
tttttcgggc cttttgggga ccatgtccta agctactgga gaggaagctt ggaagatcca    660
aaccatgtgc ttttatgaa gtttgaggag atgaaagaag aacctcgtga gcagatcaag     720
agactagccg aattcttagg atgtcttttt actaaggaag aagaagaaag cggcttggtg    780
gatgagatta tcgatctttg ctctctacgt aatctgagca gtttggagat caataagacc    840
ggaaaattgc atagtactgg tagagagaac aaaacatttt tccgtaaggg agaagttggt    900
gactggaaga actatttgac tcctgaaatg gagaacaaaa tcgacatgat cattcaagag    960
aaacttcaaa actctggttt gaaattctga                                      990
```

<210> SEQ ID NO 56
<211> LENGTH: 329
<212> TYPE: PRT
<213> ORGANISM: Arabidopsis thaliana

<400> SEQUENCE: 56

```
Met Asp Glu Lys Lys Ile Thr Met Asn Val Arg Asn Asp Glu Leu Ser
1               5                   10                  15

Glu Glu Ser Lys Thr Leu Ile Ser Ser Leu Pro Ser Asp Lys Asn Ser
            20                  25                  30

Thr Gly Val Asn Val Cys Lys Tyr Gln Gly Cys Trp Tyr Thr Pro Pro
        35                  40                  45

Ile Leu Gln Gly Val Leu Asn Phe Gln Lys Asn Phe Lys Pro Gln Asp
    50                  55                  60

Thr Asp Ile Ile Val Ala Ser Phe Pro Lys Cys Gly Thr Thr Trp Leu
65                  70                  75                  80

Lys Ala Leu Thr Phe Ala Leu Val Arg Arg Ser Lys His Pro Ser His
                85                  90                  95

Asp Asp His His Pro Leu Leu Ser Asp Asn Pro His Val Leu Ser Pro
            100                 105                 110

Ser Leu Glu Met Tyr Leu Tyr Leu Cys Ser Glu Asn Pro Asp Leu Thr
        115                 120                 125

Lys Phe Ser Ser Ser Ser Arg Leu Phe Ser Thr His Met Pro Ser His
    130                 135                 140

Thr Leu Gln Glu Gly Leu Lys Gly Ser Thr Cys Lys Ile Val Tyr Met
145                 150                 155                 160

Ser Arg Asn Val Lys Asp Thr Leu Val Ser Tyr Trp His Phe Phe Cys
                165                 170                 175

Lys Lys Gln Thr Asp Asp Asn Ile Ile Ser Ser Val Glu Asp Thr Phe
            180                 185                 190

Glu Met Phe Cys Arg Gly Val Asn Phe Phe Gly Pro Phe Trp Asp His
        195                 200                 205

Val Leu Ser Tyr Trp Arg Gly Ser Leu Glu Asp Pro Asn His Val Leu
    210                 215                 220

Phe Met Lys Phe Glu Glu Met Lys Glu Glu Pro Arg Glu Gln Ile Lys
225                 230                 235                 240

Arg Leu Ala Glu Phe Leu Gly Cys Leu Phe Thr Lys Glu Glu Glu Glu
                245                 250                 255

Ser Gly Leu Val Asp Glu Ile Ile Asp Leu Cys Ser Leu Arg Asn Leu
            260                 265                 270

Ser Ser Leu Glu Ile Asn Lys Thr Gly Lys Leu His Ser Thr Gly Arg
        275                 280                 285

Glu Asn Lys Thr Phe Phe Arg Lys Gly Glu Val Gly Asp Trp Lys Asn
```

```
                290                 295                 300
Tyr Leu Thr Pro Glu Met Glu Asn Lys Ile Asp Met Ile Ile Gln Glu
305                 310                 315                 320

Lys Leu Gln Asn Ser Gly Leu Lys Phe
                325

<210> SEQ ID NO 57
<211> LENGTH: 2479
<212> TYPE: DNA
<213> ORGANISM: Arabidopsis thaliana

<400> SEQUENCE: 57
tctcttcgag cgatgcgttg aagaaaggcg agtgaccaac aacaatggcg aaaatatctt      60
tcctctcttc ttattcttct tcttcttatc acgatcctca ttataaaccc taaattttc     120 caacagtttt tctctttctc tctaacttct ccgatctccg attttctct tctccgagat     180 gatgacggag gcgacgaagg tgttgtatat agtggtgcgt gaagaaggtg atgatgatga     240
taataatgga gatgattcgt ttaggtatac gcgtcctgtt ttgcagagta ctcttcagct     300
tatgggttgc aaagctcgtc acgccttcaa gccgtagggt ttttgagtta ataagaagtg     360
agggatcttg taatacttca ccagagaatg gaaggaacc tgaatttgct aaggaagttg     420
gtggttcaac ttgtgtagag aaacttaact gtttggttgt tgctggtgat gttgacaaga     480
ataagagtaa gccatttgag atgtacaaaa acggacaac tgttgttgtt tcacgagaga     540
tattcgttga tgttgtgtgt gatgcactgg ctgaatataa gtatgttggt cgcgaccaaa     600
gggcagattt gattctggca tgcagaatcc gagaaaggaa agaatctgta actgttttgc     660
tctgtggcac cagcggctgt ggtaaatcta cgttgtctgc attgctgggt agcaggttgg     720
gtattacgac tgtggtatca actgactcta taaggcacat gatgaggagc tttgctgatg     780
agaagcagaa tcctttgctg tgggcttcaa cataccatgc tggagagtac cttgaccctg     840
tggcagttgc cgagtcaaaa gccaaaagaa aagccaaaaa actgaaaggc tctcgaggtg     900
taaactccaa tgcccaaaag acggatgctg atcaaactc tagcaccact gagttgctaa     960
gtcataagca gatggctata aagggtata aggcacaaag tgagatggtg attgacagtc    1020
ttgataggct cattaccact tgggaagaga ggaatgagtc agtagtcgtt gaaggagtcc    1080
acttaagcct caactttgtg atgggactga tgaaaagca ccttcgatt gttcccttca    1140 tggtatacat cgctaacgag gagaaacact tggaacggtt tgctgtccga gccaagtaca    1200
tgacattgga cccagcaaag aataagtatg taaaatatat acgtaacatc agaacaatac    1260
aggattatct atgcaaacga gctgacaaac atctcgttcc taagataaac aacacaaatg    1320
tcgacaagag cgtggctaca atccacgcga cggtctttgg ttgcctgcgt agacgtgaaa    1380
ctggagagaa gctctatgat acaaccacaa acaccgtttc tgttattgac gacgagcata    1440
ggaaccaatg tgcagccaat tcattaactt ccaagggaat gtttcaggtg atccaaagac    1500
aaggctcctc taggcgattt atggctcttt gcaatactga tggtacggta gcaaaaactt    1560
ggcctgttgc ttccgttggt aagatcagga agcccgtcgt gaatactgag atggatgatg    1620
gaacagagca tcaactacat aaagctgaac cagtgaatct tcaatttggt cactttggga    1680
tcagcgcttg gcctagtgat ggcgcaacta gccacgccgg gagtgtggat gacttaagag    1740
cagatattat tgaaaccgga agcaggcatt actcttcttg ctgcagttcg cctcggacat    1800
ctgatgggcc ttcaaaagag ctgatggagg agcagtctgt gaatgggagc gatgaagatg    1860
atgaagaagg cgacgatgat tttcatgagc ctgattctga tgaagatctc agcgataaca    1920
```

```
atgacgagcg caaccgcgac gagattggat cggtggatga ggaatcgaca aagtcagatg   1980
aagagtacga tgatctggca atggaagaca agagttactg gacagacaac gaagaagaag   2040
agtctcgaga cacaatctcc atggtatcgc aaaacaacca caacgaggct tcaaagacca   2100
acaaagatga caaatactcc caaaacctcg atcttttcct caagacaacg aaccagccat   2160
tgactgaatc ccttgagctc acgagtgaat acagaaacag aatgggagta gccgcctcgg   2220
ataaagccaa gatgaggaaa cgttcactta gtattccgcc tgtcgggaaa catggttcaa   2280
tcatagatga ccagattttg gctaaccaga ctgattcagt actctaaagt gccccgtgac   2340
ctctttgcct gtggttttct ggttttttttt tctttccgtt tttttttttt ttgtgtttta   2400
acctatcagg tagcttaggt ttccaaaact cattgaagtg taaaacaaaa tttgctaatt   2460
tcatacatct ctgtgcacc                                                 2479
```

<210> SEQ ID NO 58
<211> LENGTH: 698
<212> TYPE: PRT
<213> ORGANISM: Arabidopsis thaliana

<400> SEQUENCE: 58

```
Met Met Met Ile Ile Met Glu Met Ile Arg Leu Gly Ile Arg Val Leu
1               5                   10                  15

Phe Cys Arg Val Leu Phe Ser Leu Trp Val Ala Lys Leu Val Thr Pro
            20                  25                  30

Ser Ser Arg Arg Val Phe Glu Leu Ile Arg Ser Glu Gly Ser Cys Asn
        35                  40                  45

Thr Ser Pro Glu Asn Gly Lys Glu Pro Glu Phe Ala Lys Glu Val Gly
    50                  55                  60

Gly Ser Thr Cys Val Glu Lys Leu Asn Cys Leu Val Val Ala Gly Asp
65                  70                  75                  80

Val Asp Lys Asn Lys Ser Lys Pro Phe Glu Met Tyr Lys Arg Arg Thr
                85                  90                  95

Thr Val Val Ser Arg Glu Ile Phe Val Asp Val Val Cys Asp Ala
            100                 105                 110

Leu Ala Glu Tyr Lys Tyr Val Gly Arg Asp Gln Arg Ala Asp Leu Ile
        115                 120                 125

Leu Ala Cys Arg Ile Arg Glu Arg Lys Glu Ser Val Thr Val Leu Leu
    130                 135                 140

Cys Gly Thr Ser Gly Cys Gly Lys Ser Thr Leu Ser Ala Leu Leu Gly
145                 150                 155                 160

Ser Arg Leu Gly Ile Thr Thr Val Val Ser Thr Asp Ser Ile Arg His
                165                 170                 175

Met Met Arg Ser Phe Ala Asp Glu Lys Gln Asn Pro Leu Leu Trp Ala
            180                 185                 190

Ser Thr Tyr His Ala Gly Glu Tyr Leu Asp Pro Val Ala Val Ala Glu
        195                 200                 205

Ser Lys Ala Lys Arg Lys Ala Lys Lys Leu Lys Gly Ser Arg Gly Val
    210                 215                 220

Asn Ser Asn Ala Gln Lys Thr Asp Ala Gly Ser Asn Ser Ser Thr Thr
225                 230                 235                 240

Glu Leu Leu Ser His Lys Gln Met Ala Ile Glu Gly Tyr Lys Ala Gln
                245                 250                 255

Ser Glu Met Val Ile Asp Ser Leu Asp Arg Leu Ile Thr Thr Trp Glu
            260                 265                 270
```

```
Glu Arg Asn Glu Ser Val Val Glu Gly Val His Leu Ser Leu Asn
        275                 280                 285

Phe Val Met Gly Leu Met Lys Lys His Pro Ser Ile Val Pro Phe Met
    290                 295                 300

Val Tyr Ile Ala Asn Glu Glu Lys His Leu Glu Arg Phe Ala Val Arg
305                 310                 315                 320

Ala Lys Tyr Met Thr Leu Asp Pro Ala Lys Asn Lys Tyr Val Lys Tyr
                325                 330                 335

Ile Arg Asn Ile Arg Thr Ile Gln Asp Tyr Leu Cys Lys Arg Ala Asp
                340                 345                 350

Lys His Leu Val Pro Lys Ile Asn Asn Thr Asn Val Asp Lys Ser Val
            355                 360                 365

Ala Thr Ile His Ala Thr Val Phe Gly Cys Leu Arg Arg Arg Glu Thr
        370                 375                 380

Gly Glu Lys Leu Tyr Asp Thr Thr Asn Thr Val Ser Val Ile Asp
385                 390                 395                 400

Asp Glu His Arg Asn Gln Cys Ala Ala Asn Ser Leu Thr Ser Lys Gly
                405                 410                 415

Met Phe Gln Val Ile Gln Arg Gln Gly Ser Ser Arg Arg Phe Met Ala
            420                 425                 430

Leu Cys Asn Thr Asp Gly Thr Val Ala Lys Thr Trp Pro Val Ala Ser
        435                 440                 445

Val Gly Lys Ile Arg Lys Pro Val Val Asn Thr Glu Met Asp Asp Gly
    450                 455                 460

Thr Glu His Gln Leu His Lys Ala Glu Pro Val Asn Leu Gln Phe Gly
465                 470                 475                 480

His Phe Gly Ile Ser Ala Trp Pro Ser Asp Gly Ala Thr Ser His Ala
                485                 490                 495

Gly Ser Val Asp Asp Leu Arg Ala Asp Ile Ile Glu Thr Gly Ser Arg
            500                 505                 510

His Tyr Ser Ser Cys Cys Ser Ser Pro Arg Thr Ser Asp Gly Pro Ser
        515                 520                 525

Lys Glu Leu Met Glu Glu Gln Ser Val Asn Gly Ser Asp Glu Asp Asp
    530                 535                 540

Glu Glu Gly Asp Asp Asp Phe His Glu Pro Asp Ser Asp Glu Asp Leu
545                 550                 555                 560

Ser Asp Asn Asn Asp Glu Arg Asn Arg Asp Glu Ile Gly Ser Val Asp
                565                 570                 575

Glu Glu Ser Thr Lys Ser Asp Glu Glu Tyr Asp Asp Leu Ala Met Glu
            580                 585                 590

Asp Lys Ser Tyr Trp Thr Asp Asn Glu Glu Glu Ser Arg Asp Thr
        595                 600                 605

Ile Ser Met Val Ser Gln Asn Asn His Asn Glu Ala Ser Lys Thr Asn
    610                 615                 620

Lys Asp Asp Lys Tyr Ser Gln Asn Leu Asp Leu Phe Leu Lys Thr Thr
625                 630                 635                 640

Asn Gln Pro Leu Thr Glu Ser Leu Glu Leu Thr Ser Glu Tyr Arg Asn
                645                 650                 655

Arg Met Gly Val Ala Ala Ser Asp Lys Ala Lys Met Arg Lys Arg Ser
            660                 665                 670

Leu Ser Ile Pro Pro Val Gly Lys His Gly Ser Ile Ile Asp Asp Gln
        675                 680                 685
```

Ile Leu Ala Asn Gln Thr Asp Ser Val Leu
    690                 695

<210> SEQ ID NO 59
<211> LENGTH: 2532
<212> TYPE: DNA
<213> ORGANISM: Arabidopsis thaliana

<400> SEQUENCE: 59

| | | | | | |
|---|---|---|---|---|---|
| aaagagagag | agagaagaag | aaggtatctt | ttaagaagtc | gtgaaggctc | tcttcgagcg | 60 |
| atgcgttgaa | gaaaggcgag | tgaccaacaa | caatggcgaa | aatatctttc | ctctcttctt | 120 |
| attcttcttc | ttcttatcac | gatcctcatt | ataaaccta | aattttccca | acagtttttc | 180 |
| tctttctctc | taacttctcc | gatctccgat | ttttctcttc | tccgagatga | tgacggaggc | 240 |
| gacgaaggtg | ttgtatatag | tggtgcgtga | agaaggtgat | gatgatgata | ataatggaga | 300 |
| tgattcgttt | aggtatacgc | gtcctgtttt | gcagagtact | cttcagctta | tgggttgcaa | 360 |
| agctcgtcac | gccttcaaga | tcagccgtag | ggttttgag | ttaataagaa | gtgagggatc | 420 |
| ttgtaatact | tcaccagaga | atgggaagga | acctgaattt | gctaaggaag | ttggtggttc | 480 |
| aacttgtgta | gagaaactta | actgtttggt | tgttgctggt | gatgttgaca | agaataagag | 540 |
| taagccattt | gagatgtaca | aaagacggac | aactgttgtt | gtttcacgag | agatattcgt | 600 |
| tgatgttgtg | tgtgatgcac | tggctgaata | aagtatgtt | ggtcgcgacc | aaagggcaga | 660 |
| tttgattctg | gcatgcagaa | tccgagaaag | gaaagaatct | gtaactgttt | tgctctgtgg | 720 |
| caccagcggc | tgtggtaaat | ctacgttgtc | tgcattgctg | ggtagcaggt | tgggtattac | 780 |
| gactgtggta | tcaactgact | ctataaggca | catgatgagg | agctttgctg | atgagaagca | 840 |
| gaatcctttg | ctgtgggctt | caacatacca | tgctggagag | taccttgacc | ctgtggcagt | 900 |
| tgccgagtca | aaagccaaaa | gaaaagccaa | aaaactgaaa | ggctctcgag | gtgtaaactc | 960 |
| caatgcccaa | aagacggatg | ctggatcaaa | ctctagcacc | actgagttgc | taagtcataa | 1020 |
| gcagatggct | atagaagggt | ataaggcaca | aagtgagatg | gtgattgaca | gtcttgatag | 1080 |
| gctcattacc | acttgggaag | agaggaatga | gtcagtagtc | gttgaaggag | tccacttaag | 1140 |
| cctcaacttt | gtgatgggac | tgatgaaaaa | gcacccttcg | attgttccct | tcatggtata | 1200 |
| catcgctaac | gaggagaaac | acttggaacg | gtttgctgtc | cgagccaagt | acatgacatt | 1260 |
| ggacccagca | aagaataagt | atgtaaaata | tatacgtaac | atcagaacaa | tacaggatta | 1320 |
| tctatgcaaa | cgagctgaca | aacatctcgt | tcctaagata | aacaacacaa | atgtcgacaa | 1380 |
| gagcgtggct | acaatccacg | cgacggtctt | tggttgcctg | cgtagacgtg | aaactggaga | 1440 |
| gaagctctat | gatacaacca | caaacaccgt | ttctgttatt | gacgacgagc | ataggaacca | 1500 |
| atgtgcagcc | aattcattaa | cttccaaggg | aatgtttcag | gtgatccaaa | gacaaggctc | 1560 |
| ctctaggcga | tttatggctc | tttgcaatac | tgatggtacg | gtagcaaaaa | cttggcctgt | 1620 |
| tgcttccgtt | ggtaagatca | ggaagcccgt | cgtgaatact | gagatggatg | atggaacaga | 1680 |
| gcatcaacta | cataaagctg | aaccagtgaa | tcttcaattt | ggtcactttg | ggatcagcgc | 1740 |
| ttggcctagt | gatggcgcaa | ctagccacgc | cgggagtgtg | atgacttaa | gagcagatat | 1800 |
| tattgaaacc | ggaagcaggc | attactcttc | ttgctgcagt | tcgcctcgga | catctgatgg | 1860 |
| gccttcaaaa | gagctgatgg | aggagcagtc | tgtgaatggg | agcgatgaag | atgatgaaga | 1920 |
| aggcgacgat | gattttcatg | agcctgattc | tgatgaagat | ctcagcgata | caatgacgaa | 1980 |
| gcgcaaccgc | gacgagattg | gatcggtgga | tgaggaatcg | acaaagtcag | atgaagagta | 2040 |

```
cgatgatctg gcaatggaag acaagagtta ctggacagac aacgaagaag aagagtctcg   2100
agacacaatc tccatggtat cgcaaaacaa ccacaacgag gcttcaaaga ccaacaaaga   2160
tgacaaatac tcccaaaacc tcgatctttt cctcaagaca acgaaccagc cattgactga   2220
atcccttgag ctcacgagtg aatacagaaa cagaatggga gtagccgcct cggataaagc   2280
caagatgagg aaacgttcac ttagtattcc gcctgtcggg aaacatggtt caatcataga   2340
tgaccagatt ttggctaacc agactgattc agtactctaa agtgcccgt gacctctttg    2400 cctgtggttt tctggttttt ttttctttcc gtttttttt tttttgtgtt ttaacctatc    2460
aggtagctta ggtttccaaa actcattgaa gtgtaaaaca aaatttgcta atttcataca   2520
tctctgtgca cc                                                       2532
```

<210> SEQ ID NO 60
<211> LENGTH: 717
<212> TYPE: PRT
<213> ORGANISM: Arabidopsis thaliana

<400> SEQUENCE: 60

```
Met Met Thr Glu Ala Thr Lys Val Leu Tyr Ile Val Val Arg Glu Glu
1               5                   10                  15

Gly Asp Asp Asp Asn Asn Gly Asp Ser Phe Arg Tyr Thr Arg
            20                  25                  30

Pro Val Leu Gln Ser Thr Leu Gln Leu Met Gly Cys Lys Ala Arg His
        35                  40                  45

Ala Phe Lys Ile Ser Arg Arg Val Phe Glu Leu Ile Arg Ser Glu Gly
    50                  55                  60

Ser Cys Asn Thr Ser Pro Glu Asn Gly Lys Glu Pro Glu Phe Ala Lys
65                  70                  75                  80

Glu Val Gly Gly Ser Thr Cys Val Glu Lys Leu Asn Cys Leu Val Val
                85                  90                  95

Ala Gly Asp Val Asp Lys Asn Lys Ser Lys Pro Phe Glu Met Tyr Lys
            100                 105                 110

Arg Arg Thr Thr Val Val Val Ser Arg Glu Ile Phe Val Asp Val Val
        115                 120                 125

Cys Asp Ala Leu Ala Glu Tyr Lys Tyr Val Gly Arg Asp Gln Arg Ala
    130                 135                 140

Asp Leu Ile Leu Ala Cys Arg Ile Arg Glu Arg Lys Glu Ser Val Thr
145                 150                 155                 160

Val Leu Leu Cys Gly Thr Ser Gly Cys Gly Lys Ser Thr Leu Ser Ala
                165                 170                 175

Leu Leu Gly Ser Arg Leu Gly Ile Thr Thr Val Val Ser Thr Asp Ser
            180                 185                 190

Ile Arg His Met Met Arg Ser Phe Ala Asp Glu Lys Gln Asn Pro Leu
        195                 200                 205

Leu Trp Ala Ser Thr Tyr His Ala Gly Glu Tyr Leu Asp Pro Val Ala
    210                 215                 220

Val Ala Glu Ser Lys Ala Lys Arg Lys Ala Lys Lys Leu Lys Gly Ser
225                 230                 235                 240

Arg Gly Val Asn Ser Asn Ala Gln Lys Thr Asp Ala Gly Ser Asn Ser
                245                 250                 255

Ser Thr Thr Glu Leu Leu Ser His Lys Gln Met Ala Ile Glu Gly Tyr
            260                 265                 270

Lys Ala Gln Ser Glu Met Val Ile Asp Ser Leu Asp Arg Leu Ile Thr
        275                 280                 285
```

```
Thr Trp Glu Glu Arg Asn Glu Ser Val Val Gly Val His Leu
    290                 295                 300
Ser Leu Asn Phe Val Met Gly Leu Met Lys Lys His Pro Ser Ile Val
305                 310                 315                 320
Pro Phe Met Val Tyr Ile Ala Asn Glu Glu Lys His Leu Glu Arg Phe
                    325                 330                 335
Ala Val Arg Ala Lys Tyr Met Thr Leu Asp Pro Ala Lys Asn Lys Tyr
                340                 345                 350
Val Lys Tyr Ile Arg Asn Ile Arg Thr Ile Gln Asp Tyr Leu Cys Lys
            355                 360                 365
Arg Ala Asp Lys His Leu Val Pro Lys Ile Asn Asn Thr Asn Val Asp
370                 375                 380
Lys Ser Val Ala Thr Ile His Ala Thr Val Phe Gly Cys Leu Arg Arg
385                 390                 395                 400
Arg Glu Thr Gly Glu Lys Leu Tyr Asp Thr Thr Asn Thr Val Ser
                405                 410                 415
Val Ile Asp Asp Glu His Arg Asn Gln Cys Ala Ala Asn Ser Leu Thr
                420                 425                 430
Ser Lys Gly Met Phe Gln Val Ile Gln Arg Gln Gly Ser Ser Arg Arg
            435                 440                 445
Phe Met Ala Leu Cys Asn Thr Asp Gly Thr Val Ala Lys Thr Trp Pro
450                 455                 460
Val Ala Ser Val Gly Lys Ile Arg Lys Pro Val Val Asn Thr Glu Met
465                 470                 475                 480
Asp Asp Gly Thr Glu His Gln Leu His Lys Ala Glu Pro Val Asn Leu
                485                 490                 495
Gln Phe Gly His Phe Gly Ile Ser Ala Trp Pro Ser Asp Gly Ala Thr
                500                 505                 510
Ser His Ala Gly Ser Val Asp Asp Leu Arg Ala Asp Ile Ile Glu Thr
            515                 520                 525
Gly Ser Arg His Tyr Ser Ser Cys Cys Ser Ser Pro Arg Thr Ser Asp
            530                 535                 540
Gly Pro Ser Lys Glu Leu Met Glu Glu Gln Ser Val Asn Gly Ser Asp
545                 550                 555                 560
Glu Asp Asp Glu Glu Gly Asp Asp Phe His Glu Pro Asp Ser Asp
                565                 570                 575
Glu Asp Leu Ser Asp Asn Asn Asp Glu Arg Asn Arg Asp Glu Ile Gly
                580                 585                 590
Ser Val Asp Glu Glu Ser Thr Lys Ser Asp Glu Tyr Asp Asp Leu
            595                 600                 605
Ala Met Glu Asp Lys Ser Tyr Trp Thr Asp Asn Glu Glu Glu Ser
610                 615                 620
Arg Asp Thr Ile Ser Met Val Ser Gln Asn Asn His Asn Glu Ala Ser
625                 630                 635                 640
Lys Thr Asn Lys Asp Lys Tyr Ser Gln Asn Leu Asp Leu Phe Leu
                645                 650                 655
Lys Thr Thr Asn Gln Pro Leu Thr Glu Ser Leu Glu Leu Thr Ser Glu
                660                 665                 670
Tyr Arg Asn Arg Met Gly Val Ala Ala Ser Asp Lys Ala Lys Met Arg
            675                 680                 685
Lys Arg Ser Leu Ser Ile Pro Pro Val Gly Lys His Gly Ser Ile Ile
690                 695                 700
```

-continued

Asp Asp Gln Ile Leu Ala Asn Gln Thr Asp Ser Val Leu
705                 710                 715

<210> SEQ ID NO 61
<211> LENGTH: 1589
<212> TYPE: DNA
<213> ORGANISM: Arabidopsis thaliana

<400> SEQUENCE: 61

| | | | | | |
|---|---|---|---|---|---|
| gtcaagtcac | cggagacagc | gactcacggc | ctctttggtg | gatcctcggt | ggctctctca | 60 |
| gcctctttgc | tccgcccgcg | aatctttccc | aattgtatct | atggcggaac | caccaaagct | 120 |
| tagggtttta | atggtctctg | atttcttctt | cccaaacttt | ggtggtgtcg | agaatcacat | 180 |
| ctattacctc | tctcaatgct | tgttaaagct | cggtcacaag | gtggttgtta | tgacacatgc | 240 |
| ttatgggaac | cggtctggag | ttagatacat | gactggtgga | ctcaaagtct | attatgtacc | 300 |
| ttggagacct | tttgttatgc | agactacatt | tccgacggtt | tatggaacac | ttcccattgt | 360 |
| gaggactata | cttagacgcg | agaaaatcac | ggtagttcat | ggacatcaag | ctttctctac | 420 |
| gctttgtcat | gaagctttaa | tgcatgccag | acaatgggc | tataaagttg | tgttcacaga | 480 |
| tcattccttg | tacggttttg | ctgatgttgg | tagcatccat | atgaacaagg | ttttacagtt | 540 |
| tagtttagca | gatattgatc | aggcgatttg | tgtttcacac | acgagcaagg | agaatacggt | 600 |
| tctaaggtct | ggattgtccc | cagcaaaggt | ttttatgata | ccgaatgctg | ttgatactgc | 660 |
| tatgttcaag | cccgcttctg | ttcgacccag | tactgatatt | attactatag | ttgtcataag | 720 |
| tagattggtt | tatcgaaaag | gtgcggattt | gctcgtggaa | gtcattccag | aagtatgccg | 780 |
| tttataccca | aatgttcgtt | ttgtagttgg | aggggatgga | ccaaaacatg | tgcgactcga | 840 |
| ggaaatgaga | gagaagcatt | ctctacaaga | tagagtcgaa | atgctaggtg | cagttccgca | 900 |
| ttctcgtgtg | cgctctgttt | tggttaccgg | tcatattttc | ttaaacagtt | ctttaacaga | 960 |
| agccttctgc | atagctatat | tagaggcggc | tagttgcgga | ttattaactg | tcagcactcg | 1020 |
| tgttggaggt | gtcccagagg | tcttaccaga | tgacatggtt | gtacttgctg | aaccagatcc | 1080 |
| ggatgatatg | gtacgagcta | ttgagaaggc | aatatcaata | cttccaacta | ttaaccccga | 1140 |
| ggagatgcac | aatcgaatga | agaagctcta | cagttggcaa | gatgttgcta | aaagaaccga | 1200 |
| gattgtgtat | gaccgtgcct | tgaagtgttc | aaataggagt | cttctagaac | gtctaatgcg | 1260 |
| gttcctctcg | tgtggagctt | gggcagggaa | gctattttgt | atggttatga | tcctcgatta | 1320 |
| cttgctttgg | cggttacttc | agttactgca | gcctgatgaa | gatatcgagg | aggcacccga | 1380 |
| tatctgtctt | tgccatcacc | gaggggttga | ggtatctgag | ggtctaagga | agaagataaa | 1440 |
| gtgagaaatg | ggtgagtaga | gtttcatctc | cgtcgatatt | tggcattttg | ttccttgaaa | 1500 |
| ttatacaagt | gagctcttga | ttcattgttt | tcgtaggacc | taagtaactt | cataaactta | 1560 |
| ttatctatac | agtttccaga | tatttcatt | | | | 1589 |

<210> SEQ ID NO 62
<211> LENGTH: 447
<212> TYPE: PRT
<213> ORGANISM: Arabidopsis thaliana

<400> SEQUENCE: 62

Met Ala Glu Pro Pro Lys Leu Arg Val Leu Met Val Ser Asp Phe Phe
1               5                   10                  15

Phe Pro Asn Phe Gly Gly Val Glu Asn His Ile Tyr Tyr Leu Ser Gln
            20                  25                  30

```
Cys Leu Leu Lys Leu Gly His Lys Val Val Met Thr His Ala Tyr
         35                  40                  45

Gly Asn Arg Ser Gly Val Arg Tyr Met Thr Gly Gly Leu Lys Val Tyr
 50                  55                  60

Tyr Val Pro Trp Arg Pro Phe Val Met Gln Thr Thr Phe Pro Thr Val
 65                  70                  75                  80

Tyr Gly Thr Leu Pro Ile Val Arg Thr Ile Leu Arg Arg Glu Lys Ile
                 85                  90                  95

Thr Val Val His Gly His Gln Ala Phe Ser Thr Leu Cys His Glu Ala
                100                 105                 110

Leu Met His Ala Arg Thr Met Gly Tyr Lys Val Phe Thr Asp His
        115                 120                 125

Ser Leu Tyr Gly Phe Ala Asp Val Gly Ser Ile His Met Asn Lys Val
130                 135                 140

Leu Gln Phe Ser Leu Ala Asp Ile Asp Gln Ala Ile Cys Val Ser His
145                 150                 155                 160

Thr Ser Lys Glu Asn Thr Val Leu Arg Ser Gly Leu Ser Pro Ala Lys
                165                 170                 175

Val Phe Met Ile Pro Asn Ala Val Asp Thr Ala Met Phe Lys Pro Ala
                180                 185                 190

Ser Val Arg Pro Ser Thr Asp Ile Ile Thr Ile Val Val Ile Ser Arg
                195                 200                 205

Leu Val Tyr Arg Lys Gly Ala Asp Leu Leu Val Glu Val Ile Pro Glu
                210                 215                 220

Val Cys Arg Leu Tyr Pro Asn Val Arg Phe Val Val Gly Gly Asp Gly
225                 230                 235                 240

Pro Lys His Val Arg Leu Glu Glu Met Arg Glu Lys His Ser Leu Gln
                245                 250                 255

Asp Arg Val Glu Met Leu Gly Ala Val Pro His Ser Arg Val Arg Ser
                260                 265                 270

Val Leu Val Thr Gly His Ile Phe Leu Asn Ser Ser Leu Thr Glu Ala
                275                 280                 285

Phe Cys Ile Ala Ile Leu Glu Ala Ala Ser Cys Gly Leu Leu Thr Val
290                 295                 300

Ser Thr Arg Val Gly Gly Val Pro Glu Val Leu Pro Asp Asp Met Val
305                 310                 315                 320

Val Leu Ala Glu Pro Asp Pro Asp Met Val Arg Ala Ile Glu Lys
                325                 330                 335

Ala Ile Ser Ile Leu Pro Thr Ile Asn Pro Glu Glu Met His Asn Arg
                340                 345                 350

Met Lys Lys Leu Tyr Ser Trp Gln Asp Val Ala Lys Arg Thr Glu Ile
        355                 360                 365

Val Tyr Asp Arg Ala Leu Lys Cys Ser Asn Arg Ser Leu Leu Glu Arg
370                 375                 380

Leu Met Arg Phe Leu Ser Cys Gly Ala Trp Ala Gly Lys Leu Phe Cys
385                 390                 395                 400

Met Val Met Ile Leu Asp Tyr Leu Leu Trp Arg Leu Leu Gln Leu Leu
                405                 410                 415

Gln Pro Asp Glu Asp Ile Glu Glu Ala Pro Asp Ile Cys Leu Cys His
                420                 425                 430

His Arg Gly Val Glu Val Ser Glu Gly Leu Arg Lys Lys Ile Lys
            435                 440                 445
```

```
<210> SEQ ID NO 63
<211> LENGTH: 1651
<212> TYPE: DNA
<213> ORGANISM: Arabidopsis thaliana

<400> SEQUENCE: 63
gtcaagtcac cggagacagc gactcacggc ctctttggtg gatcctcggt ggctctctca     60
gcctctttgc tccgcccgcg aatctttccc aattgtatct atggcggaac caccaaagct    120
tagggtttta atggtctctg atttcttctt cccaaacttt ggtggtgtcg agaatcacat    180
ctattacctc tctcaatgct tgttaaagct cggtcacaag gtggttgtta tgacacatgc    240
ttatgggaac cggtctggag ttagatacat gactggtgga ctcaaagtct attatgtacc    300
ttggagacct tttgttatgc agactacatt tccgacggtt tatggaacac ttcccattgt    360
gaggactata cttagacgcg agaaaatcac ggtagttcat ggacatcaag ctttctctac    420
gctttgtcat gaagctttaa tgcatgccag acaatgggc tataaagttg tgttcacaga    480
tcattccttg tacggttttg ctgatgttgg tagcatccat atgaacaagg ttttacagtt    540
tagtttagca gatattgatc aggcgatttg tgtttcacac acgagcaagg agaatacggt    600
tctaaggtct ggattgtccc cagcaaaggt ttttatgata ccgaatgctg ttgatactgc    660
tatgttcaag cccgcttctg ttcgacccag tactgatatt attactatag ttgtcataag    720
tagattggtt tatcgaaaag gtgcggattt gctcgtggaa gtcattccag aagtatgccg    780
tttataccca aatgttcgtt tgtagttgg agggatgga ccaaaacatg tgcgactcga     840
ggaaatgaga gagaagcatt ctctacaaga tagagtcgaa atgctaggtg cagttccgca    900
ttctcgtgtg cgctctgttt tggttaccgg tcatattttc ttaaacagtt ctttaacaga    960
agccttctgc atagctatat tagaggcgg tagttgcgga ttattaactg tcagcactcg   1020
tgttggaggt gtcccagagg tcttaccaga tgacatggtt gtacttgctg aaccagatcc   1080
ggatgatatg gtacgagcta ttgagaaggc aatatcaata cttccaacta ttaaccccga   1140
ggagatgcac aatcgaatga agaagctcta cagttggcaa gatgttgcta aaagaaccga   1200
gattgtgtat gaccgtgcct tgaagtgttc aaataggagt cttctagaac gtctaatgcg   1260
gttcctctcg tgtggagctt gggcagggaa gctattttgt atggttatga tcctcgatta   1320
cttgcttttgg cggttacttc agttactgca gcctgatgaa gatatcgagg aggcacccga   1380
tatctgtctt tgccatcacc gagggtgga ggtatctgag ggtctaagga agaagataaa   1440
gtgagaaatg gaaataacta tggaaaagag agacgatgat gtagcaaaga gttcagactc   1500
gccaggaata agtggttact tttgagtatc ataacattac tgagtttgtt ttactggaaa   1560
ttgtcgtgta aaaattagtt caccattgct tgtacggtga catgagccaa tcctttcgag   1620
aataaatagc atgcatggta attggtaagg c                                   1651

<210> SEQ ID NO 64
<211> LENGTH: 447
<212> TYPE: PRT
<213> ORGANISM: Arabidopsis thaliana

<400> SEQUENCE: 64

Met Ala Glu Pro Pro Lys Leu Arg Val Leu Met Val Ser Asp Phe Phe
1               5                   10                  15

Phe Pro Asn Phe Gly Gly Val Glu Asn His Ile Tyr Tyr Leu Ser Gln
            20                  25                  30

Cys Leu Leu Lys Leu Gly His Lys Val Val Val Met Thr His Ala Tyr
        35                  40                  45
```

Gly Asn Arg Ser Gly Val Arg Tyr Met Thr Gly Gly Leu Lys Val Tyr
 50                  55                  60

Tyr Val Pro Trp Arg Pro Phe Val Met Gln Thr Thr Phe Pro Thr Val
 65                  70                  75                  80

Tyr Gly Thr Leu Pro Ile Val Arg Thr Ile Leu Arg Arg Glu Lys Ile
                 85                  90                  95

Thr Val Val His Gly His Gln Ala Phe Ser Thr Leu Cys His Glu Ala
                100                 105                 110

Leu Met His Ala Arg Thr Met Gly Tyr Lys Val Val Phe Thr Asp His
            115                 120                 125

Ser Leu Tyr Gly Phe Ala Asp Val Gly Ser Ile His Met Asn Lys Val
    130                 135                 140

Leu Gln Phe Ser Leu Ala Asp Ile Asp Gln Ala Ile Cys Val Ser His
145                 150                 155                 160

Thr Ser Lys Glu Asn Thr Val Leu Arg Ser Gly Leu Ser Pro Ala Lys
                165                 170                 175

Val Phe Met Ile Pro Asn Ala Val Asp Thr Ala Met Phe Lys Pro Ala
            180                 185                 190

Ser Val Arg Pro Ser Thr Asp Ile Ile Thr Ile Val Val Ile Ser Arg
    195                 200                 205

Leu Val Tyr Arg Lys Gly Ala Asp Leu Leu Val Glu Val Ile Pro Glu
210                 215                 220

Val Cys Arg Leu Tyr Pro Asn Val Arg Phe Val Val Gly Gly Asp Gly
225                 230                 235                 240

Pro Lys His Val Arg Leu Glu Glu Met Arg Gly Lys His Ser Leu Gln
                245                 250                 255

Asp Arg Val Glu Met Leu Gly Ala Val Pro His Ser Arg Val Arg Ser
            260                 265                 270

Val Leu Val Thr Gly His Ile Phe Leu Asn Ser Ser Leu Thr Glu Ala
    275                 280                 285

Phe Cys Ile Ala Ile Leu Glu Ala Ala Ser Cys Gly Leu Leu Thr Val
290                 295                 300

Ser Thr Arg Val Gly Gly Val Pro Glu Val Leu Pro Asp Asp Met Val
305                 310                 315                 320

Val Leu Ala Glu Pro Asp Pro Asp Met Val Arg Ala Ile Glu Lys
                325                 330                 335

Ala Ile Ser Ile Leu Pro Thr Ile Asn Pro Glu Glu Met His Asn Arg
            340                 345                 350

Met Lys Lys Leu Tyr Ser Trp Gln Asp Val Ala Lys Arg Thr Glu Ile
    355                 360                 365

Val Tyr Asp Arg Ala Leu Lys Cys Ser Asn Arg Ser Leu Leu Glu Arg
    370                 375                 380

Leu Met Arg Phe Leu Ser Cys Gly Ala Trp Ala Gly Lys Leu Phe Cys
385                 390                 395                 400

Met Val Met Ile Leu Asp Tyr Leu Leu Trp Arg Leu Leu Gln Leu Leu
                405                 410                 415

Gln Pro Asp Glu Asp Ile Glu Glu Ala Pro Asp Ile Cys Leu Cys His
            420                 425                 430

His Arg Gly Val Glu Val Ser Glu Gly Leu Arg Lys Lys Ile Lys
    435                 440                 445

<210> SEQ ID NO 65
<211> LENGTH: 363

<212> TYPE: DNA
<213> ORGANISM: Arabidopsis thaliana

<400> SEQUENCE: 65

| | | | | | |
|---|---|---|---|---|---|
| atgaatcatt | ttggtaatca | ttgtactaac | acaagcggtg | ttgtttgtca | taacaattac | 60 |
| aactgtacta | ttgataactc | tatccattat | gcggatacac | gtggtgttgt | tagccatcac | 120 |
| cgagagaata | ttactggcca | tcatggactg | gtatttccgg | cggctacaat | gaacggatat | 180 |
| ggtcctgcaa | ctagttttcc | agatatgagg | gaaaatgggc | acttgatggt | gaatcaaaat | 240 |
| agacctgtga | cgctacgacc | atcaatgtcc | cagcagcaac | cacaaccaca | accactgtct | 300 |
| gatgagtata | ataaggtgga | gacggggact | gctgagcaag | tctatgtccc | ctctcgagac | 360 |
| taa | | | | | | 363 |

<210> SEQ ID NO 66
<211> LENGTH: 120
<212> TYPE: PRT
<213> ORGANISM: Arabidopsis thaliana

<400> SEQUENCE: 66

Met Asn His Phe Gly Asn His Cys Thr Asn Thr Ser Gly Val Val Cys
1               5                   10                  15

His Asn Asn Tyr Asn Cys Thr Ile Asp Asn Ser Ile His Tyr Ala Asp
            20                  25                  30

Thr Arg Gly Val Val Ser His His Arg Glu Asn Ile Thr Gly His His
        35                  40                  45

Gly Leu Val Phe Pro Ala Ala Thr Met Asn Gly Tyr Gly Pro Ala Thr
    50                  55                  60

Ser Phe Pro Asp Met Arg Glu Asn Gly His Leu Met Val Asn Gln Asn
65                  70                  75                  80

Arg Pro Val Thr Leu Arg Pro Ser Met Ser Gln Gln Pro Gln Pro
                85                  90                  95

Gln Pro Leu Ser Asp Glu Tyr Asn Lys Val Glu Thr Gly Thr Ala Glu
            100                 105                 110

Gln Val Tyr Val Pro Ser Arg Asp
        115                 120

<210> SEQ ID NO 67
<211> LENGTH: 2489
<212> TYPE: DNA
<213> ORGANISM: Arabidopsis thaliana

<400> SEQUENCE: 67

| | | | | | |
|---|---|---|---|---|---|
| gcactttctg | caaatggttc | tcttcttcct | ttaagctcaa | tctcgccact | ggagtctcaa | 60 |
| tcgggaaaga | tctccatctt | ctccggagga | aaaacggatc | cgtaaatcgt | gaattttaa | 120 |
| acagagaaga | atcaattcaa | tggaggaaga | gaaagcttct | gctgcacaga | gcttaatcga | 180 |
| tgtagttaac | gagattgctg | cgatttctga | ttatcgtata | acagtgaaga | agctttgtta | 240 |
| taatctagcg | aggagattaa | agctgcttgt | tcctatgttt | gaggaaatta | gagaaagtaa | 300 |
| cgaaccgatc | agcgaagata | cgttgaagac | tttgatgaat | ttgaaggaag | ctatgtgttc | 360 |
| agcgaaggat | tatctcaaat | tttgtagcca | agggagcaag | atttatctgg | tgatggagag | 420 |
| ggaacaagtg | acaagtaaat | tgatggaggt | gtctgttaag | ttagaacaat | ctttaagcca | 480 |
| gattccatat | gaagaactcg | atatatcgga | tgaagttaga | gaacaggttg | agctggttct | 540 |
| tagtcagttt | cggcgagcta | aaggaagagt | agatgtatca | gatgatgagc | tatatgaaga | 600 |

```
tcttcagtcg ctttgcaaca aaagtagtga tgtagatgct tatcagcctg tgctagagcg    660
ggttgcgaag aagttacatt tgatggagat tcctgaccta gctcaagaat cagtggctct    720
gcatgaaatg gttgcttcaa gcggtggaga tgttggtgaa atattgagg agatggcaat     780
ggtattaaag atgattaagg attttgtgca gacggaggat gataatggcg aggagcagaa    840
agtaggagtt aactctagaa gcaatggaca gacttctacg gcagcgagtc agaagatacc    900
tgtgattcct gatgattttc gctgtccgat ttcgctggaa atgatgagag atccagttat    960
tgtttcatca gggcagacat acgaacgcac atgtattgag aaatggatag aaggtggaca   1020
ctcgacatgt ccaaaaacac agcaggcgct aacaagcaca accctcacac caaactatgt   1080
tctccgtagt ctcatagctc agtggtgcga ggccaacgat attgagcctc caaagcctcc   1140
gagcagttta agacccagaa aagtatcgtc cttctcatct cccgcagaag cgaacaagat   1200
tgaagatctt atgtggagac ttgcgtacgg aaaccccgag gaccaacgat ctgcagctgg   1260
ggaaatccgc cttcttgcaa acgaaatgc agacaaccgc gtggccatag ccgaagctgg    1320
agccatacct cttctcgtag gtctcctctc aactcctgat tctcgtattc aagaacattc   1380
ggtaacagct cttctaaacc tctccatatg tgagaacaac aaaggagcca ttgtttcagc   1440
tggagctatt cctggtatag ttcaagtgct taagaaagga agcatggagg ccagagagaa   1500
tgcggcggct acactttca gtctatcagt gatcgatgaa ataaagtga ctatcggtgc     1560
cttaggagca attccgccac tcgttgtatt acttaatgaa ggtacacaaa gaggcaagaa   1620
agatgctgct actgcactct ttaacctctg tatataccaa ggaaacaaag gaaaagctat   1680
acgtgcagga gtgattccca cgttgactag actcttgaca gagcccggaa gcggaatggt   1740
cgatgaggca ctcgcgattt tggcgattct ctctagccac cccgaaggaa aagcaatcat   1800
aggatcctct gatgcagtcc caagtttggt tgagtttatc agaactggct cgcctagaaa   1860
cagagaaaac gcagctgctg ttctagtcca cctctgttct ggagacccac aacatcttgt   1920
cgaagcgcag aaactcggcc ttatgggtcc attgatagat ttagctggaa atgggacgga   1980
tagagggaaa cgaaaagcag cgcagttgct tgaacgcatc agccgtctcg ctgaacagca   2040
gaaggaaacg gctgtgtcac aaccggaaga agaagctgaa ccaacacatc cagaatccac   2100
cacagaagct gcagatactt aaagattgtc tttgttttgg atcctcgggt catctctttc   2160
acgtacgtat gtttattatt ctcactttt gtttgtgcta ctcatcctcc ctcgaggtag    2220
gattcacggt agacgcggaa gagggaaatg gcctccttct ccgatctact tttaacttta   2280
tggtgatatc tttgtgtgga cagagcaatc tggtccacag gagagaaaag caaatatgca   2340
tacatacacg tcaacttgta tcattgtaac actatgtttg taatcatttc cacgagcttt   2400
ttttgttttt caatacaaga tctctctgtt cgctttctta atagcattga gatactaatt   2460
gaatataatg cagattccca tttttcatg                                     2489
```

<210> SEQ ID NO 68
<211> LENGTH: 660
<212> TYPE: PRT
<213> ORGANISM: Arabidopsis thaliana

<400> SEQUENCE: 68

Met Glu Glu Glu Lys Ala Ser Ala Ala Gln Ser Leu Ile Asp Val Val
1               5                   10                  15

Asn Glu Ile Ala Ala Ile Ser Asp Tyr Arg Ile Thr Val Lys Lys Leu
            20                  25                  30

Cys Tyr Asn Leu Ala Arg Arg Leu Lys Leu Leu Val Pro Met Phe Glu

```
                 35                  40                  45
Glu Ile Arg Glu Ser Asn Glu Pro Ile Ser Glu Asp Thr Leu Lys Thr
 50                  55                  60
Leu Met Asn Leu Lys Glu Ala Met Cys Ser Ala Lys Asp Tyr Leu Lys
 65                  70                  75                  80
Phe Cys Ser Gln Gly Ser Lys Ile Tyr Leu Val Met Glu Arg Glu Gln
                 85                  90                  95
Val Thr Ser Lys Leu Met Glu Val Ser Val Lys Leu Glu Gln Ser Leu
                100                 105                 110
Ser Gln Ile Pro Tyr Glu Glu Leu Asp Ile Ser Asp Glu Val Arg Glu
                115                 120                 125
Gln Val Glu Leu Val Leu Ser Gln Phe Arg Arg Ala Lys Gly Arg Val
                130                 135                 140
Asp Val Ser Asp Asp Glu Leu Tyr Glu Asp Leu Gln Ser Leu Cys Asn
145                 150                 155                 160
Lys Ser Ser Asp Val Asp Ala Tyr Gln Pro Val Leu Glu Arg Val Ala
                165                 170                 175
Lys Lys Leu His Leu Met Glu Ile Pro Asp Leu Ala Gln Glu Ser Val
                180                 185                 190
Ala Leu His Glu Met Val Ala Ser Gly Gly Asp Val Gly Glu Asn
                195                 200                 205
Ile Glu Glu Met Ala Met Val Leu Lys Met Ile Lys Asp Phe Val Gln
210                 215                 220
Thr Glu Asp Asp Asn Gly Glu Glu Gln Lys Val Gly Val Asn Ser Arg
225                 230                 235                 240
Ser Asn Gly Gln Thr Ser Thr Ala Ala Ser Gln Lys Ile Pro Val Ile
                245                 250                 255
Pro Asp Asp Phe Arg Cys Pro Ile Ser Leu Glu Met Met Arg Asp Pro
                260                 265                 270
Val Ile Val Ser Ser Gly Gln Thr Tyr Glu Arg Thr Cys Ile Glu Lys
                275                 280                 285
Trp Ile Glu Gly Gly His Ser Thr Cys Pro Lys Thr Gln Gln Ala Leu
290                 295                 300
Thr Ser Thr Thr Leu Thr Pro Asn Tyr Val Leu Arg Ser Leu Ile Ala
305                 310                 315                 320
Gln Trp Cys Glu Ala Asn Asp Ile Glu Pro Pro Lys Pro Pro Ser Ser
                325                 330                 335
Leu Arg Pro Arg Lys Val Ser Ser Phe Ser Ser Pro Ala Glu Ala Asn
                340                 345                 350
Lys Ile Glu Asp Leu Met Trp Arg Leu Ala Tyr Gly Asn Pro Glu Asp
                355                 360                 365
Gln Arg Ser Ala Ala Gly Glu Ile Arg Leu Leu Ala Lys Arg Asn Ala
                370                 375                 380
Asp Asn Arg Val Ala Ile Ala Glu Ala Gly Ala Ile Pro Leu Leu Val
385                 390                 395                 400
Gly Leu Leu Ser Thr Pro Asp Ser Arg Ile Gln Glu His Ser Val Thr
                405                 410                 415
Ala Leu Leu Asn Leu Ser Ile Cys Glu Asn Lys Gly Ala Ile Val
                420                 425                 430
Ser Ala Gly Ala Ile Pro Gly Ile Val Gln Val Leu Lys Lys Gly Ser
                435                 440                 445
Met Glu Ala Arg Glu Asn Ala Ala Ala Thr Leu Phe Ser Leu Ser Val
                450                 455                 460
```

```
Ile Asp Glu Asn Lys Val Thr Ile Gly Ala Leu Gly Ala Ile Pro Pro
465                 470                 475                 480

Leu Val Val Leu Leu Asn Glu Gly Thr Gln Arg Gly Lys Lys Asp Ala
                485                 490                 495

Ala Thr Ala Leu Phe Asn Leu Cys Ile Tyr Gln Gly Asn Lys Gly Lys
            500                 505                 510

Ala Ile Arg Ala Gly Val Ile Pro Thr Leu Thr Arg Leu Leu Thr Glu
        515                 520                 525

Pro Gly Ser Gly Met Val Asp Glu Ala Leu Ala Ile Leu Ala Ile Leu
    530                 535                 540

Ser Ser His Pro Glu Gly Lys Ala Ile Ile Gly Ser Ser Asp Ala Val
545                 550                 555                 560

Pro Ser Leu Val Glu Phe Ile Arg Thr Gly Ser Pro Arg Asn Arg Glu
                565                 570                 575

Asn Ala Ala Ala Val Leu Val His Leu Cys Ser Gly Asp Pro Gln His
            580                 585                 590

Leu Val Glu Ala Gln Lys Leu Gly Leu Met Gly Pro Leu Ile Asp Leu
        595                 600                 605

Ala Gly Asn Gly Thr Asp Arg Gly Lys Arg Lys Ala Ala Gln Leu Leu
    610                 615                 620

Glu Arg Ile Ser Arg Leu Ala Glu Gln Gln Lys Glu Thr Ala Val Ser
625                 630                 635                 640

Gln Pro Glu Glu Glu Ala Glu Pro Thr His Pro Glu Ser Thr Thr Glu
                645                 650                 655

Ala Ala Asp Thr
            660

<210> SEQ ID NO 69
<211> LENGTH: 2264
<212> TYPE: DNA
<213> ORGANISM: Arabidopsis thaliana

<400> SEQUENCE: 69
gtctctaaaa atgaaacaag agaaaattaa tcttacaatt tccttaacgt ttgcttttc       60 cttcaacatc tttggaatca attcaaacgc gatagagagt ctctaatggt cgatgtgatg     120
gatacagatg aagaagccac aggagatgca gagaaccgtg atgaagaagt taccgcagaa     180
gaaccgattc acgatgaggt tgtggatgcg gtggagattc atgaggaaga agtgaaagaa     240
gatgatgatg attgtgaagg attggtgagc gatatcgtat cgattgtcga gttttggat     300 cagattaacg gttatcgaag aacacaacaa aaagaatgtt ttaatctcgt tagacgattg     360
aagattctta ttccattttt ggatgagatt cgaggttttg aatcaccaag ttgcaagcat     420 ttttaaatc gtttgaggaa agtgtttctt gctgccaaga aattattaga aacttgcagc     480
aatggcagta aaatctatat ggcattggat ggcgaaacaa tgatgacgag atttcattcg     540
atttacgaaa agttgaatcg tgttcttgtt aaagctcctt ttgatgaatt aatgatttct     600
ggtgatgcga agacgagat tgattcattg tgtaaacaac tgaaaaaagc aaaagaaga      660 acagatacac aagacataga gctagcagta gacatgatgg tggtattctc aaaaaccgat     720
cctcgaaacg cagatagcgc gataatagag aggctagcga aaagcttga gctacaaaca      780 attgatgatt taaagacaga aactatagcc atacaaagct taatccaaga caaggaggt      840 ttgaacatag agactaaaca acatatcatt gagcttctta acaagttcaa gaagcttcaa     900
ggtcttgaag ctaccgacat tctctaccaa cccgtcatca ataaagcaat caccaagtca     960
```

```
acgtctctaa tattacctca tgagttttg tgtcctataa cactcgaaat aatgcttgac    1020
ccggttatca tcgccactgg acagacatat gagaaggaga gtatacagaa atggtttgac    1080
gcaggacata agacttgtcc taaaacaaga caggagttag atcatctctc tcttgcacct    1140
aacttcgctt taaagaactt gattatgcag tggtgtgaga agaacaattt caagattcca    1200
gagaaagaag taagtcctga ctcacaaaat gagcagaaag atgaggtctc tttgctggtg    1260
gaagcgttat cgtcaagcca actggaagaa caacgaagat cagtgaagca gatgcgtttg    1320
ctagccagag aaaatcccga gaaccgcgtt taatagcga atgcaggagc gattcctttg    1380
ttagttcaac tcctttctta ccctgattca ggaatccaag aaaacgcggt aacgacattg    1440
ttgaatctat ctatcgacga ggtcaacaag aaactcattt caaatgaagg agctattcca    1500
aacattattg aaatccttga aaatggaaac agagaggcaa gagagaactc tgctgcagct    1560
ttgtttagtt tatcgatgct cgatgagaac aaagtaacta tcggattatc gaatgggata    1620
ccgcctttag tcgatttact acaacatggg acattaagag ggaagaaaga tgctctcact    1680
gcactcttta acttgtctct taactcagct aataaaggaa gagctatcga tgctggtatt    1740
gttcaacctt tgcttaacct tcttaaagat aaaaacttag ggatgatcga tgaagcgctt    1800
tcgattctgt tgctgcttgc atcacaccct gaaggacgtc aagccattgg acaactctcc    1860
ttcattgaaa cacttgtgga attcatcaga caaggcaccc cgaaaaacaa agagtgtgcg    1920
acctcggtgc tgcttgaact aggctctaac aactcgtctt ttatcctcgc agcgcttcaa    1980
ttcggagttt atgaatatct ggtagaaata accacctctg aacaaacag agctcagaga    2040 aaagcaaatg ctcttataca actcataagc aaatctgaac aaatttagac ttgttctaaa    2100
cattttcatc ttctactgta attataggtt tcataatttt tttatttttt ttcattctgt    2160
atcaaaccag tgtctgttgt atatttgtat atcctcttcc atttagtcat atactatttg    2220 atttcctct ctgtaatttc taactctcac gttgataatt cctc                      2264
```

<210> SEQ ID NO 70
<211> LENGTH: 660
<212> TYPE: PRT
<213> ORGANISM: Arabidopsis thaliana

<400> SEQUENCE: 70

```
Met Val Asp Val Met Asp Thr Asp Glu Glu Ala Thr Gly Asp Ala Glu
1               5                   10                  15

Asn Arg Asp Glu Glu Val Thr Ala Glu Glu Pro Ile His Asp Glu Val
            20                  25                  30

Val Asp Ala Val Glu Ile His Glu Glu Val Lys Glu Asp Asp
        35                  40                  45

Asp Cys Glu Gly Leu Val Ser Asp Ile Val Ser Ile Val Glu Phe Leu
    50                  55                  60

Asp Gln Ile Asn Gly Tyr Arg Arg Thr Gln Gln Lys Glu Cys Phe Asn
65                  70                  75                  80

Leu Val Arg Arg Leu Lys Ile Leu Ile Pro Phe Leu Asp Glu Ile Arg
                85                  90                  95

Gly Phe Glu Ser Pro Ser Cys Lys His Phe Leu Asn Arg Leu Arg Lys
            100                 105                 110

Val Phe Leu Ala Ala Lys Lys Leu Leu Glu Thr Cys Ser Asn Gly Ser
        115                 120                 125

Lys Ile Tyr Met Ala Leu Asp Gly Glu Thr Met Met Thr Arg Phe His
    130                 135                 140
```

```
Ser Ile Tyr Glu Lys Leu Asn Arg Val Leu Val Lys Ala Pro Phe Asp
145                 150                 155                 160

Glu Leu Met Ile Ser Gly Asp Ala Lys Asp Glu Ile Asp Ser Leu Cys
            165                 170                 175

Lys Gln Leu Lys Lys Ala Lys Arg Arg Thr Asp Thr Gln Asp Ile Glu
        180                 185                 190

Leu Ala Val Asp Met Met Val Val Phe Ser Lys Thr Asp Pro Arg Asn
    195                 200                 205

Ala Asp Ser Ala Ile Ile Glu Arg Leu Ala Lys Lys Leu Glu Leu Gln
210                 215                 220

Thr Ile Asp Asp Leu Lys Thr Glu Thr Ile Ala Ile Gln Ser Leu Ile
225                 230                 235                 240

Gln Asp Lys Gly Gly Leu Asn Ile Glu Thr Lys Gln His Ile Ile Glu
                245                 250                 255

Leu Leu Asn Lys Phe Lys Lys Leu Gln Gly Leu Glu Ala Thr Asp Ile
            260                 265                 270

Leu Tyr Gln Pro Val Ile Asn Lys Ala Ile Thr Lys Ser Thr Ser Leu
        275                 280                 285

Ile Leu Pro His Glu Phe Leu Cys Pro Ile Thr Leu Glu Ile Met Leu
    290                 295                 300

Asp Pro Val Ile Ile Ala Thr Gly Gln Thr Tyr Glu Lys Glu Ser Ile
305                 310                 315                 320

Gln Lys Trp Phe Asp Ala Gly His Lys Thr Cys Pro Lys Thr Arg Gln
                325                 330                 335

Glu Leu Asp His Leu Ser Leu Ala Pro Asn Phe Ala Leu Lys Asn Leu
            340                 345                 350

Ile Met Gln Trp Cys Glu Lys Asn Asn Phe Lys Ile Pro Glu Lys Glu
        355                 360                 365

Val Ser Pro Asp Ser Gln Asn Glu Gln Lys Asp Glu Val Ser Leu Leu
    370                 375                 380

Val Glu Ala Leu Ser Ser Ser Gln Leu Glu Glu Gln Arg Arg Ser Val
385                 390                 395                 400

Lys Gln Met Arg Leu Leu Ala Arg Glu Asn Pro Glu Asn Arg Val Leu
                405                 410                 415

Ile Ala Asn Ala Gly Ala Ile Pro Leu Leu Val Gln Leu Leu Ser Tyr
            420                 425                 430

Pro Asp Ser Gly Ile Gln Glu Asn Ala Val Thr Thr Leu Leu Asn Leu
        435                 440                 445

Ser Ile Asp Glu Val Asn Lys Lys Leu Ile Ser Asn Glu Gly Ala Ile
    450                 455                 460

Pro Asn Ile Ile Glu Ile Leu Glu Asn Gly Asn Arg Glu Ala Arg Glu
465                 470                 475                 480

Asn Ser Ala Ala Ala Leu Phe Ser Leu Ser Met Leu Asp Glu Asn Lys
                485                 490                 495

Val Thr Ile Gly Leu Ser Asn Gly Ile Pro Pro Leu Val Asp Leu Leu
            500                 505                 510

Gln His Gly Thr Leu Arg Gly Lys Lys Asp Ala Leu Thr Ala Leu Phe
        515                 520                 525

Asn Leu Ser Leu Asn Ser Ala Asn Lys Gly Arg Ala Ile Asp Ala Gly
    530                 535                 540

Ile Val Gln Pro Leu Leu Asn Leu Leu Lys Asp Lys Asn Leu Gly Met
545                 550                 555                 560
```

```
Ile Asp Glu Ala Leu Ser Ile Leu Leu Leu Ala Ser His Pro Glu
            565                 570                 575

Gly Arg Gln Ala Ile Gly Gln Leu Ser Phe Ile Glu Thr Leu Val Glu
        580                 585                 590

Phe Ile Arg Gln Gly Thr Pro Lys Asn Lys Glu Cys Ala Thr Ser Val
        595                 600                 605

Leu Leu Glu Leu Gly Ser Asn Asn Ser Ser Phe Ile Leu Ala Ala Leu
    610                 615                 620

Gln Phe Gly Val Tyr Glu Tyr Leu Val Glu Ile Thr Thr Ser Gly Thr
625                 630                 635                 640

Asn Arg Ala Gln Arg Lys Ala Asn Ala Leu Ile Gln Leu Ile Ser Lys
                645                 650                 655

Ser Glu Gln Ile
            660
```

<210> SEQ ID NO 71
<211> LENGTH: 1453
<212> TYPE: DNA
<213> ORGANISM: Arabidopsis thaliana

<400> SEQUENCE: 71

```
aaattttga aacccaattt cagggcacga ttccacaacc tctttctttt cttctagatc    60
tacgtaaatt catcagctag agattgaaaa atggcggacg gtgaagatat tcagccgctc   120
gtttgcgata acgggactgg aatggtcaag gctggttttg caggtgatga tgctcctaga   180
gctgtattcc caagtatcgt tggccgtcca cgtcacacgg gagtgatggt tggaatggga   240
caaaaggatg catacgtcgg agacgaggca cagtcgaaac gtggtatctt gactctcaag   300
tatccaattg agcatggtat tgtcaacaac tgggatgata tggagaagat ttggcatcac   360
actttctaca atgagctgcg tgttgccccg gaagagcatc cggttttgct aaccgaagcg   420
ccgcttaatc cgaaggctaa ccgtgagaag atgacacaga tcatgtttga acattcaac    480
actcctgcta tgtatgttgc cattcaagct gttctctccc tctatgctag tggccgtact   540
actggtattg ttttggactc tggagatggt gtgagccaca cggtaccaat ctacgagggt   600
tatgcacttc cacacgcaat cctgcgtctt gatcttgcag tcgtgaccct aaccgaccac   660
ctcatgaaaa tcctgacaga gcgtggttac tcattcacca aactgctga gcgtgagatt   720
gtcagagaca tgaaggagaa gctctcgtac attgccttgg actatgagca agagcttgag   780
acttccaaaa ccagctcatc tgtggagaag agcttcgagc tgccagacgg tcaagtgata   840
accatcgggg cagagcgttt ccggtgtcct gaagttctgt tccagccatc catgatcgga   900
atggaaaatc cgggaattca tgaaactact acaactcaa tcatgaaatg tgatgtggat    960
atcaggaagg atctttatgg aaacattgtg cttagtggtg caccacaat gtttggcggg   1020
attggtgata ggatgagtaa agaaatcacc gcgttggcgc cgagcagtat gaagatcaaa   1080
gtggttgctc caccggaaag gaagtacagt gtttggatcg gtggctctat cttggcttct   1140
ctcagtactt tccagcagat gtggattgcg aaagccgagt atgatgaatc tggaccgtcg   1200
atcgtccaca ggaagtgctt ctgatcaaaa gtcaccaagt aaaacaagag cggtaaaaat   1260
tttgatatca gttttcacc ctgaagccat ttgctataat tactcacaac ttctctattt   1320
gtgttctttt attcttgtcc ctcattgttc attttaatct ctcttttgca acaaagcaac   1380
ttaaaaaaac agatcagtca ttaacagaat gttattatta tatgtataca tattagtata   1440
cacccattat ctt                                                     1453
```

<210> SEQ ID NO 72
<211> LENGTH: 377
<212> TYPE: PRT
<213> ORGANISM: Arabidopsis thaliana

<400> SEQUENCE: 72

Met Ala Asp Gly Glu Asp Ile Gln Pro Leu Val Cys Asp Asn Gly Thr
1               5                   10                  15

Gly Met Val Lys Ala Gly Phe Ala Gly Asp Asp Ala Pro Arg Ala Val
            20                  25                  30

Phe Pro Ser Ile Val Gly Arg Pro Arg His Thr Gly Val Met Val Gly
        35                  40                  45

Met Gly Gln Lys Asp Ala Tyr Val Gly Asp Glu Ala Gln Ser Lys Arg
    50                  55                  60

Gly Ile Leu Thr Leu Lys Tyr Pro Ile Glu His Gly Ile Val Asn Asn
65                  70                  75                  80

Trp Asp Asp Met Glu Lys Ile Trp His His Thr Phe Tyr Asn Glu Leu
                85                  90                  95

Arg Val Ala Pro Glu Glu His Pro Val Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Thr Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Ser His Thr Val Pro Ile Tyr Glu Gly Tyr Ala Leu Pro His Ala
                165                 170                 175

Ile Leu Arg Leu Asp Leu Ala Gly Arg Asp Leu Thr Asp His Leu Met
            180                 185                 190

Lys Ile Leu Thr Glu Arg Gly Tyr Ser Phe Thr Thr Thr Ala Glu Arg
        195                 200                 205

Glu Ile Val Arg Asp Met Lys Glu Lys Leu Ser Tyr Ile Ala Leu Asp
    210                 215                 220

Tyr Glu Gln Glu Leu Glu Thr Ser Lys Thr Ser Ser Ser Val Glu Lys
225                 230                 235                 240

Ser Phe Glu Leu Pro Asp Gly Gln Val Ile Thr Ile Gly Ala Glu Arg
                245                 250                 255

Phe Arg Cys Pro Glu Val Leu Phe Gln Pro Ser Met Ile Gly Met Glu
            260                 265                 270

Asn Pro Gly Ile His Glu Thr Thr Tyr Asn Ser Ile Met Lys Cys Asp
        275                 280                 285

Val Asp Ile Arg Lys Asp Leu Tyr Gly Asn Ile Val Leu Ser Gly Gly
    290                 295                 300

Thr Thr Met Phe Gly Gly Ile Gly Asp Arg Met Ser Lys Glu Ile Thr
305                 310                 315                 320

Ala Leu Ala Pro Ser Ser Met Lys Ile Lys Val Val Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ala Lys Ala Glu Tyr Asp Glu Ser Gly
        355                 360                 365

Pro Ser Ile Val His Arg Lys Cys Phe
    370                 375

<210> SEQ ID NO 73
<211> LENGTH: 2972
<212> TYPE: DNA
<213> ORGANISM: Arabidopsis thaliana

<400> SEQUENCE: 73

| | | | | | |
|---|---|---|---|---|---|
| aagttaagta | cgacggtttc | tgaaataaag | aaaacatttc | ttcaatcttg | tgcttacggt | 60 |
| gatatccgtg | gattcaaatc | gatattgaga | agatggtaga | tgcgatcacg | gagttcgttg | 120 |
| tgggaaagat | cggcaactat | ctcattgaag | aagcatcaat | gtttatggca | gtcaaagagg | 180 |
| atctagaaga | gctgaagacg | gagttgacgt | gcatccatgg | ttatctcaag | gacgttgaag | 240 |
| cgcgagaaag | agaagatgag | gtctcaaaag | agtggtcaaa | actggtttta | gatttcgctt | 300 |
| atgacgtcga | agatgttttg | gacacttatc | acttgaaact | cgaagaaagg | tcacaaaggc | 360 |
| gaggcttgag | gagattgacc | aacaaaatag | gcaggaagat | ggatgcgtac | agcatagttg | 420 |
| atgatatcag | aattctcaag | agaagaattt | tggatatcac | tcgcaagagg | gagacttatg | 480 |
| gtataggagg | cttgaaagag | cctcaaggag | gagggaatac | ttcaagtttg | agagtgagac | 540 |
| aacttcggcg | tgctcgatct | gttgatcaag | aagaggttgt | agttggtttg | aagatgatg | 600 |
| ctaagattct | tttggaaaag | cttcttgatt | atgaagagaa | aaatagattt | attatctcga | 660 |
| tcttcggtat | gggaggcctt | ggaaagactg | cacttgctag | gaagctctac | aactcaaggg | 720 |
| atgtgaagga | aagattcgaa | taccgcgcat | ggacttatgt | ttctcaagag | tataaaactg | 780 |
| gagatatact | aatgagaatc | attagatctt | tgggaatgac | ttctggggaa | gagttggaaa | 840 |
| agatcagaaa | gtttgcagag | gaagagttag | aagtttacct | ttacggtctt | ctagaaggga | 900 |
| aaaaatattt | ggtggtggtg | gatgatatat | gggagcgaga | agcgtgggac | agcttaaaga | 960 |
| gagcgttacc | ttgcaaccat | gaaggaagta | gagtcatcat | cactacgcgt | attaaagccg | 1020 |
| tggctgaagg | cgtagatggg | agattctatg | ctcataagtt | aaggttcttg | acgtttgaag | 1080 |
| aaagctggga | gttgtttgaa | caaagagcat | tcaggaatat | acaaaggaag | gatgaagatt | 1140 |
| tgctgaaaac | cggaaaagaa | atggttcaaa | aatgcagagg | gttaccactt | tgtatagttg | 1200 |
| ttcttgcggg | gcttttgtcg | aggaagacac | caagcgagtg | gaatgatgtt | tgtaacagtt | 1260 |
| tatggagacg | cctaaaggat | gactccattc | atgttgcccc | tattgtgttt | gatctaagtt | 1320 |
| tcaaggagct | gcggcatgag | tccaaactct | gtttttctgta | ccttagtatc | ttcccagagg | 1380 |
| actatgagat | tgacctagag | aagttgatac | acttacttgt | agcagaaggt | tttatacaag | 1440 |
| gggatgaaga | gatgatgatg | gaagatgtgg | ctcggtacta | catcgaagag | ctgatagata | 1500 |
| gaagcttact | tgaagcagtg | agaagagaaa | gaggaaaagt | gatgtcttgt | agaatccatg | 1560 |
| atcttctgag | agacgtggct | atcaagaaat | ctaaagagct | caactttgta | aacgtgtata | 1620 |
| acgatcatgt | ggcccaacat | tcttctacta | cttgcagaag | ggaagtggtt | caccatcagt | 1680 |
| tcaagagata | ctcatctgag | aaacgcaaga | acaaacggat | gcgatccttc | ttatactttg | 1740 |
| gagaattcga | ccatttggta | gggcttgatt | ttgaaacatt | gaagctactt | cgagtgcttg | 1800 |
| atttcggaag | tctttggctt | cctttttaaaa | ttaatgggga | tctgatccac | ttgaggtacc | 1860 |
| ttggaattga | tggtaattct | atcaacgatt | ttgatatagc | agctattata | tccaagttac | 1920 |
| ggtttctaca | aacactattt | gtatctgaca | attatttcat | cgaggaaaca | atcgatctcc | 1980 |
| gtaagctcac | atcattaaga | catgtcatag | gaaatttttt | tggaggattg | cttataggcg | 2040 |
| acgtagcgaa | ccttcagacc | ttgacgtcta | tctcctttga | cagctggaac | aaaactaaaac | 2100 |

```
ctgagttgct cataaatctt cgagatttgg ggatttctga aatgtctagg tcaaaggaga    2160
gaagagttca tgtgagctgg gcttccttga ctaaactgga aagtcttcgt gttctgaagc    2220
tggcgacgcc cactgaagtc catttatcgt tggaatcaga agaagcagtt aggtccatgg    2280
atgtgatatc acgcagtctt gaatccgtga cactggttgg aataactttc gaggaagacc    2340
caatgccttt tttgcagaaa atgccgagac tggaagatct gatcttgtta agttgtaatt    2400
actcggggaa gatgagcgtc agcgaacaag gttttggtag gctgaggaag cttgacttgt    2460
taatgagaag tttagatgag ttgcagatag aagaagaggc catgcccaat ttgatcgagc    2520
tggaaataag tgtttcgaaa agagaaacaa agctgataat tccaaaccgt ttgcgagcgt    2580
ttggtcaaat ctactgctga tgagttatga gctacaagaa acgggaaaac atgtgaacca    2640
ggccttaaga tttatgtctt tttaatatca agtctgcgac ataataccac agaatgtgta    2700
gatctcttaa agcttttgaa tcagtaccaa tttacacacc acttgtaaac atttactgca    2760
gcaaagagat tcacagccgc gcagactcag gtcgtcacat gtctagaaaa gaagttgaac    2820
ttcatgtact agtaaagatc atcaaaattg tttagaaaat ttacaaacta catgattttt    2880
tgtgcaattg aaaaaaaaaa caattttaag attgaatttc tgcatcagag aaaacaattt    2940
gtagcatctt ttctttgtct ttggttacat at                                  2972

<210> SEQ ID NO 74
<211> LENGTH: 835
<212> TYPE: PRT
<213> ORGANISM: Arabidopsis thaliana

<400> SEQUENCE: 74
```

Met Val Asp Ala Ile Thr Glu Phe Val Val Gly Lys Ile Gly Asn Tyr
1               5                   10                  15

Leu Ile Glu Glu Ala Ser Met Phe Met Ala Val Lys Glu Asp Leu Glu
            20                  25                  30

Glu Leu Lys Thr Glu Leu Thr Cys Ile His Gly Tyr Leu Lys Asp Val
        35                  40                  45

Glu Ala Arg Glu Arg Glu Asp Glu Val Ser Lys Glu Trp Ser Lys Leu
    50                  55                  60

Val Leu Asp Phe Ala Tyr Asp Val Glu Asp Val Leu Asp Thr Tyr His
65                  70                  75                  80

Leu Lys Leu Glu Glu Arg Ser Gln Arg Gly Leu Arg Arg Leu Thr
            85                  90                  95

Asn Lys Ile Gly Arg Lys Met Asp Ala Tyr Ser Ile Val Asp Ile
        100                 105                 110

Arg Ile Leu Lys Arg Arg Ile Leu Asp Ile Thr Arg Lys Arg Glu Thr
        115                 120                 125

Tyr Gly Ile Gly Gly Leu Lys Glu Pro Gln Gly Gly Asn Thr Ser
    130                 135                 140

Ser Leu Arg Val Arg Gln Leu Arg Arg Ala Arg Ser Val Asp Gln Glu
145                 150                 155                 160

Glu Val Val Gly Leu Glu Asp Asp Ala Lys Ile Leu Leu Glu Lys
            165                 170                 175

Leu Leu Asp Tyr Glu Glu Lys Asn Arg Phe Ile Ser Ile Phe Gly
        180                 185                 190

Met Gly Gly Leu Gly Lys Thr Ala Leu Ala Arg Lys Leu Tyr Asn Ser
        195                 200                 205

Arg Asp Val Lys Glu Arg Phe Glu Tyr Arg Ala Trp Thr Tyr Val Ser
    210                 215                 220

-continued

```
Gln Glu Tyr Lys Thr Gly Asp Ile Leu Met Arg Ile Ile Arg Ser Leu
225                 230                 235                 240

Gly Met Thr Ser Gly Glu Leu Glu Lys Ile Arg Lys Phe Ala Glu
            245                 250                 255

Glu Glu Leu Glu Val Tyr Leu Tyr Gly Leu Leu Glu Gly Lys Lys Tyr
            260                 265                 270

Leu Val Val Val Asp Asp Ile Trp Glu Arg Glu Ala Trp Asp Ser Leu
        275                 280                 285

Lys Arg Ala Leu Pro Cys Asn His Glu Gly Ser Arg Val Ile Ile Thr
        290                 295                 300

Thr Arg Ile Lys Ala Val Ala Glu Gly Val Asp Gly Arg Phe Tyr Ala
305                 310                 315                 320

His Lys Leu Arg Phe Leu Thr Phe Glu Glu Ser Trp Glu Leu Phe Glu
                325                 330                 335

Gln Arg Ala Phe Arg Asn Ile Gln Arg Lys Asp Glu Asp Leu Leu Lys
            340                 345                 350

Thr Gly Lys Glu Met Val Gln Lys Cys Arg Gly Leu Pro Leu Cys Ile
        355                 360                 365

Val Val Leu Ala Gly Leu Leu Ser Arg Lys Thr Pro Ser Glu Trp Asn
370                 375                 380

Asp Val Cys Asn Ser Leu Trp Arg Arg Leu Lys Asp Asp Ser Ile His
385                 390                 395                 400

Val Ala Pro Ile Val Phe Asp Leu Ser Phe Lys Glu Leu Arg His Glu
                405                 410                 415

Ser Lys Leu Cys Phe Leu Tyr Leu Ser Ile Phe Pro Glu Asp Tyr Glu
            420                 425                 430

Ile Asp Leu Glu Lys Leu Ile His Leu Leu Val Ala Glu Gly Phe Ile
        435                 440                 445

Gln Gly Asp Glu Glu Met Met Met Glu Asp Val Ala Arg Tyr Tyr Ile
    450                 455                 460

Glu Glu Leu Ile Asp Arg Ser Leu Leu Glu Ala Val Arg Arg Glu Arg
465                 470                 475                 480

Gly Lys Val Met Ser Cys Arg Ile His Asp Leu Leu Arg Asp Val Ala
                485                 490                 495

Ile Lys Lys Ser Lys Glu Leu Asn Phe Val Asn Val Tyr Asn Asp His
            500                 505                 510

Val Ala Gln His Ser Ser Thr Thr Cys Arg Arg Glu Val Val His His
        515                 520                 525

Gln Phe Lys Arg Tyr Ser Ser Glu Lys Arg Lys Asn Lys Arg Met Arg
    530                 535                 540

Ser Phe Leu Tyr Phe Gly Glu Phe Asp His Leu Val Gly Leu Asp Phe
545                 550                 555                 560

Glu Thr Leu Lys Leu Leu Arg Val Leu Asp Phe Gly Ser Leu Trp Leu
                565                 570                 575

Pro Phe Lys Ile Asn Gly Asp Leu Ile His Leu Arg Tyr Leu Gly Ile
            580                 585                 590

Asp Gly Asn Ser Ile Asn Asp Phe Asp Ile Ala Ala Ile Ile Ser Lys
        595                 600                 605

Leu Arg Phe Leu Gln Thr Leu Phe Val Ser Asp Asn Tyr Phe Ile Glu
    610                 615                 620

Glu Thr Ile Asp Leu Arg Lys Leu Thr Ser Leu Arg His Val Ile Gly
625                 630                 635                 640
```

```
Asn Phe Phe Gly Gly Leu Leu Ile Gly Asp Val Ala Asn Leu Gln Thr
                645                 650                 655

Leu Thr Ser Ile Ser Phe Asp Ser Trp Asn Lys Leu Lys Pro Glu Leu
        660                 665                 670

Leu Ile Asn Leu Arg Asp Leu Gly Ile Ser Glu Met Ser Arg Ser Lys
            675                 680                 685

Glu Arg Arg Val His Val Ser Trp Ala Ser Leu Thr Lys Leu Glu Ser
690                 695                 700

Leu Arg Val Leu Lys Leu Ala Thr Pro Thr Glu Val His Leu Ser Leu
705                 710                 715                 720

Glu Ser Glu Glu Ala Val Arg Ser Met Asp Val Ile Ser Arg Ser Leu
                725                 730                 735

Glu Ser Val Thr Leu Val Gly Ile Thr Phe Glu Glu Asp Pro Met Pro
            740                 745                 750

Phe Leu Gln Lys Met Pro Arg Leu Glu Asp Leu Ile Leu Leu Ser Cys
        755                 760                 765

Asn Tyr Ser Gly Lys Met Ser Val Ser Glu Gln Gly Phe Gly Arg Leu
    770                 775                 780

Arg Lys Leu Asp Leu Leu Met Arg Ser Leu Asp Glu Leu Gln Ile Glu
785                 790                 795                 800

Glu Glu Ala Met Pro Asn Leu Ile Glu Leu Glu Ile Ser Val Ser Lys
                805                 810                 815

Arg Glu Thr Lys Leu Ile Ile Pro Asn Arg Leu Arg Ala Phe Gly Gln
            820                 825                 830

Ile Tyr Cys
        835

<210> SEQ ID NO 75
<211> LENGTH: 1213
<212> TYPE: DNA
<213> ORGANISM: Arabidopsis thaliana

<400> SEQUENCE: 75
atcacagatt tggactttc ttggttatat taaagtttt tttgtccata tattcaatga      60
ccaatctaga attcatctgt ttttgaacta acccaacact aaagaaatag atccaaaggc    120
ctctctcctc tctctcgttt ttctcatatg gttcttgata ataatttgaa agaaagatgt    180
caatgatgag cagaactcga agcagcatcg ccatgggaac accatctttc cttgagttga    240
agaaacaagc ttcatttttc ttcaaagaga agcttaaaac ggcgcgttta gctctcaccg    300
atgttactcc tcttcaacta atgactgagg aagctacgga tggtgagtca tgtggaccaa    360
atacacaaac cttagggtcc atttcaaagg ctgcttttga gtttgaagat tacttggcga    420
ttgttgaagt cttgcacaaa agattggcaa agttcgataa agaaactgg aggatggctt     480 ataactcact aatagttgtt gagcatttac tcactcatgg accagagagt gtttccgatg    540
agtttcaagg tgatatagat gttatctccc aaatgcaaac cttccaacag attgacgaga    600
aagggtttaa ttgggatta gctgttagaa agaaagcaga gaaggtttta aagctacttg     660
agaaagggga attacttaag gaagaaagga agcgagctcg tgagctgtct cgagggattc    720
aaggtttcgg tagcttaac cacaagtctt catctcattc tttgtcagag catgaagtct     780
tacaagaatc tacagtctat aggaaatgta attccaattt taccaagaat tacgatgagg    840
atgaccaaga gaacactatg gtttctccta atgacgccaa cctttttcct cagccgctgg    900
tagctgaccc gagcgaggaa tctaggacgg gtatgaaaga aaatatggat cctgaagatg    960
```

-continued

```
atgagaacac agaggtaaac ccactttggg gttttagtaa aaaggagggt caagaactag      1020
ccggagaaga cgagaaccat ccatttacgg atggcgagag taagcataca gtagtcttgc      1080
ttgatgagaa cacagattaa attttaatta cgtgatatcg caatctgtat aagagaaaaa      1140
acacgagaag aagataatgt gtgtatacca atatgtatac atatctacaa taataacact      1200
tctgttaatg act                                                         1213
```

<210> SEQ ID NO 76
<211> LENGTH: 307
<212> TYPE: PRT
<213> ORGANISM: Arabidopsis thaliana

<400> SEQUENCE: 76

```
Met Ser Met Met Ser Arg Thr Arg Ser Ile Ala Met Gly Thr Pro
1               5                   10                  15

Ser Phe Leu Glu Leu Lys Lys Gln Ala Ser Phe Phe Lys Glu Lys
                20                  25                  30

Leu Lys Thr Ala Arg Leu Ala Leu Thr Asp Val Thr Pro Leu Gln Leu
            35                  40                  45

Met Thr Glu Glu Ala Thr Asp Gly Glu Ser Cys Gly Pro Asn Thr Gln
        50                  55                  60

Thr Leu Gly Ser Ile Ser Lys Ala Ala Phe Glu Phe Glu Asp Tyr Leu
65                  70                  75                  80

Ala Ile Val Glu Val Leu His Lys Arg Leu Ala Lys Phe Asp Lys Arg
                85                  90                  95

Asn Trp Arg Met Ala Tyr Asn Ser Leu Ile Val Val Glu His Leu Leu
            100                 105                 110

Thr His Gly Pro Glu Ser Val Ser Asp Glu Phe Gln Gly Asp Ile Asp
        115                 120                 125

Val Ile Ser Gln Met Gln Thr Phe Gln Gln Ile Asp Glu Lys Gly Phe
    130                 135                 140

Asn Trp Gly Leu Ala Val Arg Lys Lys Ala Glu Lys Val Leu Lys Leu
145                 150                 155                 160

Leu Glu Lys Gly Glu Leu Leu Lys Glu Glu Arg Lys Arg Ala Arg Glu
                165                 170                 175

Leu Ser Arg Gly Ile Gln Gly Phe Gly Ser Phe Asn His Lys Ser Ser
            180                 185                 190

Ser His Ser Leu Ser Glu His Glu Val Leu Gln Glu Ser Thr Val Tyr
        195                 200                 205

Arg Lys Cys Asn Ser Asn Phe Thr Lys Asn Tyr Asp Glu Asp Gln
    210                 215                 220

Glu Asn Thr Met Val Ser Pro Asn Asp Ala Asn Leu Phe Pro Gln Pro
225                 230                 235                 240

Leu Val Ala Asp Pro Ser Glu Ser Arg Thr Gly Met Lys Glu Asn
                245                 250                 255

Met Asp Pro Glu Asp Asp Glu Asn Thr Glu Val Asn Pro Leu Leu Gly
            260                 265                 270

Phe Ser Lys Lys Glu Gly Gln Glu Leu Ala Gly Glu Asp Glu Asn His
        275                 280                 285

Pro Phe Thr Asp Gly Glu Ser Lys His Thr Val Val Leu Leu Asp Glu
    290                 295                 300

Asn Thr Asp
305
```

<210> SEQ ID NO 77
<211> LENGTH: 1413
<212> TYPE: DNA
<213> ORGANISM: Arabidopsis thaliana

<400> SEQUENCE: 77

| | | | | | |
|---|---|---|---|---|---|
| atggcgaacg | taatctcaat | ttcccatttt | acccttctcg | cattaccttta | tttacttctc | 60 |
| ctcctatctt | ccaccgccgc | cgcaattaac | gtcaccgccg | tcctctcctc | tttccctaat | 120 |
| ctctcatctt | tctcaaacct | cctcgtctct | tccggcatcg | ctgccgaact | ctccggtaga | 180 |
| aactcattaa | ccctcctcgc | cgttcccaat | tctcaattct | cctccgcctc | cttggacctc | 240 |
| acgcgccgcc | tacctccttc | cgccctagca | gatctcctcc | gcttccatgt | cctcctccag | 300 |
| ttcctttcag | attccgatct | ccgacgtatt | ccaccgtcag | gctccgccgt | cactactctc | 360 |
| tacgaagctt | ccggtcgtac | attctttgga | tctggatccg | ttaacgtaac | ccgtgacccg | 420 |
| gcttcaggat | ccgtcacgat | cggatctcca | gccaccaaaa | acgtcactgt | gttaaagctt | 480 |
| ctcgagacca | aacctcccaa | cataaccgtc | ctcaccgtgg | actccctcat | cgtccccacc | 540 |
| ggaatcgata | tcaccgcatc | ggagactctc | actccaccgc | cgacgtcaac | atctctctcc | 600 |
| cctccaccgg | cgggaatcaa | tctcactcag | atactaatca | acggacacaa | cttcaacgtc | 660 |
| gctctatccc | tcctcgtcgc | ttccggtgtc | ataacagaat | tcgaaaacga | cgaacgtggc | 720 |
| gccggcatca | cagtcttcgt | ccccaccgac | tccgccttct | ccgatctccc | ttccaacgtt | 780 |
| aacctccagt | cattaccggc | ggagcaaaaa | gcattcgtgt | taaaattcca | cgtgctacat | 840 |
| tcatactaca | ctctcggttc | actagaatca | ataaccaacc | cggttcaacc | gacattagcc | 900 |
| actgaagaaa | tgggagccgg | ttcatacact | ctcaacatct | cccgggttaa | cgggtcaatc | 960 |
| gtaacgatca | attcgggtgt | ggttttagct | gttgtgactc | aaacggcttt | tgatcaaaac | 1020 |
| ccggtttctg | ttttcggagt | atccaaagtt | cttttgccta | agaactatt | tccaaaatcg | 1080 |
| ggtcaacccg | ttgccacagc | tcctccacag | gagatttctt | tgtcgccgga | gagttctagt | 1140 |
| gaacagccgt | cacgactagt | atcaccaccg | cgtgagatag | tttcttccgg | cgcggttaaa | 1200 |
| agaccacttg | gtttcttggt | cttgtggtgt | tggtgtatag | catttgtta | tgttttggta | 1260 |
| tgattttttt | ttctttcttt | cttttatcac | ataatgtttt | gccttcgatt | agggctttat | 1320 |
| ttattttac | tggattttttt | ttttcacaag | ggtttatatt | tattcacgat | aatgttattg | 1380 |
| tatttgagtc | gaggaaaaaa | caaattcact | ttc | | | 1413 |

<210> SEQ ID NO 78
<211> LENGTH: 420
<212> TYPE: PRT
<213> ORGANISM: Arabidopsis thaliana

<400> SEQUENCE: 78

Met Ala Asn Val Ile Ser Ile Ser His Phe Thr Leu Leu Ala Leu Pro
1               5                   10                  15

Tyr Leu Leu Leu Leu Ser Ser Thr Ala Ala Ala Ile Asn Val Thr
            20                  25                  30

Ala Val Leu Ser Ser Phe Pro Asn Leu Ser Ser Phe Ser Asn Leu Leu
        35                  40                  45

Val Ser Ser Gly Ile Ala Ala Glu Leu Ser Gly Arg Asn Ser Leu Thr
    50                  55                  60

Leu Leu Ala Val Pro Asn Ser Gln Phe Ser Ser Ala Ser Leu Asp Leu
65                  70                  75                  80

Thr Arg Arg Leu Pro Pro Ser Ala Leu Ala Asp Leu Leu Arg Phe His

```
            85                  90                  95
Val Leu Leu Gln Phe Leu Ser Asp Ser Asp Leu Arg Arg Ile Pro Pro
            100                 105                 110

Ser Gly Ser Ala Val Thr Thr Leu Tyr Glu Ala Ser Gly Arg Thr Phe
            115                 120                 125

Phe Gly Ser Gly Ser Val Asn Val Thr Arg Asp Pro Ala Ser Gly Ser
            130                 135                 140

Val Thr Ile Gly Ser Pro Ala Thr Lys Asn Val Thr Val Leu Lys Leu
145                 150                 155                 160

Leu Glu Thr Lys Pro Pro Asn Ile Thr Val Leu Thr Val Asp Ser Leu
            165                 170                 175

Ile Val Pro Thr Gly Ile Asp Ile Thr Ala Ser Glu Thr Leu Thr Pro
            180                 185                 190

Pro Pro Thr Ser Thr Ser Leu Ser Pro Pro Ala Gly Ile Asn Leu
            195                 200                 205

Thr Gln Ile Leu Ile Asn Gly His Asn Phe Asn Val Ala Leu Ser Leu
            210                 215                 220

Leu Val Ala Ser Gly Val Ile Thr Glu Phe Glu Asn Asp Glu Arg Gly
225                 230                 235                 240

Ala Gly Ile Thr Val Phe Val Pro Thr Asp Ser Ala Phe Ser Asp Leu
                245                 250                 255

Pro Ser Asn Val Asn Leu Gln Ser Leu Pro Ala Glu Gln Lys Ala Phe
            260                 265                 270

Val Leu Lys Phe His Val Leu His Ser Tyr Tyr Thr Leu Gly Ser Leu
            275                 280                 285

Glu Ser Ile Thr Asn Pro Val Gln Pro Thr Leu Ala Thr Glu Glu Met
            290                 295                 300

Gly Ala Gly Ser Tyr Thr Leu Asn Ile Ser Arg Val Asn Gly Ser Ile
305                 310                 315                 320

Val Thr Ile Asn Ser Gly Val Val Leu Ala Val Val Thr Gln Thr Ala
                325                 330                 335

Phe Asp Gln Asn Pro Val Ser Val Phe Gly Val Ser Lys Val Leu Leu
            340                 345                 350

Pro Lys Glu Leu Phe Pro Lys Ser Gly Gln Pro Val Ala Thr Ala Pro
            355                 360                 365

Pro Gln Glu Ile Ser Leu Ser Pro Glu Ser Ser Glu Gln Pro Ser
            370                 375                 380

Arg Leu Val Ser Pro Pro Arg Glu Ile Val Ser Ser Gly Ala Val Lys
385                 390                 395                 400

Arg Pro Leu Gly Phe Leu Val Leu Trp Cys Trp Cys Ile Ala Phe Cys
                405                 410                 415

Tyr Val Leu Val
            420

<210> SEQ ID NO 79
<211> LENGTH: 514
<212> TYPE: DNA
<213> ORGANISM: Arabidopsis thaliana

<400> SEQUENCE: 79
atgaagaatt gaatctgtag tcgaaagaaa agagttggga aaaaaatgga cgcaagcatg     60
atggctggac ttgatggtct tcctgaagaa gacaaagcca aatggcctc catgatcgat    120 cagcttcagc tccgtgatag tttgaggatg tacaattcat ggtggagag gtgtttcgtg    180
```

```
gactgtgttg atagcttcac acgcaaatct ctgcagaaac aagaggagac ttgtgtgatg    240
cgttgcgctg agaagttcct taagcatacg atgcgtgttg gtatgcggtt tgctgagctc    300
aatcagaacg caccaaccca agactgatat agtctgcttt ttctgtttgg ttttttcgta    360
cggtttacga gtccgaaacc agaataaacc ggttgttagt tgttcaggtt actactccga    420
tactgttttt tgaacatctt gtactgtgaa attattttga ctgtatccag ttctgatatt    480
gatattgact tgtatttcaa tggagtctag agaa                                514
```

<210> SEQ ID NO 80
<211> LENGTH: 93
<212> TYPE: PRT
<213> ORGANISM: Arabidopsis thaliana

<400> SEQUENCE: 80

Met Asp Ala Ser Met Met Ala Gly Leu Asp Gly Leu Pro Glu Glu Asp
1               5                   10                  15

Lys Ala Lys Met Ala Ser Met Ile Asp Gln Leu Gln Leu Arg Asp Ser
            20                  25                  30

Leu Arg Met Tyr Asn Ser Leu Val Glu Arg Cys Phe Val Asp Cys Val
        35                  40                  45

Asp Ser Phe Thr Arg Lys Ser Leu Gln Lys Gln Glu Glu Thr Cys Val
    50                  55                  60

Met Arg Cys Ala Glu Lys Phe Leu Lys His Thr Met Arg Val Gly Met
65                  70                  75                  80

Arg Phe Ala Glu Leu Asn Gln Asn Ala Pro Thr Gln Asp
                85                  90

<210> SEQ ID NO 81
<211> LENGTH: 3847
<212> TYPE: DNA
<213> ORGANISM: Arabidopsis thaliana

<400> SEQUENCE: 81

```
gaggaaatgg gtcgcagcag ttcgaagaaa agaagaaac gaggaggtag cggaagaagg      60
ggtcagctga agaccatgg atctaatgct gatgaagata atgaacttct atctgaggag     120
atcactgctc tctctgcaat atttcaagag gactgcaaag ttgtttctga ttcgcgttcg     180
cctccgcaaa tagcaatcaa gctcaggccg tactcaaagg acatgggata tgaagacacc     240
gacatatctg ctatgcttat agttaggtgc ttaccaggat atccttacaa gtgccccaag     300
cttcagatta ctccagaaca agggttgaca cagctgatg ctgagaagct tttatctctt     360
ctcgaggacc aggcaaattc caatgctcgt gaaggtcggg ttatgatatt caacctggtg     420
gaggctgctc aagagttttt atcagaaatc attccggaaa gtcatgatga ggaatctgtt     480
ccatgcttga ctgcacatcg aagcactcag ttcattgagc aacctatgct ttcaaatata     540
gcaaaatcct gttctggtgg acctttttgtg tatggttta tagacctatt tagtggcttg     600
gaagatgcaa gaaattggag tctgactcca gatgaaaata ggggaatcgt atcttcagta     660
caatctcacc cactagacac ttcaagaatt ttgcatcaga agccagacaa gaatctgaag     720
cgatttgaag accatgctaa agaagaagtt gcactgcctg ctcccattgc caaactgaat     780
actgttcaag aggagaatgt tgatgataca agcatctctt cttttgactc aagtaaatct     840
actgacgatg tggaatctgg attattccaa aatgagaaga aggaatcaaa tcttcaagat     900
gatacagctg aagatgacag cactaactcc gaaagtgagt cgctgggggtc atggtcttct     960 gattccttag ctcaagatca agtgcctcag attagcaaga aagatctgtt gatggtccat    1020

```
ttacttcgag tagcttgcac ttcccgagga cctttggctg atgcattacc tcagataact    1080
gatgaactgc atgagcttgg tatattgtct gaagaagtgt tggatttagc ttccaaatca    1140
tctccagact ttaatagaac ctttgaacat gcattcaatc aaaacatggc ctcaaccagt    1200
gttcctcagt tttgggagcc accttctgat tcttgcgagc caaatgcatc actcccaagc    1260
tcgcgatatc tcaatgattt tgaagagttg aaaccccttg gccaaggtgg tttcggccac    1320
gttgtgttgt gcaaaaataa actggatgga agacaatatg cagtgaagaa aattcgactg    1380
aaggacaaag agatacctgt caacagtcgg atagttcgag aagtagcaac actttcccgt    1440
ttgcagcatc agcatgttgt acgttactat caggcctggt tcgaaacagg agttgttgat    1500
cccttttgctg gcgcaaattg gggatcaaaa actgcaggga gttcaatgtt cagctactca    1560
ggtgcagtgt caactgaaat tcctgagcag gacaataatc ttgagtcgac ttatctatat    1620
attcaaatgg aatattgtcc caggactctc cgccaggttt ttgaatcata taaccacttc    1680
gacaaagact ttgcatggca tttaattcgc caaattgtgg aaggcttagc tcatatccat    1740
ggacaaggaa taattcatcg ggattttaca cctaacaata ttttctttga cgctcggaat    1800
gatattaaaa ttggggattt tggtcttgca aagttcttga agctggaaca gttggatcaa    1860
gatgggggtt tctctacgga tgtggctgga agcggagtcg atagtactgg tcaagctggt    1920
acttactttt acacagcacc tgaaattgag caagattggc ctaagattga tgaaaaggcc    1980
gacatgtata gcttagggggt tgtgttcttt gaactttggc atccttttgg aaccgccatg    2040
gagagacacg ttatttttaac taacctgaag ctgaaagggg agctacctct caaatgggta    2100
aatgaatttc ccgaacaggc gtctctactg cggcgtttga tgtctccaag tccatctgat    2160
cgtccctctg ccacagaact tcttaagcat gcatttcctc ccagaatgga atctgagtta    2220
ctggacaata ttctaagaat aatgcaaact tctgaagatt caagtgttta tgatagagta    2280
gtaagtgtga tatttgatga agaagtatta gagatgaaaa gccatcagtc tagtagatcg    2340
agactctgtg cagatgatag ttatattcaa tacacagaga taaatacaga gcttcgtgat    2400
tatgttgttg aaataacaaa agaagtcttt aggcagcatt gtgcgaagca tctagaggtc    2460
ataccaatgc gcttacttag tgattgcccc cagtttagca ggaaaactgt aaagcttttg    2520
accaatggag gagatatgct tgaactatgc tatgagctac gactgccttt tgtgcattgg    2580
ataagcgtaa atcagaaatc ctcattcaag cgatatgaaa tatctcatgt ctacaggaga    2640
gcaattggcc attctccacc aaatccgtgt cttcaggcgg actttgacat tgttggaggc    2700
acactatccc tgcacagaggc agaagttctc aaggtgatag tagacatcac aacccacatc    2760
tttcatcgcg gatcttgtga cattcatttg aatcatggag atttgctgga tgcgatttgg    2820
tcctgggcag gaattaaggc agagcataga cgaaaggttg cagagcttct ttccatgatg    2880
ggatccttgc gtcctcagtc atctgagcgg aagctaaaat gggtttttcat aaggcgtcaa    2940
cttcttcagg agttgaagtt acctgaagct gttgtcaata gactgcagac tgttgcttca    3000
aggttttgtg gagatgcaga tcaagcactt cctcgtttaa gaggggctct gcgtgctgat    3060
agacctaccc gcaaagcact cgatgagttg tcaaacctct taacctacct gagagtctgg    3120
aggatagaag agcatgttca tattgatgtt ctgatgccac caactgaaag ttatcaccgg    3180
aatttgtttt ttcaggtttt cttaaccaaa gaaaatagct ctgggacatc taatgatggc    3240
gttttacttg ctgttggtgg tcgttatgat tggttggtgc aggaagtgtg tgatcgtgaa    3300
cataaaatga acctccctgg tgctgttgga gttagtcttg cactggagac aatatttcag    3360
```

-continued

```
catcttccta tggatctaag gcctattaga aatgaagtca gcaccagtgt acttgtttgt    3420
tcaagaggag gtggtggttt actggtccag cgcatggaac tagttgcgga actatgggaa    3480
aaaagtataa aggctgagtt tgttccaaca cctgatccaa gtcttactga gcagtacgaa    3540
tatgcaaatg aacatgaaat caaatgtcta gtgatcatca cagagtctgg agtagctcaa    3600
aatcaaatag agtttgtaaa ggttcgtcac cttgaactga agaaggagaa agtggtagga    3660
agagaagaac ttgtcaaatt tctgctggat gcaatggctg ttcaatttag aaacccctct    3720
gtttggagct aaagagagta aataaagagc cacttttgc ttggtgaaaa tattatttgc     3780
cactcaacag tcacaaattt tgatcattca caatcttaat gtgcatatat cttggtattg    3840
gtcagtt                                                              3847
```

<210> SEQ ID NO 82
<211> LENGTH: 1241
<212> TYPE: PRT
<213> ORGANISM: Arabidopsis thaliana

<400> SEQUENCE: 82

```
Met Gly Arg Ser Ser Lys Lys Lys Lys Arg Gly Gly Ser Gly
1               5                   10                  15

Arg Arg Gly Gln Leu Lys Asp His Gly Ser Asn Ala Asp Glu Asp Asn
            20                  25                  30

Glu Leu Leu Ser Glu Glu Ile Thr Ala Leu Ser Ala Ile Phe Gln Glu
        35                  40                  45

Asp Cys Lys Val Val Ser Asp Ser Arg Ser Pro Pro Gln Ile Ala Ile
    50                  55                  60

Lys Leu Arg Pro Tyr Ser Lys Asp Met Gly Tyr Glu Asp Thr Asp Ile
65                  70                  75                  80

Ser Ala Met Leu Ile Val Arg Cys Leu Pro Gly Tyr Pro Tyr Lys Cys
                85                  90                  95

Pro Lys Leu Gln Ile Thr Pro Glu Gln Gly Leu Thr Thr Ala Asp Ala
            100                 105                 110

Glu Lys Leu Leu Ser Leu Leu Glu Asp Gln Ala Asn Ser Asn Ala Arg
        115                 120                 125

Glu Gly Arg Val Met Ile Phe Asn Leu Val Glu Ala Ala Gln Glu Phe
    130                 135                 140

Leu Ser Glu Ile Ile Pro Glu Ser His Asp Glu Glu Ser Val Pro Cys
145                 150                 155                 160

Leu Thr Ala His Arg Ser Thr Gln Phe Ile Glu Gln Pro Met Leu Ser
                165                 170                 175

Asn Ile Ala Lys Ser Cys Ser Gly Gly Pro Phe Val Tyr Gly Phe Ile
            180                 185                 190

Asp Leu Phe Ser Gly Leu Glu Asp Ala Arg Asn Trp Ser Leu Thr Pro
        195                 200                 205

Asp Glu Asn Arg Gly Ile Val Ser Ser Val Gln Ser His Pro Leu Asp
    210                 215                 220

Thr Ser Arg Ile Leu His Gln Lys Pro Asp Lys Asn Leu Lys Arg Phe
225                 230                 235                 240

Glu Asp His Ala Lys Glu Glu Val Ala Leu Pro Ala Pro Ile Ala Lys
                245                 250                 255

Leu Asn Thr Val Gln Glu Glu Asn Val Asp Asp Thr Ser Ile Ser Ser
            260                 265                 270

Phe Asp Ser Ser Lys Ser Thr Asp Asp Val Glu Ser Gly Leu Phe Gln
        275                 280                 285
```

```
Asn Glu Lys Lys Glu Ser Asn Leu Gln Asp Asp Thr Ala Glu Asp
            290                 295                 300

Ser Thr Asn Ser Glu Ser Glu Ser Leu Gly Ser Trp Ser Ser Asp Ser
305                 310                 315                 320

Leu Ala Gln Asp Gln Val Pro Gln Ile Ser Lys Lys Asp Leu Leu Met
                325                 330                 335

Val His Leu Leu Arg Val Ala Cys Thr Ser Arg Gly Pro Leu Ala Asp
                340                 345                 350

Ala Leu Pro Gln Ile Thr Asp Glu Leu His Glu Leu Gly Ile Leu Ser
                355                 360                 365

Glu Glu Val Leu Asp Leu Ala Ser Lys Ser Ser Pro Asp Phe Asn Arg
370                 375                 380

Thr Phe Glu His Ala Phe Asn Gln Asn Met Ala Ser Thr Ser Val Pro
385                 390                 395                 400

Gln Phe Trp Glu Pro Pro Ser Asp Ser Cys Glu Pro Asn Ala Ser Leu
                405                 410                 415

Pro Ser Ser Arg Tyr Leu Asn Asp Phe Glu Glu Leu Lys Pro Leu Gly
                420                 425                 430

Gln Gly Gly Phe Gly His Val Val Leu Cys Lys Asn Lys Leu Asp Gly
                435                 440                 445

Arg Gln Tyr Ala Val Lys Lys Ile Arg Leu Lys Asp Lys Glu Ile Pro
450                 455                 460

Val Asn Ser Arg Ile Val Arg Glu Val Ala Thr Leu Ser Arg Leu Gln
465                 470                 475                 480

His Gln His Val Val Arg Tyr Tyr Gln Ala Trp Phe Glu Thr Gly Val
                485                 490                 495

Val Asp Pro Phe Ala Gly Ala Asn Trp Gly Ser Lys Thr Ala Gly Ser
                500                 505                 510

Ser Met Phe Ser Tyr Ser Gly Ala Val Ser Thr Glu Ile Pro Glu Gln
                515                 520                 525

Asp Asn Asn Leu Glu Ser Thr Tyr Leu Tyr Ile Gln Met Glu Tyr Cys
530                 535                 540

Pro Arg Thr Leu Arg Gln Val Phe Glu Ser Tyr Asn His Phe Asp Lys
545                 550                 555                 560

Asp Phe Ala Trp His Leu Ile Arg Gln Ile Val Glu Gly Leu Ala His
                565                 570                 575

Ile His Gly Gln Gly Ile Ile His Arg Asp Phe Thr Pro Asn Asn Ile
                580                 585                 590

Phe Phe Asp Ala Arg Asn Asp Ile Lys Ile Gly Asp Phe Gly Leu Ala
                595                 600                 605

Lys Phe Leu Lys Leu Glu Gln Leu Asp Gln Asp Gly Gly Phe Ser Thr
610                 615                 620

Asp Val Ala Gly Ser Gly Val Asp Ser Thr Gly Gln Ala Gly Thr Tyr
625                 630                 635                 640

Phe Tyr Thr Ala Pro Glu Ile Glu Gln Asp Trp Pro Lys Ile Asp Glu
                645                 650                 655

Lys Ala Asp Met Tyr Ser Leu Gly Val Val Phe Phe Glu Leu Trp His
                660                 665                 670

Pro Phe Gly Thr Ala Met Glu Arg His Val Ile Leu Thr Asn Leu Lys
                675                 680                 685

Leu Lys Gly Glu Leu Pro Leu Lys Trp Val Asn Glu Phe Pro Glu Gln
690                 695                 700
```

-continued

```
Ala Ser Leu Leu Arg Arg Leu Met Ser Pro Ser Pro Ser Asp Arg Pro
705                 710                 715                 720

Ser Ala Thr Glu Leu Leu Lys His Ala Phe Pro Pro Arg Met Glu Ser
            725                 730                 735

Glu Leu Leu Asp Asn Ile Leu Arg Ile Met Gln Thr Ser Glu Asp Ser
        740                 745                 750

Ser Val Tyr Asp Arg Val Val Ser Val Ile Phe Asp Glu Glu Val Leu
    755                 760                 765

Glu Met Lys Ser His Gln Ser Ser Arg Ser Arg Leu Cys Ala Asp Asp
770                 775                 780

Ser Tyr Ile Gln Tyr Thr Glu Ile Asn Thr Glu Leu Arg Asp Tyr Val
785                 790                 795                 800

Val Glu Ile Thr Lys Glu Val Phe Arg Gln His Cys Ala Lys His Leu
            805                 810                 815

Glu Val Ile Pro Met Arg Leu Leu Ser Asp Cys Pro Gln Phe Ser Arg
        820                 825                 830

Lys Thr Val Lys Leu Leu Thr Asn Gly Gly Asp Met Leu Glu Leu Cys
    835                 840                 845

Tyr Glu Leu Arg Leu Pro Phe Val His Trp Ile Ser Val Asn Gln Lys
850                 855                 860

Ser Ser Phe Lys Arg Tyr Glu Ile Ser His Val Tyr Arg Arg Ala Ile
865                 870                 875                 880

Gly His Ser Pro Pro Asn Pro Cys Leu Gln Ala Asp Phe Asp Ile Val
            885                 890                 895

Gly Gly Thr Leu Ser Leu Thr Glu Ala Glu Val Leu Lys Val Ile Val
        900                 905                 910

Asp Ile Thr Thr His Ile Phe His Arg Gly Ser Cys Asp Ile His Leu
    915                 920                 925

Asn His Gly Asp Leu Leu Asp Ala Ile Trp Ser Trp Ala Gly Ile Lys
930                 935                 940

Ala Glu His Arg Arg Lys Val Ala Glu Leu Leu Ser Met Met Gly Ser
945                 950                 955                 960

Leu Arg Pro Gln Ser Ser Glu Arg Lys Leu Lys Trp Val Phe Ile Arg
            965                 970                 975

Arg Gln Leu Leu Gln Glu Leu Lys Leu Pro Glu Ala Val Val Asn Arg
        980                 985                 990

Leu Gln Thr Val Ala Ser Arg Phe Cys Gly Asp Ala Asp Gln Ala Leu
    995                 1000                1005

Pro Arg Leu Arg Gly Ala Leu Arg Ala Asp Arg Pro Thr Arg Lys
    1010                1015                1020

Ala Leu Asp Glu Leu Ser Asn Leu Leu Thr Tyr Leu Arg Val Trp
    1025                1030                1035

Arg Ile Glu Glu His Val His Ile Asp Val Leu Met Pro Pro Thr
    1040                1045                1050

Glu Ser Tyr His Arg Asn Leu Phe Phe Gln Val Phe Leu Thr Lys
    1055                1060                1065

Glu Asn Ser Ser Gly Thr Ser Asn Asp Gly Val Leu Leu Ala Val
    1070                1075                1080

Gly Gly Arg Tyr Asp Trp Leu Val Gln Glu Val Cys Asp Arg Glu
    1085                1090                1095

His Lys Met Asn Leu Pro Gly Ala Val Gly Val Ser Leu Ala Leu
    1100                1105                1110

Glu Thr Ile Phe Gln His Leu Pro Met Asp Leu Arg Pro Ile Arg
```

```
    1115                1120                1125

Asn Glu  Val Ser Thr Ser Val  Leu Val Cys Ser Arg  Gly Gly Gly
    1130                1135                1140

Gly Leu  Leu Val Gln Arg Met  Glu Leu Val Ala Glu  Leu Trp Glu
    1145                1150                1155

Lys Ser  Ile Lys Ala Glu Phe  Val Pro Thr Pro Asp  Pro Ser Leu
    1160                1165                1170

Thr Glu  Gln Tyr Glu Tyr Ala  Asn Glu His Glu Ile  Lys Cys Leu
    1175                1180                1185

Val Ile  Ile Thr Glu Ser Gly  Val Ala Gln Asn Gln  Ile Glu Phe
    1190                1195                1200

Val Lys  Val Arg His Leu Glu  Leu Lys Lys Glu Lys  Val Val Gly
    1205                1210                1215

Arg Glu  Glu Leu Val Lys Phe  Leu Leu Asp Ala Met  Ala Val Gln
    1220                1225                1230

Phe Arg  Asn Pro Ser Val Trp  Ser
    1235                1240

<210> SEQ ID NO 83
<211> LENGTH: 3395
<212> TYPE: DNA
<213> ORGANISM: Arabidopsis thaliana
<400> SEQUENCE: 83
ctctagctcc tactttcatt acccaattac tctctcaaca cttctttagt cggcagaaaa     60
gatttttttt ttgagaagct tagcttcaaa gggtctttgg aggatgttat gatgttgtta    120
ccttgcggtc tgagatctga aaggagtaag tgtttttgtt ttcgttgcag aagaacagag    180
agacaagagg tccttctttg acttggttgt ctgaattttc cacttcaaga ttgtttccta    240
catctccgga gattgtctgg ctgacgagtc ctttgtttct tcgtcactaa ttcagctctc    300
attgtttgta atttctattc ttttagttat tgcatgccct tgattgcagt tccacagttt    360
ttgtgaactt cgtgtgactc gtttgctatt tactaatcaa gggtcatact cttagtcact    420
ctgtggaatg tctcagaaag tgaagacagt aactaagaag cgtgtgtgtt gactttgaaa    480
agaatgagaa tgttcgaaac gagagcaagg gaatggattc tccttgtaaa gcttgtgctt    540
ttcactagta tatggcagct tgcttcagct cttggttcaa tgtcttcaat tgcaatttct    600
tatggagaag gtggttctgt attctgtggt ctgaagtctg atgggtctca tcttgtggtt    660
tgctacggat cgaactcagc aatcctctat gggactcctg gtcatctcca gttcatcggt    720
ttaacgggtg gagatgggtt tatgtgtggg cttctgatgc tatctcatca gccttattgt    780
tggggaaaca gtgcatttat tcaaatggga gttcctcaac caatgaccaa aggagctgag    840
tatttagaag ttagtgctgg tgattaccat ctttgtggtt tgaggaagcc aatagtggga    900
agaagaaaga acagcaacat tatttcctct tctcttgttg attgttgggg ttacaatatg    960
acaagaaact ttgtctttga taagcagtta cattcgcttt cggctggttc ggagttcaac   1020
tgcgcgctgt cctctaaaga taagtcggtt ttctgttggg gagatgagaa tagtagtcaa   1080
gtaatcagtt taatccccaa ggaaaaaaag tttcagaaaa ttgcagctgg tggataccat   1140
gtttgtggca ttcttgacgg gttggaatcg cgagtgctat gttggggaaa gagcttagag   1200
ttcgaagagg aggttacagg gacttctaca gaagaaaaga ttcttgattt accaccaaaa   1260
gagccactct tagcagtggt aggtgggaag ttttatgctt gtggaatcaa acgctatgat   1320
catagtgcgg tctgttgggg tttttcgtg aacaggagta cacctgctcc tacaggtatc   1380
```

```
ggcttttatg atcttgcagc ggggaattac ttcacttgcg gagttctcac agggacttct    1440
atgtcacctg tttgttgggg tcttggtttc cctgcttcta tcccttttagc tgtctcacca   1500 ggactctgta tagacactcc ttgtccacca ggaactcatg aactcagtaa ccaagaaaac    1560
tcgccttgca aatttactgg ctctcacatt tgcttgccct gtagcaccag ttgccctcct    1620
ggaatgtatc agaaaagcgt atgcacagag agatctgatc aagtttgtgt ttacaactgc    1680
tccagttgtt cctcacatga ttgctcctca aactgctctt cttcggctac cagtggaggc    1740
aaggaaaaag gaaagttttg gtcactgcag ctacctattg caactgcaga gattggattt    1800
gctctatttt tggtagcggt tgtctcgata cagcggctt tatacattag gtacagattg     1860
aggaattgta ggtgctcaga aaatgataca aggtcttcta agattcagc ctttacgaaa     1920 gataatggca aaatccgtcc ggatcttgat gagctgcaaa agcgcagaag gctagagtt    1980 ttcacttatg aggaacttga aaagccgct gatggattca agaagaatc aatagtgggg     2040 aaagggagtt tctcatgtgt gtacaaagga gtactgagag atggaaccac tgttgcagtg   2100
aagagagcga taatgtcatc agacaaacag aagaattcaa atgagtttcg cacggagctt   2160
gatctgttat caagactcaa ccatgctcat cttcttagcc ttcttggata ctgtgaagaa    2220
tgtggagaaa ggctttttagt ttatgagttt atggcacacg gctcactgca caaccatctt   2280 catgaaaga caaggccttg aaagagcaa ctagattggg tcaaaagagt aacgattgct     2340
gtccaagctg ctagaggaat cgaatacttg catggttacg cttgccctcc cgtgattcac   2400
cgggatatta aatcatcaaa cattcttata gatgaagaac acaatgctcg agtagctgat   2460
tttggtctct ccttacttgg tcctgtcgat agcggctctc ctttggcaga actaccagca    2520
ggaactctcg gttaccttga tcccgagtac tatcgacttc actatctcac aaccaaatcc   2580
gatgtctaca gctttggagt cctgcttctc gagatcctaa gcggaagaaa agccattgac   2640
atgcactacg aagaagggaa catagtagaa tgggcagttc ctttgatcaa gcaggagat    2700 ataaacgcac tcttggaccc ggtcttgaaa catccatctg aaatcgaagc tttgaaaaga   2760
atcgtgagtg tggcttgcaa atgcgtgaga atgagaggga agatagacc atcaatggat    2820 aaagtgacaa cagcattgga acgagcgctt gcacagctaa tgggaaaccc gagcagtgag   2880
cagccaatat taccaacaga agtggttctt gggagcagca gaatgcacaa gaagtcatgg   2940
aggatcggtt caaaaaggtc tggttccgag aacacggaat tcagaggcgg atcatggata   3000
acattcccga gcgtgacatc atcgcagagg aggaaatcat cggcatctga aggagatgtc   3060
gcagaggagg aggatgaagg gaggaagcaa caagaagcat tgaggagtct tgaggaagag   3120 ataggggccag cttctcctgg acagagcttg ttcttgcatc ataatttctg aaaacaagtg   3180
tctgttttct caagtcttta gtaactaatg acatatataa gatattttac tctgatgtat    3240
aatgtgttcc ttaaggcagg aaagtaacaa agaggcagag agactcttca agcaagaatg   3300
tatcaagttt tttttttcaac taattattac aaagttcttt tgtataagtg aacctggtta   3360
tttattattg tactagtggt ttttacctgt tgatt                                3395
```

<210> SEQ ID NO 84
<211> LENGTH: 895
<212> TYPE: PRT
<213> ORGANISM: Arabidopsis thaliana

<400> SEQUENCE: 84

Met Arg Met Phe Glu Thr Arg Ala Arg Glu Trp Ile Leu Leu Val Lys
1               5                   10                  15

```
Leu Val Leu Phe Thr Ser Ile Trp Gln Leu Ala Ser Ala Leu Gly Ser
             20                  25                  30

Met Ser Ser Ile Ala Ile Ser Tyr Gly Glu Gly Gly Ser Val Phe Cys
         35                  40                  45

Gly Leu Lys Ser Asp Gly Ser His Leu Val Val Cys Tyr Gly Ser Asn
     50                  55                  60

Ser Ala Ile Leu Tyr Gly Thr Pro Gly His Leu Gln Phe Ile Gly Leu
65                  70                  75                  80

Thr Gly Gly Asp Gly Phe Met Cys Gly Leu Leu Met Leu Ser His Gln
                 85                  90                  95

Pro Tyr Cys Trp Gly Asn Ser Ala Phe Ile Gln Met Gly Val Pro Gln
            100                 105                 110

Pro Met Thr Lys Gly Ala Glu Tyr Leu Glu Val Ser Ala Gly Asp Tyr
        115                 120                 125

His Leu Cys Gly Leu Arg Lys Pro Ile Val Gly Arg Arg Lys Asn Ser
    130                 135                 140

Asn Ile Ile Ser Ser Ser Leu Val Asp Cys Trp Gly Tyr Asn Met Thr
145                 150                 155                 160

Arg Asn Phe Val Phe Asp Lys Gln Leu His Ser Leu Ser Ala Gly Ser
                165                 170                 175

Glu Phe Asn Cys Ala Leu Ser Ser Lys Asp Lys Ser Val Phe Cys Trp
            180                 185                 190

Gly Asp Glu Asn Ser Ser Gln Val Ile Ser Leu Ile Pro Lys Glu Lys
        195                 200                 205

Lys Phe Gln Lys Ile Ala Ala Gly Gly Tyr His Val Cys Gly Ile Leu
    210                 215                 220

Asp Gly Leu Glu Ser Arg Val Leu Cys Trp Gly Lys Ser Leu Glu Phe
225                 230                 235                 240

Glu Glu Glu Val Thr Gly Thr Ser Thr Glu Glu Lys Ile Leu Asp Leu
                245                 250                 255

Pro Pro Lys Glu Pro Leu Leu Ala Val Val Gly Gly Lys Phe Tyr Ala
            260                 265                 270

Cys Gly Ile Lys Arg Tyr Asp His Ser Ala Val Cys Trp Gly Phe Phe
        275                 280                 285

Val Asn Arg Ser Thr Pro Ala Pro Thr Gly Ile Gly Phe Tyr Asp Leu
    290                 295                 300

Ala Ala Gly Asn Tyr Phe Thr Cys Gly Val Leu Thr Gly Thr Ser Met
305                 310                 315                 320

Ser Pro Val Cys Trp Gly Leu Gly Phe Pro Ala Ser Ile Pro Leu Ala
                325                 330                 335

Val Ser Pro Gly Leu Cys Ile Asp Thr Pro Cys Pro Pro Gly Thr His
            340                 345                 350

Glu Leu Ser Asn Gln Glu Asn Ser Pro Cys Lys Phe Thr Gly Ser His
        355                 360                 365

Ile Cys Leu Pro Cys Ser Thr Ser Cys Pro Pro Gly Met Tyr Gln Lys
    370                 375                 380

Ser Val Cys Thr Glu Arg Ser Asp Gln Val Cys Val Tyr Asn Cys Ser
385                 390                 395                 400

Ser Cys Ser Ser His Asp Cys Ser Ser Asn Cys Ser Ser Ala Thr
                405                 410                 415

Ser Gly Gly Lys Glu Lys Gly Lys Phe Trp Ser Leu Gln Leu Pro Ile
            420                 425                 430
```

```
Ala Thr Ala Glu Ile Gly Phe Ala Leu Phe Leu Val Ala Val Val Ser
            435                 440                 445

Ile Thr Ala Ala Leu Tyr Ile Arg Tyr Arg Leu Arg Asn Cys Arg Cys
    450                 455                 460

Ser Glu Asn Asp Thr Arg Ser Ser Lys Asp Ser Ala Phe Thr Lys Asp
465                 470                 475                 480

Asn Gly Lys Ile Arg Pro Asp Leu Asp Glu Leu Gln Lys Arg Arg Arg
                485                 490                 495

Ala Arg Val Phe Thr Tyr Glu Glu Leu Glu Lys Ala Ala Asp Gly Phe
                500                 505                 510

Lys Glu Glu Ser Ile Val Gly Lys Gly Ser Phe Ser Cys Val Tyr Lys
            515                 520                 525

Gly Val Leu Arg Asp Gly Thr Thr Val Ala Val Lys Arg Ala Ile Met
530                 535                 540

Ser Ser Asp Lys Gln Lys Asn Ser Asn Glu Phe Arg Thr Glu Leu Asp
545                 550                 555                 560

Leu Leu Ser Arg Leu Asn His Ala His Leu Leu Ser Leu Leu Gly Tyr
                565                 570                 575

Cys Glu Glu Cys Gly Glu Arg Leu Leu Val Tyr Glu Phe Met Ala His
            580                 585                 590

Gly Ser Leu His Asn His Leu His Gly Lys Asn Lys Ala Leu Lys Glu
            595                 600                 605

Gln Leu Asp Trp Val Lys Arg Val Thr Ile Ala Val Gln Ala Ala Arg
    610                 615                 620

Gly Ile Glu Tyr Leu His Gly Tyr Ala Cys Pro Pro Val Ile His Arg
625                 630                 635                 640

Asp Ile Lys Ser Ser Asn Ile Leu Ile Asp Glu Glu His Asn Ala Arg
                645                 650                 655

Val Ala Asp Phe Gly Leu Ser Leu Leu Gly Pro Val Asp Ser Gly Ser
                660                 665                 670

Pro Leu Ala Glu Leu Pro Ala Gly Thr Leu Gly Tyr Leu Asp Pro Glu
            675                 680                 685

Tyr Tyr Arg Leu His Tyr Leu Thr Thr Lys Ser Asp Val Tyr Ser Phe
            690                 695                 700

Gly Val Leu Leu Leu Glu Ile Leu Ser Gly Arg Lys Ala Ile Asp Met
705                 710                 715                 720

His Tyr Glu Glu Gly Asn Ile Val Glu Trp Ala Val Pro Leu Ile Lys
                725                 730                 735

Ala Gly Asp Ile Asn Ala Leu Leu Asp Pro Val Leu Lys His Pro Ser
                740                 745                 750

Glu Ile Glu Ala Leu Lys Arg Ile Val Ser Val Ala Cys Lys Cys Val
            755                 760                 765

Arg Met Arg Gly Lys Asp Arg Pro Ser Met Asp Lys Val Thr Thr Ala
770                 775                 780

Leu Glu Arg Ala Leu Ala Gln Leu Met Gly Asn Pro Ser Ser Glu Gln
785                 790                 795                 800

Pro Ile Leu Pro Thr Glu Val Val Leu Gly Ser Ser Arg Met His Lys
                805                 810                 815

Lys Ser Trp Arg Ile Gly Ser Lys Arg Ser Gly Ser Glu Asn Thr Glu
                820                 825                 830

Phe Arg Gly Gly Ser Trp Ile Thr Phe Pro Ser Val Thr Ser Ser Gln
            835                 840                 845

Arg Arg Lys Ser Ser Ala Ser Glu Gly Asp Val Ala Glu Glu Glu Asp
```

```
                      850                 855                 860
Glu Gly Arg Lys Gln Gln Glu Ala Leu Arg Ser Leu Glu Glu Glu Ile
 865                 870                 875                 880

Gly Pro Ala Ser Pro Gly Gln Ser Leu Phe Leu His His Asn Phe
                 885                 890                 895

<210> SEQ ID NO 85
<211> LENGTH: 2198
<212> TYPE: DNA
<213> ORGANISM: Arabidopsis thaliana

<400> SEQUENCE: 85
ggtttcagaa aactaagtat ggctcaggag gaaaaaaact tgttgcttga agataatctg      60
aaatcattaa tatgcaactt catgccttgt tgctctataa atttaatatc gtcacatgtc     120
ctgttgtttc tcctaatgat ttcttgtttg gaacctaatc atgtgttgtt gtatctatct     180
aacaattgca gaaaataat ttgaacccgg taagttttgg ggtccctggg aatcaagata      240
gttcagcgac aacttctaga gcaccagcga ttagaacatg gaatgtgaaa agaggttttg     300 gtgaattttat ttctgtttct tatagatttc tcttgtctca ttttgttata ccatttatga    360
agactggtta aatgttattg cagattctta tggtaacaaa ttggatgtac ctagagagga    420
ttatgttcaa ggtgcagtgg ctagagaacc aggcattatc cttgggaata atacaccgta    480
tcaggttcga ttcacttttt ttgaaatatg tatttgtatg aaagtgaagt cggcttacaa    540
ccactaggat gagtcagctg tagttttcac taagttggtt ttcattgagc aaattgataa    600
aatccgctat tttcgccttt atggtagatg gtacaatagt cataccgcta taatgtacga    660
tagtttctca aagaaattta ttgaaatagg tgcatcaatg ttttgtcct taatactctg     720 ccaacttcta acgtctctta aatgtttcta tggaaaatgc aggaaagaaa tggaaatgat    780
ggtttgattg attttacatc tgctcctcct tatatgagga aattgaatga aaagggccca    840
acagcaaact ccaagagagc agattctcgg ctagaaaata aatgagaga tgtagacagt     900 ggtgataatc ctagttcgtc ttcgtttgag tttcatgtca gtttggaaga gggtattagc    960 cttttcagttg atctaaattt taatccatca gattggatca atagcatgag agatgaggtc   1020
aatgtatgtg atagcatgcg ccgcagaaaa tccccacatt ctgatcttgg cattacagag   1080
tgtaagaaac agaagagttc agggcaagac acggatggtc atgtaaggag agaatcatct   1140
ttaagtccgc caatgaaaga caatgctcac ttaccttctg atcaccatcc caatggtgaa   1200
cgatctctag catcatctgc catagaacca tgcaacagaa tcaaagagag ctcagacact   1260
tgcaaggaaa aaagcgggct taacttgtcc ataccctgatt cttcaggacc ttgccagatt   1320
gcatcatctt gtgtcgaatc atatagtaaa agctgctgtg taaatccagt tgacttggac   1380
tgtattattc ctccagggaa gaagttggca agtgaatctg atatggttgc tgcagaacag   1440
aatcattcag ctggtgatct ccttgtagaa attccgaaaa atccatccat ggaaagcttt   1500
caaatagtcg gaaactcaag tactgttata tgtccacggg gagctggctc tgaattatca   1560
tcatcagaag cagaggccta tcactcaaac cagccgtgtt ctcctcgtaa gaccagtaga   1620
tcctcgacta tctcttctcc agagttcatc atcgatagag agtctactag ttattctgag   1680
tcattcaagt tccgttgcaa tggaggcaaa agtttgccac caaacacgga ggagcaggaa   1740
aagagcgaag ttttaagtga gcaggcgcgg tcagagtgac ttgtttgaag ggtgaagcat   1800
ccattatgtt gtataatatt gttcaagtaa tagaaaaatg ctatataca tgatgtagag   1860 atagtcaaga aatggccttt cctctaacca agaggtttct actgctgctt ttttttgag   1920
```

-continued

```
gtatgatttt gtgctctctc tataaatata cgattgatac aacaaagagt aatgaagact    1980 ttattttgg ttgttggctt gcacttaggc catcaaacac atggagatga gagcattgag     2040
tcaaatatta ctgaaggttt tttgcaatga cctagggaga agtcagtttt taggtcagta    2100
tgcaattctt tttggttcgt cttttattat ttgtaaggct gtcttgtctg taaacgcaat    2160
tctgtgttgt taaacacatc attcataaac caatcttg                            2198
```

<210> SEQ ID NO 86
<211> LENGTH: 345
<212> TYPE: PRT
<213> ORGANISM: Arabidopsis thaliana

<400> SEQUENCE: 86

```
Met Phe Leu Trp Lys Met Gln Glu Arg Asn Gly Asn Asp Gly Leu Ile
 1               5                  10                  15

Asp Phe Thr Ser Ala Pro Pro Tyr Met Arg Lys Leu Asn Glu Lys Gly
            20                  25                  30

Pro Thr Ala Asn Ser Lys Arg Ala Asp Ser Arg Leu Glu Asn Arg Met
        35                  40                  45

Arg Asp Val Asp Ser Gly Asp Asn Pro Ser Ser Ser Phe Glu Phe
    50                  55                  60

His Val Ser Leu Glu Glu Gly Ile Ser Leu Ser Val Asp Leu Asn Phe
65                  70                  75                  80

Asn Pro Ser Asp Trp Ile Asn Ser Met Arg Asp Glu Val Asn Val Cys
                85                  90                  95

Asp Ser Met Arg Arg Arg Lys Ser Pro His Ser Asp Leu Gly Ile Thr
            100                 105                 110

Glu Cys Lys Lys Gln Lys Ser Ser Gly Gln Asp Thr Asp Gly His Val
        115                 120                 125

Arg Arg Glu Ser Ser Leu Ser Pro Pro Met Lys Asp Asn Ala His Leu
    130                 135                 140

Pro Ser Asp His His Pro Asn Gly Glu Arg Ser Leu Ala Ser Ser Ala
145                 150                 155                 160

Ile Glu Pro Cys Asn Arg Ile Lys Glu Ser Ser Asp Thr Cys Lys Glu
                165                 170                 175

Lys Ser Gly Leu Asn Leu Ser Ile Pro Asp Ser Ser Gly Pro Cys Gln
            180                 185                 190

Ile Ala Ser Ser Cys Val Glu Ser Tyr Ser Lys Ser Cys Cys Val Asn
        195                 200                 205

Pro Val Asp Leu Asp Cys Ile Ile Pro Pro Gly Lys Lys Leu Ala Ser
    210                 215                 220

Glu Ser Asp Met Val Ala Ala Glu Gln Asn His Ser Ala Gly Asp Leu
225                 230                 235                 240

Leu Val Glu Ile Pro Lys Asn Pro Ser Met Glu Ser Phe Gln Ile Val
                245                 250                 255

Gly Asn Ser Ser Thr Val Ile Cys Pro Arg Gly Ala Gly Ser Glu Leu
            260                 265                 270

Ser Ser Ser Glu Ala Glu Ala Tyr His Ser Asn Gln Pro Cys Ser Pro
        275                 280                 285

Arg Lys Thr Ser Arg Ser Ser Thr Ile Ser Ser Pro Glu Phe Ile Ile
    290                 295                 300

Asp Arg Glu Ser Thr Ser Tyr Ser Glu Ser Phe Lys Phe Arg Cys Asn
305                 310                 315                 320
```

Gly Gly Lys Ser Leu Pro Pro Asn Thr Glu Glu Gln Glu Lys Ser Glu
             325                 330                 335

Val Leu Ser Glu Gln Ala Arg Ser Glu
             340                 345

<210> SEQ ID NO 87
<211> LENGTH: 1768
<212> TYPE: DNA
<213> ORGANISM: Arabidopsis thaliana

<400> SEQUENCE: 87

| | | | | | |
|---|---|---|---|---|---|
| gttctgtctg | cttaggtccc | tgcagagatt | tcgaaatcgc | tacttccaat | ttctccagaa |   60 |
| actttctttc | tcggcaaaat | tcccggaaaa | agccactcga | tcagcagatg | gtcaggaagg |  120 |
| aagatgtgga | tttctattgc | ggattttcaa | ggaaagagct | tcagagttta | tgcaagaagt |  180 |
| ataatttgcc | tgccaataga | tcaagttccg | atatggctga | atcattggct | tcttacttcg |  240 |
| agaaaaataa | tttgaacccg | gtaagttttg | gggtccctgg | gaatcaagat | agttcagcga |  300 |
| caacttctag | agcaccagcg | attagaacat | ggaatgtgaa | aagagattct | tatggtaaca |  360 |
| aattggatgt | acctagagag | gattatgttc | aaggtgcagt | ggctagagaa | ccaggcatta |  420 |
| tccttgggaa | taatacaccg | tatcaggaaa | gaaatgaaa  | tgatggtttg | attgatttta |  480 |
| catctgctcc | tccttatatg | aggaaattga | atgaaaaggg | cccaacagca | aactccaaga |  540 |
| gagcagattc | tcggctagaa | aatagaatga | gagatgtaga | cagtggtgat | aatcctagtt |  600 |
| cgtcttcgtt | tgagtttcat | gtcagtttgg | aagagggtat | tagcctttca | gttgatctaa |  660 |
| attttaatcc | atcagattgg | atcaatagca | tgagagatga | ggtcaatgta | tgtgatagca |  720 |
| tgcgccgcag | aaaatcccca | cattctgatc | ttggcattac | agagtgtaag | aaacagaaga |  780 |
| gttcagggca | agacacggat | ggtcatgtaa | ggagagaatc | atctttaagt | ccgccaatga |  840 |
| aagacaatgc | tcacttacct | tctgatcacc | atcccaatgg | tgaacgatct | ctagcatcat |  900 |
| ctgccataga | accatgcaac | agaatcaaag | agagctcaga | cacttgcaag | gaaaaaagcg |  960 |
| ggcttaactt | gtccatacct | gattcttcag | gaccttgcca | gattgcatca | tcttgtgtcg | 1020 |
| aatcatatag | taaaagctgc | tgtgtaaatc | cagttgactt | ggactgtatt | attcctccag | 1080 |
| ggaagaagtt | ggcaagtgaa | tctgatatgg | ttgctgcaga | acagaatcat | tcagctggtg | 1140 |
| atctccttgt | agaaattccg | aaaaatccat | ccatggaaag | ctttcaaata | gtcggaaact | 1200 |
| caagtactgt | tatatgtcca | cggggagctg | gctctgaatt | atcatcatca | gaagcagagg | 1260 |
| cctatcactc | aaaccagccg | tgttctcctc | gtaagaccag | tagatcctcg | actatctctt | 1320 |
| ctccagagtt | catcatcgat | agagagtcta | ctagttattc | tgagtcattc | aagttccgtt | 1380 |
| gcaatggagg | caaagtttg  | ccaccaaaca | cggaggagca | ggaaaagagc | gaagttttaa | 1440 |
| gtgagcaggc | gcggtcagag | tgacttgttt | gaagggtgaa | gcatccatta | tgttgtataa | 1500 |
| tattgttcaa | gtaatagaaa | aatggctata | tacatgatgt | agagatagtc | aagaaatggc | 1560 |
| ctttcctcta | accaagaggt | ttctactgct | gcttttttt  | tgaggccatc | aaacacatgg | 1620 |
| agatgagagc | attgagtcaa | atattactga | aggttttttg | caatgaccta | gggagaagtc | 1680 |
| agttttagg  | tcagtatgca | attcttttg  | gttcgtcttt | tattatttgt | aaggctgtct | 1740 |
| tgtctgtaaa | cgcaattctg | tgttgtta   |            |            |            | 1768 |

<210> SEQ ID NO 88
<211> LENGTH: 451
<212> TYPE: PRT
<213> ORGANISM: Arabidopsis thaliana

<400> SEQUENCE: 88

Met Val Arg Lys Glu Asp Val Asp Phe Tyr Cys Gly Phe Ser Arg Lys
1               5                   10                  15

Glu Leu Gln Ser Leu Cys Lys Lys Tyr Asn Leu Pro Ala Asn Arg Ser
            20                  25                  30

Ser Ser Asp Met Ala Glu Ser Leu Ala Ser Tyr Phe Glu Lys Asn Asn
        35                  40                  45

Leu Asn Pro Val Ser Phe Gly Val Pro Gly Asn Gln Asp Ser Ser Ala
    50                  55                  60

Thr Thr Ser Arg Ala Pro Ala Ile Arg Thr Trp Asn Val Lys Arg Asp
65                  70                  75                  80

Ser Tyr Gly Asn Lys Leu Asp Val Pro Arg Glu Asp Tyr Val Gln Gly
                85                  90                  95

Ala Val Ala Arg Glu Pro Gly Ile Ile Leu Gly Asn Asn Thr Pro Tyr
            100                 105                 110

Gln Glu Arg Asn Gly Asn Asp Gly Leu Ile Asp Phe Thr Ser Ala Pro
        115                 120                 125

Pro Tyr Met Arg Lys Leu Asn Glu Lys Gly Pro Thr Ala Asn Ser Lys
    130                 135                 140

Arg Ala Asp Ser Arg Leu Glu Asn Arg Met Arg Asp Val Asp Ser Gly
145                 150                 155                 160

Asp Asn Pro Ser Ser Ser Phe Glu Phe His Val Ser Leu Glu Glu
                165                 170                 175

Gly Ile Ser Leu Ser Val Asp Leu Asn Phe Asn Pro Ser Asp Trp Ile
            180                 185                 190

Asn Ser Met Arg Asp Glu Val Asn Val Cys Asp Ser Met Arg Arg
        195                 200                 205

Lys Ser Pro His Ser Asp Leu Gly Ile Thr Glu Cys Lys Lys Gln Lys
    210                 215                 220

Ser Ser Gly Gln Asp Thr Asp Gly His Val Arg Arg Glu Ser Ser Leu
225                 230                 235                 240

Ser Pro Pro Met Lys Asp Asn Ala His Leu Pro Ser Asp His His Pro
                245                 250                 255

Asn Gly Glu Arg Ser Leu Ala Ser Ser Ala Ile Glu Pro Cys Asn Arg
            260                 265                 270

Ile Lys Glu Ser Ser Asp Thr Cys Lys Glu Lys Ser Gly Leu Asn Leu
        275                 280                 285

Ser Ile Pro Asp Ser Ser Gly Pro Cys Gln Ile Ala Ser Ser Cys Val
    290                 295                 300

Glu Ser Tyr Ser Lys Ser Cys Cys Val Asn Pro Val Asp Leu Asp Cys
305                 310                 315                 320

Ile Ile Pro Pro Gly Lys Lys Leu Ala Ser Glu Ser Asp Met Val Ala
                325                 330                 335

Ala Glu Gln Asn His Ser Ala Gly Asp Leu Leu Val Glu Ile Pro Lys
            340                 345                 350

Asn Pro Ser Met Glu Ser Phe Gln Ile Val Gly Asn Ser Ser Thr Val
        355                 360                 365

Ile Cys Pro Arg Gly Ala Gly Ser Glu Leu Ser Ser Glu Ala Glu
    370                 375                 380

Ala Tyr His Ser Asn Gln Pro Cys Ser Pro Arg Lys Thr Ser Arg Ser
385                 390                 395                 400

Ser Thr Ile Ser Ser Pro Glu Phe Ile Ile Asp Arg Glu Ser Thr Ser

```
                405                 410                 415
Tyr Ser Glu Ser Phe Lys Phe Arg Cys Asn Gly Gly Lys Ser Leu Pro
        420                 425                 430

Pro Asn Thr Glu Glu Gln Glu Lys Ser Glu Val Leu Ser Glu Gln Ala
            435                 440                 445

Arg Ser Glu
    450

<210> SEQ ID NO 89
<211> LENGTH: 1817
<212> TYPE: DNA
<213> ORGANISM: Arabidopsis thaliana

<400> SEQUENCE: 89
ctttctcggc aaaattcccg gaaaaagcca ctcgatcagc agatggtcag gaaggaagat      60
gtggatttct attgcggatt ttcaaggaaa gagcttcaga gtttatgcaa gaagtataat     120
ttgcctgcca atagatcaag ttccgatatg gctgaatcat tggcttctta cttcgagaaa     180
aataatttga acccggtaag ttttggggtc cctgggaatc aagatagttc agcgacaact     240
tctagagcac cagcgattag aacatggaat gtgaaaagag attcttatgg taacaaattg     300
gatgtaccta gagaggatta tgttcaaggt gcagtggcta gagaaccagg cattatcctt     360
gggaataata caccgtatca ggaaagaaat ggaaatgatg gtttgattga ttttacatct     420
gctcctcctt atatgaggaa attgaatgaa aagggcccaa cagcaaactc caagagagca     480
gattctcggc tagaaaatag aatgagagat gtagacagtg gtgataatcc tagttcgtct     540
tcgtttgagt ttcatgtcag tttggaagag ggtattagcc tttcagttga tctaaatttt     600
aatccatcag attggatcaa tagcatgaga atgaggtca atgtatgtga tagcatgcgc     660
cgcagaaaat ccccacattc tgatcttggc attacagagt gtaagaaaca gaagagttca     720
gggcaagaca cggatggtca tgtaaggaga gaatcatctt taagtccgcc aatgaaagac     780
aatgctcact taccttctga tcaccatccc aatggtgaac gatctctagc atcatctgcc     840
atagaaccat gcaacagaat caaagagagc tcagacactt gcaaggaaaa aagcgggctt     900
aacttgtcca tacctgattc ttcaggacct tgccagattg catcatcttg tgtcgaatca     960
tatagtaaaa gctgctgtgt aaatccagtt gacttggact gtattattcc tccagggaag    1020
aagttggcaa gtgaatctga tatggttgct gcagaacaga atcattcagc tggtgatctc    1080
cttgtagaaa ttccgaaaaa tccatccatg gaaagctttc aaatagtcgg aaactcaagt    1140
actgttatat gtccacgggg agctggctct gaattatcat catcagaagc agaggcctat    1200
cactcaaacc agccgtgttc tcctcgtaag accagtagat cctcgactat ctcttctcca    1260
gagttcatca tcgatagaga gtctactagt tattctgagt cattcaagtt ccgttgcaat    1320
ggaggcaaaa gtttgccacc aaacacggag gagcaggaaa agagcgaagt tttaagtgag    1380
caggcgcggt cagagtgact tgtttgaagg gtgaagcatc cattatgttg tataatattg    1440
ttcaagtaat agaaaaatgg ctatatacat gatgtagaga tagtcaagaa atggcctttc    1500
ctctaaccaa gaggtttcta ctgctgcttt ttttttgagg tatgattttg tgctctctct    1560
ataaatatac gattgataca acaaagagta atgaagactt tatttttggt tgttggcttg    1620
cacttaggcc atcaaacaca tggagatgag agcattgagt caaatattac tgaaggtttt    1680
ttgcaatgac ctaggagaa gtcagttttt aggtcagtat gcaattcttt ttggttcgtc    1740
ttttattatt tgtaaggctg tcttgtctgt aaacgcaatt ctgtgttgtt aaacacatca    1800
```
ttcataaacc aatcttg                                              1817

<210> SEQ ID NO 90
<211> LENGTH: 451
<212> TYPE: PRT
<213> ORGANISM: Arabidopsis thaliana

<400> SEQUENCE: 90

Met Val Arg Lys Glu Asp Val Asp Phe Tyr Cys Gly Phe Ser Arg Lys
1               5                   10                  15

Glu Leu Gln Ser Leu Cys Lys Lys Tyr Asn Leu Pro Ala Asn Arg Ser
            20                  25                  30

Ser Ser Asp Met Ala Glu Ser Leu Ala Ser Tyr Phe Glu Lys Asn Asn
        35                  40                  45

Leu Asn Pro Val Ser Phe Gly Val Pro Gly Asn Gln Asp Ser Ser Ala
    50                  55                  60

Thr Thr Ser Arg Ala Pro Ala Ile Arg Thr Trp Asn Val Lys Arg Asp
65                  70                  75                  80

Ser Tyr Gly Asn Lys Leu Asp Val Pro Arg Glu Asp Tyr Val Gln Gly
                85                  90                  95

Ala Val Ala Arg Glu Pro Gly Ile Ile Leu Gly Asn Asn Thr Pro Tyr
            100                 105                 110

Gln Glu Arg Asn Gly Asn Asp Gly Leu Ile Asp Phe Thr Ser Ala Pro
        115                 120                 125

Pro Tyr Met Arg Lys Leu Asn Glu Lys Gly Pro Thr Ala Asn Ser Lys
    130                 135                 140

Arg Ala Asp Ser Arg Leu Glu Asn Arg Met Arg Asp Val Asp Ser Gly
145                 150                 155                 160

Asp Asn Pro Ser Ser Ser Phe Glu Phe His Val Ser Leu Glu Glu
                165                 170                 175

Gly Ile Ser Leu Ser Val Asp Leu Asn Phe Asn Pro Ser Asp Trp Ile
            180                 185                 190

Asn Ser Met Arg Asp Glu Val Asn Val Cys Asp Ser Met Arg Arg Arg
        195                 200                 205

Lys Ser Pro His Ser Asp Leu Gly Ile Thr Glu Cys Lys Lys Gln Lys
    210                 215                 220

Ser Ser Gly Gln Asp Thr Asp Gly His Val Arg Arg Glu Ser Ser Leu
225                 230                 235                 240

Ser Pro Pro Met Lys Asp Asn Ala His Leu Pro Ser Asp His His Pro
                245                 250                 255

Asn Gly Glu Arg Ser Leu Ala Ser Ser Ala Ile Glu Pro Cys Asn Arg
            260                 265                 270

Ile Lys Glu Ser Ser Asp Thr Cys Lys Glu Lys Ser Gly Leu Asn Leu
        275                 280                 285

Ser Ile Pro Asp Ser Ser Gly Pro Cys Gln Ile Ala Ser Ser Cys Val
    290                 295                 300

Glu Ser Tyr Ser Lys Ser Cys Cys Val Asn Pro Val Asp Leu Asp Cys
305                 310                 315                 320

Ile Ile Pro Pro Gly Lys Lys Leu Ala Ser Glu Ser Asp Met Val Ala
                325                 330                 335

Ala Glu Gln Asn His Ser Ala Gly Asp Leu Leu Val Glu Ile Pro Lys
            340                 345                 350

Asn Pro Ser Met Glu Ser Phe Gln Ile Val Gly Asn Ser Ser Thr Val
        355                 360                 365

```
Ile Cys Pro Arg Gly Ala Gly Ser Glu Leu Ser Ser Ser Glu Ala Glu
    370                 375                 380

Ala Tyr His Ser Asn Gln Pro Cys Ser Pro Arg Lys Thr Ser Arg Ser
385                 390                 395                 400

Ser Thr Ile Ser Ser Pro Glu Phe Ile Ile Asp Arg Glu Ser Thr Ser
            405                 410                 415

Tyr Ser Glu Ser Phe Lys Phe Arg Cys Asn Gly Gly Lys Ser Leu Pro
        420                 425                 430

Pro Asn Thr Glu Glu Gln Glu Lys Ser Glu Val Leu Ser Glu Gln Ala
    435                 440                 445

Arg Ser Glu
    450

<210> SEQ ID NO 91
<211> LENGTH: 768
<212> TYPE: DNA
<213> ORGANISM: Arabidopsis thaliana

<400> SEQUENCE: 91
aagttcctct gtataccaaa ctatcaaaaa aactctctcc atttctgttc tcaacaaagc      60
caagagttat ggtgagagtc tttcttctct acaacctctt taactccttt cttctttgtt     120
tagttcccaa gaagcttaga gttttcttcc ctccttcttg gtacatcgac gacaagaacc     180
caccaccgcc tgatgaatcg gaaactgaat ctccggtaga tctaaaacga gtgtttcaga     240
tgttcgacaa gaacggagat ggacgcatca caaggaaga gctgaacgat tctctagaga     300
atctaggaat ctttatgcct gacaaagatc tgatccagat gatccagaag atggatgcaa     360
atggagatgg gtgtgtagac ataaacgagt ttgagtctct ttatggttcg attgtggagg     420
aaaaggagga aggggacatg agagacgcgt tcaatgtgtt tgatcaagac ggtgatggat     480
ttatcactgt tgaggagttg aattctgtga tgacttcctt ggggctcaag caaggtaaaa     540
ccctagaatg ttgtaaagag atgattatgc aagtggatga agatggagat ggtagagtca     600
attacaagga attccttcag atgatgaaaa gtggtgactt tagcaataga tcatgagttt     660
attctgacat ggagaagaag gaccaatata tttacctcta gtcctctact atatatgatt     720
aatgtatcag ctttctccaa gttaagaaat ttgggcaggg atcgaatc                  768

<210> SEQ ID NO 92
<211> LENGTH: 195
<212> TYPE: PRT
<213> ORGANISM: Arabidopsis thaliana

<400> SEQUENCE: 92

Met Val Arg Val Phe Leu Leu Tyr Asn Leu Phe Asn Ser Phe Leu Leu
1               5                   10                  15

Cys Leu Val Pro Lys Lys Leu Arg Val Phe Phe Pro Pro Ser Trp Tyr
            20                  25                  30

Ile Asp Asp Lys Asn Pro Pro Pro Asp Ser Glu Thr Glu Ser
        35                  40                  45

Pro Val Asp Leu Lys Arg Val Phe Gln Met Phe Asp Lys Asn Gly Asp
    50                  55                  60

Gly Arg Ile Thr Lys Glu Leu Asn Asp Ser Leu Glu Asn Leu Gly
65                  70                  75                  80

Ile Phe Met Pro Asp Lys Asp Leu Ile Gln Met Ile Gln Lys Met Asp
                85                  90                  95

Ala Asn Gly Asp Gly Cys Val Asp Ile Asn Glu Phe Glu Ser Leu Tyr
```

```
            100                 105                 110
Gly Ser Ile Val Glu Glu Lys Glu Glu Gly Asp Met Arg Asp Ala Phe
        115                 120                 125

Asn Val Phe Asp Gln Asp Gly Asp Gly Phe Ile Thr Val Glu Glu Leu
    130                 135                 140

Asn Ser Val Met Thr Ser Leu Gly Leu Lys Gln Gly Lys Thr Leu Glu
145                 150                 155                 160

Cys Cys Lys Glu Met Ile Met Gln Val Asp Glu Asp Gly Asp Gly Arg
                165                 170                 175

Val Asn Tyr Lys Glu Phe Leu Gln Met Met Lys Ser Gly Asp Phe Ser
            180                 185                 190

Asn Arg Ser
        195

<210> SEQ ID NO 93
<211> LENGTH: 447
<212> TYPE: DNA
<213> ORGANISM: Arabidopsis thaliana

<400> SEQUENCE: 93
atgccgatat tccagtggct taaacggtgt ctctgtggag acacaaacat aactattgat        60
caggcaatag ctttggttga tgaagagatc gccaacttgc gaaaattgga gcgagggtat       120
caaactaata tccgcaacgc agaaaatgcc agagatcaaa ctaatgtcca gatagaaagg       180
gacagcttca cgatactat tcgactttta caagcagagt gtaatctcat caacctagag        240
atcccaaccc tcaatgaaga gaaatttgcg attacaaggt tgaaatcagc aaaacatttc       300
tttggtgctg ttagttcgct caaggaaggt aaagccctag agtgttgtaa agaaatgatt       360
aagcaagtgg atgaagatgg acatggtaga gtcgattaca aggagtttct tcagatgatg       420
aaaactggtg actttagcaa tagatga                                          447

<210> SEQ ID NO 94
<211> LENGTH: 148
<212> TYPE: PRT
<213> ORGANISM: Arabidopsis thaliana

<400> SEQUENCE: 94

Met Pro Ile Phe Gln Trp Leu Lys Arg Cys Leu Cys Gly Asp Thr Asn
1               5                   10                  15

Ile Thr Ile Asp Gln Ala Ile Ala Leu Val Asp Glu Glu Ile Ala Asn
            20                  25                  30

Leu Arg Lys Leu Glu Arg Gly Tyr Gln Thr Asn Ile Arg Asn Ala Glu
        35                  40                  45

Asn Ala Arg Asp Gln Thr Asn Val Gln Ile Glu Arg Asp Ser Phe Asn
    50                  55                  60

Asp Thr Ile Arg Leu Leu Gln Ala Glu Cys Asn Leu Ile Asn Leu Glu
65                  70                  75                  80

Ile Pro Thr Leu Asn Glu Glu Lys Phe Ala Ile Thr Arg Leu Lys Ser
                85                  90                  95

Ala Lys His Phe Phe Gly Ala Val Ser Ser Leu Lys Glu Gly Lys Ala
            100                 105                 110

Leu Glu Cys Cys Lys Glu Met Ile Lys Gln Val Asp Glu Asp Gly His
        115                 120                 125

Gly Arg Val Asp Tyr Lys Glu Phe Leu Gln Met Met Lys Thr Gly Asp
    130                 135                 140
```

Phe Ser Asn Arg
145

<210> SEQ ID NO 95
<211> LENGTH: 2627
<212> TYPE: DNA
<213> ORGANISM: Arabidopsis thaliana

<400> SEQUENCE: 95

| | | | | | |
|---|---|---|---|---|---|
| aacggaatat | ttttttctg | ggagctgaaa | atcgttggtg | acgatggcgg | attctctttc | 60 |
| tagggtttac | ggaactctgt | ttagtggtgt | taatatatct | ctcttctcgg | atccaccgtt | 120 |
| gaaaaccccc | tgaagagtgt | tttttttcc | gggtttaagg | tcttttacgt | ttcgtttttt | 180 |
| cttgagattt | cgtcttccgc | tgtgagtttc | tgttctcgcg | gcgagttttt | gtgtagatct | 240 |
| gagggttttc | aaggcaagag | aaagtgtcgg | tgatgtcgat | tttctcactc | gcgagctctt | 300 |
| ctgattcaca | aagagatgac | taataatgg | cgttgaaggc | ggtggttatt | gtatattgtg | 360 |
| tggtttctct | cgtcagtgtt | caattagctg | atgctcaaca | tgaaggactg | ccagtttcac | 420 |
| caacgttatc | accttcaact | tcaccagtta | tcactgatct | gccctacca | gctgaatttc | 480 |
| cgcggtttca | cagaaagtat | ttcgcaccac | aacaagcaga | agcacctcag | cattctcccc | 540 |
| cttatagtcg | tttggtcgct | tctgatcatc | cctaccag | ctcacatttc | tccaaacctt | 600 |
| ccatgaaaag | gaatgctcag | tctcctggag | ccggcttggc | tgatattgct | ccagcacaat | 660 |
| ctagcaatgg | tgttcttcct | gatgccttaa | ctcagccacc | tttgtcgccc | tccatttcaa | 720 |
| attgttgcaa | atcagatatg | gtgcttaaac | gaagaagtat | tggttgccac | tgcgtgtatc | 780 |
| ctataaaact | ggacatcctt | ctcttgaatg | tttcagaaac | tcctagttgg | aacatgttct | 840 |
| tgaacgaatt | tgctacccag | cttggtctcc | tacctcacca | aatcgagctg | attaacttct | 900 |
| atgtgctaag | cttatcaagg | atgaacatat | cgatggatat | cacccctcat | tctggaatta | 960 |
| gtttctcagc | tagtcaggca | tccgcaataa | actcttccct | tatcagccac | aagattcaat | 1020 |
| ttagccctac | tttggtggga | gattacaaac | ttctaaacct | tacttggttt | gaggcccctg | 1080 |
| caccttcgca | agcacctcta | gtggcttctt | cacctcataa | agcaccatca | caaggatcct | 1140 |
| cagcaactac | gtcagtaaga | tctccaggga | aaaagaggca | tcccaatctt | attcttatct | 1200 |
| tttctatagc | cgctggtgtg | cttatacttg | ccataatcac | tgtacttgtt | atttgttccc | 1260 |
| gcgcactccg | agaagagaaa | gctccagatc | ctcacaaaga | agctgtaaaa | ccaaggaacc | 1320 |
| tggacgctgg | ttcatttggg | ggatctcttc | ctcacccagc | aagtacacgg | tttctgtcat | 1380 |
| atgaagaact | caaagaggca | actagcaatt | ttgaatctgc | tagcattcta | ggagaaggtg | 1440 |
| ggtttggcaa | ggtttacaga | ggcatcttag | ccgatggtac | tgctgtagcg | attaagaagc | 1500 |
| tcacaagtgg | tgggccacaa | ggtgataaag | aattccaggt | ggagattgat | atgcttagcc | 1560 |
| gtcttcatca | tcgtaatctt | gtgaaacttg | tgggttacta | tagtagtcga | gattcttctc | 1620 |
| agcacctact | ttgttatgag | cttgttccaa | atggcagcct | cgaggcttgg | ctccatgggc | 1680 |
| ctctcgggtt | gaactgtcct | cttgattggg | acaccagaat | gaagattgca | cttgatgctg | 1740 |
| caagaggact | tgcatacctt | catgaagact | cgcaaccctc | cgttatacac | agagattttta | 1800 |
| aagcctctaa | tatactcctt | gaaaacaact | tcaacgccaa | agttgcagat | tttggcctag | 1860 |
| ccaaacaagc | tcctgaaggc | aggggtaatc | acttatctac | tcgtgttatg | gcacatttg | 1920 |
| gatatgttgc | gcctgaatat | gcaatgacgg | gacacctact | cgtcaagagt | gatgtttata | 1980 |
| gttacggtgt | ggtccttctc | gaattgttaa | ctggtagaaa | acctgtggat | atgtcacaac | 2040 |

```
cttcaggcca agaaaatctc gtcacttgga caaggccagt tttaagagac aaagaccggt    2100
tagaagaact agtcgattca agacttgaag gaaaataccc gaaagaagat ttcataagag    2160
tatgcacaat cgctgcagct tgtgttgcac ctgaagctag ccagagacca acgatgggcg    2220
aagtggttca gtcacttaaa atggttcaac gggtggttga gtatcaagac ccggttttaa    2280
acacttcaaa taaagctcgt cctaaccgga gacaatcatc agctacgttc gagtcagaag    2340
taacctcttc tatgttctct tctggtcctt attctggtct aagcgctttt gatcatgaaa    2400
atattacacg aacaactgtt ttctcagaag atcttcacga aggccgatga tagaagccag    2460
ggttttcttc tttttatttg tttttctccc acttacggtg agaaaattc caccagagaa     2520 gcttttgagt ttgggacatt attacagctc tttggatttt ggattctcct ttattggagg    2580
atagaatttt gtatatattt ttgcgttaat taattaatat ttgccac                  2627
```

<210> SEQ ID NO 96
<211> LENGTH: 725
<212> TYPE: PRT
<213> ORGANISM: Arabidopsis thaliana

<400> SEQUENCE: 96

```
Met Ser Ile Phe Ser Leu Ala Ser Ser Asp Ser Gln Arg Asp Asp
1               5                   10                  15

Leu Ile Met Ala Leu Lys Ala Val Val Ile Val Tyr Cys Val Val Ser
        20                  25                  30

Leu Val Ser Val Gln Leu Ala Asp Ala Gln His Glu Gly Leu Pro Val
            35                  40                  45

Ser Pro Thr Leu Ser Pro Ser Thr Ser Pro Val Ile Thr Asp Leu Pro
    50                  55                  60

Leu Pro Ala Glu Phe Pro Arg Phe His Arg Lys Tyr Phe Ala Pro Gln
65                  70                  75                  80

Gln Ala Glu Ala Pro Gln His Ser Pro Tyr Ser Arg Leu Val Ala
                85                  90                  95

Ser Asp His Pro Pro Thr Ser Ser His Phe Ser Lys Pro Ser Met Lys
            100                 105                 110

Arg Asn Ala Gln Ser Pro Gly Ala Gly Leu Ala Asp Ile Ala Pro Ala
        115                 120                 125

Gln Ser Ser Asn Gly Val Leu Pro Asp Ala Leu Thr Gln Pro Pro Leu
    130                 135                 140

Ser Pro Ser Ile Ser Asn Cys Cys Lys Ser Asp Met Val Leu Lys Arg
145                 150                 155                 160

Arg Ser Ile Gly Cys His Cys Val Tyr Pro Ile Lys Leu Asp Ile Leu
                165                 170                 175

Leu Leu Asn Val Ser Glu Thr Pro Ser Trp Asn Met Phe Leu Asn Glu
            180                 185                 190

Phe Ala Thr Gln Leu Gly Leu Leu Pro His Gln Ile Glu Leu Ile Asn
        195                 200                 205

Phe Tyr Val Leu Ser Leu Ser Arg Met Asn Ile Ser Met Asp Ile Thr
    210                 215                 220

Pro His Ser Gly Ile Ser Phe Ser Ala Ser Gln Ala Ser Ala Ile Asn
225                 230                 235                 240

Ser Ser Leu Ile Ser His Lys Ile Gln Phe Ser Pro Thr Leu Val Gly
                245                 250                 255

Asp Tyr Lys Leu Leu Asn Leu Thr Trp Phe Glu Ala Pro Ala Pro Ser
            260                 265                 270
```

```
Gln Ala Pro Leu Val Ala Ser Ser Pro His Lys Ala Pro Ser Gln Gly
            275                 280                 285

Ser Ser Ala Thr Thr Ser Val Arg Ser Pro Gly Lys Lys Arg His Pro
290                 295                 300

Asn Leu Ile Leu Ile Phe Ser Ile Ala Ala Gly Val Leu Ile Leu Ala
305                 310                 315                 320

Ile Ile Thr Val Leu Val Ile Cys Ser Arg Ala Leu Arg Glu Glu Lys
                325                 330                 335

Ala Pro Asp Pro His Lys Glu Ala Val Lys Pro Arg Asn Leu Asp Ala
            340                 345                 350

Gly Ser Phe Gly Gly Ser Leu Pro His Pro Ala Ser Thr Arg Phe Leu
        355                 360                 365

Ser Tyr Glu Glu Leu Lys Glu Ala Thr Ser Asn Phe Glu Ser Ala Ser
    370                 375                 380

Ile Leu Gly Glu Gly Gly Phe Gly Lys Val Tyr Arg Gly Ile Leu Ala
385                 390                 395                 400

Asp Gly Thr Ala Val Ala Ile Lys Lys Leu Thr Ser Gly Pro Gln
                405                 410                 415

Gly Asp Lys Glu Phe Gln Val Glu Ile Asp Met Leu Ser Arg Leu His
            420                 425                 430

His Arg Asn Leu Val Lys Leu Val Gly Tyr Tyr Ser Ser Arg Asp Ser
        435                 440                 445

Ser Gln His Leu Leu Cys Tyr Glu Leu Val Pro Asn Gly Ser Leu Glu
    450                 455                 460

Ala Trp Leu His Gly Pro Leu Gly Leu Asn Cys Pro Leu Asp Trp Asp
465                 470                 475                 480

Thr Arg Met Lys Ile Ala Leu Asp Ala Ala Arg Gly Leu Ala Tyr Leu
                485                 490                 495

His Glu Asp Ser Gln Pro Ser Val Ile His Arg Asp Phe Lys Ala Ser
            500                 505                 510

Asn Ile Leu Leu Glu Asn Asn Phe Asn Ala Lys Val Ala Asp Phe Gly
        515                 520                 525

Leu Ala Lys Gln Ala Pro Glu Gly Arg Gly Asn His Leu Ser Thr Arg
    530                 535                 540

Val Met Gly Thr Phe Gly Tyr Val Ala Pro Glu Tyr Ala Met Thr Gly
545                 550                 555                 560

His Leu Leu Val Lys Ser Asp Val Tyr Ser Tyr Gly Val Val Leu Leu
                565                 570                 575

Glu Leu Leu Thr Gly Arg Lys Pro Val Asp Met Ser Gln Pro Ser Gly
            580                 585                 590

Gln Glu Asn Leu Val Thr Trp Thr Arg Pro Val Leu Arg Asp Lys Asp
        595                 600                 605

Arg Leu Glu Glu Leu Val Asp Ser Arg Leu Glu Gly Lys Tyr Pro Lys
    610                 615                 620

Glu Asp Phe Ile Arg Val Cys Thr Ile Ala Ala Cys Val Ala Pro
625                 630                 635                 640

Glu Ala Ser Gln Arg Pro Thr Met Gly Glu Val Val Gln Ser Leu Lys
                645                 650                 655

Met Val Gln Arg Val Val Glu Tyr Gln Asp Pro Val Leu Asn Thr Ser
            660                 665                 670

Asn Lys Ala Arg Pro Asn Arg Arg Gln Ser Ser Ala Thr Phe Glu Ser
        675                 680                 685

Glu Val Thr Ser Ser Met Phe Ser Ser Gly Pro Tyr Ser Gly Leu Ser
```

Ala Phe Asp His Glu Asn Ile Thr Arg Thr Thr Val Phe Ser Glu Asp
705                 710                 715                 720

Leu His Glu Gly Arg
            725

<210> SEQ ID NO 97
<211> LENGTH: 2876
<212> TYPE: DNA
<213> ORGANISM: Arabidopsis thaliana

<400> SEQUENCE: 97

```
ccgttcgtcc ttctcacaag tctgattgcg gaaaaagcag agagagagag aaagttcgag     60
cggaagagaa gcggaaagct cgaggagtca tcaatggtga cggacgatag caactcctct    120
ggacgaatca agtctcatgt agatgatgat gatgatggtg aagaagaaga agatagactc    180
gagggtttgg aaaacagatt aagtgagctt aaaaggaaaa ttcaaggaga aagagttagg    240
tctattaaag agaaatttga ggctaataga agaaagtgg atgctcatgt ttctcccttt     300
tcatctgctg catcgagccg agctaccgca gaggataatg gaaatagcaa tatgctttct    360
tcgagaatga gaatgccact ctgcaagtta atggtttttt ctcatggtgt gggagataga    420
gactatgttc ctactaagga tgttatatca gcaagtgtca agcttcctat tgctgagaga    480
ataccgccat acactacctg atatttttg gacagaaatc aaagaatggc tgaagatcag    540
tctgtggttg gtcgaagaca aatctactat gaacaacatg gtggtgagac gctaatatgc    600
agcgatagtg aggaagaacc agaacctgag gaggaaaaac gtgaatttc cgagggtgaa    660 gattccatta tatggttaat tgggcaggag tatggcatgg gtgaggaagt gcaggatgcc    720
ctttgccagt tgctaagcgt agatgcttct gatatcctgg aaagatacaa tgagctcaag    780
ttgaaggata agcagaatac cgaggaattt tctaattccg gattcaagct gggaatatct    840
ctggaaaagg gccttggtgc agctctagat tcttttgata tcttttctg ccgccgttgc    900 ttggtatttg actgtcgtct gcatggatgt ctcagcctt tgattagtgc tagtgaaaaa    960 cagcctatt ggtctgatta tgaaggtgat aggaaaccct gcagcaaaca ttgttacctc   1020
cagctcaagg cggtcagaga agtaccagaa acatgcagta attttgcatc taaagcagaa   1080
gagaaagctt cagaagagga atgcagcaag gctgtctcct ctgatgttcc ccatgctgct   1140
gctagtggtg tcagtctgca agttgagaag actgatattg gtatcaagaa tgtagattca   1200
tcctctggtg tagaacaaga gcatggaatt agaggaaagc gtgaggtccc aattctaaaa   1260
gactccaatg atctgcctaa tttatcgaac aagaaacaga gaccgcagc ctcagataca   1320 aaaatgtcat ttgttaattc tgtccctagc ttagatcagg cattggatag cacaaagggt   1380
gatcaaggtg aacaactga caataaagta aacagagact cagaagctga tgcaaaagaa   1440
gtaggtgagc ctattccaga caattcggtc catgatggtg gttcctcaat ttgtcagcca   1500
caccatggta gtgaaacgg agcaataatc attgcagaaa tgtctgagac aagtcgacca   1560
tctacagagt ggaatcctat cgagaaggat ctttacttga agggagtcga atctttgga    1620 agaaacagct gtcttattgc aagaaacctg ctttctggct tgaagacatg cctagatgtg   1680
tccaattaca tgcgtgaaaa cgaagtttca gttttcgaa gatctagtac cccaaatttg   1740
ctgttggatg atggcaggac tgacccaggg aatgataatg atgaggtgcc tccaaggaca   1800
agattgttcc gtagaaaagg caaaacccgg aagctaaaat actctacaaa gtctgctggt   1860
catccgtctg tctggaaaag aatagctggt ggcaaaaacc agtcctgtaa acaatacacg   1920
```

-continued

```
ccgtgtggat gcctgtcaat gtgcggaaag gattgcccct gtctaactaa tgaaacttgc    1980
tgcgagaaat attgcgggtg ctcaaaaagc tgtaaaaatc gtttccgagg atgtcattgt    2040
gcaaagagtc aatgcagaag taggcagtgt ccctgctttg ctgctggcag agaatgtgat    2100
ccagatgttt gcagaaattg ctgggttagt tgtggagatg gttctctcgg tgaagcacca    2160
agacgcggag aagggcaatg cggaaacatg agacttctcc tgaggcaaca acagaggatc    2220
ctattgggaa agtctgatgt tgctggatgg ggtgcttttc taaagaactc ggtcagcaaa    2280
aatgaatacc ttggagaata caccggtgaa ttgatctcac accatgaggc ggataagcgt    2340
gggaaaatat atgaccgggc aaattcgtcc ttcctctttg acttgaatga tcagtacgtc    2400
ctcgatgctc aacgcaaagg tgacaagctg aaatttgcca atcactcagc taaacccaat    2460
tgctacgcta aggtgatgtt tgtagcagga gatcacaggg tcgggatttt tgcaaacgaa    2520
cgaatagaag ctagcgaaga gcttttctat gactatagat atggaccaga ccaagcacca    2580
gtgtgggctc gcaaacctga aggctccaag aaagatgatt cagccattac tcatcgtaga    2640
gccagaaagc accaatctca ttgatgatta ctggctaaga gaagtaactt ttataaaaat    2700
aacttataga gttgtgagag atgatatttg aagtttgata acttaagctt gtctttatta    2760
attaattatt atagagttga gattttattt tattttgaca tcgagtttgg actttgtata    2820
ggtgataaaa caatttatga attattgggg tcaataagta aaaatgtatc atttcg       2876
```

<210> SEQ ID NO 98
<211> LENGTH: 856
<212> TYPE: PRT
<213> ORGANISM: Arabidopsis thaliana

<400> SEQUENCE: 98

```
Met Val Thr Asp Asp Ser Asn Ser Ser Gly Arg Ile Lys Ser His Val
1               5                   10                  15

Asp Asp Asp Asp Asp Gly Glu Glu Glu Asp Arg Leu Glu Gly Leu
            20                  25                  30

Glu Asn Arg Leu Ser Glu Leu Lys Arg Lys Ile Gln Gly Glu Arg Val
        35                  40                  45

Arg Ser Ile Lys Glu Lys Phe Glu Ala Asn Arg Lys Lys Val Asp Ala
    50                  55                  60

His Val Ser Pro Phe Ser Ser Ala Ala Ser Ser Arg Ala Thr Ala Glu
65                  70                  75                  80

Asp Asn Gly Asn Ser Asn Met Leu Ser Ser Arg Met Arg Met Pro Leu
                85                  90                  95

Cys Lys Leu Asn Gly Phe Ser His Gly Val Gly Asp Arg Asp Tyr Val
            100                 105                 110

Pro Thr Lys Asp Val Ile Ser Ala Ser Val Lys Leu Pro Ile Ala Glu
        115                 120                 125

Arg Ile Pro Pro Tyr Thr Thr Trp Ile Phe Leu Asp Arg Asn Gln Arg
    130                 135                 140

Met Ala Glu Asp Gln Ser Val Val Gly Arg Arg Gln Ile Tyr Tyr Glu
145                 150                 155                 160

Gln His Gly Gly Glu Thr Leu Ile Cys Ser Asp Ser Glu Glu Pro
                165                 170                 175

Glu Pro Glu Glu Glu Lys Arg Glu Phe Ser Glu Gly Glu Asp Ser Ile
            180                 185                 190

Ile Trp Leu Ile Gly Gln Glu Tyr Gly Met Gly Glu Glu Val Gln Asp
        195                 200                 205
```

-continued

```
Ala Leu Cys Gln Leu Leu Ser Val Asp Ala Ser Asp Ile Leu Glu Arg
    210                 215                 220

Tyr Asn Glu Leu Lys Leu Lys Asp Lys Gln Asn Thr Glu Glu Phe Ser
225                 230                 235                 240

Asn Ser Gly Phe Lys Leu Gly Ile Ser Leu Glu Lys Gly Leu Gly Ala
                245                 250                 255

Ala Leu Asp Ser Phe Asp Asn Leu Phe Cys Arg Arg Cys Leu Val Phe
            260                 265                 270

Asp Cys Arg Leu His Gly Cys Ser Gln Pro Leu Ile Ser Ala Ser Glu
        275                 280                 285

Lys Gln Pro Tyr Trp Ser Asp Tyr Glu Gly Asp Arg Lys Pro Cys Ser
    290                 295                 300

Lys His Cys Tyr Leu Gln Leu Lys Ala Val Arg Glu Val Pro Glu Thr
305                 310                 315                 320

Cys Ser Asn Phe Ala Ser Lys Ala Glu Glu Lys Ala Ser Glu Glu Glu
                325                 330                 335

Cys Ser Lys Ala Val Ser Ser Asp Val Pro His Ala Ala Ser Gly
            340                 345                 350

Val Ser Leu Gln Val Glu Lys Thr Asp Ile Gly Ile Lys Asn Val Asp
        355                 360                 365

Ser Ser Ser Gly Val Glu Gln Glu His Gly Ile Arg Gly Lys Arg Glu
    370                 375                 380

Val Pro Ile Leu Lys Asp Ser Asn Asp Leu Pro Asn Leu Ser Asn Lys
385                 390                 395                 400

Lys Gln Lys Thr Ala Ala Ser Asp Thr Lys Met Ser Phe Val Asn Ser
                405                 410                 415

Val Pro Ser Leu Asp Gln Ala Leu Asp Ser Thr Lys Gly Asp Gln Gly
            420                 425                 430

Gly Thr Thr Asp Asn Lys Val Asn Arg Asp Ser Glu Ala Asp Ala Lys
        435                 440                 445

Glu Val Gly Glu Pro Ile Pro Asp Asn Ser Val His Asp Gly Gly Ser
    450                 455                 460

Ser Ile Cys Gln Pro His His Gly Ser Gly Asn Gly Ala Ile Ile Ile
465                 470                 475                 480

Ala Glu Met Ser Glu Thr Ser Arg Pro Ser Thr Glu Trp Asn Pro Ile
                485                 490                 495

Glu Lys Asp Leu Tyr Leu Lys Gly Val Glu Ile Phe Gly Arg Asn Ser
            500                 505                 510

Cys Leu Ile Ala Arg Asn Leu Leu Ser Gly Leu Lys Thr Cys Leu Asp
        515                 520                 525

Val Ser Asn Tyr Met Arg Glu Asn Glu Val Ser Val Phe Arg Arg Ser
    530                 535                 540

Ser Thr Pro Asn Leu Leu Leu Asp Asp Gly Arg Thr Asp Pro Gly Asn
545                 550                 555                 560

Asp Asn Asp Glu Val Pro Pro Arg Thr Arg Leu Phe Arg Arg Lys Gly
                565                 570                 575

Lys Thr Arg Lys Leu Lys Tyr Ser Thr Lys Ser Ala Gly His Pro Ser
            580                 585                 590

Val Trp Lys Arg Ile Ala Gly Gly Lys Asn Gln Ser Cys Lys Gln Tyr
        595                 600                 605

Thr Pro Cys Gly Cys Leu Ser Met Cys Gly Lys Asp Cys Pro Cys Leu
    610                 615                 620
```

```
Thr Asn Glu Thr Cys Cys Glu Lys Tyr Cys Gly Cys Ser Lys Ser Cys
625                 630                 635                 640

Lys Asn Arg Phe Arg Gly Cys His Cys Ala Lys Ser Gln Cys Arg Ser
            645                 650                 655

Arg Gln Cys Pro Cys Phe Ala Ala Gly Arg Glu Cys Asp Pro Asp Val
        660                 665                 670

Cys Arg Asn Cys Trp Val Ser Cys Gly Asp Gly Ser Leu Gly Glu Ala
    675                 680                 685

Pro Arg Arg Gly Glu Gly Gln Cys Gly Asn Met Arg Leu Leu Leu Arg
690                 695                 700

Gln Gln Gln Arg Ile Leu Leu Gly Lys Ser Asp Val Ala Gly Trp Gly
705                 710                 715                 720

Ala Phe Leu Lys Asn Ser Val Ser Lys Asn Glu Tyr Leu Gly Glu Tyr
            725                 730                 735

Thr Gly Glu Leu Ile Ser His His Glu Ala Asp Lys Arg Gly Lys Ile
        740                 745                 750

Tyr Asp Arg Ala Asn Ser Ser Phe Leu Phe Asp Leu Asn Asp Gln Tyr
    755                 760                 765

Val Leu Asp Ala Gln Arg Lys Gly Asp Lys Leu Lys Phe Ala Asn His
770                 775                 780

Ser Ala Lys Pro Asn Cys Tyr Ala Lys Val Met Phe Val Ala Gly Asp
785                 790                 795                 800

His Arg Val Gly Ile Phe Ala Asn Glu Arg Ile Glu Ala Ser Glu Glu
            805                 810                 815

Leu Phe Tyr Asp Tyr Arg Tyr Gly Pro Asp Gln Ala Pro Val Trp Ala
        820                 825                 830

Arg Lys Pro Glu Gly Ser Lys Lys Asp Asp Ser Ala Ile Thr His Arg
    835                 840                 845

Arg Ala Arg Lys His Gln Ser His
850                 855

<210> SEQ ID NO 99
<211> LENGTH: 2052
<212> TYPE: DNA
<213> ORGANISM: Arabidopsis thaliana

<400> SEQUENCE: 99
atggatgttt ctgaagcacg tctaagtaga attgagtcac agagttcaat tgattcgtct      60
catgaccaaa ggagacaagg atatttctcc atgaacaaga taaacaacgg tcttcgctca     120
ctcagttcac gaggtttcct tcgaaacaga ggaaaagcca taccgctgcc aatgaaagat     180
accgagaaga ctgtgccgga gttcttagtt aatctcaaat tttccgatct tttcgatctc     240
cctggtgaat atgtgctgat gaatgcggag atgcttagca cacttgggaa cgaagaatgg     300
ctggagaaat tgagaagcca tggaacacca ctaacatgtc tcaagaacga tcgaggagat     360
tctgttcttc atcttgctgc tacatggagt catctagaac tagttaagaa cattgtctct     420
gaatgttctt gccttctaat ggagtcaaac tctaaggacc agcttccact tcatgtggca     480
gctcgaatgg tcacttagc tgttgttgag gatcttgttg cgtcggttac attttttctca     540 gctagactgc tgaagaaga tagggagata ctgaatccat atcttctgaa ggacataaat     600
ggagatactg ctctgaactt ggccttgaaa ggacactata cggaggttgc tctctgtttg     660
gtgaatgcaa accgacaagc ttccttctt gcatgtaaag acggaatatc tcccttgtat     720
ttagcagtag aagccaagga tgcatcactt gtaaaagcaa tgttgggaaa tgatggtcct     780
```

```
caaaggaaaa atttgaactt agaagggaga aaatatcttg cacacgctgc attgaattcc    840
ttgagcacag atatccttga tgttattctt aatgaatatc caagtcttgt ggatgagcga    900
gatgaagaag gaaggacttg tctttcgttt ggagcatcca ttgggtatca taaaggagta    960
tgcaacctgt taaaccgatc aagaaagggt gttttttgtat gtgatgatga tggttcctat   1020
ccaatccacc tggcagtaga gaaaggtcgt attaaagttg tcaaagagat ttgcaaacgt   1080
tgtccatatt caaagctttt gcttaacaaa aaaggtcaga acctccttca catcgcagct   1140
gaaagtggga aatttagaat tctacgccac ttgacagcac atgaacaaat aaaccatcta   1200
gctaacgaga agatgtggga tgggaataca ccactgcatc tagccacaat atattggcgt   1260
cctcgagctg ttcgtgagct tggagggaag aaaaacctgt tgatacaaaa caataacggc   1320
ttggtagctc tggatattgc tgagtcaaaa ctgcaaccac actacatctt tcgagagagg   1380
ttgacactgc tagctttagt acaacttcac ttccaaaatg atcctagatg cgcacatact   1440
atgattcaaa caagaccaat aatgcctcaa ggcggaaaca agattacat caacgctctt   1500
ctagtagtgg cagctcttat aaccaccgta acgtttacgt ctggatttac tataccaggt   1560
ggttttaaag actctactcc aaacgtgggc atggcaaatc taataactaa ccctcgtctc   1620
atccttttcc tgatatttga cattttggca ctggaaacct catttttagc agtagttct   1680
ctcatattgg cgcaattagg tgatccgaca ttatatcaga gttccgtaag ggtggccatg   1740
atatcactgt atttcgctat gtatttcatg accttagcat tctttttgt catggttat    1800
gcagctggga atgttagatg gcttgtttat gtcatcttct gtttaatttt ctccattta   1860
actctggcgt tctcaaggtt tatgcctcat cttctactac attattgtgg ctctagttat   1920
aagttgatga tgccatttgt tagttttgca aattcatgtg atgatgacgg acacgaaagt   1980
cctcagttct ctgcgcacaa gtctgagaag atctcaaaca tgatcaagt tgaaatgtca   2040
gacactactt aa                                                       2052
```

<210> SEQ ID NO 100
<211> LENGTH: 683
<212> TYPE: PRT
<213> ORGANISM: Arabidopsis thaliana

<400> SEQUENCE: 100

```
Met Asp Val Ser Glu Ala Arg Leu Ser Arg Ile Glu Ser Gln Ser Ser
1               5                   10                  15

Ile Asp Ser Ser His Asp Gln Arg Arg Gln Gly Tyr Phe Ser Met Asn
            20                  25                  30

Lys Ile Asn Asn Gly Leu Arg Ser Leu Ser Ser Arg Gly Phe Leu Arg
        35                  40                  45

Asn Arg Gly Lys Ala Ile Pro Leu Pro Met Lys Asp Thr Glu Lys Thr
    50                  55                  60

Val Pro Glu Phe Leu Val Asn Leu Lys Phe Ser Asp Leu Phe Asp Leu
65                  70                  75                  80

Pro Gly Glu Tyr Val Leu Met Asn Ala Glu Met Leu Ser Thr Leu Gly
                85                  90                  95

Asn Glu Glu Trp Leu Glu Lys Leu Arg Ser His Gly Thr Pro Leu Thr
            100                 105                 110

Cys Leu Lys Asn Asp Arg Gly Asp Ser Val Leu His Leu Ala Ala Thr
        115                 120                 125

Trp Ser His Leu Glu Leu Val Lys Asn Ile Val Ser Glu Cys Ser Cys
    130                 135                 140
```

```
Leu Leu Met Glu Ser Asn Ser Lys Asp Gln Leu Pro Leu His Val Ala
145                 150                 155                 160

Ala Arg Met Gly His Leu Ala Val Val Glu Asp Leu Val Ala Ser Val
                165                 170                 175

Thr Phe Phe Ser Ala Arg Leu Ala Glu Glu Asp Arg Glu Ile Leu Asn
            180                 185                 190

Pro Tyr Leu Leu Lys Asp Ile Asn Gly Asp Thr Ala Leu Asn Leu Ala
        195                 200                 205

Leu Lys Gly His Tyr Thr Glu Val Ala Leu Cys Leu Val Asn Ala Asn
    210                 215                 220

Arg Gln Ala Ser Phe Leu Ala Cys Lys Asp Gly Ile Ser Pro Leu Tyr
225                 230                 235                 240

Leu Ala Val Glu Ala Lys Asp Ala Ser Leu Val Lys Ala Met Leu Gly
                245                 250                 255

Asn Asp Gly Pro Gln Arg Lys Asn Leu Asn Leu Glu Gly Arg Lys Tyr
            260                 265                 270

Leu Ala His Ala Ala Leu Asn Ser Leu Ser Thr Asp Ile Leu Asp Val
        275                 280                 285

Ile Leu Asn Glu Tyr Pro Ser Leu Val Asp Glu Arg Asp Glu Glu Gly
    290                 295                 300

Arg Thr Cys Leu Ser Phe Gly Ala Ser Ile Gly Tyr His Lys Gly Val
305                 310                 315                 320

Cys Asn Leu Leu Asn Arg Ser Arg Lys Gly Val Phe Val Cys Asp Asp
                325                 330                 335

Asp Gly Ser Tyr Pro Ile His Leu Ala Val Glu Lys Gly Arg Ile Lys
            340                 345                 350

Val Val Lys Glu Ile Cys Lys Arg Cys Pro Tyr Ser Lys Leu Leu Leu
        355                 360                 365

Asn Lys Lys Gly Gln Asn Leu Leu His Ile Ala Ala Glu Ser Gly Lys
    370                 375                 380

Phe Arg Ile Leu Arg His Leu Thr Ala His Glu Gln Ile Asn His Leu
385                 390                 395                 400

Ala Asn Glu Lys Asp Val Asp Gly Asn Thr Pro Leu His Leu Ala Thr
                405                 410                 415

Ile Tyr Trp Arg Pro Arg Ala Val Arg Glu Leu Gly Gly Lys Lys Asn
            420                 425                 430

Leu Leu Ile Gln Asn Asn Asn Gly Leu Val Ala Leu Asp Ile Ala Glu
        435                 440                 445

Ser Lys Leu Gln Pro His Tyr Ile Phe Arg Glu Arg Leu Thr Leu Leu
    450                 455                 460

Ala Leu Val Gln Leu His Phe Gln Asn Asp Pro Arg Cys Ala His Thr
465                 470                 475                 480

Met Ile Gln Thr Arg Pro Ile Met Pro Gln Gly Gly Asn Lys Asp Tyr
                485                 490                 495

Ile Asn Ala Leu Leu Val Val Ala Ala Leu Ile Thr Thr Val Thr Phe
            500                 505                 510

Thr Ser Gly Phe Thr Ile Pro Gly Gly Phe Lys Asp Ser Thr Pro Asn
        515                 520                 525

Val Gly Met Ala Asn Leu Ile Thr Asn Pro Arg Leu Ile Leu Phe Leu
    530                 535                 540

Ile Phe Asp Ile Leu Ala Leu Glu Thr Ser Phe Leu Ala Val Val Ser
545                 550                 555                 560

Leu Ile Leu Ala Gln Leu Gly Asp Pro Thr Leu Tyr Gln Ser Ser Val
```

```
                565                 570                 575
Arg Val Ala Met Ile Ser Leu Tyr Phe Ala Met Tyr Phe Met Thr Leu
            580                 585                 590

Ala Phe Phe Phe Val Met Val Ile Ala Ala Gly Asn Val Arg Trp Leu
            595                 600                 605

Val Tyr Val Ile Phe Cys Leu Ile Phe Ser Ile Leu Thr Leu Ala Phe
        610                 615                 620

Ser Arg Phe Met Pro His Leu Leu Leu His Tyr Cys Gly Ser Ser Tyr
625             630                 635                 640

Lys Leu Met Met Pro Phe Val Ser Phe Ala Asn Ser Cys Asp Asp Asp
                645                 650                 655

Gly His Glu Ser Pro Gln Phe Ser Ala His Lys Ser Glu Lys Ile Ser
            660                 665                 670

Asn Asn Asp Gln Val Glu Met Ser Asp Thr Thr
            675                 680
```